US010000463B2

(12) United States Patent
Iwase et al.

(10) Patent No.: US 10,000,463 B2
(45) Date of Patent: Jun. 19, 2018

(54) HALOGEN-SUBSTITUTED HETEROCYCLIC COMPOUND

(71) Applicant: UBE INDUSTRIES, LTD., Ube-shi, Yamaguchi (JP)

(72) Inventors: Noriaki Iwase, Ube (JP); Hiroshi Nishida, Ube (JP); Makoto Okudo, Ube (JP); Masaaki Ito, Ube (JP); Shigeyuki Kono, Ube (JP); Masaaki Matoyama, Ube (JP); Shigeru Ushiyama, Ube (JP); Eiji Okanari, Ube (JP); Hirofumi Matsunaga, Ube (JP); Kenji Nishikawa, Ube (JP); Tomio Kimura, Tokyo (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days. days.

(21) Appl. No.: 14/752,623

(22) Filed: Jun. 26, 2015

(65) Prior Publication Data
US 2015/0376160 A1 Dec. 31, 2015

Related U.S. Application Data

(63) Continuation of application No. PCT/JP2013/085277, filed on Dec. 27, 2013.

(30) Foreign Application Priority Data

Dec. 28, 2012 (JP) .................................. 2012-286425
May 2, 2013 (JP) .................................. 2013-097171

(51) Int. Cl.
*C07D 333/36* (2006.01)
*C07D 409/04* (2006.01)
*C07D 409/14* (2006.01)
*C07D 417/12* (2006.01)
*A61K 31/381* (2006.01)
*A61K 31/427* (2006.01)
*A61K 31/443* (2006.01)
*C07D 409/12* (2006.01)

(52) U.S. Cl.
CPC .......... *C07D 333/36* (2013.01); *A61K 31/381* (2013.01); *A61K 31/427* (2013.01); *A61K 31/443* (2013.01); *C07D 409/04* (2013.01); *C07D 409/12* (2013.01); *C07D 409/14* (2013.01); *C07D 417/12* (2013.01)

(58) Field of Classification Search
CPC .................................................. C07D 333/36
USPC ........................................... 549/69; 514/447
See application file for complete search history.

(56) References Cited

U.S. PATENT DOCUMENTS

| 2003/0114505 A1 | 6/2003 | Ueno et al. |
| 2004/0067908 A1 | 4/2004 | Nakade et al. |
| 2006/0194850 A1 | 8/2006 | Yamamoto et al. |
| 2011/0082164 A1 | 4/2011 | Clark et al. |
| 2011/0082181 A1 | 4/2011 | Seiders et al. |
| 2011/0196005 A1 | 8/2011 | Hutchinson et al. |
| 2012/0015991 A1 | 1/2012 | Hutchinson et al. |
| 2012/0196839 A1 | 8/2012 | Hutchinson et al. |
| 2012/0258987 A1 | 10/2012 | Seiders et al. |
| 2013/0072449 A1 | 3/2013 | Buckman et al. |
| 2013/0253004 A1 | 9/2013 | Seiders et al. |
| 2013/0253023 A1 | 9/2013 | Brittain et al. |

FOREIGN PATENT DOCUMENTS

| WO | WO 01/60819 A1 | 8/2001 |
| WO | WO 02/062389 A1 | 8/2002 |
| WO | WO 2005/012269 A1 | 2/2005 |
| WO | WO 2010/077882 A2 | 7/2010 |
| WO | WO 2010/077883 A2 | 7/2010 |
| WO | WO 2010/141761 A2 | 12/2010 |
| WO | WO 2010/141768 A2 | 12/2010 |
| WO | WO 2011/017350 A2 | 2/2011 |
| WO | WO 2011/041461 A2 | 4/2011 |
| WO | WO 2011/041462 A2 | 4/2011 |
| WO | WO 2011/041694 A2 | 4/2011 |
| WO | WO 2011/041729 A2 | 4/2011 |
| WO | WO 2011/091167 A2 | 7/2011 |
| WO | WO 2011/159632 A1 | 12/2011 |
| WO | WO 2011/159633 A1 | 12/2011 |
| WO | WO 2011/159635 A1 | 12/2011 |
| WO | WO 2012/078593 A2 | 6/2012 |
| WO | WO 2012/078805 A1 | 6/2012 |
| WO | WO 2012/138648 A1 | 10/2012 |
| WO | WO 2012/138797 A1 | 10/2012 |
| WO | WO 2013/025733 A1 | 2/2013 |

OTHER PUBLICATIONS

Ren et al., "Comparing the differential, etc.," Microvascular Research 85 (2013) 59-67.*
Ikeda et al., "Autotaxin in liver fibrosis" Clinica Chimica Acta 413 (2012) 1817-1821.*
Pradere et al., "LPA1 Receptor, etc.," J Am. Soc. Nephrol. 18:3110-3118, 2007.*
Zhao et al., "Lysophosphatidic acid, etc.," Biochimica et Biophysica Acta 1831 (2013) 86-92.*
Rancoule et al, "Lysophosphatidic acid, etc.," Expert Opin. Investig. Drugs (2011) 20(5), 657-667.*
Takuwa et al., "Sphingosine-1-phospate, etc.," Biochimica et Biophysica Acta1831 (2013) 185-192.*
Hama et al., "LPA3, a unique, etc.," Progress in Lipid Research 49 (2010) 335-342.*
Robinson, "Medical Therapy, etc.," Eur J Surg 1998: Suppl 582:90-98.*
Simone, Oncology: Introduction, Cecil Textbook of Medicine, ed Bennett et al. W.B. Saunders CO. 20th ed. vol. 1, 1996, pp. 1004-1010.*
Gura, Systems for Identifying New Drugs Are Often Faulty, Cancer Models, Science, vol. 278. No. 5340, pp. 1041-1042, Nov. 1997.*

(Continued)

*Primary Examiner* — Patricia L Morris
(74) *Attorney, Agent, or Firm* — Birch, Stewart, Kolasch & Birch, LLP

(57) ABSTRACT

A novel α-halogen-substituted thiophene compound or a pharmacologically acceptable salt thereof, which has a potent LPA receptor-antagonist activity and is useful as a medicament is provided.

18 Claims, No Drawings

(56) References Cited

OTHER PUBLICATIONS

Johnson et al., Relationships between drug activity in NCI preclinical in vitro and in vivo and early clinical trials, British Journal of Cancer (2001) 64(10): 1424-1431.*

Golub et al., "Molecular Classification, etc.," Science, 286, 1999, 531-537.*

Castelino et al., "Amelioration of Dermal Fibrosis by Genetic Deletion or Pharmacologic Antagonism of Lysophosphatidic Acid Receptor 1 in a Mouse Model of Scleroderma", Arthritis & Rheumatism, May 2011, vol. 63, No. 5, pp. 1405-1415.

Gräler et al., "Lysophospholipids and their G protein-coupled receptors in inflammation and immunity", Biochimica et Biophysica Acta, 2002, 1582, pp. 168-174.

Guo et al., "Mitogenic Signaling in Androgen Sensitive and Insensitive Prostate Cancer Cell Lines", The Journal of Urology, Mar. 2000, vol. 163, pp. 1027-1032.

Ikeda et al., "Effects of Lysophosphatidic Acid on Proliferation of Stellate Cells and Hepatocytes in Culture", Biochemical and Biophysical Research Communications, 1998, vol. 248, No. 2, pp. 436-440, Article No. RC988983.

Imamura et al., "Induction of in Vitro Tumor Cell Invasion of Cellular Monolayers by Lysophosphatidic Acid or Phospholipase D", Biochemical and Biophysical Research Communications, Jun. 15, 1993, vol. 193, No. 2, pp. 497-503.

Inoue et al., "Initiation of neuropathic pain requires lysophosphatidic acid receptor signaling", Nature Medicine, Jul. 2004, vol. 10, No. 7, pp. 712-718, 755.

International Search Report, issued in PCT/JP2013/085277, dated Mar. 25, 2014.

Pradère et al., "LPA1 Receptor Activation Promotes Renal Interstitial Fibrosis", J Am Soc Nephrol, 2007, 18, pp. 3310-3118.

Qian et al., "Discovery of Highly Selective and Orally Active Lysophosphatidic Acid Receptor-1 Antagonists with Potent Activity on Human Lung Fibroblasts", Journal of Medicinal Chemistry, 2012, 55, 7920-7939.

Swaney et al., "A novel, orally active LPA1 receptor antagonist inhibits lung fibrosis in the mouse bleomycin model", British Journal of Pharmacology, 2010, 160, pp. 1699-1713.

Swaney et al., "Pharmacokinetic and Pharmacodynamic Characterization of an Oral Lysophosphatidic Acid Type 1 Receptor-Selective Antagonist", The Journal of Pharmacology and Experimental Therapeutics, 2011, vol. 336, No. 3, pp. 693-700.

Tager et al., "The lysophosphatidic acid receptor LPA1 links pulmonary fibrosis to lung injury by mediating fibroblast recruitment and vascular leak", Nature Medicine, Jan. 2008, vol. 14, No. 1, pp. 45-54.

Tangkijvanich et al., "Rho and p38 MAP Kinase Signaling Pathways Mediate LPA-Stimulated Hepatic Myofibroblast Migration", Journal of Biomedical Science, 2003, 10, pp. 352-358.

Xu et al., "Lysophospholiqids activate ovarian and breast cancer cells", Biochem. J, 1995, 309, pp. 933-940.

Yanase et al., "Lysophosphatidic Acid Enhances Collagen Gel Contraction by Hepatic Stellate Cells: Association with Rho-Kinase", Biochemical and Biophysical Research Communications, 2000, vol. 277, No. 1, pp. 72-78.

Zhao et al., "Regulation of Lysophosphatidic Acid Receptor Expression and Function in Human Synoviocytes: Implications for Rheumatoid Arthritis", Molecular Pharmacology, 2008, vol. 73, No. 2, pp. 587-600.

Zhou et al., "Phosphatidic Acid and Lysophosphatidic Acid Induce Haptotactic Migration of Human Monocytes", The Journal of Biological Chemistry, Oct. 27, 1995, vol. 270, No. 43, pp. 25549-25556.

* cited by examiner

US 10,000,463 B2

HALOGEN-SUBSTITUTED HETEROCYCLIC COMPOUND

CROSS REFERENCE TO RELATED APPLICATIONS

This application is a Continuation of PCT International Application No. PCT/JP2013/085277 filed on Dec. 27, 2013, which claims priority under 35 U.S.C. § 119(a) to Patent Application No. 2012-286425 filed in Japan on Dec. 28, 2012 and Patent Application No. 2013-097171 filed in Japan on May 2, 2013, all of which are hereby expressly incorporated by reference into the present application.

TECHNICAL FIELD

The present invention relates to a novel α-halogen-substituted thiophene compound or a pharmacologically acceptable salt thereof. Since the α-halogen-substituted thiophene compound of the present invention has an antagonist activity on a lysophosphatidic acid (LPA) receptor, it would be useful for the prevention and/or the treatment of diseases caused by LPA.

BACKGROUND ART

Lysophosphatidic acid (LPA) is a physiologically active phospholipid which is present in a living body. LPA transduces a signal in a cell and modulates the proliferation, differentiation, survival, migration, adhesion, infiltration, morphogenesis of a cell by binding to a specific G-protein-coupled receptor (LPA1, LPA2, LPA3, LPA4, LPA5, LPA6). Further, it has been known that LPA is involved with a disease accompanied with fibrosis in various organs.

Regarding liver, it has been reported that LPA accelerates the proliferation or contraction of stellate cell which plays an important role in the process of hepatic fibrosis, or the migration of myofibroblast (refer to Non-Patent Documents 1, 2 and 3).

Regarding kidney, it has been reported that the production of LPA or the expression of LPA1 is facilitated in a mouse with unilateral ureteral ligation, which is an animal model of renal fibrosis, and that the renal fibrosis is suppressed by LPA1 deficiency or administration of an LPA receptor-antagonist (refer to Non-Patent Documents 4 and 5).

Regarding lung, it has been reported that the LPA concentration in bronchoalveolar lavage fluid of a patient with idiopathic pulmonary fibrosis is elevated; and that LPA1 is most expressed in fibroblast having an important role in the process of pulmonary fibrosis and LPA makes the fibroblast migrate. Further, it has been reported that fibrosis is suppressed by LPA1 deficiency or administration of an LPA receptor-antagonist in a mouse to which bleomycin was intratracheally administered, which is an animal model of pulmonary fibrosis (refer to Non-Patent Documents 6 and 7).

Regarding skin, it has been reported that fibrosis of skin is suppressed by LPA1 deficiency or administration of an LPA receptor-antagonist in a mouse to which bleomycin was subcutaneously administered, which is a sclerodermia animal model (refer to Non-Patent Document 8).

It has also been known to that LPA is involved with immunological or inflammatory diseases. It has been reported that LPA facilitates the migration of human monocyte; and that LPA is involved with the proliferation or infiltration of T cells. Further, it has been reported that synovial cells of patient with rheumatoid arthritis express LPA receptor and migrate or produce IL-6 and IL-8 by the LPA stimulation; and that these actions are inhibited by an LPA receptor antagonist (refer to Non-Patent Documents 9, 10 and 11).

In addition, it has been reported that LPA and LPA1 are involved with the development of neuropathic pain (refer to Patent Document 12); that LPA is involved with urologic diseases by contracting an extracted urethra specimen and a prostatic specimen to increase the intraurethral pressure (refer to Patent Document 1); and that LPA is involved with cancer-related diseases by accelerating the infiltration of cancer cells, by accelerating the proliferation of ovary cancer cells, or by accelerating the proliferation of prostate cancer cells (refer to Non-Patent Documents 13, 14 and 15).

Based on these findings, a medicament which antagonizes the LPA receptor (particularly, LPA1 receptor) is considered to be useful for the prevention and/or treatment of a disease accompanying fibrosis, an immunological or inflammatory disease, a central or peripheral nervous system disease, an urologic disease, a cancer-related disease, etc.

On the other hand, as a compound having antagonizing action of LPA receptor, ([1,1'-biphenyl]-4-yl)acetic acid derivatives are disclosed in Patent Documents 2 to 19, and Non-Patent Documents 7, 8, 16 and 17; (2'-methoxy-[1,1'-biphenyl]-4-yl) acetic acid derivatives are disclosed in Patent Document 17; and 3-chloroisothiazole derivatives are disclosed in Patent Document 19, but there is no disclosure on the compound of the present invention.

PRIOR ART DOCUMENTS

Patent Documents

Patent Document 1: WO 2002/062389
Patent Document 2: WO 2010/077882
Patent Document 3: WO 2010/077883
Patent Document 4: WO 2010/141761
Patent Document 5: WO 2010/141768
Patent Document 6: WO 2011/017350
Patent Document 7: WO 2011/041461
Patent Document 8: WO 2011/041462
Patent Document 9: WO 2011/041694
Patent Document 10: WO 2011/041729
Patent Document 11: WO 2011/091167
Patent Document 12: WO 2011/159632
Patent Document 13: WO 2011/159633
Patent Document 14: WO 2011/159635
Patent Document 15: WO 2012/078593
Patent Document 16: WO 2012/078805
Patent Document 17: WO 2012/138648
Patent Document 18: WO 2012/138797
Patent Document 19: WO 2013/025733

Non-Patent Document

Non-Patent Document 1: Biochemical and Biophysical Research Communications, 248 (1998) 436-440
Non-Patent Document 2: Biochemical and Biophysical Research Communications, 277 (2000) 72-78
Non-Patent Document 3: Journal of Biomedical Science, 10 (2003) 352-358
Non-Patent Document 4: Journal of the American Society of Nephrology, 18 (2007) 3110-3118
Non-Patent Document 5: The Journal of Pharmacology and Experimental Therapeutics, 336 (2011) 693-700
Non-Patent Document 6: Nature Medicine, 14 (2008) 45-54

Non-Patent Document 7: British Journal of Pharmacology, 160 (2010) 1699-1713

Non-Patent Document 8: Arthritis & Rheumatism, 63 (2011) 1405-1415

Non-Patent Document 9: Journal of Biological Chemistry, 270 (1995) 25549-25556

Non-Patent Document 10: Biochimica et Biophysica Acta, 1582 (2002) 168-174

Non-Patent Document 11: Molecular Pharmacology, 73 (2008) 587-600

Non-Patent Document 12: Nature Medicine, 10 (2004) 712-718

Non-Patent Document 13: Biochemical and Biophysical Research Communications, 193 (1993) 497-503

Non-Patent Document 14: Biochemical Journal, 309 (1995) 933-940

Non-Patent Document 15: The Journal of Urology, 163 (2000) 1027-1032

Non-Patent Document 16: The Journal of Pharmacology and Experimental Therapeutics, 336 (2011) 693-700

Non-Patent Document 17: Journal of Medicinal Chemistry, 55 (2012) 7920-7939

DISCLOSURE OF THE INVENTION

Problems to be Solved by the Invention

The present inventors carried out a research on various halogen-substituted heterocyclic compounds in order to develop an excellent medicament for the treatment or prevention of a disease accompanying fibrosis, an immunological or inflammatory disease, a central or peripheral nervous system disease, an urologic disease, a cancer-related disease, etc., and found out that a novel α-halogen-substituted thiophene compound having a specific structure has an excellent LPA receptor-antagonist action and is useful as a medicament (particularly, for the prevention and/or treatment of a disease accompanying fibrosis, an immunological or inflammatory disease, a central or peripheral nervous system disease, an urologic disease, a cancer-related disease) to accomplish the present invention.

The present invention provides a novel α-halogen-substituted thiophene compound or a pharmacologically acceptable salt thereof which has a potent LPA receptor-antagonist action and is useful as a medicament for the treatment and/or prevention (preferably, a medicament for the treatment) of, particularly, a disease accompanying fibrosis, an immunological or inflammatory disease, a central or peripheral nervous system disease, an urologic disease or a cancer-related disease.

Means for Solving the Problems

The present invention provides:
(1) A compound represented by the general formula (I):

[Chemical Formula 1]

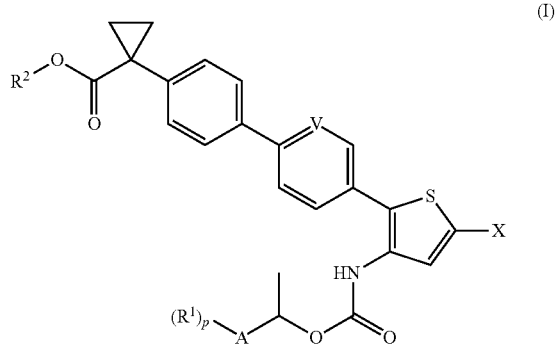

(I)

wherein
A represents, a phenyl ring, a thiophene ring, or an isothiazole ring;
$R^1$ is the same or different, and represents a halogen atom, or a $C_1$-$C_3$ alkyl group;
$R^2$ represents a hydrogen atom, or a $C_1$-$C_6$ alkyl group;
p represents an integer of 0 to 5;
V represents $CR^3$ wherein $R^3$ represents a hydrogen atom, an amino group, a nitro group, or a $C_1$-$C_3$ alkoxy group, or V represents a nitrogen atom;
X represents a halogen atom,
or a pharmacologically acceptable salt thereof.
(2) The compound according to (1) which is represented by the general formula (Ia):

[Chemical Formula 2]

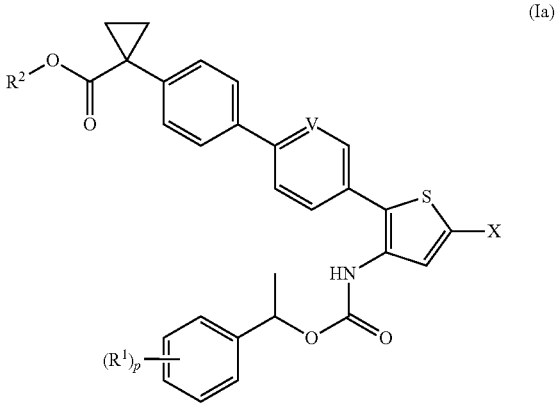

(Ia)

wherein
$R^1$ is the same or different, and represents a halogen atom, or a $C_1$-$C_3$ alkyl group,
$R^2$ represents a hydrogen atom, or a $C_1$-$C_6$ alkyl group;
p represents an integer of 0 to 5;
V represents CH or a nitrogen atom;
X represents a halogen atom,
or a pharmacologically acceptable salt thereof.
(3) The compound according to (2) wherein, in the general formula (Ia), the group:

[Chemical Formula 3]

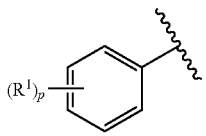

is selected from a group consisting of the groups:

[Chemical Formula 4]

is selected from a group consisting of the groups:

[Chemical Formula 6]

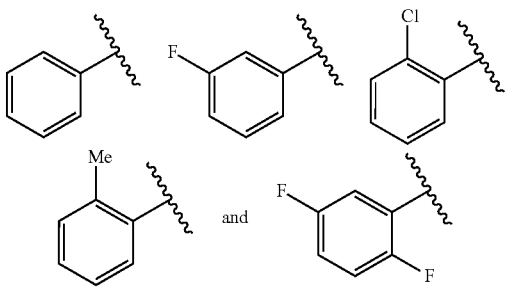

or a pharmacologically acceptable salt thereof.

(5) The compound according to (2) which is selected from a group consisting of:
  (RS)-1-{4'-[5-bromo-3-({[1-(2-chlorophenyl)ethoxy]carbonyl}amino)-thiophen-2-yl]-[1,1'-biphenyl]-4-yl}cyclopropanecarboxylic acid,
  (RS)-1-{4'-[5-chloro-3-({[1-(2-chlorophenyl)ethoxy]carbonyl}amino)-thiophen-2-yl]-[1,1'-biphenyl]-4-yl}cyclopropanecarboxylic acid,
  (R)-1-{4'-[5-chloro-3-({[1-(2-chlorophenyl)ethoxy]carbonyl}amino)thiophen-2-yl]-[1,1'-biphenyl]-4-yl}cyclopropanecarboxylic acid,
  (R)-1-[4'-(5-chloro-3-{[(1-phenylethoxy)carbonyl]amino}thiophen-2-yl)-[1,1'-biphenyl]-4-yl]cyclopropanecarboxylic acid,
  (R)-1-{4'-[5-chloro-3-({[1-(2-fluorophenyl)ethoxy]carbonyl}amino)thiophen-2-yl]-[1,1'-biphenyl]-4-yl}cyclopropanecarboxylic acid,
  (R)-1-{4'-[5-chloro-3-({[1-(3-fluorophenyl)ethoxy]carbonyl}amino)thiophen-2-yl]-[1,1'-biphenyl]-4-yl}cyclopropanecarboxylic acid,
  (R)-1-{4'-[5-chloro-3-({[1-(4-fluorophenyl)ethoxy]carbonyl}amino)thiophen-2-yl]-[1,1'-biphenyl]-4-yl}cyclopropanecarboxylic acid,
  (R)-1-{4'-[5-chloro-3-({[1-(4-chlorophenyl)ethoxy]carbonyl}amino)thiophen-2-yl]-[1,1'-biphenyl]-4-yl}cyclopropanecarboxylic acid,
  (R)-1-{4'-[5-chloro-3-({[1-(o-tolyl)ethoxy]carbonyl}amino)thiophen-2-yl]-[1,1'-biphenyl]-4-yl}cyclopropanecarboxylic acid,
  (R)-1-{4'-[5-chloro-3-({[1-(2,4-difluorophenyl)ethoxy]carbonyl}amino)-thiophen-2-yl]-[1,1'-biphenyl]-4-yl}cyclopropanecarboxylic acid,
  (R)-1-{4'-[5-chloro-3-({[1-(2,5-difluorophenyl)ethoxy]carbonyl}amino)-thiophen-2-yl]-[1,1'-biphenyl]-4-yl}cyclopropanecarboxylic acid,
  (R)-1-{4'-[5-chloro-3-({[1-(3,4-difluorophenyl)ethoxy]carbonyl}amino)-thiophen-2-yl]-[1,1'-biphenyl]-4-yl}cyclopropanecarboxylic acid,
  (R)-1-{4'-[5-chloro-3-({[1-(2-chloro-4-fluorophenyl)ethoxy]carbonyl}amino)-thiophen-2-yl]-[1,1'-biphenyl]-4-yl}cyclopropanecarboxylic acid,
  (R)-1-{4'-[5-(5-chloro-3-{[(1-phenylethoxy)carbonyl]amino}thiophen-2-yl)-pyridin-2-yl]phenyl}cyclopropanecarboxylic acid,
  (R)-1-[4'-(5-fluoro-3-{[(1-phenylethoxy)carbonyl]amino}thiophen-2-yl)[1,1'-biphenyl]-4-yl]cyclopropanecarboxylic acid,
  (R)-1-{4'-[5-fluoro-3-({[1-(2-fluorophenyl)ethoxy]carbonyl}amino)thiophen-2-yl]-[1,1'-biphenyl]-4-yl}cyclopropanecarboxylic acid, or a pharmacologically acceptable salt thereof.

(4) The compound according to (2) wherein, in the general formula (Ia), the group:

[Chemical Formula 5]

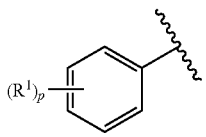

(R)-1-{4'-[5-fluoro-3-({[1-(4-fluorophenyl)ethoxy]carbonyl}amino)thiophen-2-yl]-[1,1'-biphenyl]-4-yl}cyclopropanecarboxylic acid, (R)-1-{4'-[3-({[1-(2-chlorophenyl)ethoxy]carbonyl}amino)-5-fluorothiophen-2-yl]-[1,1'-biphenyl]-4-yl}cyclopropanecarboxylic acid, (R)-1-{4'-[3-({[1-(4-chlorophenyl)ethoxy]carbonyl}amino)-5-fluorothiophen-2-yl]-[1,1'-biphenyl]-4-yl}cyclopropanecarboxylic acid, (R)-1-{4'-[5-fluoro-3-({[1-(o-tolyl)ethoxy]carbonyl}amino)thiophen-2-yl]-[1,1'-biphenyl]-4-yl}cyclopropanecarboxylic acid, (R)-1-{4'-[3-({[1-(3,4-difluorophenyl)ethoxy]carbonyl}amino)-5-fluorothiophen-2-yl]-[1,1'-biphenyl]-4-yl}cyclopropanecarboxylic acid, (R)-1-{4'-[3-({[1-(2,4-difluorophenyl)ethoxy]carbonyl}amino)-5-fluorothiophen-2-yl]-[1,1'-biphenyl]-4-yl}cyclopropanecarboxylic acid, (R)-1-{4'-[3-({[1-(2-chloro-4-fluorophenyl)ethoxy]carbonyl}amino)-5-fluorothiophen-2-yl]-[1,1'-biphenyl]-4-yl}cyclopropanecarboxylic acid, (RS)-1-{4'-[3-({[1-(4-chloro-2-fluorophenyl)ethoxy]carbonyl}amino)-5-fluorothiophen-2-yl]-[1,1'-biphenyl]-4-yl}cyclopropanecarboxylic acid, (RS)-1-{4'-[5-fluoro-3-({[1-(2,4,5-trifluorophenyl)ethoxy]carbonyl}amino)-thiophen-2-yl]-[1,1'-biphenyl]-4-yl}cyclopropanecarboxylic acid, or a pharmacologically acceptable salt thereof.

(6) The compound according to (1) wherein, in the general formula (I), V represents $CR^3$ in which $R^3$ represents a hydrogen atom, an amino group, a nitro group, or a $C_1$-$C_3$ alkoxy group, or V represents a nitrogen atom with the proviso that in a case where A represents a phenyl ring, V is not CH or a nitrogen atom, or a pharmacologically acceptable salt thereof.

(7) The compound according to (6) which is represented by the general formula (Ib):

[Chemical Formula 7]

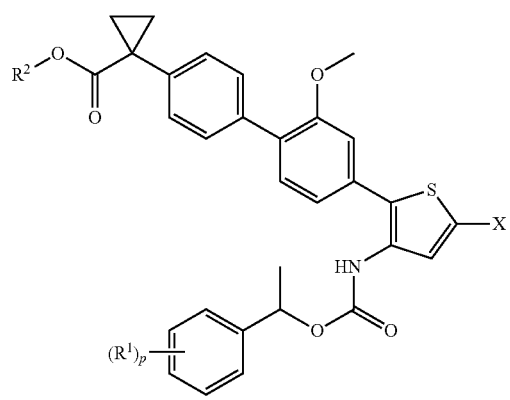

(Ib)

wherein $R^1$ is the same or different, and represents a halogen atom, or a $C_1$-$C_3$ alkyl group;

$R^2$ represents a hydrogen atom or a $C_1$-$C_6$ alkyl group;

p represents an integer of 0 to 5;

X represents a halogen atom, or a pharmacologically acceptable salt thereof.

(8) The compound according to (7) wherein, in the general formula (Ib), the group:

[Chemical Formula 8]

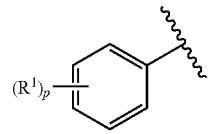

is selected from a group consisting of the groups:

[Chemical Formula 9]

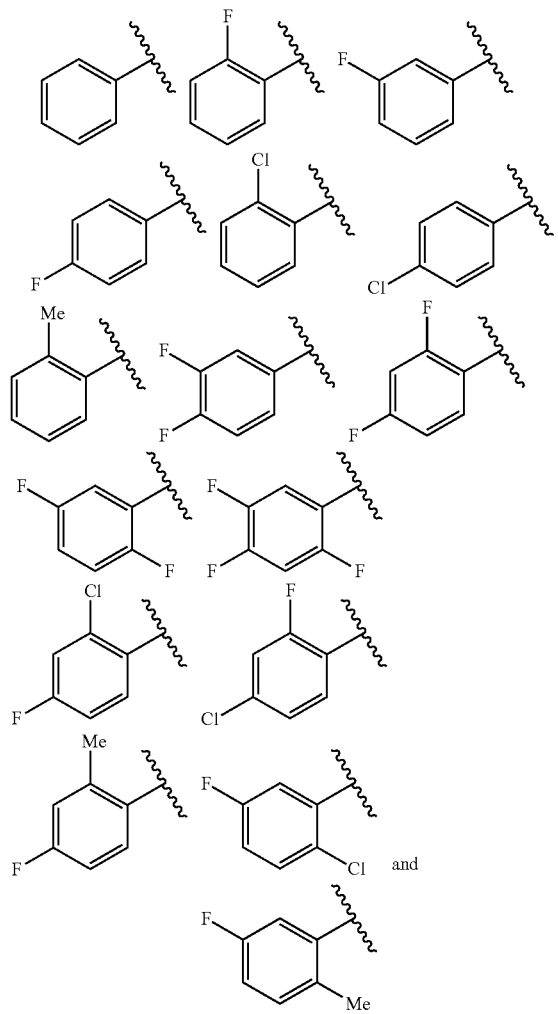

and or a pharmacologically acceptable salt thereof.

(9) The compound according to (7) wherein, in the general formula (Ib), the group:

[Chemical Formula 10]

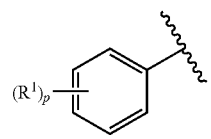

is selected from a group consisting of the groups:

[Chemical Formula 11]

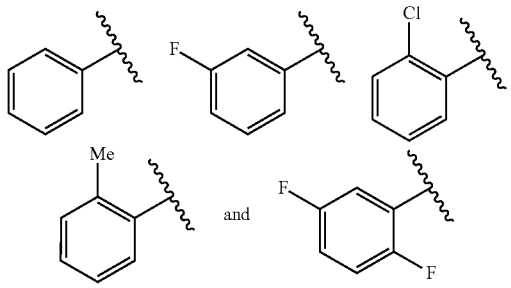

or a pharmacologically acceptable salt thereof.

(10) The compound according to (7) which is selected from a group consisting of:
(R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid,
(R)-1-{4'-[5-chloro-3-({[1-(2-fluorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(3-fluorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(4-fluorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(2-chlorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(4-chlorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(o-tolyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(3,4-difluorophenyl)ethoxy]carbonyl}amino)-thiophen-2-yl]-2'-methoxy-[1,1'-biphenyl]-4-yl}cyclopropanecarboxylic acid,
(R)-1-{4'-[5-chloro-3-({[1-(2,5-difluorophenyl)ethoxy]carbonyl}amino)-thiophen-2-yl]-2'-methoxy-[1,1'-biphenyl]-4-yl}cyclopropanecarboxylic acid,
(R)-1-{4'-[5-chloro-3-({[1-(2,4-difluorophenyl)ethoxy]carbonyl}amino)-thiophen-2-yl]-2'-methoxy-[1,1'-biphenyl]-4-yl}cyclopropanecarboxylic acid,
(RS)-1-{4'-[5-chloro-3-({[1-(2-chloro-5-fluorophenyl)ethoxy]carbonyl}-amino)thiophen-2-yl]-2'-methoxy-[1,1'-biphenyl]-4-yl}cyclopropanecarboxylic acid,
(R)-1-{4'-[5-chloro-3-({[1-(2-chloro-4-fluorophenyl)ethoxy]carbonyl}amino)-thiophen-2-yl]-2'-methoxy-[1,1'-biphenyl]-4-yl}cyclopropanecarboxylic acid,
(RS)-1-{4'-[5-chloro-3-({[1-(5-fluoro-2-methylphenyl)ethoxy]carbonyl}-amino)thiophen-2-yl]-2'-methoxy-[1,1'-biphenyl]-4-yl}cyclopropanecarboxylic acid,
(RS)-1-{4'-[5-chloro-3-({[1-(4-fluoro-2-methylphenyl)ethoxy]carbonyl}-amino)thiophen-2-yl]-2'-methoxy-[1,1'-biphenyl]-4-yl}cyclopropanecarboxylic acid,
(R)-1-[4'-(5-fluoro-3-{[(1-phenylethoxy)carbonyl]amino}thiophen-2-yl)-2'-methoxy-[1,1'-biphenyl]-4-yl]cyclopropanecarboxylic acid,
(R)-1-{4'-[5-fluoro-3-({[1-(2-fluorophenyl)ethoxy]carbonyl}amino)thiophen-2-yl]-2'-methoxy-[1,1'-biphenyl]-4-yl}cyclopropanecarboxylic acid,
(R)-1-{4'-[5-fluoro-3-({[1-(3-fluorophenyl)ethoxy]carbonyl}amino)thiophen-2-yl]-2'-methoxy-[1,1'-biphenyl]-4-yl}cyclopropanecarboxylic acid,
(R)-1-{4'-[5-fluoro-3-({[1-(4-fluorophenyl)ethoxy]carbonyl}amino)thiophen-2-yl]-2'-methoxy-[1,1'-biphenyl]-4-yl}cyclopropanecarboxylic acid,
(R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid,
(R)-1-{4'-[3-({[1-(4-chlorophenyl)ethoxy]carbonyl}amino)-5-fluorothiophen-2-yl]-2'-methoxy-[1,1'-biphenyl]-4-yl}cyclopropanecarboxylic acid,
(R)-1-{4'-[5-fluoro-3-({[1-(o-tolyl)ethoxy]carbonyl}amino)thiophen-2-yl]-2'-methoxy-[1,1'-biphenyl]-4-yl}cyclopropanecarboxylic acid,
(R)-1-{4'-[3-({[1-(3,4-difluorophenyl)ethoxy]carbonyl}amino)-5-fluorothiophen-2-yl]-2'-methoxy-[1,1'-biphenyl]-4-yl}cyclopropanecarboxylic acid,
(R)-1-{4'-[3-({[1-(2,5-difluorophenyl)ethoxy]carbonyl}amino)-5-fluorothiophen-2-yl]-2'-methoxy-[1,1'-biphenyl]-4-yl}cyclopropanecarboxylic acid,
(R)-1-{4'-[3-({[1-(2,4-difluorophenyl)ethoxy]carbonyl}amino)-5-fluorothiophen-2-yl]-2'-methoxy-[1,1'-biphenyl]-4-yl}cyclopropanecarboxylic acid,
(RS)-1-{4'-[3-({[1-(2-chloro-5-fluorophenyl)ethoxy]carbonyl}amino)-5-fluorothiophen-2-yl]-2'-methoxy-[1,1'-biphenyl]-4-yl}cyclopropanecarboxylic acid,
(R)-1-{4'-[3-({[1-(2-chloro-4-fluorophenyl)ethoxy]carbonyl}amino)-5-fluorothiophen-2-yl]-2'-methoxy-[1,1'-biphenyl]-4-yl}cyclopropanecarboxylic acid,
(RS)-1-{4'-[5-fluoro-3-({[1-(5-fluoro-2-methylphenyl)ethoxy]carbonyl}-amino)thiophen-2-yl]-2'-methoxy-[1,1'-biphenyl]-4-yl}cyclopropanecarboxylic acid, and
(RS)-1-{4'-[5-fluoro-3-({[1-(4-fluoro-2-methylphenyl)ethoxy]carbonyl}-amino)thiophen-2-yl]-2'-methoxy-[1,1'-biphenyl]-4-yl}cyclopropanecarboxylic acid,
or a pharmacologically acceptable salt thereof.

(11) The compound according to (6) wherein, in the general formula (I), V represents $CR^3$ in which $R^3$ represents a hydrogen atom or a methoxy group, or V represents a nitrogen atom; and the group:

[Chemical Formula 12]

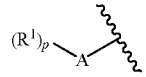

is selected from a group consisting of the groups:

[Chemical Formula 13]

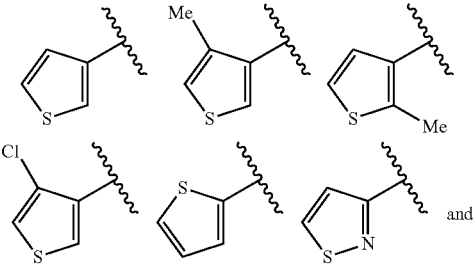

-continued

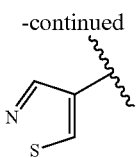

or a pharmacologically acceptable salt thereof.

(12) The compound according to (6) wherein, in the general formula (I), the group:

[Chemical Formula 14]

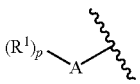

is selected from a group consisting of the groups:

[Chemical Formula 15]

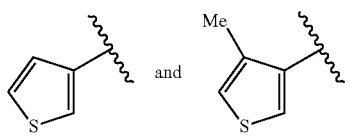

or a pharmacologically acceptable salt thereof.

(13) The compound according to (11) which is selected from a group consisting of:
(RS)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid,
(R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid,
(RS)-1-{4'-[5-chloro-3-({[1-(thiophen-3-yl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(thiophen-3-yl)ethoxy]carbonyl}amino)thiophen-2-yl]-2'-methoxy-[1,1'-biphenyl]-4-yl}cyclopropanecarboxylic acid,
(RS)-1-{4'-[5-chloro-3-({[1-(4-methylthiophen-3-yl)ethoxy]carbonyl}amino)-thiophen-2-yl]-[1,1'-biphenyl]-4-yl}cyclopropanecarboxylic acid,
(R)-1-{4'-[5-chloro-3-({[1-(4-methylthiophen-3-yl)ethoxy]carbonyl}amino)-thiophen-2-yl]-[1,1'-biphenyl]-4-yl}cyclopropanecarboxylic acid,
(RS)-1-{4'-[5-chloro-3-({[1-(4-methylthiophen-3-yl)ethoxy]carbonyl}amino)-thiophen-2-yl]-2'-methoxy-[1,1'-biphenyl]-4-yl}cyclopropanecarboxylic acid,
(RS)-1-{4'-[5-chloro-3-({[1-(4-chlorothiophen-3-yl)ethoxy]carbonyl}amino)-thiophen-2-yl]-2'-methoxy-[1,1'-biphenyl]-4-yl}cyclopropanecarboxylic acid,
(RS)-1-{4'-[5-chloro-3-({[(1-(isothiazol-3-yl)ethoxy]carbonyl}amino)-thiophen-2-yl]-[1,1'-biphenyl]-4-yl}cyclopropanecarboxylic acid,
(RS)-1-{4'-[5-chloro-3-({[1-(isothiazol-4-yl)ethoxy]carbonyl}amino)thiophen-2-yl]-[1,1'-biphenyl]-4-yl}cyclopropanecarboxylic acid,
(RS)-1-(4-{5-[5-chloro-3-({[1-(thiophen-3-yl)ethoxy]carbonyl}amino)-thiophen-2-yl]pyridin-2-yl}phenyl)cyclopropanecarboxylic acid,
(RS)-1-(4-{5-[5-chloro-3-({[1-(4-methylthiophen-3-yl)ethoxy]carbonyl}amino)thiophen-2-yl]pyridin-2-yl}phenyl)cyclopropanecarboxylic acid,
(RS)-1-{4-[5-fluoro-3-({[1-(thiophen-3-yl)ethoxy]carbonyl}amino)thiophen-2-yl]-[1,1'-biphenyl]-4-yl}cyclopropanecarboxylic acid,
(R)-1-{4'-[5-fluoro-3-({[1-(thiophen-3-yl)ethoxy]carbonyl}amino)thiophen-2-yl]-[1,1'-biphenyl]-4-yl}cyclopropanecarboxylic acid,
(RS)-1-{4'-[5-fluoro-3-({[1-(thiophen-3-yl)ethoxy]carbonyl}amino)thiophen-2-yl]-2'-methoxy-[1,1'-biphenyl]-4-yl}cyclopropanecarboxylic acid,
(RS)-1-{4'-[5-fluoro-3-({[1-(4-methylthiophen-3-yl)ethoxy]carbonyl}amino)-thiophen-2-yl]-[1,1'-biphenyl]-4-yl}cyclopropanecarboxylic acid,
(R)-1-{4-[5-fluoro-3-({[1-(4-methylthiophen-3-yl)ethoxy]carbonyl}amino)-thiophen-2-yl]-[1,1'-biphenyl]-4-yl}cyclopropanecarboxylic acid,
(RS)-1-{4'-[5-fluoro-3-({[1-(2-methylthiophen-3-yl)ethoxy]carbonyl}amino)-thiophen-2-yl]-[1,1'-biphenyl]-4-yl}cyclopropanecarboxylic acid,
(RS)-1-{4'-[5-fluoro-3-({[1-(4-methylthiophen-3-yl)ethoxy]carbonyl}amino)-thiophen-2-yl]-2'-methoxy-[1,1'-biphenyl]-4-yl}cyclopropanecarboxylic acid,
(RS)-1-{4'-[3-({[1-(4-chlorothiophen-3-yl)ethoxy]carbonyl}amino)-5-fluoro-thiophen-2-yl]-[1,1'-biphenyl]-4-yl}cyclopropanecarboxylic acid,
(RS)-1-{4'-[3-({[1-(4-chlorothiophen-3-yl)ethoxy]carbonyl}amino)-5-fluoro-thiophen-2-yl]-2'-methoxy-[1,1'-biphenyl]-4-yl}cyclopropanecarboxylic acid,
(R)-1-{4'-[5-chloro-3-({[1-(thiophen-2-yl)ethoxy]carbonyl}amino)thiophen-2-yl]-[1,1'-biphenyl]-4-yl}cyclopropanecarboxylic acid,
(R)-1-{4'-[5-chloro-3-({[1-(thiophen-2-yl)ethoxy]carbonyl}amino)thiophen-2-yl]-2'-methoxy-[1,1'-biphenyl]-4-yl}cyclopropanecarboxylic acid,
(R)-1-{4'-[5-fluoro-3-({[1-(thiophen-2-yl)ethoxy]carbonyl}amino)thiophen-2-yl]-[1,1'-biphenyl]-4-yl}cyclopropanecarboxylic acid, and
(R)-1-{4'-[5-fluoro-3-({[1-(thiophen-2-yl)ethoxy]carbonyl}amino)thiophen-2-yl]-2'-methoxy-[1,1'-biphenyl]-4-yl}cyclopropanecarboxylic acid,
or a pharmacologically acceptable salt thereof.

(14) (R)-1-{4'-[5-chloro-3-({[1-(2-chlorophenyl)ethoxy]carbonyl}-amino)thiophen-2-yl]-[1,1'-biphenyl]-4-yl}cyclopropanecarboxylic acid, or a pharmacologically acceptable salt thereof.

(15) (R)-1-{4'-[5-chloro-3-({[1-(3-fluorophenyl)ethoxy]carbonyl}-amino)thiophen-2-yl]-[1,1'-biphenyl]-4-yl}cyclopropanecarboxylic acid, or a pharmacologically acceptable salt thereof.

(16) (R)-1-{4'-[3-({[1-(2-chlorophenyl)ethoxy]carbonyl}amino)-5-fluorothiophen-2-yl]-[1,1'-biphenyl]-4-yl}cyclopropanecarboxylic acid, or a pharmacologically acceptable salt thereof

(17) (R)-1-{4'-[5-fluoro-3-({[1-(o-tolyl)ethoxy]carbonyl}-amino)thiophen-2-yl]-[1,1'-biphenyl]-4-yl}cyclopropanecarboxylic acid, or a pharmacologically acceptable salt thereof.

(18) (R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid, or a pharmacologically acceptable salt thereof.

(19) (R)-1-{4'-[5-chloro-3-({[1-(2,5-difluorophenyl)ethoxy]carbonyl}-amino)thiophen-2-yl]-2'-methoxy-[1,1'-biphenyl]-4-yl}cyclopropanecarboxylic acid, or a pharmacologically acceptable salt thereof.

(20) (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid, or a pharmacologically acceptable salt thereof.

(21) (R)-1-{4'-[5-chloro-3-({[1-(thiophen-3-yl)ethoxy]carbonyl}-amino)thiophen-2-yl]-[1,1'-biphenyl]-4-yl}cyclopropanecarboxylic acid, or a pharmacologically acceptable salt thereof.

(22) (R)-1-{4'-[5-chloro-3-({[1-(thiophen-3-yl)ethoxy]carbonyl}-amino)thiophen-2-yl]-2'-methoxy-[1,1'-biphenyl]-4-yl}cyclopropanecarboxylic acid, or a pharmacologically acceptable salt thereof.

(23) (R)-1-{4'-[5-chloro-3-({[1-(4-methylthiophen-3-yl)ethoxy]-carbonyl}amino)thiophen-2-yl]-[1,1'-biphenyl]-4-yl}cyclopropanecarboxylic acid, or a pharmacologically acceptable salt thereof.

(24) (R)-1-{4'-[5-fluoro-3-({[1-(thiophen-3-yl)ethoxy]carbonyl}-amino)thiophen-2-yl]-[1,1'-biphenyl]-4-yl}cyclopropanecarboxylic acid, or a pharmacologically acceptable salt thereof.

(25) (R)-1-{4'-[5-fluoro-3-({[1-(4-methylthiophen-3-yl)ethoxy]-carbonyl}amino)thiophen-2-yl]-[1,1'-biphenyl]-4-yl}cyclopropanecarboxylic acid, or a pharmacologically acceptable salt thereof.

(26) An LPA receptor antagonist comprising the compound or a pharmacologically acceptable salt thereof according to anyone of (1) to (25) as an active ingredient.

(27) A pharmaceutical composition comprising the compound or a pharmacologically acceptable salt thereof according to anyone of (1) to (25) as an active ingredient.

(28) The pharmaceutical composition according to (27) for the treatment or prevention of a disease accompanying fibrosis, an immunological or inflammatory disease, a central or peripheral nervous system disease, an urologic disease or a cancer-related disease.

Specific examples of the compound represented by the general formula (I) of the present invention can include, for example, the compounds as shown in the following Tables 1 to 3. In addition, in the following Tables 1 to 3, Me represents a methyl group; Et represents an ethyl group; n-Pr represents a n-propyl group, iso-Pr represents an isopropyl group; "racemic" and "(R)-" represent the configuration of the carbon atom marked with "*" in the general formula (I) as shown below.

[Chemical Formula 16]

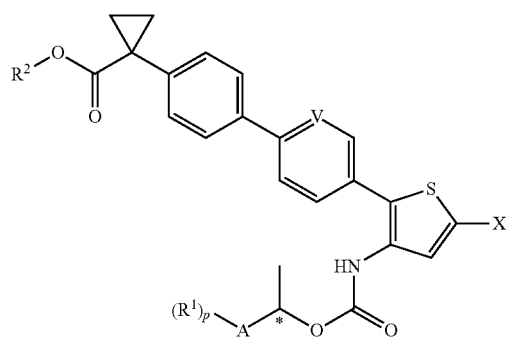

(I)

TABLE 1

| Compound No. | V | X | $(R^1)_p$—A— | $R^2$ | Configuration |
|---|---|---|---|---|---|
| I-1 | CH | Br | phenyl | Et | racemic |
| I-2 | CH | Br | phenyl | Et | (R)— |
| I-3 | CH | Br | phenyl | H | racemic |
| I-4 | CH | Br | phenyl | H | (R)— |
| I-5 | CH | Br | 3-fluorophenyl | Et | racemic |
| I-6 | CH | Br | 3-fluorophenyl | Et | (R)— |
| I-7 | CH | Br | 3-fluorophenyl | H | racemic |
| I-8 | CH | Br | 3-fluorophenyl | H | (R)— |
| I-9 | CH | Br | 2-chlorophenyl | Et | racemic |
| I-10 | CH | Br | 2-chlorophenyl | Et | (R)— |
| I-11 | CH | Br | 2-chlorophenyl | H | racemic |
| I-12 | CH | Br | 2-chlorophenyl | H | (R)— |
| I-13 | CH | Br | o-tolyl | Et | racemic |
| I-14 | CH | Br | o-tolyl | Et | (R)— |
| I-15 | CH | Br | o-tolyl | H | racemic |
| I-16 | CH | Br | o-tolyl | H | (R)— |
| I-17 | CH | Br | 2,5-difluorophenyl | Et | racemic |
| I-18 | CH | Br | 2,5-difluorophenyl | Et | (R)— |
| I-19 | CH | Br | 2,5-difluorophenyl | H | racemic |
| I-20 | CH | Br | 2,5-difluorophenyl | H | (R)— |
| I-21 | CH | Cl | phenyl | Et | racemic |
| I-22 | CH | Cl | phenyl | Et | (R)— |
| I-23 | CH | Cl | phenyl | H | racemic |
| I-24 | CH | Cl | phenyl | H | (R)— |
| I-25 | CH | Cl | 2-fluorophenyl | Et | racemic |
| I-26 | CH | Cl | 2-fluorophenyl | Et | (R)— |
| I-27 | CH | Cl | 2-fluorophenyl | H | racemic |
| I-28 | CH | Cl | 2-fluorophenyl | H | (R)— |
| I-29 | CH | Cl | 3-fluorophenyl | iso-Pr | racemic |
| I-30 | CH | Cl | 3-fluorophenyl | iso-Pr | (R)— |
| I-31 | CH | Cl | 3-fluorophenyl | n-Pr | racemic |
| I-32 | CH | Cl | 3-fluorophenyl | n-Pr | (R)— |
| I-33 | CH | Cl | 3-fluorophenyl | Et | racemic |
| I-34 | CH | Cl | 3-fluorophenyl | Et | (R)— |
| I-35 | CH | Cl | 3-fluorophenyl | Me | racemic |
| I-36 | CH | Cl | 3-fluorophenyl | Me | (R)— |
| I-37 | CH | Cl | 3-fluorophenyl | H | racemic |
| I-38 | CH | Cl | 3-fluorophenyl | H | (R)— |
| I-39 | CH | Cl | 4-fluorophenyl | Et | racemic |
| I-40 | CH | Cl | 4-fluorophenyl | Et | (R)— |
| I-41 | CH | Cl | 4-fluorophenyl | H | racemic |
| I-42 | CH | Cl | 4-fluorophenyl | H | (R)— |
| I-43 | CH | Cl | 2-chlorophenyl | iso-Pr | racemic |
| I-44 | CH | Cl | 2-chlorophenyl | iso-Pr | (R)— |
| I-45 | CH | Cl | 2-chlorophenyl | n-Pr | racemic |
| I-46 | CH | Cl | 2-chlorophenyl | n-Pr | (R)— |
| I-47 | CH | Cl | 2-chlorophenyl | Et | racemic |
| I-48 | CH | Cl | 2-chlorophenyl | Et | (R)— |
| I-49 | CH | Cl | 2-chlorophenyl | Me | racemic |
| I-50 | CH | Cl | 2-chlorophenyl | Me | (R)— |
| I-51 | CH | Cl | 2-chlorophenyl | H | racemic |
| I-52 | CH | Cl | 2-chlorophenyl | H | (R)— |
| I-53 | CH | Cl | 4-chlorophenyl | Et | racemic |
| I-54 | CH | Cl | 4-chlorophenyl | Et | (R)— |
| I-55 | CH | Cl | 4-chlorophenyl | H | racemic |
| I-56 | CH | Cl | 4-chlorophenyl | H | (R)— |
| I-57 | CH | Cl | o-tolyl | Et | racemic |
| I-58 | CH | Cl | o-tolyl | Et | (R)— |
| I-59 | CH | Cl | o-tolyl | H | racemic |
| I-60 | CH | Cl | o-tolyl | H | (R)— |
| I-61 | CH | Cl | 2,4-difluorophenyl | Et | racemic |
| I-62 | CH | Cl | 2,4-difluorophenyl | Et | (R)— |
| I-63 | CH | Cl | 2,4-difluorophenyl | H | racemic |
| I-64 | CH | Cl | 2,4-difluorophenyl | H | (R)— |
| I-65 | CH | Cl | 2,5-difluorophenyl | Et | racemic |
| I-66 | CH | Cl | 2,5-difluorophenyl | Et | (R)— |
| I-67 | CH | Cl | 2,5-difluorophenyl | H | racemic |
| I-68 | CH | Cl | 2,5-difluorophenyl | H | (R)— |
| I-69 | CH | Cl | 3,4-difluorophenyl | Et | racemic |
| I-70 | CH | Cl | 3,4-difluorophenyl | Et | (R)— |
| I-71 | CH | Cl | 3,4-difluorophenyl | H | racemic |
| I-72 | CH | Cl | 3,4-difluorophenyl | H | (R)— |
| I-73 | CH | Cl | 2-chloro-4-fluorophenyl | Et | racemic |
| I-74 | CH | Cl | 2-chloro-4-fluorophenyl | Et | (R)— |
| I-75 | CH | Cl | 2-chloro-4-fluorophenyl | H | racemic |
| I-76 | CH | Cl | 2-chloro-4-fluorophenyl | H | (R)— |
| I-77 | CH | Cl | 2-chloro-5-fluorophenyl | Et | racemic |
| I-78 | CH | Cl | 2-chloro-5-fluorophenyl | Et | (R)— |

TABLE 1-continued

| Compound No. | V | X | (R¹)ₚ—A— | R² | Configuration |
|---|---|---|---|---|---|
| I-79 | CH | Cl | 2-chloro-5-fluorophenyl | H | racemic |
| I-80 | CH | Cl | 2-chloro-5-fluorophenyl | H | (R)— |
| I-81 | CH | Cl | 4-chloro-2-fluorophenyl | Et | racemic |
| I-82 | CH | Cl | 4-chloro-2-fluorophenyl | Et | (R)— |
| I-83 | CH | Cl | 4-chloro-2-fluorophenyl | H | racemic |
| I-84 | CH | Cl | 4-chloro-2-fluorophenyl | H | (R)— |
| I-85 | CH | Cl | 4-fluoro-2-methylphenyl | Et | racemic |
| I-86 | CH | Cl | 4-fluoro-2-methylphenyl | Et | (R)— |
| I-87 | CH | Cl | 4-fluoro-2-methylphenyl | H | racemic |
| I-88 | CH | Cl | 4-fluoro-2-methylphenyl | H | (R)— |
| I-89 | CH | Cl | 5-fluoro-2-methylphenyl | Et | racemic |
| I-90 | CH | Cl | 5-fluoro-2-methylphenyl | Et | (R)— |
| I-91 | CH | Cl | 5-fluoro-2-methylphenyl | H | racemic |
| I-92 | CH | Cl | 5-fluoro-2-methylphenyl | H | (R)— |
| I-93 | CH | Cl | 2,4,5-trifluorophenyl | Et | racemic |
| I-94 | CH | Cl | 2,4,5-trifluorophenyl | Et | (R)— |
| I-95 | CH | Cl | 2,4,5-trifluorophenyl | H | racemic |
| I-96 | CH | Cl | 2,4,5-trifluorophenyl | H | (R)— |
| I-97 | CH | F | phenyl | Et | racemic |
| I-98 | CH | F | phenyl | Et | (R)— |
| I-99 | CH | F | phenyl | H | racemic |
| I-100 | CH | F | phenyl | H | (R)— |
| I-101 | CH | F | 2-fluorophenyl | Et | racemic |
| I-102 | CH | F | 2-fluorophenyl | Et | (R)— |
| I-103 | CH | F | 2-fluorophenyl | H | racemic |
| I-104 | CH | F | 2-fluorophenyl | H | (R)— |
| I-105 | CH | F | 3-fluorophenyl | Et | racemic |
| I-106 | CH | F | 3-fluorophenyl | Et | (R)— |
| I-107 | CH | F | 3-fluorophenyl | H | racemic |
| I-108 | CH | F | 3-fluorophenyl | H | (R)— |
| I-109 | CH | F | 4-fluorophenyl | Et | racemic |
| I-110 | CH | F | 4-fluorophenyl | Et | (R)— |
| I-111 | CH | F | 4-fluorophenyl | H | racemic |
| I-112 | CH | F | 4-fluorophenyl | H | (R)— |
| I-113 | CH | F | 2-chlorophenyl | iso-Pr | racemic |
| I-114 | CH | F | 2-chlorophenyl | iso-Pr | (R)— |
| I-115 | CH | F | 2-chlorophenyl | n-Pr | racemic |
| I-116 | CH | F | 2-chlorophenyl | n-Pr | (R)— |
| I-117 | CH | F | 2-chlorophenyl | Et | racemic |
| I-118 | CH | F | 2-chlorophenyl | Et | (R)— |
| I-119 | CH | F | 2-chlorophenyl | Me | racemic |
| I-120 | CH | F | 2-chlorophenyl | Me | (R)— |
| I-121 | CH | F | 2-chlorophenyl | H | racemic |
| I-122 | CH | F | 2-chlorophenyl | H | (R)— |
| I-123 | CH | F | 4-chlorophenyl | Et | racemic |
| I-124 | CH | F | 4-chlorophenyl | Et | (R)— |
| I-125 | CH | F | 4-chlorophenyl | H | racemic |
| I-126 | CH | F | 4-chlorophenyl | H | (R)— |
| I-127 | CH | F | o-tolyl | iso-Pr | racemic |
| I-128 | CH | F | o-tolyl | iso-Pr | (R)— |
| I-129 | CH | F | o-tolyl | n-Pr | racemic |
| I-130 | CH | F | o-tolyl | n-Pr | (R)— |
| I-131 | CH | F | o-tolyl | Et | racemic |
| I-132 | CH | F | o-tolyl | Et | (R)— |
| I-133 | CH | F | o-tolyl | Me | racemic |
| I-134 | CH | F | o-tolyl | Me | (R)— |
| I-135 | CH | F | o-tolyl | H | racemic |
| I-136 | CH | F | o-tolyl | H | (R)— |
| I-137 | CH | F | 2,4-difluorophenyl | Et | racemic |
| I-138 | CH | F | 2,4-difluorophenyl | Et | (R)— |
| I-139 | CH | F | 2,4-difluorophenyl | H | racemic |
| I-140 | CH | F | 2,4-difluorophenyl | H | (R)— |
| I-141 | CH | F | 2,5-difluorophenyl | Et | racemic |
| I-142 | CH | F | 2,5-difluorophenyl | Et | (R)— |
| I-143 | CH | F | 2,5-difluorophenyl | H | racemic |
| I-144 | CH | F | 2,5-difluorophenyl | H | (R)— |
| I-145 | CH | F | 3,4-difluorophenyl | Et | racemic |
| I-146 | CH | F | 3,4-difluorophenyl | Et | (R)— |
| I-147 | CH | F | 3,4-difluorophenyl | H | racemic |
| I-148 | CH | F | 3,4-difluorophenyl | H | (R)— |
| I-149 | CH | F | 2-chloro-4-fluorophenyl | Et | racemic |
| I-150 | CH | F | 2-chloro-4-fluorophenyl | Et | (R)— |
| I-151 | CH | F | 2-chloro-4-fluorophenyl | H | racemic |
| I-152 | CH | F | 2-chloro-4-fluorophenyl | H | (R)— |
| I-153 | CH | F | 2-chloro-5-fluorophenyl | Et | racemic |
| I-154 | CH | F | 2-chloro-5-fluorophenyl | Et | (R)— |
| I-155 | CH | F | 2-chloro-5-fluorophenyl | H | racemic |
| I-156 | CH | F | 2-chloro-5-fluorophenyl | H | (R)— |
| I-157 | CH | F | 4-chloro-2-fluorophenyl | Et | racemic |
| I-158 | CH | F | 4-chloro-2-fluorophenyl | Et | (R)— |
| I-159 | CH | F | 4-chloro-2-fluorophenyl | H | racemic |
| I-160 | CH | F | 4-chloro-2-fluorophenyl | H | (R)— |
| I-161 | CH | F | 4-fluoro-2-methylphenyl | Et | racemic |
| I-162 | CH | F | 4-fluoro-2-methylphenyl | Et | (R)— |
| I-163 | CH | F | 4-fluoro-2-methylphenyl | H | racemic |
| I-164 | CH | F | 4-fluoro-2-methylphenyl | H | (R)— |
| I-165 | CH | F | 5-fluoro-2-methylphenyl | Et | racemic |
| I-166 | CH | F | 5-fluoro-2-methylphenyl | Et | (R)— |
| I-167 | CH | F | 5-fluoro-2-methylphenyl | H | racemic |
| I-168 | CH | F | 5-fluoro-2-methylphenyl | H | (R)— |
| I-169 | CH | F | 2,4,5-trifluorophenyl | Et | racemic |
| I-170 | CH | F | 2,4,5-trifluorophenyl | Et | (R)— |
| I-171 | CH | F | 2,4,5-trifluorophenyl | H | racemic |
| I-172 | CH | F | 2,4,5-trifluorophenyl | H | (R)— |
| I-173 | N | Br | phenyl | Et | racemic |
| I-174 | N | Br | phenyl | Et | (R)— |
| I-175 | N | Br | phenyl | H | racemic |
| I-176 | N | Br | phenyl | H | (R)— |
| I-177 | N | Br | 3-fluorophenyl | Et | racemic |
| I-178 | N | Br | 3-fluorophenyl | Et | (R)— |
| I-179 | N | Br | 3-fluorophenyl | H | racemic |
| I-180 | N | Br | 3-fluorophenyl | H | (R)— |
| I-181 | N | Br | 2-chlorophenyl | Et | racemic |
| I-182 | N | Br | 2-chlorophenyl | Et | (R)— |
| I-183 | N | Br | 2-chlorophenyl | H | racemic |
| I-184 | N | Br | 2-chlorophenyl | H | (R)— |
| I-185 | N | Br | o-tolyl | Et | racemic |
| I-186 | N | Br | o-tolyl | Et | (R)— |
| I-187 | N | Br | o-tolyl | H | racemic |
| I-188 | N | Br | o-tolyl | H | (R)— |
| I-189 | N | Br | 2,5-difluorophenyl | Et | racemic |
| I-190 | N | Br | 2,5-difluorophenyl | Et | (R)— |
| I-191 | N | Br | 2,5-difluorophenyl | H | racemic |
| I-192 | N | Br | 2,5-difluorophenyl | H | (R)— |
| I-193 | N | Cl | phenyl | Et | racemic |
| I-194 | N | Cl | phenyl | Et | (R)— |
| I-195 | N | Cl | phenyl | H | racemic |
| I-196 | N | Cl | phenyl | H | (R)— |
| I-197 | N | Cl | 2-fluorophenyl | Et | racemic |
| I-198 | N | Cl | 2-fluorophenyl | Et | (R)— |
| I-199 | N | Cl | 2-fluorophenyl | H | racemic |
| I-200 | N | Cl | 2-fluorophenyl | H | (R)— |
| I-201 | N | Cl | 3-fluorophenyl | Et | racemic |
| I-202 | N | Cl | 3-fluorophenyl | Et | (R)— |
| I-203 | N | Cl | 3-fluorophenyl | H | racemic |
| I-204 | N | Cl | 3-fluorophenyl | H | (R)— |
| I-205 | N | Cl | 4-fluorophenyl | Et | racemic |
| I-206 | N | Cl | 4-fluorophenyl | Et | (R)— |
| I-207 | N | Cl | 4-fluorophenyl | H | racemic |
| I-208 | N | Cl | 4-fluorophenyl | H | (R)— |
| I-209 | N | Cl | 2-chlorophenyl | Et | racemic |
| I-210 | N | Cl | 2-chlorophenyl | Et | (R)— |
| I-211 | N | Cl | 2-chlorophenyl | H | racemic |
| I-212 | N | Cl | 2-chlorophenyl | H | (R)— |
| I-213 | N | Cl | 4-chlorophenyl | Et | racemic |
| I-214 | N | Cl | 4-chlorophenyl | Et | (R)— |
| I-215 | N | Cl | 4-chlorophenyl | H | racemic |
| I-216 | N | Cl | 4-chlorophenyl | H | (R)— |
| I-217 | N | Cl | o-tolyl | Et | racemic |
| I-218 | N | Cl | o-tolyl | Et | (R)— |
| I-219 | N | Cl | o-tolyl | H | racemic |
| I-220 | N | Cl | o-tolyl | H | (R)— |
| I-221 | N | Cl | 2,4-difluorophenyl | Et | racemic |
| I-222 | N | Cl | 2,4-difluorophenyl | Et | (R)— |
| I-223 | N | Cl | 2,4-difluorophenyl | H | racemic |
| I-224 | N | Cl | 2,4-difluorophenyl | H | (R)— |
| I-225 | N | Cl | 2,5-difluorophenyl | Et | racemic |
| I-226 | N | Cl | 2,5-difluorophenyl | Et | (R)— |
| I-227 | N | Cl | 2,5-difluorophenyl | H | racemic |
| I-228 | N | Cl | 2,5-difluorophenyl | H | (R)— |
| I-229 | N | Cl | 3,4-difluorophenyl | Et | racemic |
| I-230 | N | Cl | 3,4-difluorophenyl | Et | (R)— |
| I-231 | N | Cl | 3,4-difluorophenyl | H | racemic |
| I-232 | N | Cl | 3,4-difluorophenyl | H | (R)— |
| I-233 | N | Cl | 2-chloro-4-fluorophenyl | Et | racemic |
| I-234 | N | Cl | 2-chloro-4-fluorophenyl | Et | (R)— |

TABLE 1-continued

| Compound No. | V | X | (R¹)ₚ—A— | R² | Configuration |
|---|---|---|---|---|---|
| I-235 | N | Cl | 2-chloro-4-fluorophenyl | H | racemic |
| I-236 | N | Cl | 2-chloro-4-fluorophenyl | H | (R)— |
| I-237 | N | Cl | 2-chloro-5-fluorophenyl | Et | racemic |
| I-238 | N | Cl | 2-chloro-5-fluorophenyl | Et | (R)— |
| I-239 | N | Cl | 2-chloro-5-fluorophenyl | H | racemic |
| I-240 | N | Cl | 2-chloro-5-fluorophenyl | H | (R)— |
| I-241 | N | Cl | 4-chloro-2-fluorophenyl | Et | racemic |
| I-242 | N | Cl | 4-chloro-2-fluorophenyl | Et | (R)— |
| I-243 | N | Cl | 4-chloro-2-fluorophenyl | H | racemic |
| I-244 | N | Cl | 4-chloro-2-fluorophenyl | H | (R)— |
| I-245 | N | Cl | 4-fluoro-2-methylphenyl | Et | racemic |
| I-246 | N | Cl | 4-fluoro-2-methylphenyl | Et | (R)— |
| I-247 | N | Cl | 4-fluoro-2-methylphenyl | H | racemic |
| I-248 | N | Cl | 4-fluoro-2-methylphenyl | H | (R)— |
| I-249 | N | Cl | 5-fluoro-2-methylphenyl | Et | racemic |
| I-250 | N | Cl | 5-fluoro-2-methylphenyl | Et | (R)— |
| I-251 | N | Cl | 5-fluoro-2-methylphenyl | H | racemic |
| I-252 | N | Cl | 5-fluoro-2-methylphenyl | H | (R)— |
| I-253 | N | Cl | 2,4,5-trifluorophenyl | Et | racemic |
| I-254 | N | Cl | 2,4,5-trifluorophenyl | Et | (R)— |
| I-255 | N | Cl | 2,4,5-trifluorophenyl | H | racemic |
| I-256 | N | Cl | 2,4,5-trifluorophenyl | H | (R)— |
| I-257 | N | F | phenyl | Et | racemic |
| I-258 | N | F | phenyl | Et | (R)— |
| I-259 | N | F | phenyl | H | racemic |
| I-260 | N | F | phenyl | H | (R)— |
| I-261 | N | F | 2-fluorophenyl | Et | racemic |
| I-262 | N | F | 2-fluorophenyl | Et | (R)— |
| I-263 | N | F | 2-fluorophenyl | H | racemic |
| I-264 | N | F | 2-fluorophenyl | H | (R)— |
| I-265 | N | F | 3-fluorophenyl | Et | racemic |
| I-266 | N | F | 3-fluorophenyl | Et | (R)— |
| I-267 | N | F | 3-fluorophenyl | H | racemic |
| I-268 | N | F | 3-fluorophenyl | H | (R)— |
| I-269 | N | F | 4-fluorophenyl | Et | racemic |
| I-270 | N | F | 4-fluorophenyl | Et | (R)— |
| I-271 | N | F | 4-fluorophenyl | H | racemic |
| I-272 | N | F | 4-fluorophenyl | H | (R)— |
| I-273 | N | F | 2-chlorophenyl | Et | racemic |
| I-274 | N | F | 2-chlorophenyl | Et | (R)— |
| I-275 | N | F | 2-chlorophenyl | H | racemic |
| I-276 | N | F | 2-chlorophenyl | H | (R)— |
| I-277 | N | F | 4-chlorophenyl | Et | racemic |
| I-278 | N | F | 4-chlorophenyl | Et | (R)— |
| I-279 | N | F | 4-chlorophenyl | H | racemic |
| I-280 | N | F | 4-chlorophenyl | H | (R)— |
| I-281 | N | F | o-tolyl | Et | racemic |
| I-282 | N | F | o-tolyl | Et | (R)— |
| I-283 | N | F | o-tolyl | H | racemic |
| I-284 | N | F | o-tolyl | H | (R)— |
| I-285 | N | F | 3,4-difluorophenyl | Et | racemic |
| I-286 | N | F | 3,4-difluorophenyl | Et | (R)— |
| I-287 | N | F | 3,4-difluorophenyl | H | racemic |
| I-288 | N | F | 3,4-difluorophenyl | H | (R)— |
| I-289 | N | F | 2,4-difluorophenyl | Et | racemic |
| I-290 | N | F | 2,4-difluorophenyl | Et | (R)— |
| I-291 | N | F | 2,4-difluorophenyl | H | racemic |
| I-292 | N | F | 2,4-difluorophenyl | H | (R)— |
| I-293 | N | F | 2,5-difluorophenyl | Et | racemic |
| I-294 | N | F | 2,5-difluorophenyl | Et | (R)— |
| I-295 | N | F | 2,5-difluorophenyl | H | racemic |
| I-296 | N | F | 2,5-difluorophenyl | H | (R)— |
| I-297 | N | F | 2-chloro-4-fluorophenyl | Et | racemic |
| I-298 | N | F | 2-chloro-4-fluorophenyl | Et | (R)— |
| I-299 | N | F | 2-chloro-4-fluorophenyl | H | racemic |
| I-300 | N | F | 2-chloro-4-fluorophenyl | H | (R)— |
| I-301 | N | F | 2-chloro-5-fluorophenyl | Et | racemic |
| I-302 | N | F | 2-chloro-5-fluorophenyl | Et | (R)— |
| I-303 | N | F | 2-chloro-5-fluorophenyl | H | racemic |
| I-304 | N | F | 2-chloro-5-fluorophenyl | H | (R)— |
| I-305 | N | F | 4-chloro-2-fluorophenyl | Et | racemic |
| I-306 | N | F | 4-chloro-2-fluorophenyl | Et | (R)— |
| I-307 | N | F | 4-chloro-2-fluorophenyl | H | racemic |
| I-308 | N | F | 4-chloro-2-fluorophenyl | H | (R)— |
| I-309 | N | F | 4-fluoro-2-methylphenyl | Et | racemic |
| I-310 | N | F | 4-fluoro-2-methylphenyl | Et | (R)— |
| I-311 | N | F | 4-fluoro-2-methylphenyl | H | racemic |
| I-312 | N | F | 4-fluoro-2-methylphenyl | H | (R)— |
| I-313 | N | F | 5-fluoro-2-methylphenyl | Et | racemic |
| I-314 | N | F | 5-fluoro-2-methylphenyl | Et | (R)— |
| I-315 | N | F | 5-fluoro-2-methylphenyl | H | racemic |
| I-316 | N | F | 5-fluoro-2-methylphenyl | H | (R)— |
| I-317 | N | F | 2,4,5-trifluorophenyl | Et | racemic |
| I-318 | N | F | 2,4,5-trifluorophenyl | Et | (R)— |
| I-319 | N | F | 2,4,5-trifluorophenyl | H | racemic |
| I-320 | N | F | 2,4,5-trifluorophenyl | H | (R)— |

TABLE 2

| Compound No. | V | X | (R¹)p—A— | R² | Configuration |
|---|---|---|---|---|---|
| I-321 | C—OMe | Br | phenyl | Et | racemic |
| I-322 | C—OMe | Br | phenyl | Et | (R)— |
| I-323 | C—OMe | Br | phenyl | H | racemic |
| I-324 | C—OMe | Br | phenyl | H | (R)— |
| I-325 | C—OMe | Br | 3-fluorophenyl | Et | racemic |
| I-326 | C—OMe | Br | 3-fluorophenyl | Et | (R)— |
| I-327 | C—OMe | Br | 3-fluorophenyl | H | racemic |
| I-328 | C—OMe | Br | 3-fluorophenyl | H | (R)— |
| I-329 | C—OMe | Br | 2-chlorophenyl | Et | racemic |
| I-330 | C—OMe | Br | 2-chlorophenyl | Et | (R)— |
| I-331 | C—OMe | Br | 2-chlorophenyl | H | racemic |
| I-332 | C—OMe | Br | 2-chlorophenyl | H | (R)— |
| I-333 | C—OMe | Br | o-tolyl | Et | racemic |
| I-334 | C—OMe | Br | o-tolyl | Et | (R)— |
| I-335 | C—OMe | Br | o-tolyl | H | racemic |
| I-336 | C—OMe | Br | o-tolyl | H | (R)— |
| I-337 | C—OMe | Br | 2,5-difluorophenyl | Et | racemic |
| I-338 | C—OMe | Br | 2,5-difluorophenyl | Et | (R)— |
| I-339 | C—OMe | Br | 2,5-difluorophenyl | H | racemic |
| I-340 | C—OMe | Br | 2,5-difluorophenyl | H | (R)— |
| I-341 | C—OMe | Cl | phenyl | iso-Pr | racemic |
| I-342 | C—OMe | Cl | phenyl | iso-Pr | (R)— |
| I-343 | C—OMe | Cl | phenyl | n-Pr | racemic |
| I-344 | C—OMe | Cl | phenyl | n-Pr | (R)— |
| I-345 | C—OMe | Cl | phenyl | Et | racemic |
| I-346 | C—OMe | Cl | phenyl | Et | (R)— |
| I-347 | C—OMe | Cl | phenyl | Me | racemic |
| I-348 | C—OMe | Cl | phenyl | Me | (R)— |
| I-349 | C—OMe | Cl | phenyl | H | racemic |
| I-350 | C—OMe | Cl | phenyl | H | (R)— |
| I-351 | C—OMe | Cl | 2-fluorophenyl | Et | racemic |
| I-352 | C—OMe | Cl | 2-fluorophenyl | Et | (R)— |
| I-353 | C—OMe | Cl | 2-fluorophenyl | H | racemic |
| I-354 | C—OMe | Cl | 2-fluorophenyl | H | (R)— |
| I-355 | C—OMe | Cl | 3-fluorophenyl | Et | racemic |
| I-356 | C—OMe | Cl | 3-fluorophenyl | Et | (R)— |
| I-357 | C—OMe | Cl | 3-fluorophenyl | H | racemic |
| I-358 | C—OMe | Cl | 3-fluorophenyl | H | (R)— |
| I-359 | C—OMe | Cl | 4-fluorophenyl | Et | racemic |
| I-360 | C—OMe | Cl | 4-fluorophenyl | Et | (R)— |
| I-361 | C—OMe | Cl | 4-fluorophenyl | H | racemic |
| I-362 | C—OMe | Cl | 4-fluorophenyl | H | (R)— |
| I-363 | C—OMe | Cl | 2-chlorophenyl | Et | racemic |
| I-364 | C—OMe | Cl | 2-chlorophenyl | Et | (R)— |
| I-365 | C—OMe | Cl | 2-chlorophenyl | H | racemic |
| I-366 | C—OMe | Cl | 2-chlorophenyl | H | (R)— |
| I-367 | C—OMe | Cl | 4-chlorophenyl | Et | racemic |
| I-368 | C—OMe | Cl | 4-chlorophenyl | Et | (R)— |
| I-369 | C—OMe | Cl | 4-chlorophenyl | H | racemic |
| I-370 | C—OMe | Cl | 4-chlorophenyl | H | (R)— |
| I-371 | C—OMe | Cl | o-tolyl | Et | racemic |
| I-372 | C—OMe | Cl | o-tolyl | Et | (R)— |
| I-373 | C—OMe | Cl | o-tolyl | H | racemic |
| I-374 | C—OMe | Cl | o-tolyl | H | (R)— |
| I-375 | C—OMe | Cl | 2,4-difluorophenyl | Et | racemic |
| I-376 | C—OMe | Cl | 2,4-difluorophenyl | Et | (R)— |
| I-377 | C—OMe | Cl | 2,4-difluorophenyl | H | racemic |
| I-378 | C—OMe | Cl | 2,4-difluorophenyl | H | (R)— |
| I-379 | C—OMe | Cl | 2,5-difluorophenyl | iso-Pr | racemic |
| I-380 | C—OMe | Cl | 2,5-difluorophenyl | iso-Pr | (R)— |
| I-381 | C—OMe | Cl | 2,5-difluorophenyl | n-Pr | racemic |

TABLE 2-continued

| Compound No. | V | X | (R¹)p—A— | R² | Configuration |
|---|---|---|---|---|---|
| I-382 | C—OMe | Cl | 2,5-difluorophenyl | n-Pr | (R)— |
| I-383 | C—OMe | Cl | 2,5-difluorophenyl | Et | racemic |
| I-384 | C—OMe | Cl | 2,5-difluorophenyl | Et | (R)— |
| I-385 | C—OMe | Cl | 2,5-difluorophenyl | Me | racemic |
| I-386 | C—OMe | Cl | 2,5-difluorophenyl | Me | (R)— |
| I-387 | C—OMe | Cl | 2,5-difluorophenyl | H | racemic |
| I-388 | C—OMe | Cl | 2,5-difluorophenyl | H | (R)— |
| I-389 | C—OMe | Cl | 3,4-difluorophenyl | Et | racemic |
| I-390 | C—OMe | Cl | 3,4-difluorophenyl | Et | (R)— |
| I-391 | C—OMe | Cl | 3,4-difluorophenyl | H | racemic |
| I-392 | C—OMe | Cl | 3,4-difluorophenyl | H | (R)— |
| I-393 | C—OMe | Cl | 2-chloro-4-fluorophenyl | Et | racemic |
| I-394 | C—OMe | Cl | 2-chloro-4-fluorophenyl | Et | (R)— |
| I-395 | C—OMe | Cl | 2-chloro-4-fluorophenyl | H | racemic |
| I-396 | C—OMe | Cl | 2-chloro-4-fluorophenyl | H | (R)— |
| I-397 | C—OMe | Cl | 2-chloro-5-fluorophenyl | Et | racemic |
| I-398 | C—OMe | Cl | 2-chloro-5-fluorophenyl | Et | (R)— |
| I-399 | C—OMe | Cl | 2-chloro-5-fluorophenyl | H | racemic |
| I-400 | C—OMe | Cl | 2-chloro-5-fluorophenyl | H | (R)— |
| I-401 | C—OMe | Cl | 4-chloro-2-fluorophenyl | Et | racemic |
| I-402 | C—OMe | Cl | 4-chloro-2-fluoro phenyl | Et | (R)— |
| I-403 | C—OMe | Cl | 4-chloro-2-fluorophenyl | H | racemic |
| I-404 | C—OMe | Cl | 4-chloro-2-fluorophenyl | H | (R)— |
| I-405 | C—OMe | Cl | 4-fluoro-2-methylphenyl | Et | racemic |
| I-406 | C—OMe | Cl | 4-fluoro-2-methylphenyl | Et | (R)— |
| I-407 | C—OMe | Cl | 4-fluoro-2-methylphenyl | H | racemic |
| I-408 | C—OMe | Cl | 4-fluoro-2-methylphenyl | H | (R)— |
| I-409 | C—OMe | Cl | 5-fluoro-2-methylphenyl | Et | racemic |
| I-410 | C—OMe | Cl | 5-fluoro-2-methylphenyl | Et | (R)— |
| I-411 | C—OMe | Cl | 5-fluoro-2-methylphenyl | H | racemic |
| I-412 | C—OMe | Cl | 5-fluoro-2-methylphenyl | H | (R)— |
| I-413 | C—OMe | Cl | 2,4,5-trifluorophenyl | Et | racemic |
| I-414 | C—OMe | Cl | 2,4,5-trifluorophenyl | Et | (R)— |
| I-415 | C—OMe | Cl | 2,4,5-trifluorophenyl | H | racemic |
| I-416 | C—OMe | Cl | 2,4,5-trifluorophenyl | H | (R)— |
| I-417 | C—OMe | F | phenyl | Et | racemic |
| I-418 | C—OMe | F | phenyl | Et | (R)— |
| I-419 | C—OMe | F | phenyl | H | racemic |
| I-420 | C—OMe | F | phenyl | H | (R)— |
| I-421 | C—OMe | F | 2-fluorophenyl | Et | racemic |
| I-422 | C—OMe | F | 2-fluorophenyl | Et | (R)— |
| I-423 | C—OMe | F | 2-fluorophenyl | H | racemic |
| I-424 | C—OMe | F | 2-fluorophenyl | H | (R)— |
| I-425 | C—OMe | F | 3-fluorophenyl | Et | racemic |
| I-426 | C—OMe | F | 3-fluorophenyl | Et | (R)— |
| I-427 | C—OMe | F | 3-fluorophenyl | H | racemic |
| I-428 | C—OMe | F | 3-fluorophenyl | H | (R)— |
| I-429 | C—OMe | F | 4-fluorophenyl | Et | racemic |
| I-430 | C—OMe | F | 4-fluorophenyl | Et | (R)— |
| I-431 | C—OMe | F | 4-fluorophenyl | H | racemic |
| I-432 | C—OMe | F | 4-fluorophenyl | H | (R)— |
| I-433 | C—OMe | F | 2-chlorophenyl | iso-Pr | racemic |
| I-434 | C—OMe | F | 2-chlorophenyl | iso-Pr | (R)— |
| I-435 | C—OMe | F | 2-chlorophenyl | n-Pr | racemic |
| I-436 | C—OMe | F | 2-chlorophenyl | n-Pr | (R)— |
| I-437 | C—OMe | F | 2-chlorophenyl | Et | racemic |
| I-438 | C—OMe | F | 2-chlorophenyl | Et | (R)— |
| I-439 | C—OMe | F | 2-chlorophenyl | Me | racemic |
| I-440 | C—OMe | F | 2-chlorophenyl | Me | (R)— |
| I-441 | C—OMe | F | 2-chlorophenyl | H | racemic |
| I-442 | C—OMe | F | 2-chlorophenyl | H | (R)— |
| I-443 | C—OMe | F | 4-chlorophenyl | Et | racemic |
| I-444 | C—OMe | F | 4-chlorophenyl | Et | (R)— |
| I-445 | C—OMe | F | 4-chlorophenyl | H | racemic |
| I-446 | C—OMe | F | 4-chlorophenyl | H | (R)— |
| I-447 | C—OMe | F | o-tolyl | Et | racemic |
| I-448 | C—OMe | F | o-tolyl | Et | (R)— |
| I-449 | C—OMe | F | o-tolyl | H | racemic |
| I-450 | C—OMe | F | o-tolyl | H | (R)— |
| I-451 | C—OMe | F | 2,4-difluorophenyl | Et | racemic |
| I-452 | C—OMe | F | 2,4-difluorophenyl | Et | (R)— |
| I-453 | C—OMe | F | 2,4-difluorophenyl | H | racemic |
| I-454 | C—OMe | F | 2,4-difluorophenyl | H | (R)— |
| I-455 | C—OMe | F | 2,5-difluorophenyl | Et | racemic |
| I-456 | C—OMe | F | 2,5-difluorophenyl | Et | (R)— |
| I-457 | C—OMe | F | 2,5-difluorophenyl | H | racemic |
| I-458 | C—OMe | F | 2,5-difluorophenyl | H | (R)— |
| I-459 | C—OMe | F | 3,4-difluorophenyl | Et | racemic |
| I-460 | C—OMe | F | 3,4-difluorophenyl | Et | (R)— |
| I-461 | C—OMe | F | 3,4-difluorophenyl | H | racemic |
| I-462 | C—OMe | F | 3,4-difluorophenyl | H | (R)— |
| I-463 | C—OMe | F | 2-chloro-4-fluorophenyl | Et | racemic |
| I-464 | C—OMe | F | 2-chloro-4-fluorophenyl | Et | (R)— |
| I-465 | C—OMe | F | 2-chloro-4-fluorophenyl | H | racemic |
| I-466 | C—OMe | F | 2-chloro-4-fluorophenyl | H | (R)— |
| I-467 | C—OMe | F | 2-chloro-5-fluorophenyl | Et | racemic |
| I-468 | C—OMe | F | 2-chloro-5-fluorophenyl | Et | (R)— |
| I-469 | C—OMe | F | 2-chloro-5-fluorophenyl | H | racemic |
| I-470 | C—OMe | F | 2-chloro-5-fluorophenyl | H | (R)— |
| I-471 | C—OMe | F | 4-chloro-2-fluorophenyl | Et | racemic |
| I-472 | C—OMe | F | 4-chloro-2-fluorophenyl | Et | (R)— |
| I-473 | C—OMe | F | 4-chloro-2-fluorophenyl | H | racemic |
| I-474 | C—OMe | F | 4-chloro-2-fluorophenyl | H | (R)— |
| I-475 | C—OMe | F | 4-fluoro-2-methylphenyl | Et | racemic |
| I-476 | C—OMe | F | 4-fluoro-2-methylphenyl | Et | (R)— |
| I-477 | C—OMe | F | 4-fluoro-2-methylphenyl | H | racemic |
| I-478 | C—OMe | F | 4-fluoro-2-methylphenyl | H | (R)— |
| I-479 | C—OMe | F | 5-fluoro-2-methylphenyl | Et | racemic |
| I-480 | C—OMe | F | 5-fluoro-2-methylphenyl | Et | (R)— |
| I-481 | C—OMe | F | 5-fluoro-2-methylphenyl | H | racemic |
| I-482 | C—OMe | F | 5-fluoro-2-methylphenyl | H | (R)— |
| I-483 | C—OMe | F | 2,4,5-trifluorophenyl | Et | racemic |
| I-484 | C—OMe | F | 2,4,5-trifluorophenyl | Et | (R)— |
| I-485 | C—OMe | F | 2,4,5-trifluorophenyl | H | racemic |
| I-486 | C—OMe | F | 2,4,5-trifluorophenyl | H | (R)— |
| I-487 | C—NO$_2$ | Cl | phenyl | Et | racemic |
| I-488 | C—NO$_2$ | Cl | phenyl | Et | (R)— |
| I-489 | C—NO$_2$ | Cl | phenyl | H | racemic |
| I-490 | C—NO$_2$ | Cl | phenyl | H | (R)— |
| I-491 | C—NO$_2$ | Cl | 3-fluorophenyl | Et | racemic |
| I-492 | C—NO$_2$ | Cl | 3-fluorophenyl | Et | (R)— |
| I-493 | C—NO$_2$ | Cl | 3-fluorophenyl | H | racemic |
| I-494 | C—NO$_2$ | Cl | 3-fluorophenyl | H | (R)— |
| I-495 | C—NO$_2$ | Cl | 4-fluorophenyl | Et | racemic |
| I-496 | C—NO$_2$ | Cl | 4-fluorophenyl | Et | (R)— |
| I-497 | C—NO$_2$ | Cl | 4-fluorophenyl | H | racemic |
| I-498 | C—NO$_2$ | Cl | 4-fluorophenyl | H | (R)— |
| I-499 | C—NO$_2$ | Cl | 2-chlorophenyl | Et | racemic |
| I-500 | C—NO$_2$ | Cl | 2-chlorophenyl | Et | (R)— |
| I-501 | C—NO$_2$ | Cl | 2-chlorophenyl | H | racemic |
| I-502 | C—NO$_2$ | Cl | 2-chlorophenyl | H | (R)— |
| I-503 | C—NO$_2$ | Cl | o-tolyl | Et | racemic |
| I-504 | C—NO$_2$ | Cl | o-tolyl | Et | (R)— |
| I-505 | C—NO$_2$ | Cl | o-tolyl | H | racemic |
| I-506 | C—NO$_2$ | Cl | o-tolyl | H | (R)— |
| I-507 | C—NO$_2$ | Cl | 2,5-difluorophenyl | Et | racemic |
| I-508 | C—NO$_2$ | Cl | 2,5-difluorophenyl | Et | (R)— |
| I-509 | C—NO$_2$ | Cl | 2,5-difluorophenyl | H | racemic |
| I-510 | C—NO$_2$ | Cl | 2,5-difluorophenyl | H | (R)— |
| I-511 | C—NO$_2$ | F | phenyl | Et | racemic |
| I-512 | C—NO$_2$ | F | phenyl | Et | (R)— |
| I-513 | C—NO$_2$ | F | phenyl | H | racemic |
| I-514 | C—NO$_2$ | F | phenyl | H | (R)— |
| I-515 | C—NO$_2$ | F | 3-fluorophenyl | Et | racemic |
| I-516 | C—NO$_2$ | F | 3-fluorophenyl | Et | (R)— |
| I-517 | C—NO$_2$ | F | 3-fluorophenyl | H | racemic |
| I-518 | C—NO$_2$ | F | 3-fluorophenyl | H | (R)— |
| I-519 | C—NO$_2$ | F | 2-chlorophenyl | Et | racemic |
| I-520 | C—NO$_2$ | F | 2-chlorophenyl | Et | (R)— |
| I-521 | C—NO$_2$ | F | 2-chlorophenyl | H | racemic |
| I-522 | C—NO$_2$ | F | 2-chlorophenyl | H | (R)— |
| I-523 | C—NO$_2$ | F | o-tolyl | Et | racemic |
| I-524 | C—NO$_2$ | F | o-tolyl | Et | (R)— |
| I-525 | C—NO$_2$ | F | o-tolyl | H | racemic |
| I-526 | C—NO$_2$ | F | o-tolyl | H | (R)— |
| I-527 | C—NO$_2$ | F | 2,5-difluorophenyl | Et | racemic |
| I-528 | C—NO$_2$ | F | 2,5-difluorophenyl | Et | (R)— |
| I-529 | C—NO$_2$ | F | 2,5-difluorophenyl | H | racemic |
| I-530 | C—NO$_2$ | F | 2,5-difluorophenyl | H | (R)— |
| I-531 | C—NH$_2$ | Cl | phenyl | Et | racemic |
| I-532 | C—NH$_2$ | Cl | phenyl | Et | (R)— |
| I-533 | C—NH$_2$ | Cl | phenyl | H | racemic |
| I-534 | C—NH$_2$ | Cl | phenyl | H | (R)— |
| I-535 | C—NH$_2$ | Cl | 3-fluorophenyl | Et | racemic |

TABLE 2-continued

| Compound No. | V | X | (R¹)p—A— | R² | Configuration |
|---|---|---|---|---|---|
| I-536 | C—NH₂ | Cl | 3-fluorophenyl | Et | (R)— |
| I-537 | C—NH₂ | Cl | 3-fluorophenyl | H | racemic |
| I-538 | C—NH₂ | Cl | 3-fluorophenyl | H | (R)— |
| I-539 | C—NH₂ | Cl | 2-chlorophenyl | Et | racemic |
| I-540 | C—NH₂ | Cl | 2-chlorophenyl | Et | (R)— |
| I-541 | C—NH₂ | Cl | 2-chlorophenyl | H | racemic |
| I-542 | C—NH₂ | Cl | 2-chlorophenyl | H | (R)— |
| I-543 | C—NH₂ | Cl | o-tolyl | Et | racemic |
| I-544 | C—NH₂ | Cl | o-tolyl | Et | (R)— |
| I-545 | C—NH₂ | Cl | o-tolyl | H | racemic |
| I-546 | C—NH₂ | Cl | o-tolyl | H | (R)— |
| I-547 | C—NH₂ | Cl | 2,5-difluorophenyl | Et | racemic |
| I-548 | C—NH₂ | Cl | 2,5-difluorophenyl | Et | (R)— |
| I-549 | C—NH₂ | Cl | 2,5-difluorophenyl | H | racemic |
| I-550 | C—NH₂ | Cl | 2,5-difluorophenyl | H | (R)— |
| I-551 | C—NH₂ | F | phenyl | Et | racemic |
| I-552 | C—NH₂ | F | phenyl | Et | (R)— |
| I-553 | C—NH₂ | F | phenyl | H | racemic |
| I-554 | C—NH₂ | F | phenyl | H | (R)— |
| I-555 | C—NH₂ | F | 3-fluorophenyl | Et | racemic |
| I-556 | C—NH₂ | F | 3-fluorophenyl | Et | (R)— |
| I-557 | C—NH₂ | F | 3-fluorophenyl | H | racemic |
| I-558 | C—NH₂ | F | 3-fluorophenyl | H | (R)— |
| I-559 | C—NH₂ | F | 2-chlorophenyl | Et | racemic |
| I-560 | C—NH₂ | F | 2-chlorophenyl | Et | (R)— |
| I-561 | C—NH₂ | F | 2-chlorophenyl | H | racemic |
| I-562 | C—NH₂ | F | 2-chlorophenyl | H | (R)— |
| I-563 | C—NH₂ | F | o-tolyl | Et | racemic |
| I-564 | C—NH₂ | F | o-tolyl | Et | (R)— |
| I-565 | C—NH₂ | F | o-tolyl | H | racemic |
| I-566 | C—NH₂ | F | o-tolyl | H | (R)— |
| I-567 | C—NH₂ | F | 2,5-difluorophenyl | Et | racemic |
| I-568 | C—NH₂ | F | 2,5-difluorophenyl | Et | (R)— |
| I-569 | C—NH₂ | F | 2,5-difluorophenyl | H | racemic |
| I-570 | C—NH₂ | F | 2,5-difluorophenyl | H | (R)— |

TABLE 3

| Compound No. | V | X | (R¹)p—A— | R² | Configuration |
|---|---|---|---|---|---|
| I-571 | CH | Br | thiophen-3-yl | Et | racemic |
| I-572 | CH | Br | thiophen-3-yl | Et | (R)— |
| I-573 | CH | Br | thiophen-3-yl | H | racemic |
| I-574 | CH | Br | thiophen-3-yl | H | (R)— |
| I-575 | CH | Br | 4-methylthiophen-3-yl | Et | racemic |
| I-576 | CH | Br | 4-methylthiophen-3-yl | Et | (R)— |
| I-577 | CH | Br | 4-methylthiophen-3-yl | H | racemic |
| I-578 | CH | Br | 4-methylthiophen-3-yl | H | (R)— |
| I-579 | CH | Br | 4-fluorothiophen-3-yl | Et | racemic |
| I-580 | CH | Br | 4-fluorothiophen-3-yl | Et | (R)— |
| I-581 | CH | Br | 4-fluorothiophen-3-yl | H | racemic |
| I-582 | CH | Br | 4-fluorothiophen-3-yl | H | (R)— |
| I-583 | CH | Br | thiophen-2-yl | Et | racemic |
| I-584 | CH | Br | thiophen-2-yl | Et | (R)— |
| I-585 | CH | Br | thiophen-2-yl | H | racemic |
| I-586 | CH | Br | thiophen-2-yl | H | (R)— |
| I-587 | CH | Cl | thiophen-3-yl | iso-Pr | racemic |
| I-588 | CH | Cl | thiophen-3-yl | iso-Pr | (R)— |
| I-589 | CH | Cl | thiophen-3-yl | n-Pr | racemic |
| I-590 | CH | Cl | thiophen-3-yl | n-Pr | (R)— |
| I-591 | CH | Cl | thiophen-3-yl | Et | racemic |
| I-592 | CH | Cl | thiophen-3-yl | Et | (R)— |
| I-593 | CH | Cl | thiophen-3-yl | Me | racemic |
| I-594 | CH | Cl | thiophen-3-yl | Me | (R)— |
| I-595 | CH | Cl | thiophen-3-yl | H | racemic |
| I-596 | CH | Cl | thiophen-3-yl | H | (R)— |
| I-597 | CH | Cl | 4-methylthiophen-3-yl | iso-Pr | racemic |
| I-598 | CH | Cl | 4-methylthiophen-3-yl | iso-Pr | (R)— |
| I-599 | CH | Cl | 4-methylthiophen-3-yl | n-Pr | racemic |
| I-600 | CH | Cl | 4-methylthiophen-3-yl | n-Pr | (R)— |
| I-601 | CH | Cl | 4-methylthiophen-3-yl | Et | racemic |
| I-602 | CH | Cl | 4-methylthiophen-3-yl | Et | (R)— |
| I-603 | CH | Cl | 4-methylthiophen-3-yl | Me | racemic |
| I-604 | CH | Cl | 4-methylthiophen-3-yl | Me | (R)— |
| I-605 | CH | Cl | 4-methylthiophen-3-yl | H | racemic |
| I-606 | CH | Cl | 4-methylthiophen-3-yl | H | (R)— |
| I-607 | CH | Cl | 4-fluorothiophen-3-yl | Et | racemic |
| I-608 | CH | Cl | 4-fluorothiophen-3-yl | Et | (R)— |
| I-609 | CH | Cl | 4-fluorothiophen-3-yl | H | racemic |
| I-610 | CH | Cl | 4-fluorothiophen-3-yl | H | (R)— |
| I-611 | CH | Cl | 4-chlorothiophen-3-yl | Et | racemic |
| I-612 | CH | Cl | 4-chlorothiophen-3-yl | Et | (R)— |
| I-613 | CH | Cl | 4-chlorothiophen-3-yl | H | racemic |
| I-614 | CH | Cl | 4-chlorothiophen-3-yl | H | (R)— |
| I-615 | CH | Cl | 2-methylthiophen-3-yl | Et | racemic |
| I-616 | CH | Cl | 2-methylthiophen-3-yl | Et | (R)— |
| I-617 | CH | Cl | 2-methylthiophen-3-yl | H | racemic |
| I-618 | CH | Cl | 2-methylthiophen-3-yl | H | (R)— |
| I-619 | CH | Cl | isothiazol-3-yl | Et | racemic |
| I-620 | CH | Cl | isothiazol-3-yl | Et | (R)— |
| I-621 | CH | Cl | isothiazol-3-yl | H | racemic |
| I-622 | CH | Cl | isothiazol-3-yl | H | (R)— |
| I-623 | CH | Cl | isothiazol-4-yl | Et | racemic |
| I-624 | CH | Cl | isothiazol-4-yl | Et | (R)— |
| I-625 | CH | Cl | isothiazol-4-yl | H | racemic |
| I-626 | CH | Cl | isothiazol-4-yl | H | (R)— |
| I-627 | CH | Cl | thiophen-2-yl | Et | racemic |
| I-628 | CH | Cl | thiophen-2-yl | Et | (R)— |
| I-629 | CH | Cl | thiophen-2-yl | H | racemic |
| I-630 | CH | Cl | thiophen-2-yl | H | (R)— |
| I-631 | CH | F | thiophen-3-yl | iso-Pr | racemic |
| I-632 | CH | F | thiophen-3-yl | iso-Pr | (R)— |
| I-633 | CH | F | thiophen-3-yl | n-Pr | racemic |
| I-634 | CH | F | thiophen-3-yl | n-Pr | (R)— |
| I-635 | CH | F | thiophen-3-yl | Et | racemic |
| I-636 | CH | F | thiophen-3-yl | Et | (R)— |
| I-637 | CH | F | thiophen-3-yl | Me | racemic |
| I-638 | CH | F | thiophen-3-yl | Me | (R)— |
| I-639 | CH | F | thiophen-3-yl | H | racemic |
| I-640 | CH | F | thiophen-3-yl | H | (R)— |
| I-641 | CH | F | 4-methylthiophen-3-yl | iso-Pr | racemic |
| I-642 | CH | F | 4-methylthiophen-3-yl | iso-Pr | (R)— |
| I-643 | CH | F | 4-methylthiophen-3-yl | n-Pr | racemic |
| I-644 | CH | F | 4-methylthiophen-3-yl | n-Pr | (R)— |
| I-645 | CH | F | 4-methylthiophen-3-yl | Et | racemic |
| I-646 | CH | F | 4-methylthiophen-3-yl | Et | (R)— |
| I-647 | CH | F | 4-methylthiophen-3-yl | Me | racemic |
| I-648 | CH | F | 4-methylthiophen-3-yl | Me | (R)— |
| I-649 | CH | F | 4-methylthiophen-3-yl | H | racemic |
| I-650 | CH | F | 4-methylthiophen-3-yl | H | (R)— |
| I-651 | CH | F | 4-fluorothiophen-3-yl | Et | racemic |
| I-652 | CH | F | 4-fluorothiophen-3-yl | Et | (R)— |
| I-653 | CH | F | 4-fluorothiophen-3-yl | H | racemic |
| I-654 | CH | F | 4-fluorothiophen-3-yl | H | (R)— |
| I-655 | CH | F | 4-chlorothiophen-3-yl | Et | racemic |
| I-656 | CH | F | 4-chlorothiophen-3-yl | Et | (R)— |
| I-657 | CH | F | 4-chlorothiophen-3-yl | H | racemic |
| I-658 | CH | F | 4-chlorothiophen-3-yl | H | (R)— |
| I-659 | CH | F | 2-methylthiophen-3-yl | Et | racemic |
| I-660 | CH | F | 2-methylthiophen-3-yl | Et | (R)— |
| I-661 | CH | F | 2-methylthiophen-3-yl | H | racemic |
| I-662 | CH | F | 2-methylthiophen-3-yl | H | (R)— |
| I-663 | CH | F | isothiazol-3-yl | Et | racemic |
| I-664 | CH | F | isothiazol-3-yl | Et | (R)— |
| I-665 | CH | F | isothiazol-3-yl | H | racemic |
| I-666 | CH | F | isothiazol-3-yl | H | (R)— |
| I-667 | CH | F | isothiazol-4-yl | Et | racemic |
| I-668 | CH | F | isothiazol-4-yl | Et | (R)— |
| I-669 | CH | F | isothiazol-4-yl | H | racemic |
| I-670 | CH | F | isothiazol-4-yl | H | (R)— |
| I-671 | CH | F | thiophen-2-yl | Et | racemic |
| I-672 | CH | F | thiophen-2-yl | Et | (R)— |
| I-673 | CH | F | thiophen-2-yl | H | racemic |
| I-674 | CH | F | thiophen-2-yl | H | (R)— |
| I-675 | N | Br | thiophen-3-yl | Et | racemic |
| I-676 | N | Br | thiophen-3-yl | Et | (R)— |
| I-677 | N | Br | thiophen-3-yl | H | racemic |
| I-678 | N | Br | thiophen-3-yl | H | (R)— |
| I-679 | N | Br | 4-methylthiophen-3-yl | Et | racemic |
| I-680 | N | Br | 4-methylthiophen-3-yl | Et | (R)— |

TABLE 3-continued

| Compound No. | V | X | (R¹)p—A— | R² | Configuration |
|---|---|---|---|---|---|
| I-681 | N | Br | 4-methylthiophen-3-yl | H | racemic |
| I-682 | N | Br | 4-methylthiophen-3-yl | H | (R)— |
| I-683 | N | Br | 4-fluorothiophen-3-yl | Et | racemic |
| I-684 | N | Br | 4-fluorothiophen-3-yl | Et | (R)— |
| I-685 | N | Br | 4-fluorothiophen-3-yl | H | racemic |
| I-686 | N | Br | 4-fluorothiophen-3-yl | H | (R)— |
| I-687 | N | Br | thiophen-2-yl | Et | racemic |
| I-688 | N | Br | thiophen-2-yl | Et | (R)— |
| I-689 | N | Br | thiophen-2-yl | H | racemic |
| I-690 | N | Br | thiophen-2-yl | H | (R)— |
| I-691 | N | Cl | thiophen-3-yl | Et | racemic |
| I-692 | N | Cl | thiophen-3-yl | Et | (R)— |
| I-693 | N | Cl | thiophen-3-yl | H | racemic |
| I-694 | N | Cl | thiophen-3-yl | H | (R)— |
| I-695 | N | Cl | 4-methylthiophen-3-yl | Et | racemic |
| I-696 | N | Cl | 4-methylthiophen-3-yl | Et | (R)— |
| I-697 | N | Cl | 4-methylthiophen-3-yl | H | racemic |
| I-698 | N | Cl | 4-methylthiophen-3-yl | H | (R)— |
| I-699 | N | Cl | 4-fluorothiophen-3-yl | Et | racemic |
| I-700 | N | Cl | 4-fluorothiophen-3-yl | Et | (R)— |
| I-701 | N | Cl | 4-fluorothiophen-3-yl | H | racemic |
| I-702 | N | Cl | 4-fluorothiophen-3-yl | H | (R)— |
| I-703 | N | Cl | 4-chlorothiophen-3-yl | Et | racemic |
| I-704 | N | Cl | 4-chlorothiophen-3-yl | Et | (R)— |
| I-705 | N | Cl | 4-chlorothiophen-3-yl | H | racemic |
| I-706 | N | Cl | 4-chlorothiophen-3-yl | H | (R)— |
| I-707 | N | Cl | 2-methylthiophen-3-yl | Et | racemic |
| I-708 | N | Cl | 2-methylthiophen-3-yl | Et | (R)— |
| I-709 | N | Cl | 2-methylthiophen-3-yl | H | racemic |
| I-710 | N | Cl | 2-methylthiophen-3-yl | H | (R)— |
| I-711 | N | Cl | isothiazol-3-yl | Et | racemic |
| I-712 | N | Cl | isothiazol-3-yl | Et | (R)— |
| I-713 | N | Cl | isothiazol-3-yl | H | racemic |
| I-714 | N | Cl | isothiazol-3-yl | H | (R)— |
| I-715 | N | Cl | isothiazol-4-yl | Et | racemic |
| I-716 | N | Cl | isothiazol-4-yl | Et | (R)— |
| I-717 | N | Cl | isothiazol-4-yl | H | racemic |
| I-718 | N | Cl | isothiazol-4-yl | H | (R)— |
| I-719 | N | Cl | thiophen-2-yl | Et | racemic |
| I-720 | N | Cl | thiophen-2-yl | Et | (R)— |
| I-721 | N | Cl | thiophen-2-yl | H | racemic |
| I-722 | N | Cl | thiophen-2-yl | H | (R)— |
| I-723 | N | F | thiophen-3-yl | Et | racemic |
| I-724 | N | F | thiophen-3-yl | Et | (R)— |
| I-725 | N | F | thiophen-3-yl | H | racemic |
| I-726 | N | F | thiophen-3-yl | H | (R)— |
| I-727 | N | F | 4-methylthiophen-3-yl | Et | racemic |
| I-728 | N | F | 4-methylthiophen-3-yl | Et | (R)— |
| I-729 | N | F | 4-methylthiophen-3-yl | H | racemic |
| I-730 | N | F | 4-methylthiophen-3-yl | H | (R)— |
| I-731 | N | F | 4-fluorothiophen-3-yl | Et | racemic |
| I-732 | N | F | 4-fluorothiophen-3-yl | Et | (R)— |
| I-733 | N | F | 4-fluorothiophen-3-yl | H | racemic |
| I-734 | N | F | 4-fluorothiophen-3-yl | H | (R)— |
| I-735 | N | F | 4-chlorothiophen-3-yl | Et | racemic |
| I-736 | N | F | 4-chlorothiophen-3-yl | Et | (R)— |
| I-737 | N | F | 4-chlorothiophen-3-yl | H | racemic |
| I-738 | N | F | 4-chlorothiophen-3-yl | H | (R)— |
| I-739 | N | F | 2-methylthiophen-3-yl | Et | racemic |
| I-740 | N | F | 2-methylthiophen-3-yl | Et | (R)— |
| I-741 | N | F | 2-methylthiophen-3-yl | H | racemic |
| I-742 | N | F | 2-methylthiophen-3-yl | H | (R)— |
| I-743 | N | F | isothiazol-3-yl | Et | racemic |
| I-744 | N | F | isothiazol-3-yl | Et | (R)— |
| I-745 | N | F | isothiazol-3-yl | H | racemic |
| I-746 | N | F | isothiazol-3-yl | H | (R)— |
| I-747 | N | F | isothiazol-4-yl | Et | racemic |
| I-748 | N | F | isothiazol-4-yl | Et | (R)— |
| I-749 | N | F | isothiazol-4-yl | H | racemic |
| I-750 | N | F | isothiazol-4-yl | H | (R)— |
| I-751 | N | F | thiophen-2-yl | Et | racemic |
| I-752 | N | F | thiophen-2-yl | Et | (R)— |
| I-753 | N | F | thiophen-2-yl | H | racemic |
| I-754 | N | F | thiophen-2-yl | H | (R)— |
| I-755 | C—OMe | Br | thiophen-3-yl | Et | racemic |
| I-756 | C—OMe | Br | thiophen-3-yl | Et | (R)— |
| I-757 | C—OMe | Br | thiophen-3-yl | H | racemic |
| I-758 | C—OMe | Br | thiophen-3-yl | H | (R)— |
| I-759 | C—OMe | Br | 4-methylthiophen-3-yl | Et | racemic |
| I-760 | C—OMe | Br | 4-methylthiophen-3-yl | Et | (R)— |
| I-761 | C—OMe | Br | 4-methylthiophen-3-yl | H | racemic |
| I-762 | C—OMe | Br | 4-methylthiophen-3-yl | H | (R)— |
| I-763 | C—OMe | Br | 4-fluorothiophen-3-yl | Et | racemic |
| I-764 | C—OMe | Br | 4-fluorothiophen-3-yl | Et | (R)— |
| I-765 | C—OMe | Br | 4-fluorothiophen-3-yl | H | racemic |
| I-766 | C—OMe | Br | 4-fluorothiophen-3-yl | H | (R)— |
| I-767 | C—OMe | Br | thiophen-2-yl | Et | racemic |
| I-768 | C—OMe | Br | thiophen-2-yl | Et | (R)— |
| I-769 | C—OMe | Br | thiophen-2-yl | H | racemic |
| I-770 | C—OMe | Br | thiophen-2-yl | H | (R)— |
| I-771 | C—OMe | Cl | thiophen-3-yl | iso-Pr | racemic |
| I-772 | C—OMe | Cl | thiophen-3-yl | iso-Pr | (R)— |
| I-773 | C—OMe | Cl | thiophen-3-yl | n-Pr | racemic |
| I-774 | C—OMe | Cl | thiophen-3-yl | n-Pr | (R)— |
| I-775 | C—OMe | Cl | thiophen-3-yl | Et | racemic |
| I-776 | C—OMe | Cl | thiophen-3-yl | Et | (R)— |
| I-777 | C—OMe | Cl | thiophen-3-yl | Me | racemic |
| I-778 | C—OMe | Cl | thiophen-3-yl | Me | (R)— |
| I-779 | C—OMe | Cl | thiophen-3-yl | H | racemic |
| I-780 | C—OMe | Cl | thiophen-3-yl | H | (R)— |
| I-781 | C—OMe | Cl | 4-methylthiophen-3-yl | Et | racemic |
| I-782 | C—OMe | Cl | 4-methylthiophen-3-yl | Et | (R)— |
| I-783 | C—OMe | Cl | 4-methylthiophen-3-yl | H | racemic |
| I-784 | C—OMe | Cl | 4-methylthiophen-3-yl | H | (R)— |
| I-785 | C—OMe | Cl | 4-fluorothiophen-3-yl | Et | racemic |
| I-786 | C—OMe | Cl | 4-fluorothiophen-3-yl | Et | (R)— |
| I-787 | C—OMe | Cl | 4-fluorothiophen-3-yl | H | racemic |
| I-788 | C—OMe | Cl | 4-fluorothiophen-3-yl | H | (R)— |
| I-789 | C—OMe | Cl | 4-chlorothiophen-3-yl | Et | racemic |
| I-790 | C—OMe | Cl | 4-chlorothiophen-3-yl | Et | (R)— |
| I-791 | C—OMe | Cl | 4-chlorothiophen-3-yl | H | racemic |
| I-792 | C—OMe | Cl | 4-chlorothiophen-3-yl | H | (R)— |
| I-793 | C—OMe | Cl | 2-methylthiophen-3-yl | Et | racemic |
| I-794 | C—OMe | Cl | 2-methylthiophen-3-yl | Et | (R)— |
| I-795 | C—OMe | Cl | 2-methylthiophen-3-yl | H | racemic |
| I-796 | C—OMe | Cl | 2-methylthiophen-3-yl | H | (R)— |
| I-797 | C—OMe | Cl | isothiazol-3-yl | Et | racemic |
| I-798 | C—OMe | Cl | isothiazol-3-yl | Et | (R)— |
| I-799 | C—OMe | Cl | isothiazol-3-yl | H | racemic |
| I-800 | C—OMe | Cl | isothiazol-3-yl | H | (R)— |
| I-801 | C—OMe | Cl | isothiazol-4-yl | Et | racemic |
| I-802 | C—OMe | Cl | isothiazol-4-yl | Et | (R)— |
| I-803 | C—OMe | Cl | isothiazol-4-yl | H | racemic |
| I-804 | C—OMe | Cl | isothiazol-4-yl | H | (R)— |
| I-805 | C—OMe | Cl | thiophen-2-yl | Et | racemic |
| I-806 | C—OMe | Cl | thiophen-2-yl | Et | (R)— |
| I-807 | C—OMe | Cl | thiophen-2-yl | H | racemic |
| I-808 | C—OMe | Cl | thiophen-2-yl | H | (R)— |
| I-809 | C—OMe | F | thiophen-3-yl | Et | racemic |
| I-810 | C—OMe | F | thiophen-3-yl | Et | (R)— |
| I-811 | C—OMe | F | thiophen-3-yl | H | racemic |
| I-812 | C—OMe | F | thiophen-3-yl | H | (R)— |
| I-813 | C—OMe | F | 4-methylthiophen-3-yl | Et | racemic |
| I-814 | C—OMe | F | 4-methylthiophen-3-yl | Et | (R)— |
| I-815 | C—OMe | F | 4-methylthiophen-3-yl | H | racemic |
| I-816 | C—OMe | F | 4-methylthiophen-3-yl | H | (R)— |
| I-817 | C—OMe | F | 4-fluorothiophen-3-yl | Et | racemic |
| I-818 | C—OMe | F | 4-fluorothiophen-3-yl | Et | (R)— |
| I-819 | C—OMe | F | 4-fluorothiophen-3-yl | H | racemic |
| I-820 | C—OMe | F | 4-fluorothiophen-3-yl | H | (R)— |
| I-821 | C—OMe | F | 4-chlorothiophen-3-yl | Et | racemic |
| I-822 | C—OMe | F | 4-chlorothiophen-3-yl | Et | (R)— |
| I-823 | C—OMe | F | 4-chlorothiophen-3-yl | H | racemic |
| I-824 | C—OMe | F | 4-chlorothiophen-3-yl | H | (R)— |
| I-825 | C—OMe | F | 2-methylthiophen-3-yl | Et | racemic |
| I-826 | C—OMe | F | 2-methylthiophen-3-yl | Et | (R)— |
| I-827 | C—OMe | F | 2-methylthiophen-3-yl | H | racemic |
| I-828 | C—OMe | F | 2-methylthiophen-3-yl | H | (R)— |
| I-829 | C—OMe | F | isothiazol-3-yl | Et | racemic |
| I-830 | C—OMe | F | isothiazol-3-yl | Et | (R)— |
| I-831 | C—OMe | F | isothiazol-3-yl | H | racemic |
| I-832 | C—OMe | F | isothiazol-3-yl | H | (R)— |
| I-833 | C—OMe | F | isothiazol-4-yl | Et | racemic |
| I-834 | C—OMe | F | isothiazol-4-yl | Et | (R)— |

TABLE 3-continued

| Compound No. | V | X | (R¹)p—A— | R² | Configuration |
|---|---|---|---|---|---|
| I-835 | C—OMe | F | isothiazol-4-yl | H | racemic |
| I-836 | C—OMe | F | isothiazol-4-yl | H | (R)— |
| I-837 | C—OMe | F | thiophen-2-yl | Et | racemic |
| I-838 | C—OMe | F | thiophen-2-yl | Et | (R)— |
| I-839 | C—OMe | F | thiophen-2-yl | H | racemic |
| I-840 | C—OMe | F | thiophen-2-yl | H | (R)— |
| I-841 | C—NO₂ | Cl | thiophen-3-yl | Et | racemic |
| I-842 | C—NO₂ | Cl | thiophen-3-yl | Et | (R)— |
| I-843 | C—NO₂ | Cl | thiophen-3-yl | H | racemic |
| I-844 | C—NO₂ | Cl | thiophen-3-yl | H | (R)— |
| I-845 | C—NO₂ | Cl | 4-methylthiophen-3-yl | Et | racemic |
| I-846 | C—NO₂ | Cl | 4-methylthiophen-3-yl | Et | (R)— |
| I-847 | C—NO₂ | Cl | 4-methylthiophen-3-yl | H | racemic |
| I-848 | C—NO₂ | Cl | 4-methylthiophen-3-yl | H | (R)— |
| I-849 | C—NO₂ | Cl | 4-fluorothiophen-3-yl | Et | racemic |
| I-850 | C—NO₂ | Cl | 4-fluorothiophen-3-yl | Et | (R)— |
| I-851 | C—NO₂ | Cl | 4-fluorothiophen-3-yl | H | racemic |
| I-852 | C—NO₂ | Cl | 4-fluorothiophen-3-yl | H | (R)— |
| I-853 | C—NO₂ | Cl | thiophen-2-yl | Et | racemic |
| I-854 | C—NO₂ | Cl | thiophen-2-yl | Et | (R)— |
| I-855 | C—NO₂ | Cl | thiophen-2-yl | H | racemic |
| I-856 | C—NO₂ | Cl | thiophen-2-yl | H | (R)— |
| I-857 | C—NO₂ | F | thiophen-3-yl | Et | racemic |
| I-858 | C—NO₂ | F | thiophen-3-yl | Et | (R)— |
| I-859 | C—NO₂ | F | thiophen-3-yl | H | racemic |
| I-860 | C—NO₂ | F | thiophen-3-yl | H | (R)— |
| I-861 | C—NO₂ | F | 4-methylthiophen-3-yl | Et | racemic |
| I-862 | C—NO₂ | F | 4-methylthiophen-3-yl | Et | (R)— |
| I-863 | C—NO₂ | F | 4-methylthiophen-3-yl | H | racemic |
| I-864 | C—NO₂ | F | 4-methylthiophen-3-yl | H | (R)— |
| I-865 | C—NO₂ | F | 4-fluorothiophen-3-yl | Et | racemic |
| I-866 | C—NO₂ | F | 4-fluorothiophen-3-yl | Et | (R)— |
| I-867 | C—NO₂ | F | 4-fluorothiophen-3-yl | H | racemic |
| I-868 | C—NO₂ | F | 4-fluorothiophen-3-yl | H | (R)— |
| I-869 | C—NO₂ | F | thiophen-2-yl | Et | racemic |
| I-870 | C—NO₂ | F | thiophen-2-yl | Et | (R)— |
| I-871 | C—NO₂ | F | thiophen-2-yl | H | racemic |
| I-872 | C—NO₂ | F | thiophen-2-yl | H | (R)— |
| I-873 | C—NH₂ | Cl | thiophen-3-yl | Et | racemic |
| I-874 | C—NH₂ | Cl | thiophen-3-yl | Et | (R)— |
| I-875 | C—NH₂ | Cl | thiophen-3-yl | H | racemic |
| I-876 | C—NH₂ | Cl | thiophen-3-yl | H | (R)— |
| I-877 | C—NH₂ | Cl | 4-methylthiophen-3-yl | Et | racemic |
| I-878 | C—NH₂ | Cl | 4-methylthiophen-3-yl | Et | (R)— |
| I-879 | C—NH₂ | Cl | 4-methylthiophen-3-yl | H | racemic |
| I-880 | C—NH₂ | Cl | 4-methylthiophen-3-yl | H | (R)— |
| I-881 | C—NH₂ | Cl | 4-fluorothiophen-3-yl | Et | racemic |
| I-882 | C—NH₂ | Cl | 4-fluorothiophen-3-yl | Et | (R)— |
| I-883 | C—NH₂ | Cl | 4-fluorothiophen-3-yl | H | racemic |
| I-884 | C—NH₂ | Cl | 4-fluorothiophen-3-yl | H | (R)— |
| I-885 | C—NH₂ | Cl | thiophen-2-yl | Et | racemic |
| I-886 | C—NH₂ | Cl | thiophen-2-yl | Et | (R)— |
| I-887 | C—NH₂ | Cl | thiophen-2-yl | H | racemic |
| I-888 | C—NH₂ | Cl | thiophen-2-yl | H | (R)— |
| I-889 | C—NH₂ | F | thiophen-3-yl | Et | racemic |
| I-890 | C—NH₂ | F | thiophen-3-yl | Et | (R)— |
| I-891 | C—NH₂ | F | thiophen-3-yl | H | racemic |
| I-892 | C—NH₂ | F | thiophen-3-yl | H | (R)— |
| I-893 | C—NH₂ | F | 4-methylthiophen-3-yl | Et | racemic |
| I-894 | C—NH₂ | F | 4-methylthiophen-3-yl | Et | (R)— |
| I-895 | C—NH₂ | F | 4-methylthiophen-3-yl | H | racemic |
| I-896 | C—NH₂ | F | 4-methylthiophen-3-yl | H | (R)— |
| I-897 | C—NH₂ | F | 4-fluorothiophen-3-yl | Et | racemic |
| I-898 | C—NH₂ | F | 4-fluorothiophen-3-yl | Et | (R)— |
| I-899 | C—NH₂ | F | 4-fluorothiophen-3-yl | H | racemic |
| I-900 | C—NH₂ | F | 4-fluorothiophen-3-yl | H | (R)— |
| I-901 | C—NH₂ | F | thiophen-2-yl | Et | racemic |
| I-902 | C—NH₂ | F | thiophen-2-yl | Et | (R)— |
| I-903 | C—NH₂ | F | thiophen-2-yl | H | racemic |
| I-904 | C—NH₂ | F | thiophen-2-yl | H | (R)— |

Effects of the Invention

The α-halogen-substituted thiophene compound represented by the general formula (I) of the present invention, and, a pharmacologically acceptable salt thereof have a potent LPA receptor-antagonist activity and is thereby useful as a medicament, as a medicament for the treatment and/or prevention of a disease accompanying fibrosis, an immunological or inflammatory disease, a central or peripheral nervous system disease, an urologic disease or a cancer-related disease.

BEST MODE FOR CARRYING OUT THE INVENTION

In the compounds represented by the above general formulae (I), (Ia), and (Ib), a preferred embodiment of each substituent group is shown below.

"Halogen atom" represented by $R^1$, and "halogen atom" represented by X each have the same significance, being, for example, a fluorine atom, a chlorine atom, a bromine atom, or an iodine atom.

"Halogen atom" represented by X is preferably a fluorine atom, a chlorine atom, or a bromine atom, and is more preferably a fluorine atom or a chlorine atom.

"Halogen atom" represented by $R^1$ is preferably a fluorine atom or a chlorine atom.

"$C_1$-$C_3$ alkyl group" represented by $R^1$ includes, for example, a straight or branched $C_1$-$C_3$ alkyl group such as a methyl group, an ethyl group, a propyl group, or an isopropyl group.

"$C_1$-$C_3$ alkyl group" represented by $R^1$ is preferably a methyl group, or an ethyl group, and more preferably a methyl group.

$R^1$ is preferably a fluorine atom, a chlorine atom, or a methyl group.

"$C_1$-$C_6$ alkyl group" represented by $R^2$ includes, for example, a straight or branched $C_1$-$C_6$ alkyl group such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1-ethylpropyl group, a 1,2-dimethylpropyl group, a hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1-ethyl-1-methylpropyl group, a 1-ethyl-2-methylpropyl group, a 1,1,2-trimethylpropyl group, or a 1,2,2-trimethylpropyl group, etc.

"$C_1$-$C_6$ alkyl group" represented by $R^2$ is preferably a $C_1$-$C_3$ alkyl group, and more preferably an ethyl group.

$R^2$ is preferably a hydrogen atom, or an ethyl group, and more preferably a hydrogen atom.

"$C_1$-$C_3$ alkoxy group" represented by $R^3$ includes, for example, a straight or branched $C_1$-$C_3$ alkoxy group such as a methoxy group, an ethoxy group, a propoxy group or an isopropoxy group.

"$C_1$-$C_3$ alkoxy group" represented by $R^3$ is preferably a methoxy group, or an ethoxy group, and more preferably a methoxy group.

V is preferably $CR^3$ (wherein $R^3$ represents a hydrogen atom, an amino group, a nitro group, or a methoxy group), or a nitrogen atom, more preferably $CR^3$ (wherein $R^3$ represents a hydrogen atom, or a methoxy group), or a nitrogen atom, and particularly preferably CR³ (wherein R³ represents a hydrogen atom, or a methoxy group).

p is preferably 0 to 3, and more preferably 0 to 2.

A is preferably selected from the groups:

[Chemical Formula 17]

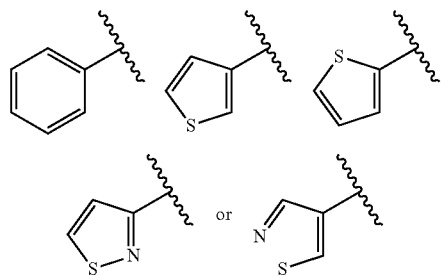

and more preferably selected from the groups:

[Chemical Formula 18]

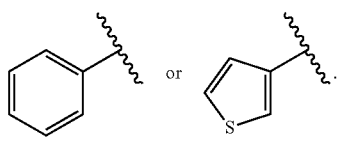

"Phenyl ring" represented by A in combination with p and the substituent group R¹ includes, for example, the groups:

[Chemical Formula 19]

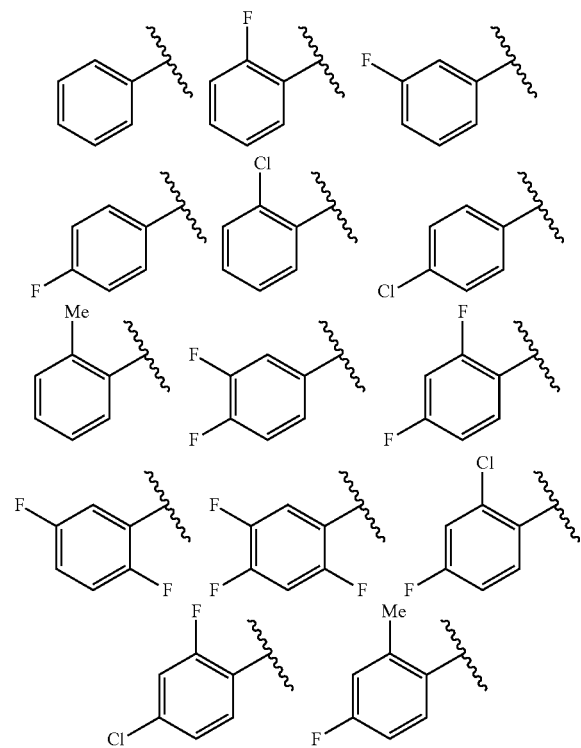

wherein Me represents a methyl group, preferably includes the groups:

[Chemical Formula 20]

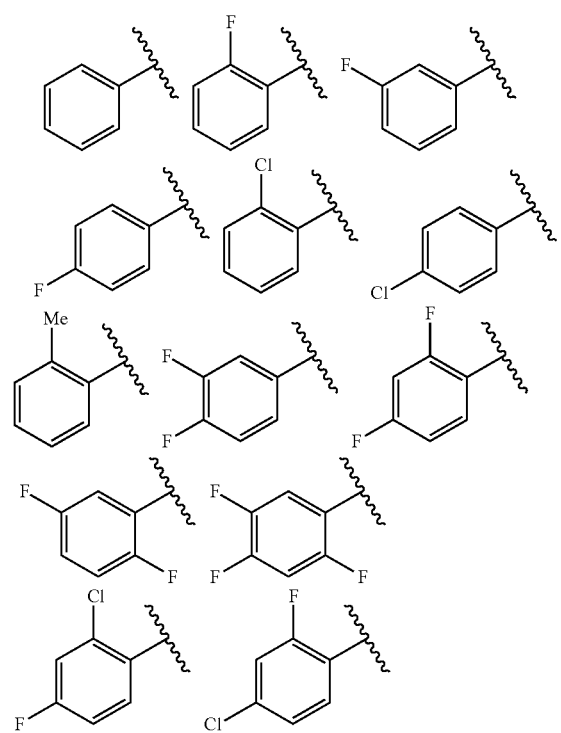

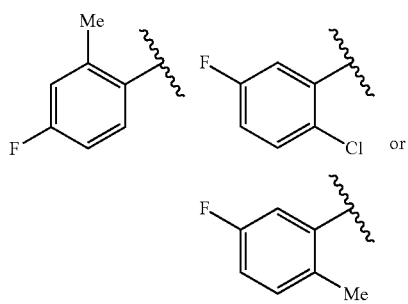

wherein Me represents a methyl group,
and more preferably includes the groups:

[Chemical Formula 21]

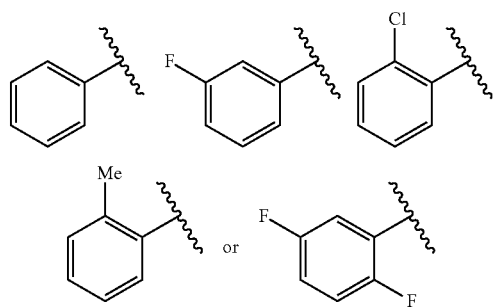

wherein Me represents a methyl group.

"Thiophene ring" or "isothiazole ring" represented by A in combination with p and the substituent group $R^1$ includes, for example, the groups:

[Chemical Formula 22]

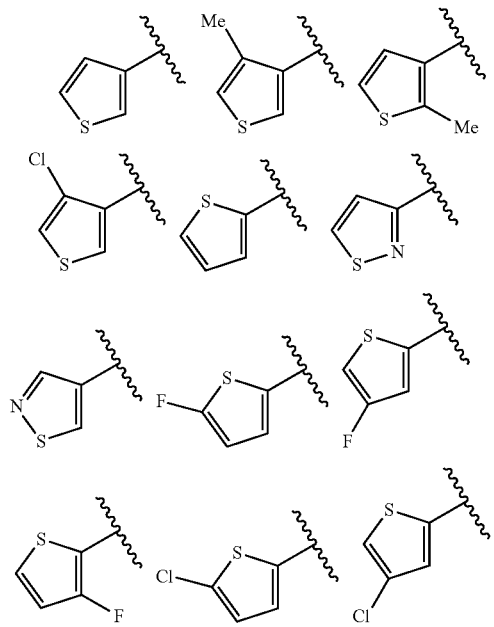

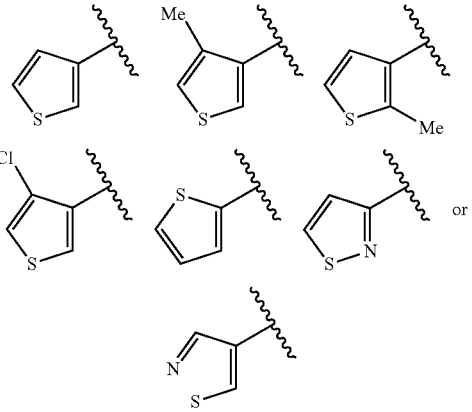

wherein Me represents a methyl group,
preferably includes the groups:

[Chemical Formula 23]

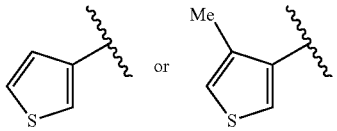

wherein Me represents a methyl group,
and more preferably includes the groups:

[Chemical Formula 24]

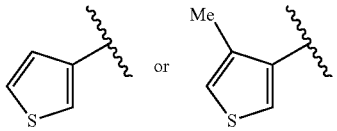

wherein Me represents a methyl group.

In a case where the compounds represented by the general formulae (I), (Ia), and (Ib) have an optical isomer, a geometrical isomer, or a rotational isomer, these isomers are included within the scope of the present invention, and in a case where proton tautomerism is present, these tautomers are also included within the scope of the present invention.

In the general formula (I), the group:

[Chemical Formula 25]

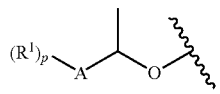

is preferably the group:

[Chemical Formula 26]

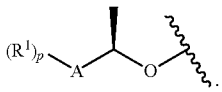

In the general formulae (Ia) and (Ib), the group:

[Chemical Formula 27]

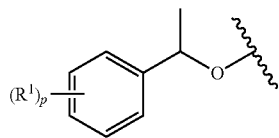

is preferably the group:

[Chemical Formula 28]

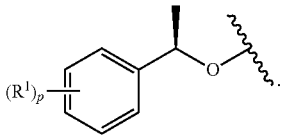

The compounds represented by the formulae (I), (Ia), and (Ib) of the present invention, in a case where each $R^2$ is a hydrogen atom, may be treated with a base to convert them to a pharmacologically acceptable basic salt. Such a salt includes, for example, a metal salt such as a sodium salt, a potassium salt, a calcium salt, or a magnesium salt; an inorganic salt such as an ammonium salt; or an organic amine salt such as a triethylamine salt or a guanidine salt, etc.

Further, in a case where $R^3$ is an amino group, or V is a nitrogen atom, they may be treated with an acid to convert them to a pharmacological acceptable acid salt. Such a salt includes, for example, an inorganic acid salt such as hydrochloride, hydrobromide, hydroiodide, nitrate, sulfate or phosphate; or an organic acid salt such as acetate, trifluoroacetate, benzoate, oxalate, malonate, succinate, maleate, fumarate, tartrate, citrate, methanesulfonate, ethanesulfonate, trifluoromethanesulfonate, benzenesulfonate, p-toluenesulfonate, glutamate, or aspartate, etc.

Further, the compounds represented by the general formulae (I), (Ia), and (Ib) of the present invention or a pharmacologically acceptable salt thereof can be present as a hydrate or a solvate, and they are included within the present invention.

The compound represented by the formula (I) of the present invention may comprise a non-natural ratio of isotope in one or more constituent atoms. The isotope includes, for example, deuterium ($^2H$), tritium ($^3H$), carbon-14 ($^{14}C$), fluorine-18 ($^{18}F$), sulfur-35 ($^{35}S$), or iodine-125 ($^{125}I$), etc. These compounds are useful as a medicament for the treatment or prevention, a reagent for research, for example, an assay reagent, and a diagnostic agent, for example, an in vivo image diagnostic agent. Every isotope variant of the compound represented by the formula (I) of the present invention is included within the present invention whether or not it is radioactive.

A general process for preparing the compound of the present invention is shown below. In a case where there is a partial structure which inhibits a desired reaction or is subjected to a side reaction in the process for preparation as shown below (for example, a hydroxyl group, an amino group, a carbonyl group, a carboxyl group, an amide group, or a thiol group, etc.), the desired compound can be obtained by introducing a protective group to the partial structure, carrying out the desired reaction and then removing said protective group. Such a reaction for introducing and removing the protective group can be carried out according to a method which is usually used in the organic synthetic chemistry (for example, a method as described in Protective Groups in Organic Synthesis, the 4th edition, T. W. Greene, P. G. M. Wuts, John Wiley & Sons Inc., 2006, etc.) Further, each specific process for preparing the compound of the present invention will be explained in detail in the following examples.

[Chemical Formula 29]

Step 1

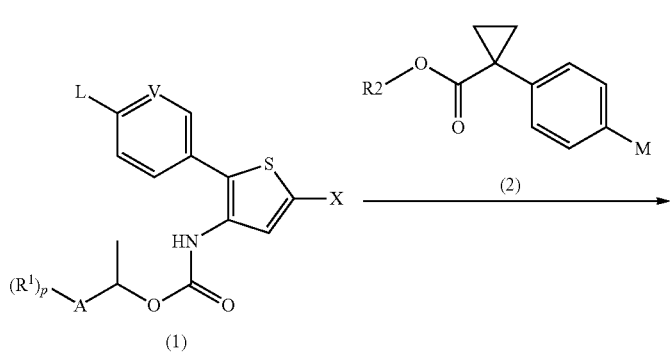

-continued
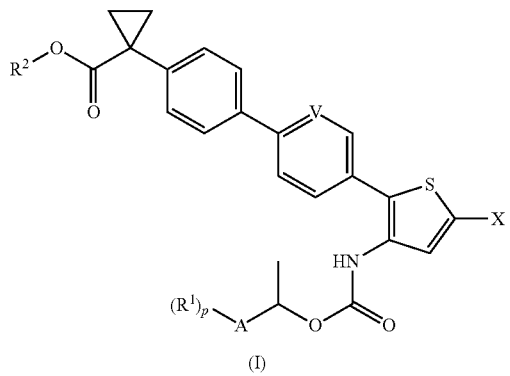
[Chemical Formula 30]
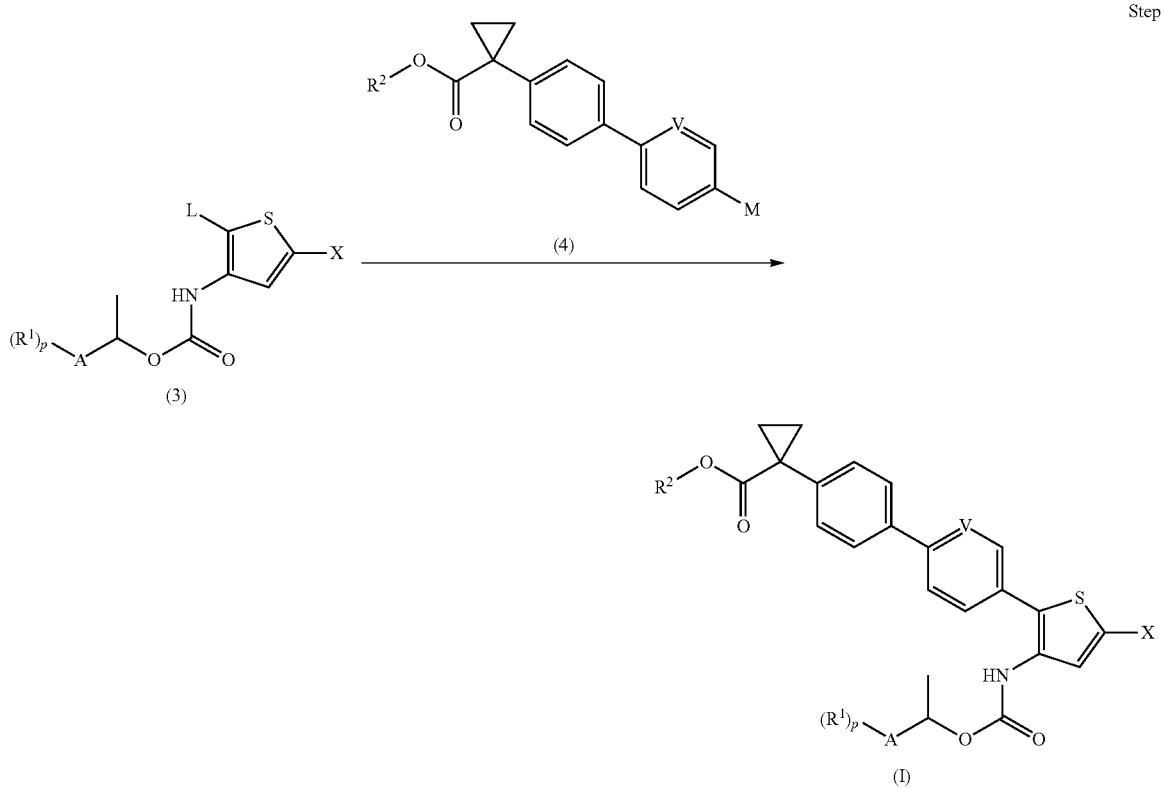
Step 2
[Chemical Formula 31]
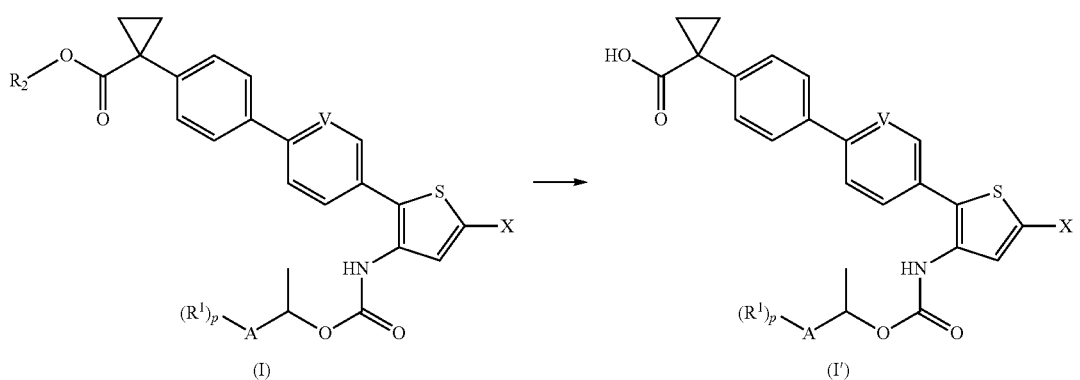
Step 3

[Chemical Formula 32]
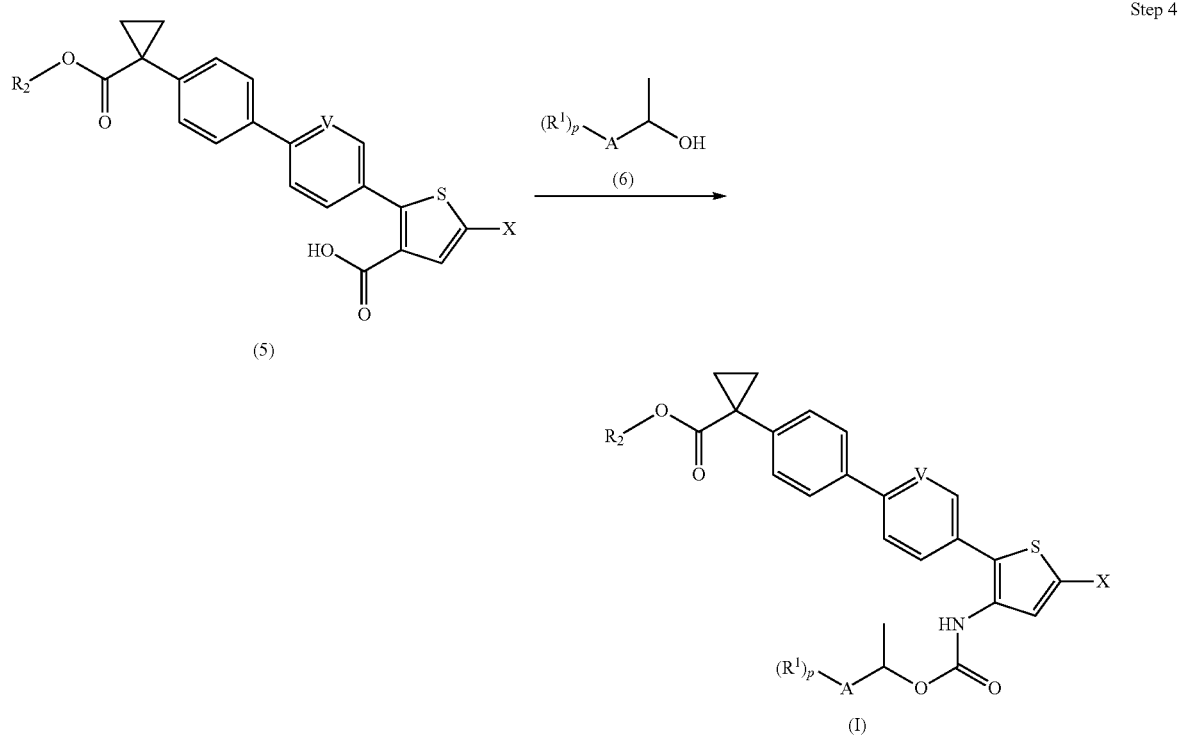
Step 4
[Chemical Formula 33]
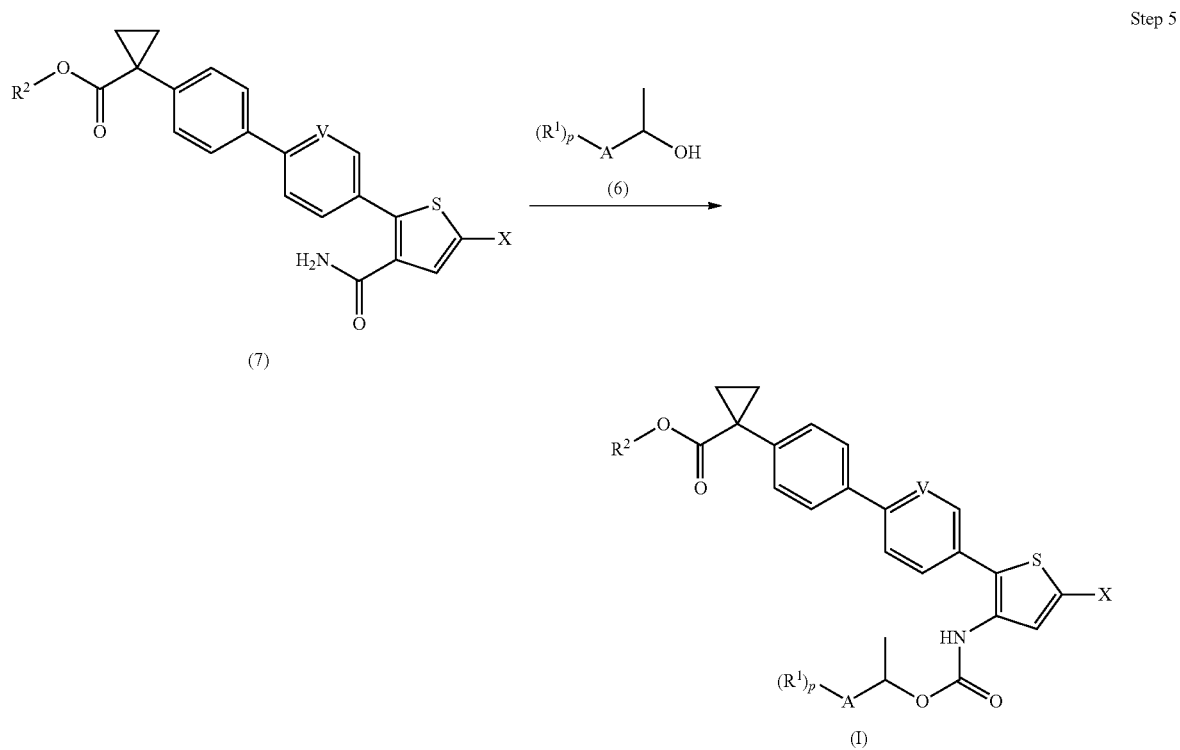
Step 5

[Chemical Formula 34]

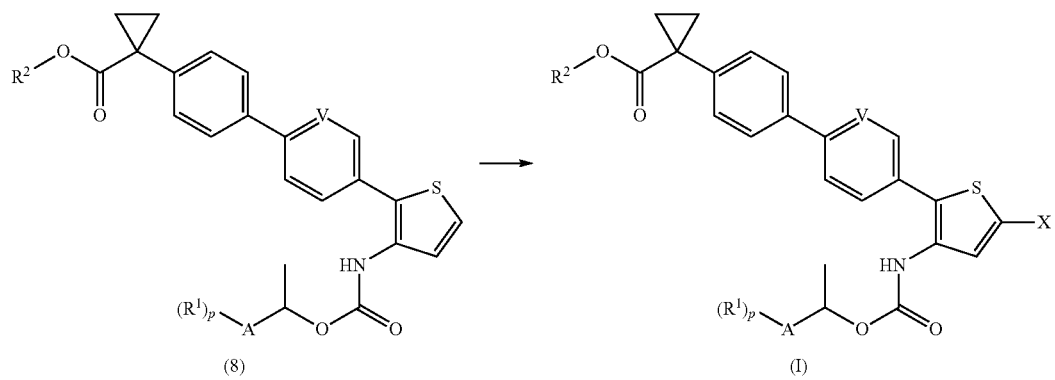

Step 6

[Chemical Formula 35]

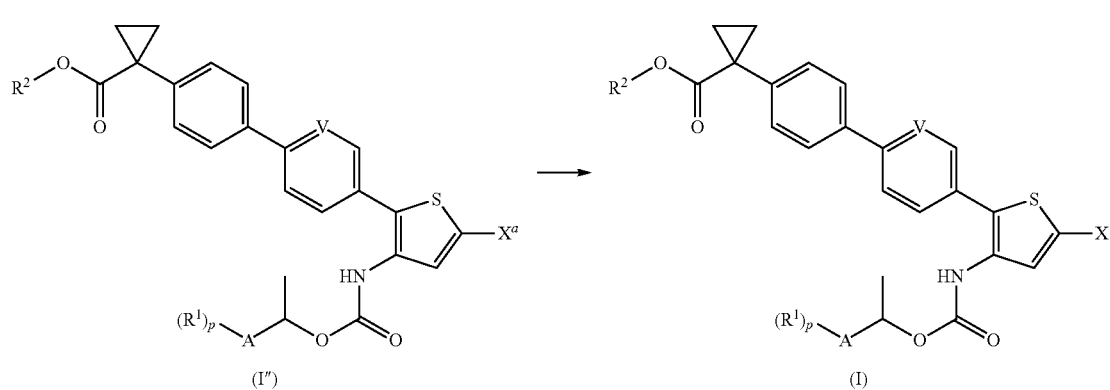

Step 7

[Chemical Formula 36]

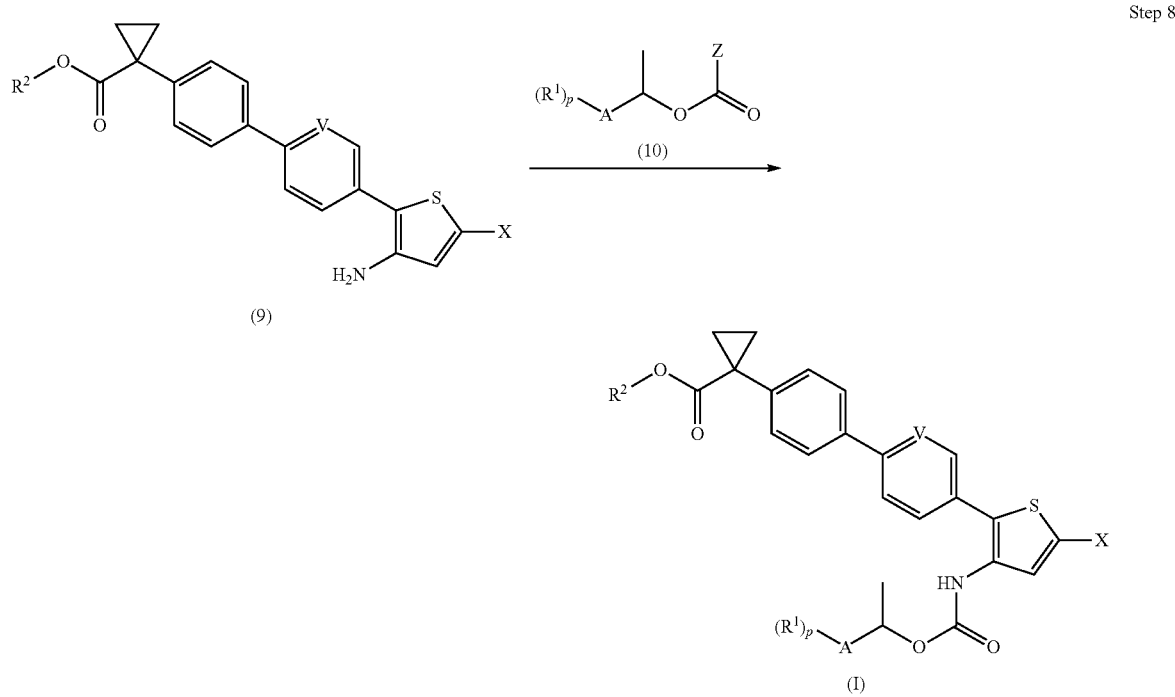

Step 8 wherein A, $R^1$, $R^2$, V, X and p have the same meanings as above. $X^a$ represents a chlorine atom, a bromine atom, or an iodine atom. L and M represent a substituent group neces- sary for a coupling reaction, and for example, in a case where L represents a chlorine atom, a bromine atom, an iodine atom, or a trifluoromethanesulfonyloxy group, etc., M represents a boronic acid, a boronic acid ester, a trialkyltin, etc., and in a case where L represents a boronic acid, a boronic acid ester, a trialkyltin, etc., M represents a chlorine atom, a bromine atom, an iodine atom, or a trifluoromethanesulfonyloxy group, etc. Z represents a leaving group such as a halogen group, or a 4-nitrophenoxy group.

Although the choice of the synthetic route is limited depending on the kind of X, the compound of the general formula (I) of the present invention can usually be synthesized through anyone of the above Steps 1 to 8.

Step 1 and Step 2: Compound (1) and Compound (2), or Compound (3) and Compound (4) are each reacted in a reaction solvent in the presence of a coupling catalyst, a ligand, and/or a base, for example, according to a method as described in Tetrahedron, 58 (2002), pages 9633-9695, etc., to synthesize the compound of the general formula (I).

Unless the reaction is inhibited, the reaction solvent is not particularly limited, and includes, for example, ethers such as 1,4-dioxane, 1,2-dimethoxyethane, or tetrahydrofuran; alcohols such as methanol or ethanol; amides such as N,N-dimethylformamide, N,N-dimethylacetamide, or 1-methyl-2-pyrrolidone; aromatic hydrocarbons such as toluene or xylene; sulfoxides such as dimethylsulfoxide; water; or a mixed solvent thereof. The solvent is preferably a mixed solvent of 1,4-dioxane/water.

The coupling catalyst include a palladium catalyst such as tetrakis(triphenylphosphine)palladium (O), [1,1'-bis(diphenylphosphino)-ferrocene]palladium (II) dichloride methylene chloride adduct, bis(triphenylphosphine)palladium (II) dichloride, tris(dibenzylideneacetone)dipalladium (O), or palladium (II) acetate; or a nickel catalyst such as bis(triphenylphosphine) nickel (II) dichloride.

The ligand includes triphenylphosphine, [1,1'-bis(diphenylphosphino)-ferrocene], dibenzylideneacetone, triphenylarsine, tri(o-tolyl)phosphine, tri-tert-butylphosphine, or tricyclohexylphosphine, etc., although it may be contained in the coupling catalyst itself.

The base includes a fluoride salt such as potassium fluoride or cesium fluoride; a carbonate such as sodium hydrogencarbonate, sodium carbonate, potassium carbonate, cesium carbonate, or thallium carbonate; a metal hydroxide such as sodium hydroxide, potassium hydroxide, barium hydroxide, or thallium hydroxide; a phosphate such as potassium phosphate; or an organic amine such as triethylamine or diisopropylethylamine. The base is preferably sodium carbonate.

Step 3: In a case where a compound where $R^2$ in the general formula (I) is a $C_1$-$C_6$ alkyl group, the compound of the general formula (I) can be subjected to a hydrolysis reaction in a reaction solvent in the presence of an acid or a base to synthesize the compound of the general formula (I').

Unless the reaction is inhibited, the reaction solvent is not particularly limited, and includes, for example, alcohols such as methanol, ethanol, or isopropylalcohol; ethers such as tetrahydrofuran, 1,4-dioxane, or 1,2-dimethoxyethane; water; or a mixed solvent thereof. The solvent is preferably a mixed solvent of isopropylalcohol/water, or isopropylalcohol/tetrahydrofuran/water.

The acid or the base includes an inorganic acid such as hydrochloric acid or sulfuric acid; an organic acid such as acetic acid or trifluoroacetic acid; a sulfonic acid such as methanesulfonic acid, benzenesulfonic acid, or p-toluenesulfonic acid; an alkaline metal hydroxide such as lithium hydroxide, sodium hydroxide, or potassium hydroxide; or an alkaline metal carbonate such as potassium carbonate or sodium carbonate, and it is preferably a base and more preferably lithium hydroxide or sodium hydroxide.

Step 4: Compound (5) can be subjected to a Curtius rearrangement reaction in a reaction solvent or without a solvent by using Compound (6), diphenylphosphoryl azide, and a base to synthesize the compound of the general formula (I), for example, according to a method as described in Journal of the American Chemical Society, 94 (1972), pages 6203-6205, etc.

Unless the reaction is inhibited, the reaction solvent is not particularly limited, and includes, for example, aromatic hydrocarbons such as toluene or xylene; or amides such as N,N-dimethylformamide, N,N-dimethylacetamide, or 1-methyl-2-pyrrolidone. It is preferably toluene.

The base includes organic amines such as triethylamine or diisopropylethylamine, and it is preferably triethylamine.

Step 5: Compound (7) can be subjected to a Hofmann rearrangement reaction in a reaction solvent or without a solvent, in the presence or absence of a base, by using Compound (6) and/or an oxidizing agent to synthesize the compound of the general formula (I), for example, according to a method as described in Organic Synthesis, 66 (1988), pages 132-137, etc.

Unless the reaction is inhibited, the reaction solvent is not particularly limited, and includes, for example, aromatic hydrocarbons such as toluene or xylene; amides such as N,N-dimethylformamide, N,N-dimethylacetamide, or 1-methyl-2-pyrrolidone; alkyl halides such as methylene chloride or 1,2-dichloroethane; aromatic hydrocarbon halides such as chlorobenzene or 1,2-dichlorobenzene; or nitriles such as acetnitrile or propionitrile. It is preferably toluene.

The base includes organic amines such as triethylamine or diisopropylethylamine; or pyridines such as pyridine, 2,6-lutidine, or 4-picoline. It is preferably pyridine.

The oxidizing agent includes a high-valence iodine compound such as [bis(acetoxy)iodo]benzene, [bis(trifluoroacetoxy)iodo]benzene, or iodosylbenzene, and it is preferably [bis(trifluoroacetoxy)iodo]benzene.

Step 6: Compound (8) can be halogenated in a reaction solvent, by using a halogenating agent to synthesize the compound of the general formula (I), for example, according to a method as described in Tetrahedron, 64 (2008), pages 9733-9737, or Bioorganic and Medicinal Chemistry Letters, 21 (2011), pages 528-530, etc.

Unless the reaction is inhibited, the reaction solvent is not particularly limited, and includes, for example, alkyl halides such as methylene chloride or 1,2-dichloroethane; ethers such as 1,4-dioxane, 1,2-dimethoxyethane, or tetrahydrofuran; alcohols such as methanol or ethanol; nitriles such as acetnitrile or propionitrile; amides such as N,N-dimethylformamide, N,N-dimethylacetamide, or 1-methyl-2-pyrrolidone; aromatic hydrocarbons such as toluene or xylene; hydrocarbons such as hexane, cyclohexane, or heptane; organic acids such as acetic acid or trifluoroacetic acid; water; or a mixed solvent thereof. It is preferably N,N-dimethylformamide.

The halogenating agent includes iodine, N-iodosuccinimide, bromine, N-bromosuccinimide, 1,2-dibromoethane, 1,2-dibromo-1,1,2,2-tetrafluoroethane, chlorine, N-chlorosuccinimide, xenon difluoride, N-fluorodibenzenesulfonamide, or N-fluoro-N'-(chloromethyl)triethylenediamine bis(tetrafluoroborate), etc.

Compound (8) can be converted to an anion in an reaction solvent by using a base and subsequently treated with a halogenating agent to synthesize the compound of the general formula (I), for example, according to a method as described in Tetrahedron Letters, 51 (2010), pages 4526-4529, or Journal of Medicinal Chemistry, 54 (2011), pages 2687-2700, etc.

Unless the reaction is inhibited, the reaction solvent is not particularly limited, and includes, for example, ethers such as tetrahydrofuran, 1,4-dioxane, diethylether, or 1,2-dimethoxyethane; hydrocarbons such as hexane, cyclohexane, or heptane; or a mixed solvent thereof.

The base includes alkyl lithiums such as n-butyl lithium, sec-butyl lithium, or tert-butyl lithium; lithium amides such as lithium diisopropyl amide, or lithium 2,2,6,6-tetramethylpiperidide; Grignard reagents such as ethylmagnesium bromide, ethylmagnesium chloride, isopropylmagnesium chloride, or phenylmagnesium chloride; magnesium amides such as diisopropyl amide magnesium chloride, or 2,2,6,6-tetramethylpiperidine chloride magnesium; or disilazane bases such as lithium 1,1,1,3,3,3-hexamethyldisilazane, or potassium 1,1,1,3,3,3-hexamethyldisilazane.

The halogenating agent includes iodine, N-iodosuccinimide, bromine, N-bromosuccinimide, carbon tetrabromide, 1,2-dibromoethane, 1,2-dibromo-1,1,2,2-tetrafluoroethane, chlorine, N-chlorosuccinimide, carbon tetrachloride, xenon difluoride, N-fluorodibenzenesulfonamide, or N-fluoro-N'-(chloromethyl)triethylenediaminebis(tetrafluoroborate), etc.

Step 7: In the compound of the general formula (I"), the halogen group $X^a$ can be subjected to a halogen-metal exchange in a reaction solvent and subsequently treated with a halogenating agent to synthesize the compound of the general formula (I), for example, according to a method as described in Angewandte Chemie—International Edition, 49 (2010), pages 2215-2218.

Unless the reaction is inhibited, the reaction solvent is not particularly limited, and includes, for example, ethers such as tetrahydrofuran, 1,4-dioxane, diethylether, or 1,2-dimethoxyethane; hydrocarbons such as n-hexane or cyclohexane; alkyl halides such as methylene chloride; or a mixed solvent thereof.

The base includes alkyl lithiums such as n-butyl lithium, sec-butyl lithium, or tert-butyl lithium; or Grignard reagents such as ethylmagnesium bromide, ethylmagnesium chloride, isopropylmagnesium chloride, or phenylmagnesium chloride.

The halogenating agent includes iodine, N-iodo-succinimide, bromine, N-bromo-succinimide, carbon tetrabromide, 1,2-dibromoethane, 1,2-dibromo-1,1,2,2-tetrafluoroethane, chlorine, N-chlorosuccinimide, carbon tetrachloride, xenon difluoride, N-fluorodibenzenesulfonamide, or N-fluoro-N'-(chloromethyl)triethylenediamine bis(tetrafluoroborate), etc.

Step 8: Compound (9) and Compound (10) can be reacted in a reaction solvent in the presence or absence of a base to synthesize the compound of the general formula (I), for example, according to a method as described in Bioorganic and Medicinal Chemistry Letters, 11 (2001), pages 9-12, etc.

Unless the reaction is inhibited, the reaction solvent is not particularly limited, and includes, for example, acetate esters such as ethyl acetate or isopropyl acetate; halogenated hydrocarbons such as methylene chloride, or 1,2-dichloroethane; ethers such as 1,4-dioxane or 1,2-dimethoxyethane; ketones such as acetone, methylethylketone, or methylisobutylketone; aromatic hydrocarbons such as toluene or xylene; nitriles such as acetonitrile or propionitrile; amides such as N,N-dimethylformamide, N,N-dimethylacetamide, or 1-methyl-2-pyrrolidone; alcohols such as methanol, ethanol, or isopropyl alcohol; water; or a mixed solvent thereof.

The base includes organic bases such as triethylamine or diisopropylethylamine; pyridines such as pyridine, 4-picoline, or 2,6-lutidine; alkaline metal hydroxides such as sodium hydroxide or potassium hydroxide; or alkaline metal carbonate salts such as sodium hydrogencarbonate, sodium carbonate, or potassium carbonate.

A general process for preparing a synthetic intermediate of the compound of the present invention is explained below. In a case where there is a partial structure in the compound which inhibits a desired reaction or is subjected to a side reaction in the process for preparation as shown below (for example, a hydroxyl group, an amino group, a carbonyl group, a carboxyl group, an amide group, or a thiol group, etc.), the desired compound can be obtained by introducing a protective group to the partial structure, carrying out the desired reaction and then removing said protective group. Such a reaction for introducing and removing the protective group can be carried out according to a method which is usually used in the organic synthetic chemistry (for example, a method as described in Protective Groups in Organic Synthesis, the $4^{th}$ edition, T. W. Greene, P. G. M. Wuts, John Wiley & Sons Inc., 2006, etc.) Further, each specific process for preparing the synthetic intermediate of the compound of the present invention will be explained in detail in the following examples.

Further, A, $R^1$, $R^2$, V, X, $X^a$, p, L, M, and Z in the following synthetic route represent the same meanings as above. $L^a$ represents the same meaning as L.

Step 9

[Chemical Formula 37]

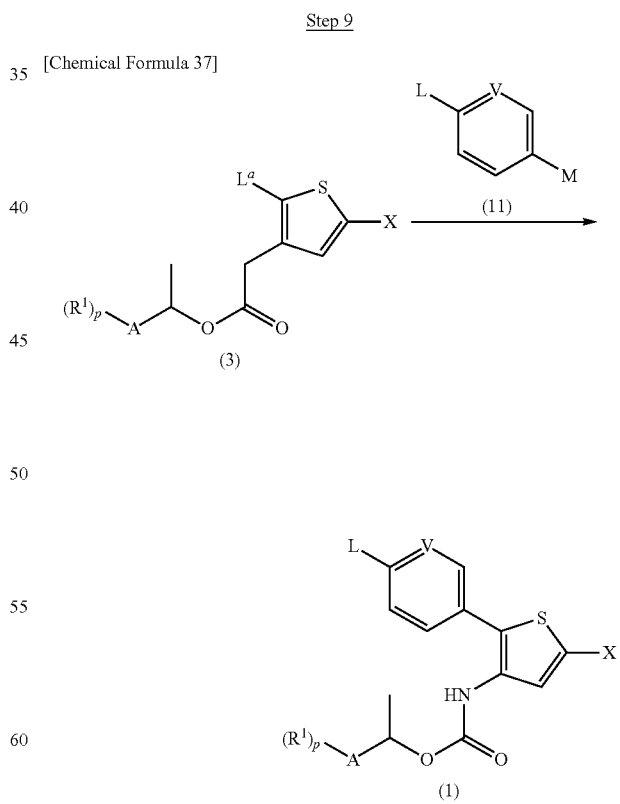

Step 9: Compound (3) and Compound (11) can be reacted in the similar manner to in Step 1 to synthesize Compound (1).

Step 10

[Chemical Formula 38]

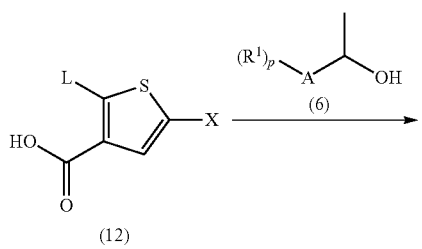

Step 10: Compound (12) and Compound (6) can be reacted in the similar manner to in Step 4 to synthesize Compound (3).

[Chemical Formula 39]

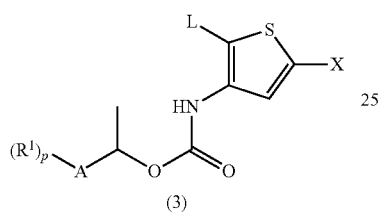

Step 11: Compound (12) can be treated in the similar manner to in Step 6 to synthesize Compound (13).

Step 12

[Chemical Formula 40]

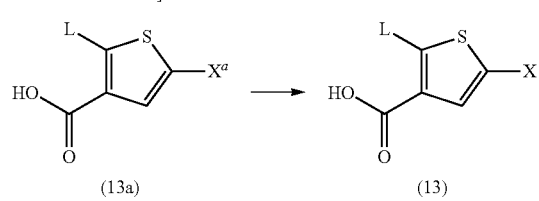

Step 12: Compound (13a) can be treated in the similar manner to in Step 7 to synthesize Compound (13).

Step 13

[Chemical Formula 41]

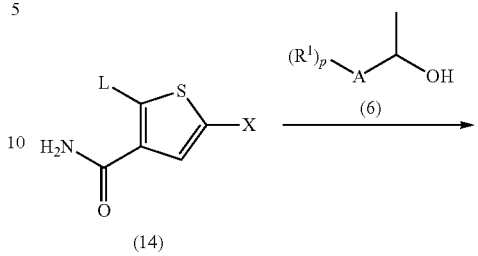

Step 13: Compound (14) and Compound (6) can be reacted in the similar manner to in Step 5 to synthesize Compound (3).

Step 14

[Chemical Formula 42]

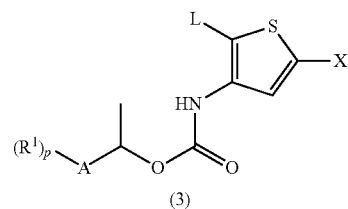

Step 14: Compound (15) can be treated in the similar manner to in Step 6 to synthesize Compound (14).

Step 15

[Chemical Formula 43]

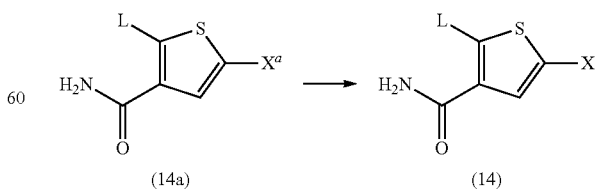

Step 15: Compound (14a) can be treated in the similar manner to in Step 7 to synthesize Compound (14).

Step 16

[Chemical Formula 44]

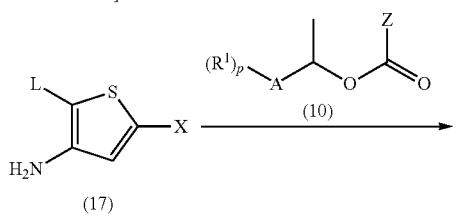

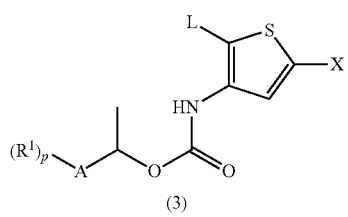

Step 16: Compound (16) and Compound (10) can be reacted in the similar manner to in Step 8 to synthesize Compound (3).

Step 17

[Chemical Formula 45]

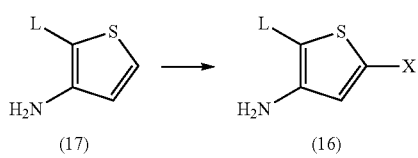

Step 17: Compound (17) can be treated in the similar manner to in Step 6 to synthesize Compound (16).

Step 18

[Chemical Formula 46]

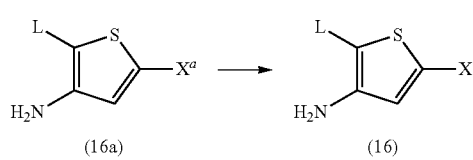

Step 18: Compound (16a) can be treated in the similar manner to in Step 7 to synthesize Compound (16).

Step 19

[Chemical Formula 47]

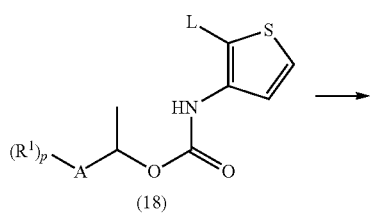

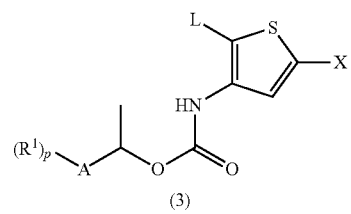

Step 19: Compound (18) can be treated in the similar manner to in Step 6 to synthesize Compound (3).

[Chemical Formula 48]

Step 20

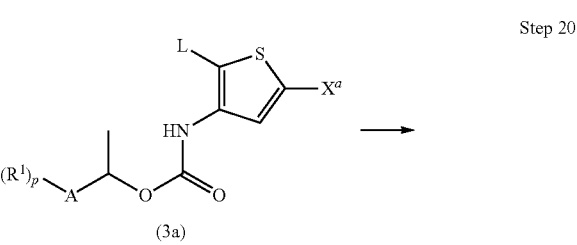

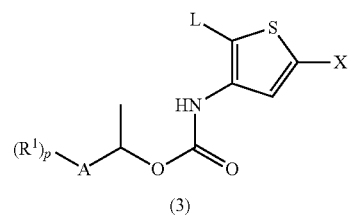

Step 20: Compound (3a) can be treated in the similar manner to in Step 7 to synthesize Compound (3).

Step 21

[Chemical Formula 49]

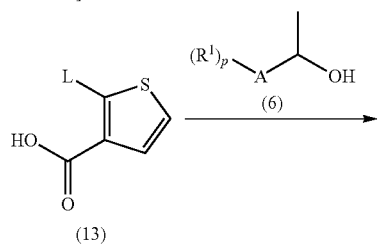

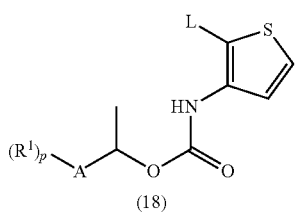

Step 21: Compound (13) and Compound (6) can be reacted in the similar manner to in Step 4 to synthesize Compound (18).

Step 22

[Chemical Formula 50]

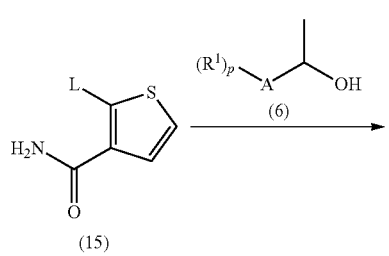

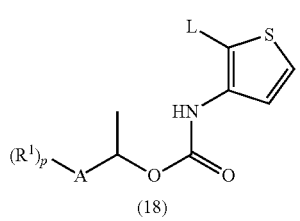

Step 22: Compound (15) and Compound (6) can be reacted in the similar manner to in Step 5 to synthesize Compound (18).

Step 23

[Chemical Formula 51]

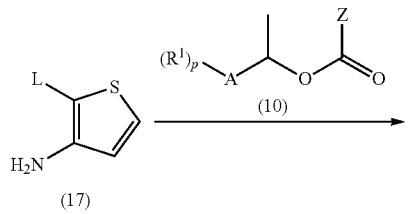

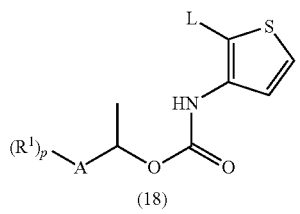

Step 23: Compound (17) and Compound (10) can be reacted in the similar manner to in Step 8 to synthesize Compound (18).

[Chemical Formula 52]

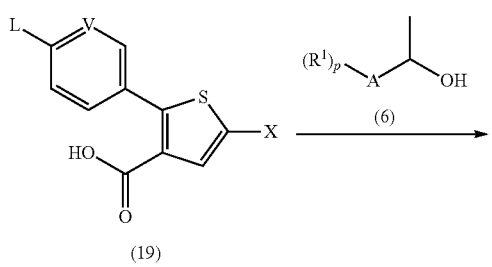

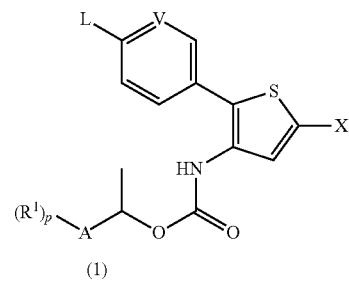

Step 24: Compound (19) and Compound (6) can be reacted in the similar manner to in Step 4 to synthesize Compound (1).

Step 25

[Chemical Formula 53]

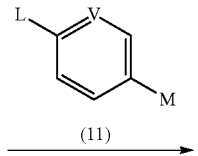

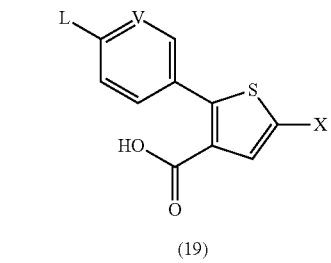

Step 25: Compound (12) and Compound (11) can be reacted in the similar manner to in Step 1 to synthesize Compound (19).

Step 26

[Chemical Formula 54]

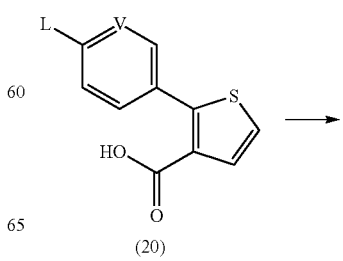

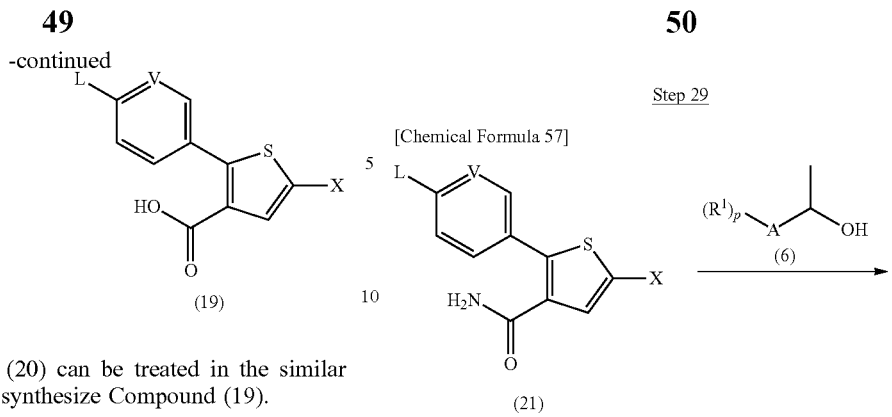

(19)

Step 26: Compound (20) can be treated in the similar manner to in Step 6 to synthesize Compound (19).

Step 27

[Chemical Formula 55]

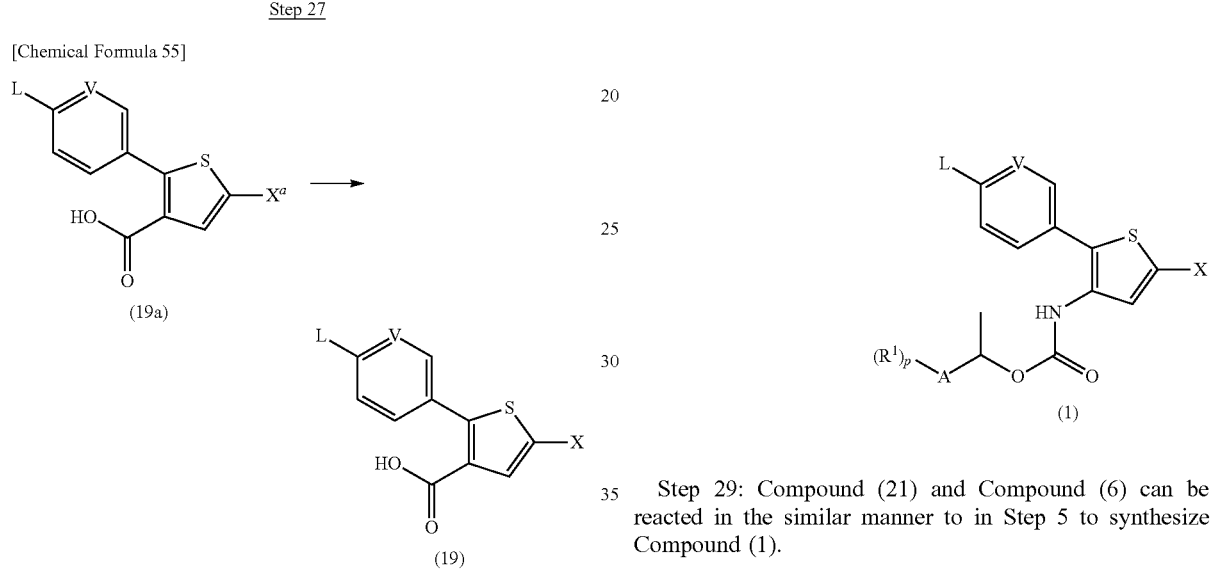

Step 27: Compound (19a) can be treated in the similar manner to in Step 7 to synthesize Compound (19).

[Chemical Formula 56]

Step 28

Step 28: Compound (13) and Compound (11) can be reacted in the similar manner to in Step 1 to synthesize Compound (20).

Step 29

[Chemical Formula 57]

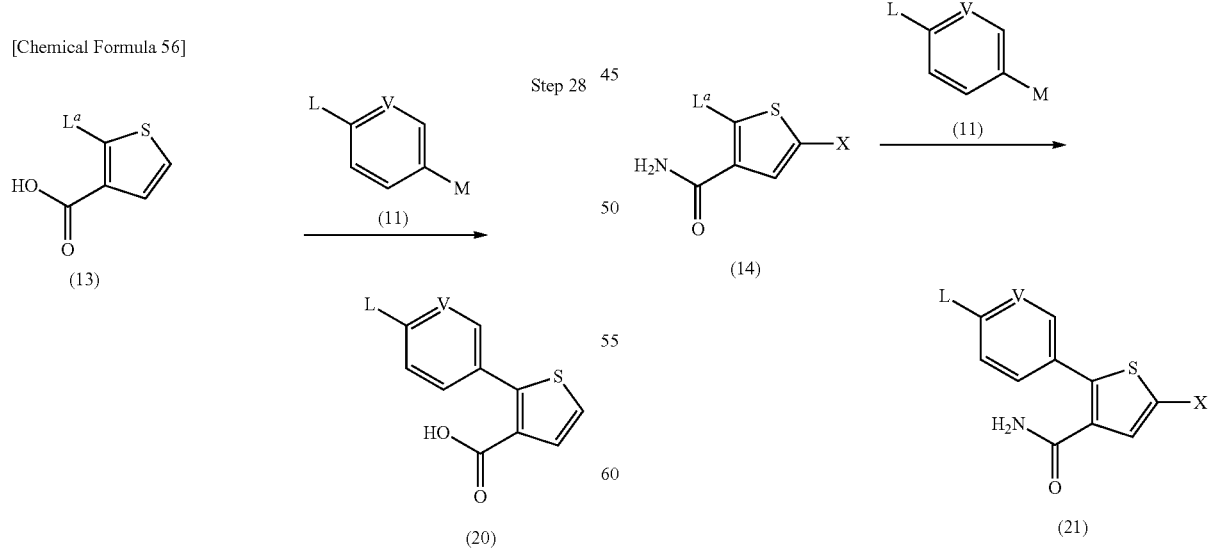

Step 29: Compound (21) and Compound (6) can be reacted in the similar manner to in Step 5 to synthesize Compound (1).

Step 30

[Chemical Formula 58]

Step 30: Compound (14) and Compound (11) can be reacted in the similar manner to in Step 1 to synthesize Compound (21).

Step 31

[Chemical Formula 59]

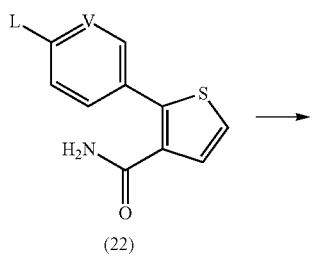

(22)

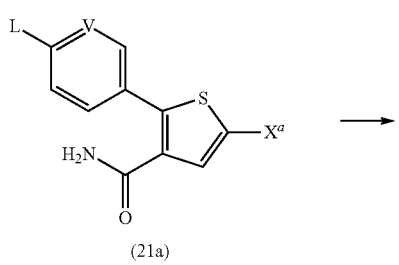

(21)

Step 31: Compound (22) can be treated in the similar manner to in Step 6 to synthesize Compound (21).

[Chemical Formula 60]

Step 32

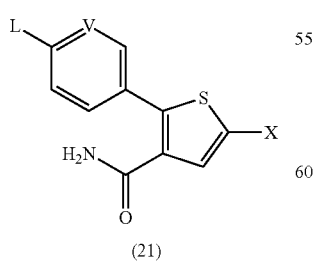

(21a)

(21)

Step 32: Compound (21a) can be treated in the similar manner to in Step 7 to synthesize Compound (21).

Step 33

[Chemical Formula 61]

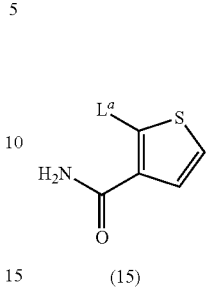

(15)

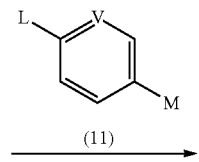

(11)

(22)

Step 33: Compound (15) and Compound (11) can be reacted in the similar manner to in Step 1 to synthesize Compound (22).

Step 34

[Chemical Formula 62]

(23)

(10)

(1)

Step 34: Compound (23) and Compound (10) can be reacted in the similar manner to in Step 8 to synthesize Compound (1).

Step 35

[Chemical Formula 63]

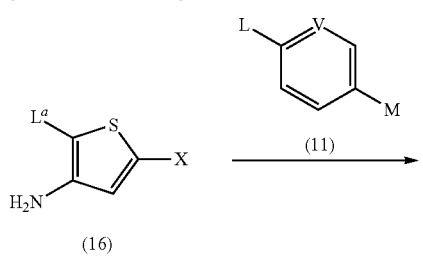

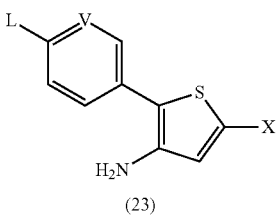

Step 35: Compound (16) and Compound (11) can be reacted in the similar manner to in Step 1 to synthesize Compound (23).

[Chemical Formula 64]

Step 36

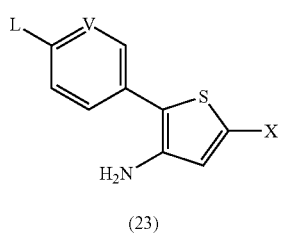

Step 36: Compound (24) can be treated in the similar manner to in Step 6 to synthesize Compound (23).

Step 37

[Chemical Formula 65]

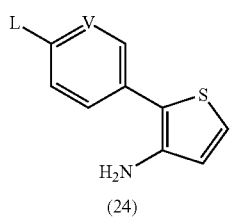

Step 37: Compound (23a) can be treated in the similar manner to in Step 7 to synthesize Compound (23).

Step 38

[Chemical Formula 66]

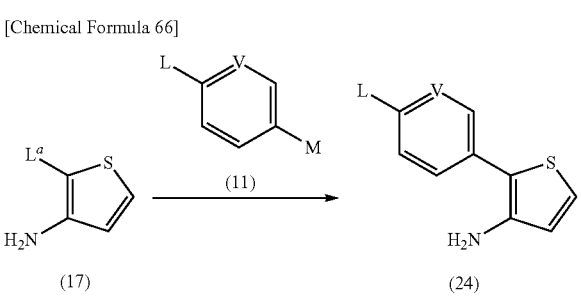

Step 38: Compound (17) and Compound (11) can be reacted in the similar manner to in Step 1 to synthesize Compound (24).

Step 39

[Chemical Formula 67]

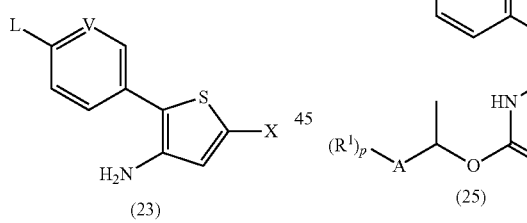
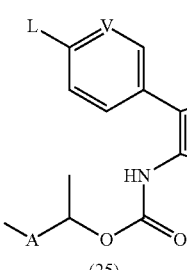

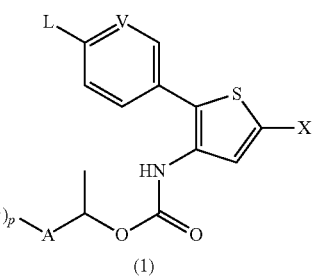

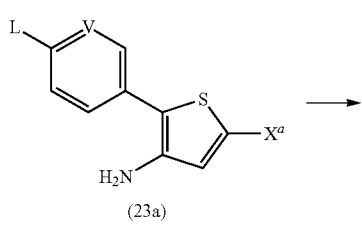

Step 39: Compound (25) can be treated in the similar manner to in Step 6 to synthesize Compound (1).

[Chemical Formula 68]

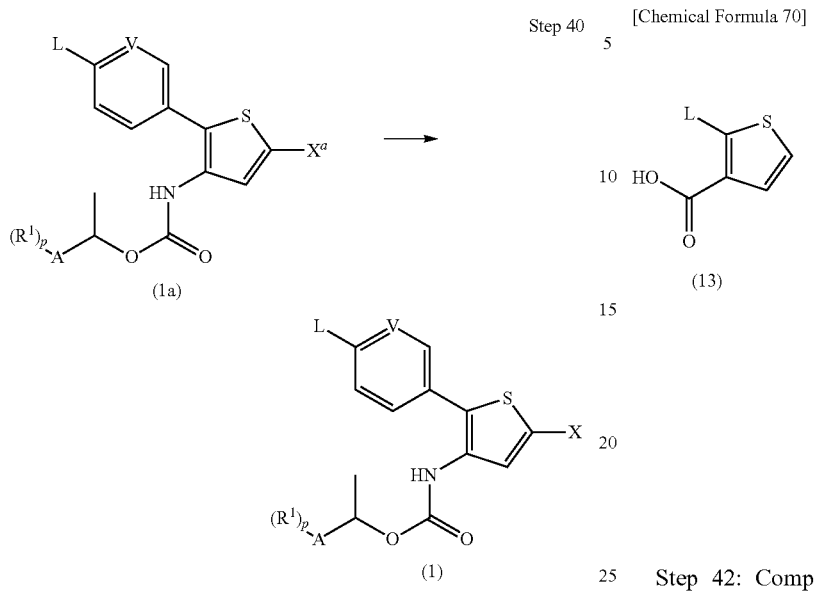

Step 40: Compound (1a) can be treated in the similar manner to in Step 7 to synthesize Compound (1).

[Chemical Formula 69]

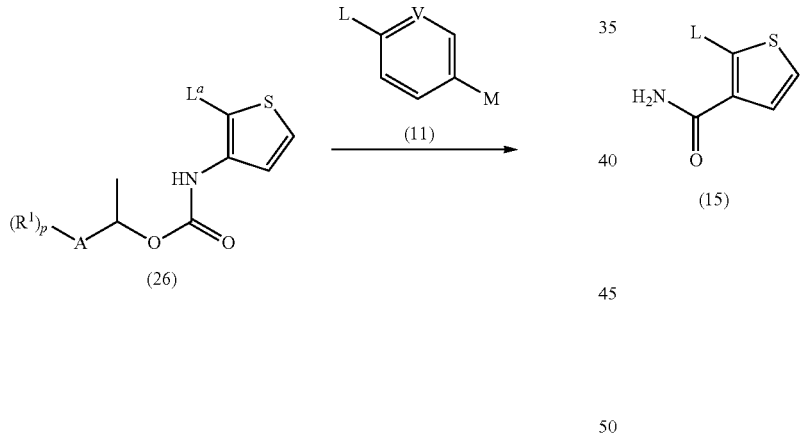

Step 41: Compound (26) and Compound (11) can be reacted in the similar manner to in Step 1 to synthesize Compound (25).

Step 42

[Chemical Formula 70]

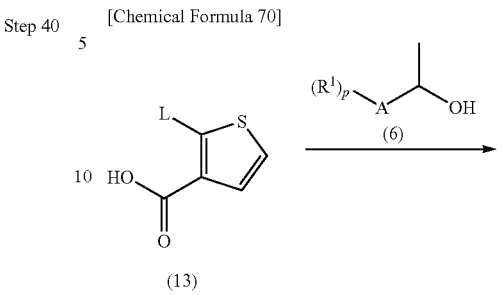

Step 42: Compound (13) and Compound (6) can be reacted in the similar manner to in Step 4 to synthesize Compound (26).

Step 43

[Chemical Formula 71]

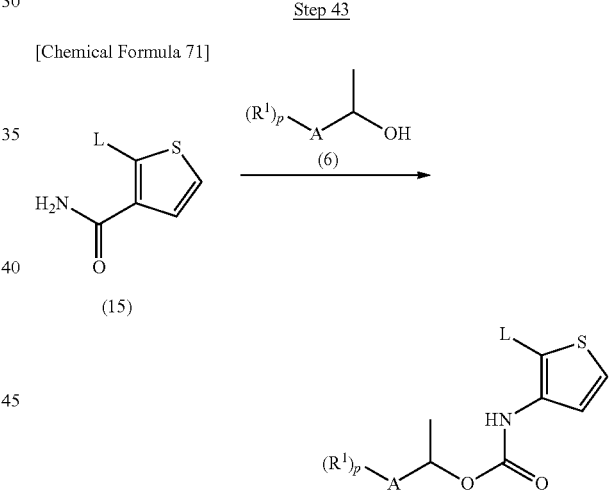

Step 43: Compound (15) and Compound (6) can be reacted in the similar manner to in Step 5 to synthesize Compound (26).

[Chemical Formula 72]

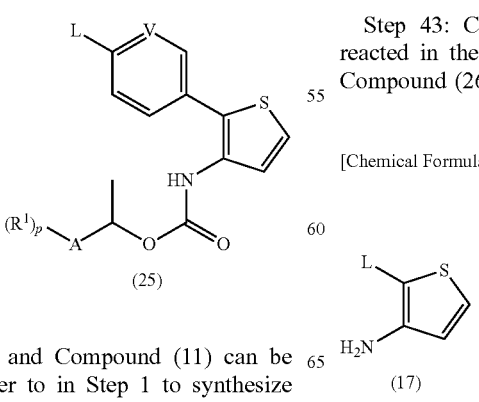

Step 44

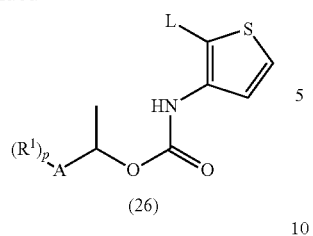

(26)

Step 44: Compound (17) and Compound (10) can be reacted in the similar manner to in Step 8 to synthesize Compound (26).

Step 45

[Chemical Formula 73]

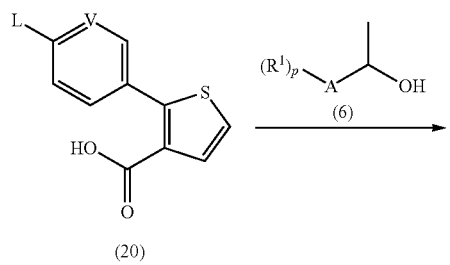

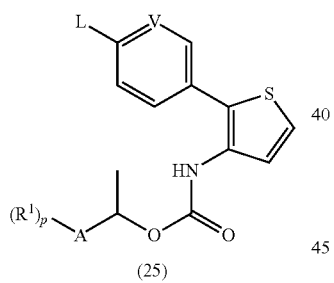

(25)

Step 45: Compound (20) and Compound (6) can be reacted in the similar manner to in Step 4 to synthesize Compound (25).

Step 46

[Chemical Formula 74]

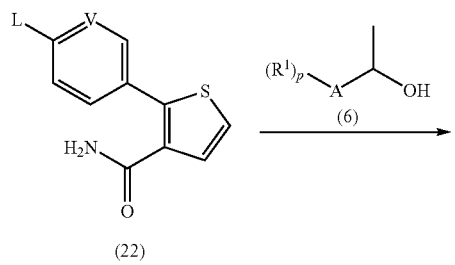

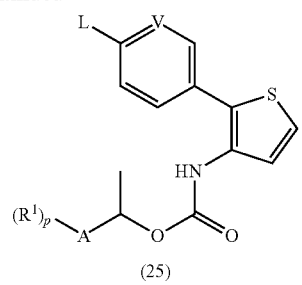

(25)

Step 46: Compound (22) and Compound (6) can be reacted in the similar manner to in Step 5 to synthesize Compound (25).

Step 75

[Chemical Formula 75]

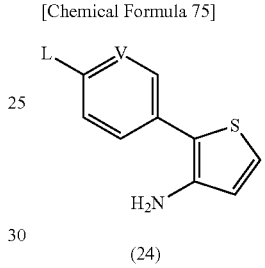

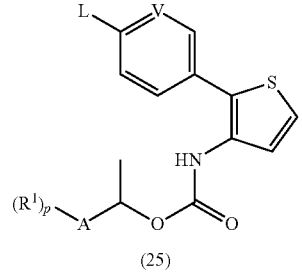

(25)

Step 47: Compound (24) and Compound (10) can be reacted in the similar manner to in Step 8 to synthesize Compound (25).

[Chemical Formula 76]

Step 48

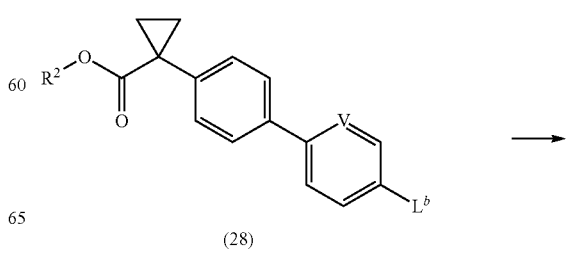

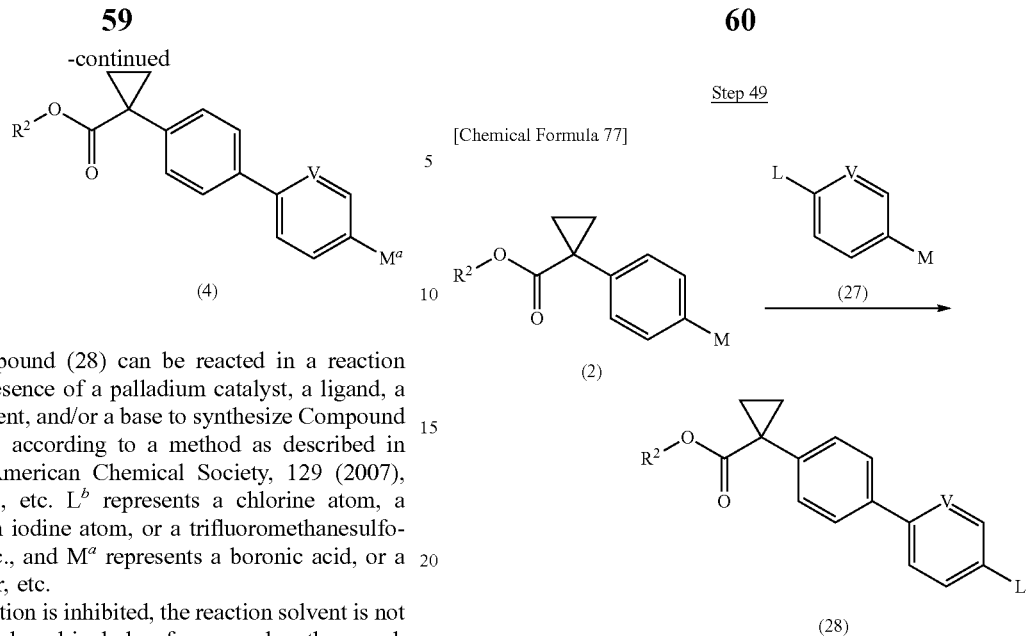

(4)

Step 48: Compound (28) can be reacted in a reaction solvent in the presence of a palladium catalyst, a ligand, a boronic acid reagent, and/or a base to synthesize Compound (4), for example, according to a method as described in Journal of the American Chemical Society, 129 (2007), pages 4595-4605, etc. $L^b$ represents a chlorine atom, a bromine atom, an iodine atom, or a trifluoromethanesulfonyloxy group, etc., and $M^a$ represents a boronic acid, or a boronic acid ester, etc.

Unless the reaction is inhibited, the reaction solvent is not particularly limited, and includes, for example, ethers such as 1,4-dioxane, 1,2-dimethoxyethane, or tetrahydrofuran; amides such as N,N-dimethyformamide, N,N-dimethylacetamide, or 1-methyl-2-pyrrolidone; aromatic hydrocarbons such as toluene or xylene; sulfoxides such as dimethylsulfoxide; water; or a mixed solvent thereof. It is preferably 1,4-dioxane.

The palladium catalyst includes tetrakis(triphenylphosphine)palladium (O), [1,1'-bis(diphenylphosphino) ferrocene]palladium (II) dichloride methylene chloride adduct, bis(triphenylphosphine)palladium (II) dichloride, tris(dibenzylideneacetone)dipalladium (O), or palladium (II) acetate, etc. It is preferably [1,1'-bis(diphenylphosphino) ferrocene] palladium (II) dichloride methylene chloride adduct.

The ligand includes triphenylphosphine, [1,1'-bis(diphenylphosphino)-ferrocene], dibenzylideneacetone, triphenylarsine, tri(o-tolyl)phosphine, tri-tert-butylphosphine, or tricyclohexyiphosphine, etc., although it may be contained in the coupling catalyst itself.

The boronic acid reagent includes 4,4,4',4',5,5,5',5'-octamethyl-2,2'-bi(1,3,2-dioxaborolane), 4,4,5,5-tetramethyl-1,3,2-dioxaborolane, etc.

The base includes potassium acetate, sodium acetate, etc.

Further, in Compound (28) in which $L^b$ represents a chlorine atom, a bromine atom, or an iodine atom, the halogen group $L^b$ can be subjected to a halogen-metal exchange in a reaction solvent, by using a base, and then treated with a boronic acid agent to synthesize Compound (4), for example, according to a method as described in Angewandte Chemie—International Edition, 45 (2006), pages 1404-1408, etc.

Unless the reaction is inhibited, the reaction solvent is not particularly limited, and includes, for example, ethers such as tetrahydrofuran, 1,4-dioxane, diethylether, or 1,2-dimethoxyethane; hydrocarbons such as hexane, cyclohexane, or heptane; or a mixed solvent thereof.

The base includes alkyl lithiums such as n-butyl lithium, sec-butyl lithium, or tert-butyl lithium; or Grignard reagents such as ethylmagnesium bromide, ethylmagnesium chloride, isopropylmagnesium chloride or phenylmagnesium chloride.

The boronic acid reagent includes trimethyl borate, triisopropyl borate, trihexadecyl borate, or 2-isopropoxy-4,4,5,5-tetramethyl-1,3,2-dioxaborolane, etc.

Step 49

[Chemical Formula 77]

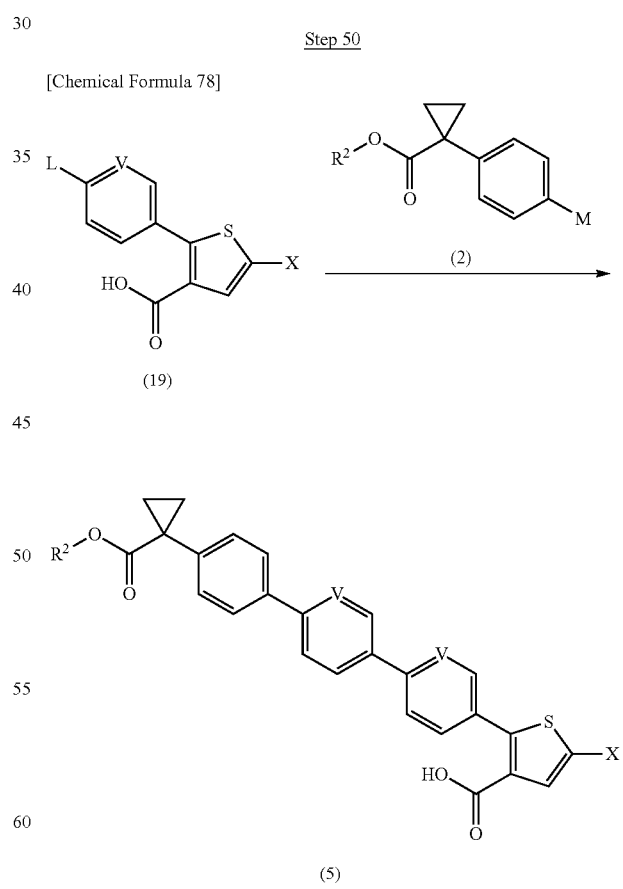

Step 49: Compound (2) and Compound (27) can be reacted in the similar manner to in Step 1 to synthesize Compound (28).

Step 50

[Chemical Formula 78]

Step 50: Compound (19) and Compound (2) can be reacted in the similar manner to in Step 1 to synthesize Compound (5).

Step 51
[Chemical Formula 79]
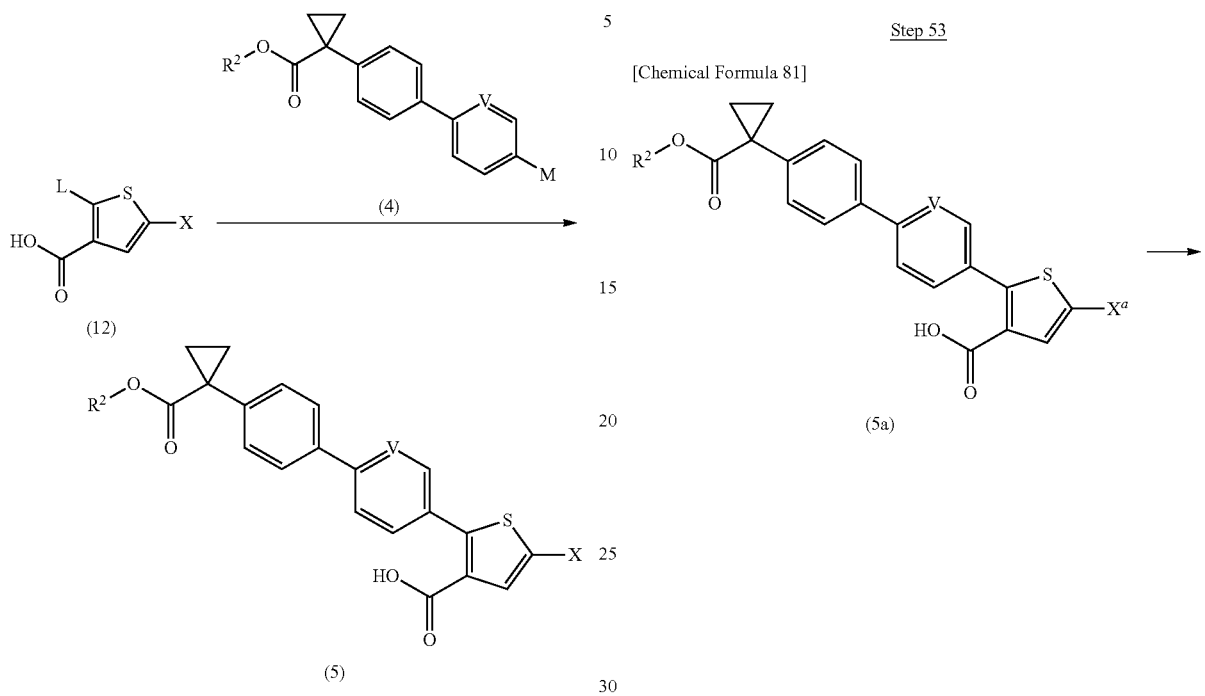
Step 51: Compound (12) and Compound (4) can be reacted in the similar manner to in Step 1 to synthesize Compound (5).
Step 52
[Chemical Formula 80]
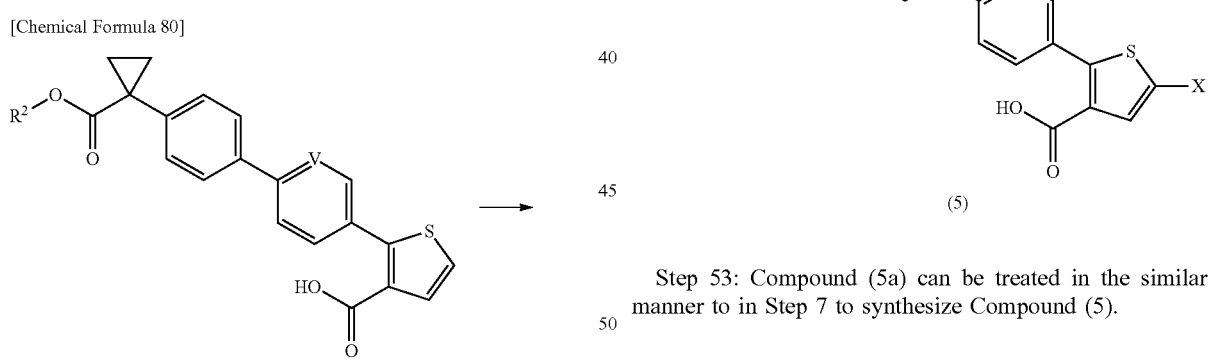
Step 52: Compound (29) can be treated in the similar manner to in Step 6 to synthesize Compound (5).
Step 53
[Chemical Formula 81]
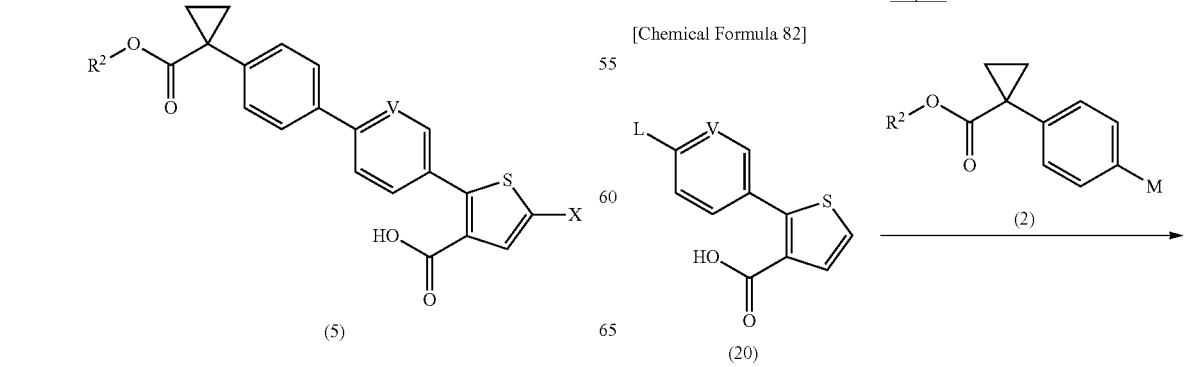
Step 53: Compound (5a) can be treated in the similar manner to in Step 7 to synthesize Compound (5).
Step 54
[Chemical Formula 82]

-continued

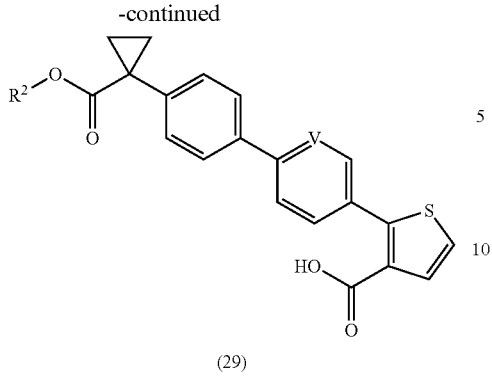

(29)

Step 54: Compound (20) and Compound (2) can be reacted in the similar manner to in Step 1 to synthesize Compound (29).

[Chemical Formula 83]

Step 55

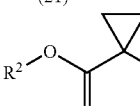

(13)

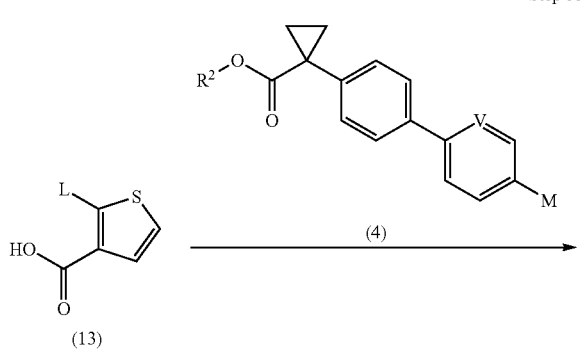

(29)

Step 55: Compound (13) and Compound (4) can be reacted in the similar manner to in Step 1 to synthesize Compound (29).

Step 56

[Chemical Formula 84]

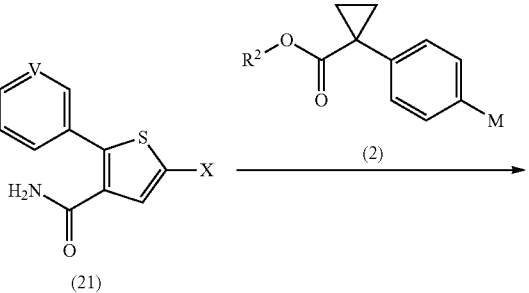

(21)

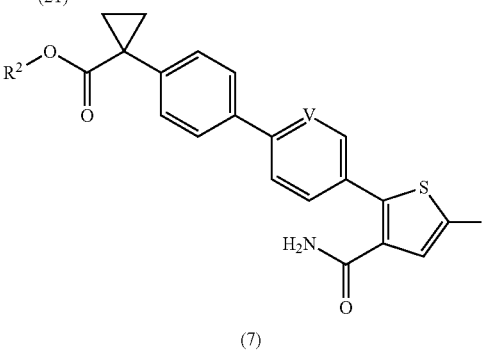

(7)

Step 56: Compound (21) and Compound (2) can be reacted in the similar manner to in Step 1 to synthesize Compound (7).

Step 57

[Chemical Formula 85]

(14)

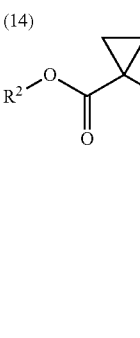

(7)

Step 57: Compound (14) and Compound (4) can be reacted in the similar manner to in Step 1 to synthesize Compound (7).

[Chemical Formula 86]
Step 58
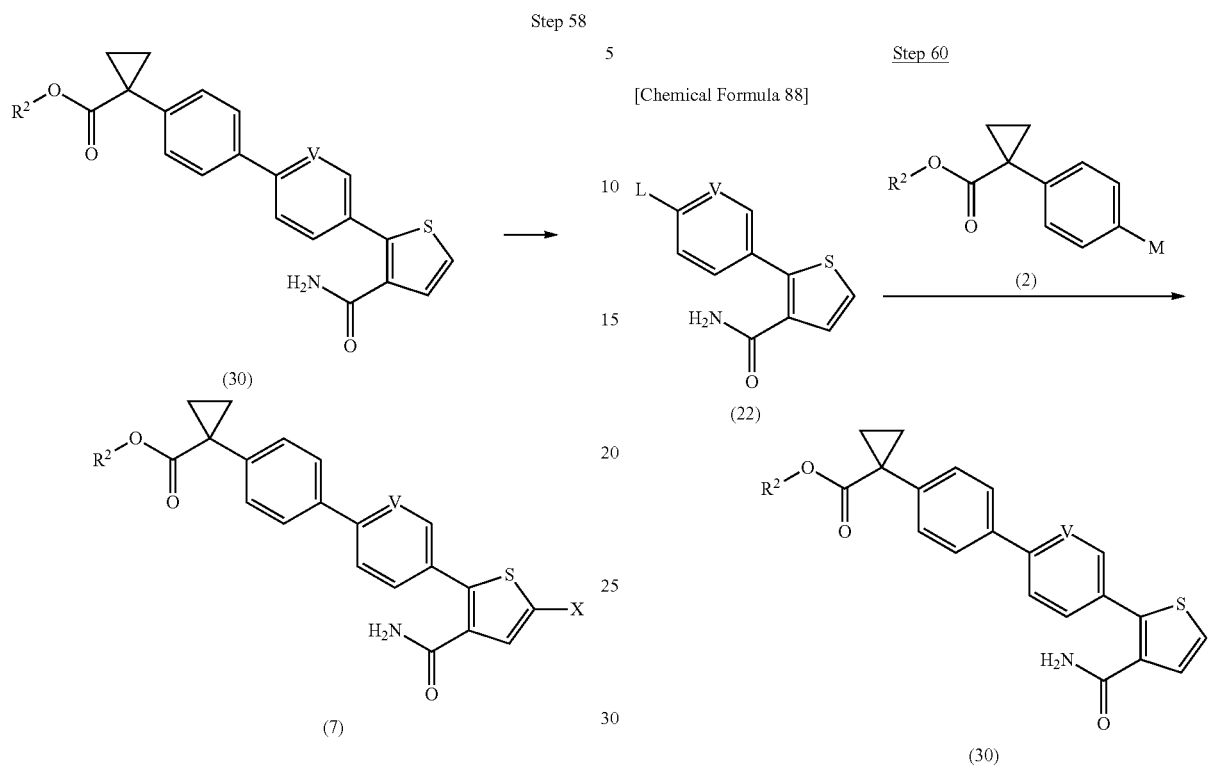
Step 58: Compound (30) can be treated in the similar manner to in Step 6 to synthesize Compound (7).
Step 59
[Chemical Formula 87]
Step 59: Compound (7a) can be treated in the similar manner to in Step 7 to synthesize Compound (7).
Step 60
[Chemical Formula 88]
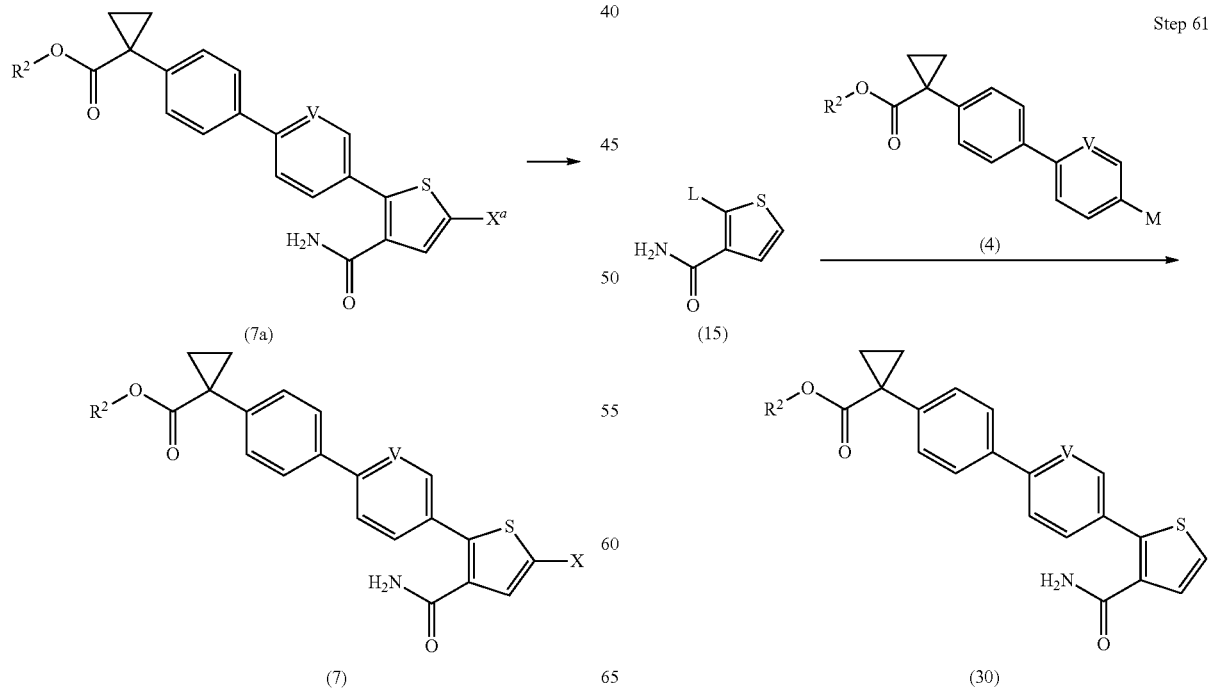
Step 60: Compound (22) and Compound (2) can be reacted in the similar manner to in Step 1 to synthesize Compound (30).
[Chemical Formula 89]
Step 61

Step 61: Compound (15) and Compound (4) can be reacted in the similar manner to in Step 1 to synthesize Compound (30).

Step 62

[Chemical Formula 90]

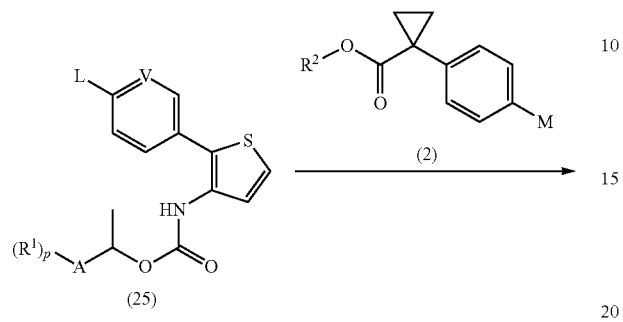

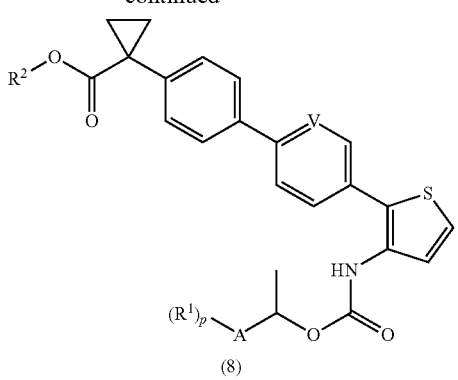

Step 62: Compound (25) and Compound (2) can be reacted in the similar manner to in Step 1 to synthesize Compound (8).

Step 63

[Chemical Formula 91]

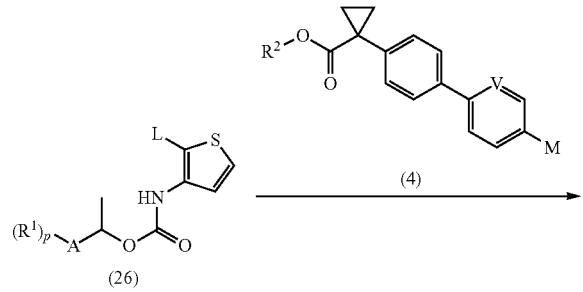

Step 63: Compound (26) and Compound (4) can be reacted in the similar manner to in Step 1 to synthesize Compound (8).

[Chemical Formula 92]

Step 64

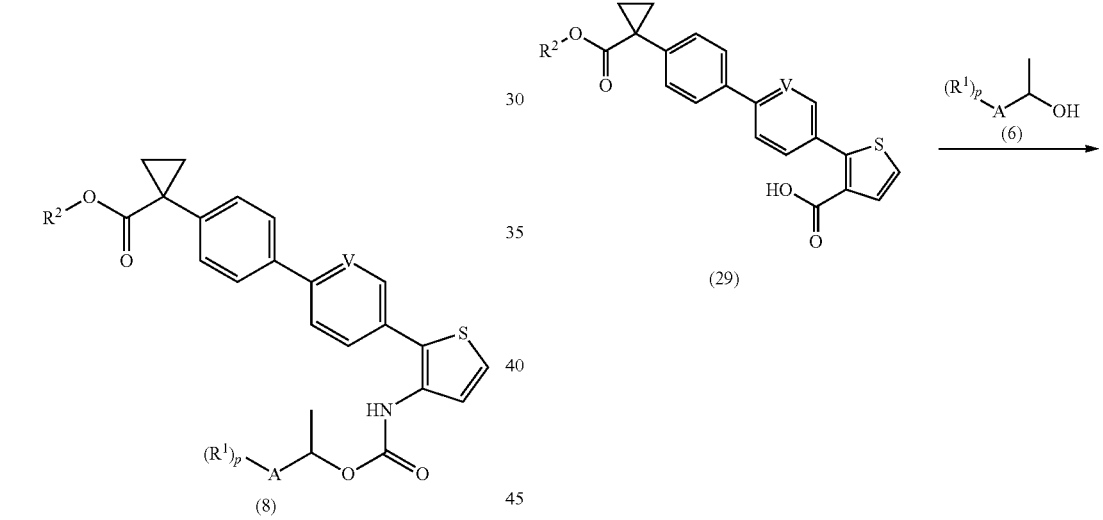

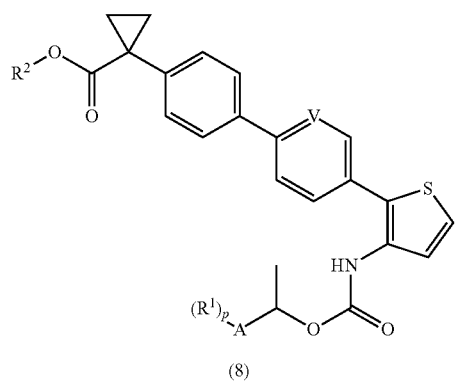

Step 64: Compound (29) and Compound (6) can be reacted in the similar manner to in Step 4 to synthesize Compound (8).

Step 65

[Chemical Formula 93]

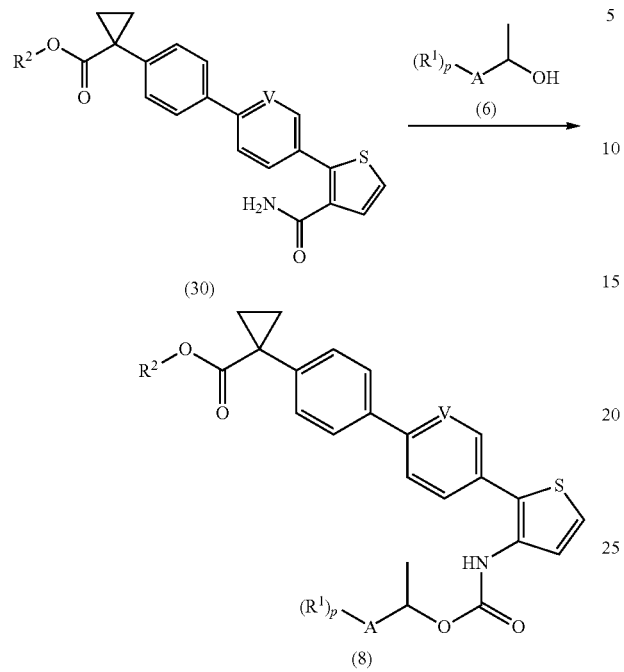

Step 65: Compound (30) and Compound (6) can be reacted in the similar manner to in Step 5 to synthesize Compound (8).

Step 66

[Chemical Formula 94]

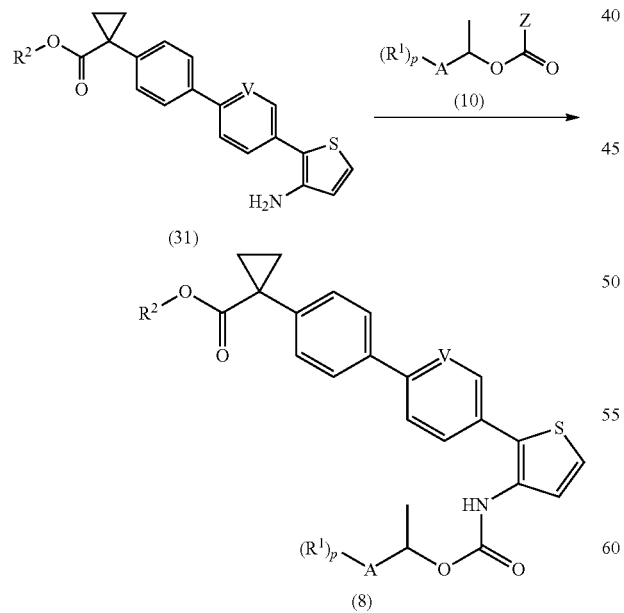

Step 66: Compound (31) and Compound (10) can be reacted in the similar manner to in Step 8 to synthesize Compound (8).

[Chemical Formula 95]

Step 67

Step 67: Compound (24) and Compound (2) can be reacted in the similar manner to in Step 1 to synthesize Compound (31).

Step 68

[Chemical Formula 96]

Step 68: Compound (17) and Compound (4) can be reacted in the similar manner to in Step 1 to synthesize Compound (31).

Step 69

[Chemical Formula 97]

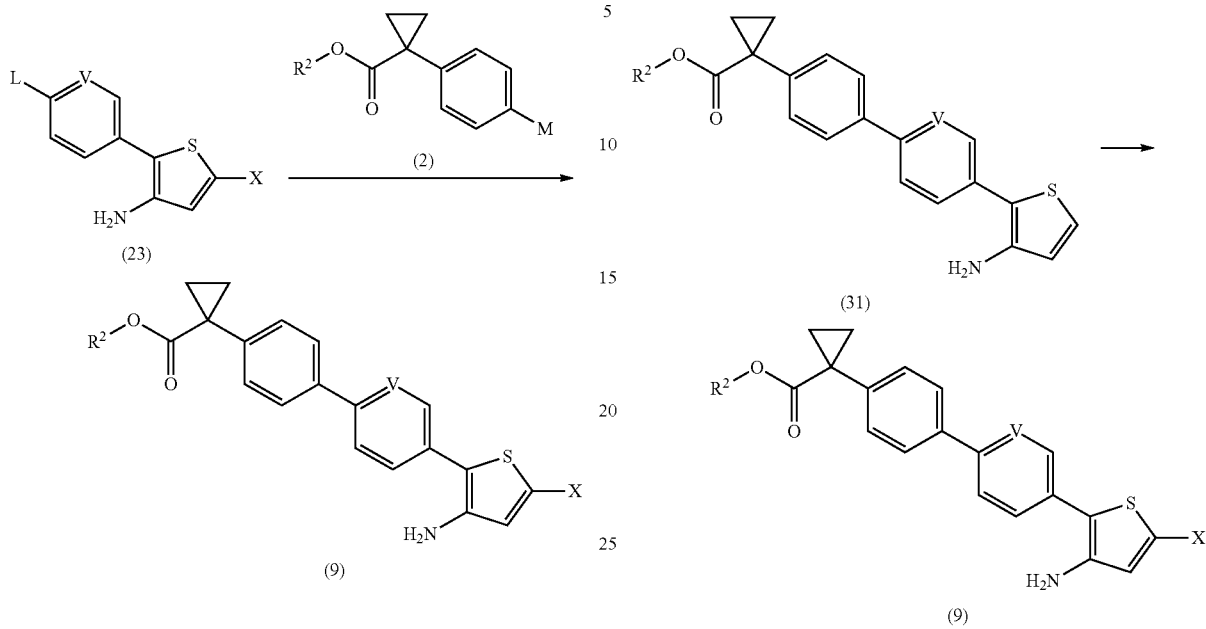

Step 69: Compound (23) and Compound (2) can be reacted in the similar manner to in Step 1 to synthesize Compound (9).

Step 70

[Chemical Formula 98]

Step 70: Compound (14) and Compound (4) can be reacted in the similar manner to in Step 1 to synthesize Compound (9).

Step 71

[Chemical Formula 99]

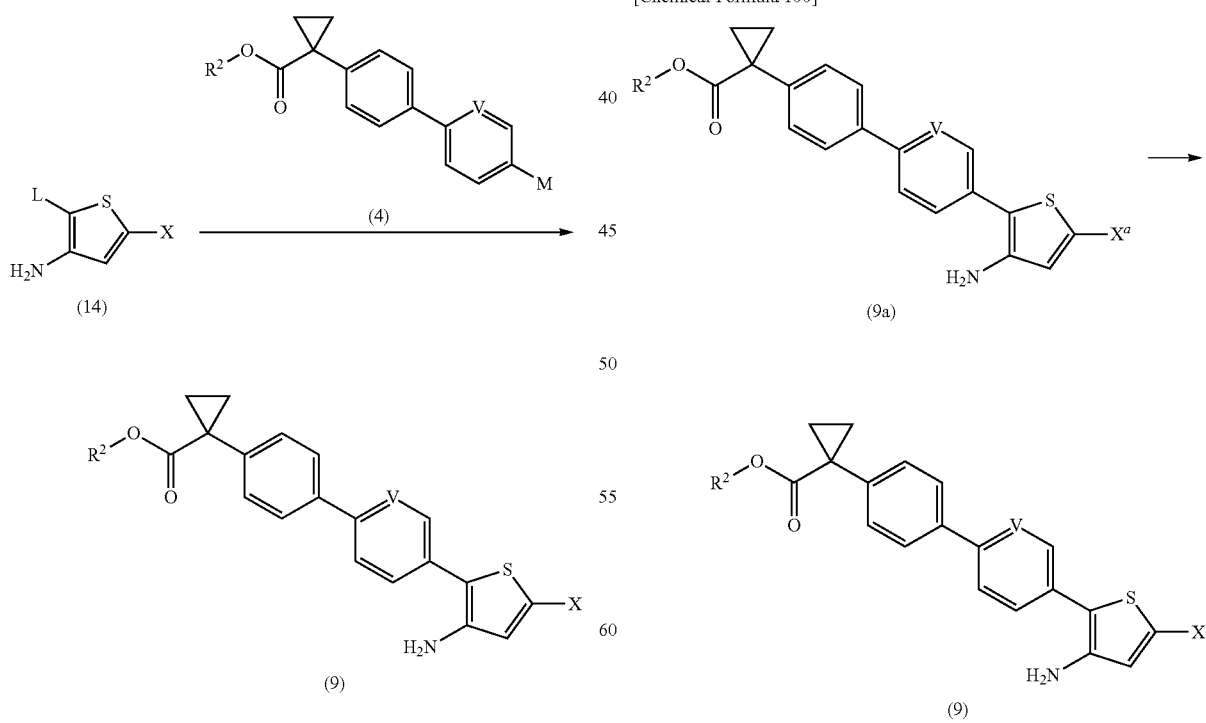

Step 71: Compound (31) can be treated in the similar manner to in Step 6 to synthesize Compound (9).

Step 72

[Chemical Formula 100]

Step 72: Compound (9a) can be treated in the similar manner to in Step 7 to synthesize Compound (9).

Step 73

[Chemical Formula 101]

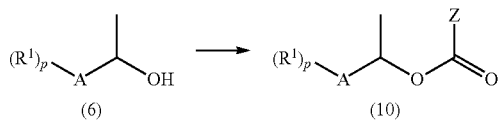

Step 73: Compound (6) can be reacted with a carbonyl compound in a reaction solvent in the presence or absence of a base to synthesize Compound (10), for example, according to a method as described in Journal of Medicinal Chemistry, 42 (1999), pages 941-946, or Journal of Organic Chemistry, 60 (1995), pages 730-734, etc.

Unless the reaction is inhibited, the reaction solvent is not particularly limited, and includes, for example, aromatic hydrocarbons such as toluene or xylene; halogenated hydrocarbons such as methylene chloride or 1,2-dichloroethane; ethers such as tetrahydrofuran, 1,4-dioxane, diethylether, or 1,2-dimethoxyethane; hydrocarbons such as n-hexane or cyclohexane; or nitriles such as acetonitrile or propionitrile.

The base includes organic amines such as triethylamine or diisopropylethylamine; pyridines such as pyridine, 2,6-lutidine, or 4-picoline.

The carbonyl compound includes phosgene, diphosgene, triphosgene, bromoformyl bromide, carbonyldiimidazole, or 4-nitrophenyl chloroformate, etc.

Step 74

[Chemical Formula 102]

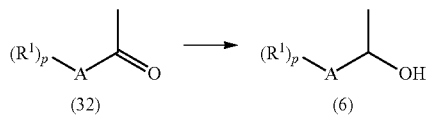

Step 74: Compound (32) can be reduced with a reducing agent in a reaction solvent to synthesize Compound (6), for example, according to a method as described in Tetrahedron Letters, 47 (2006), pages 5261-5264, etc.

Unless the reaction is inhibited, the reaction solvent is not particularly limited, and includes, for example, aromatic hydrocarbons such as toluene or xylene; ethers such as tetrahydrofuran, 1,4-dioxane, diethylether, or 1,2-dimethoxyethane; hydrocarbons such as n-hexane or cyclohexane; alcohols such as methanol, ethanol, or isopropylalcohol; water; or a mixed solvent thereof The reducing agent includes borohydrides such as lithium borohydride, sodium borohydride, potassium borohydride, or trimethoxy sodium borohydride; or aluminum hydrides such as lithium aluminum hydride, sodium aluminum hydride, diisobutylaluminium hydride, or trimethoxy lithium aluminum hydride.

Further, an optically active Compound (6) can be synthesized by using (R)- or (S)-5,5-diphenyl-2-methyl-3,4-propano-1,3,2-oxazaborolidine etc., for example, according to a method as described in Journal of Organic Chemistry, 56 (1991), pages 763-769, etc.

Step 75

[Chemical Formula 103]

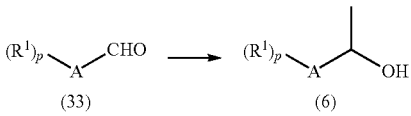

Step 75: Compound (33) can be methylated with a methylating agent in a reaction solvent to synthesize Compound (6), for example, according to a method as described in Journal of Medicinal Chemistry, 51 (2008), pages 282-297, etc.

Unless the reaction is inhibited, the reaction solvent is not particularly limited, and includes, for example, aromatic hydrocarbons such as toluene or xylene; ethers such as tetrahydrofuran, 1,4-dioxane, diethylether, or 1,2-dimethoxyethane; hydrocarbons such as n-hexane or cyclohexane; or a mixed solvent thereof.

The methylating agent includes methyl Grignard reagents such as methylmagnesium chloride, methylmagnesium bromide, or methylmagnesium iodide; methyl lithium, dimethyl zinc, or trimethylaluminum, etc.

Further, an optically active Compound (6) can be synthesized by using a complex of (2R)- or (2S)-3-exo-(dimethylamino)isonorbornenol, or (R,R)- or (S,S)-6,6'-{(1E,1'E)-[cyclohexane-1,2-diylbis(azanylylidene)]bis(methanylylidene)}bis(2,4-di-tert-butylphenol) with chromium (I) chloride, etc., for example, according to a method as described in Tetrahedron, 55 (1999), pages 3605-3614, or Journal of the American Chemical Society, 128 (2006), pages 4940-4941, etc.

Step 76

[Chemical Formula 104]

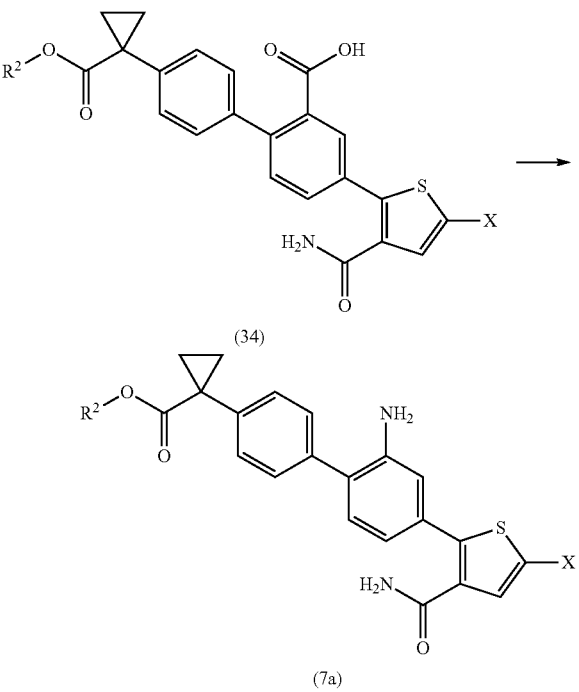

Step 76: Compound (34) can be subjected to a Curtius rearrangement reaction in a reaction solvent by using diphenylphosphorylazide and a base to synthesize Compound (7a), for example, according to a method as described in Bioorganic and Medicinal Chemistry Letters, 17 (2007), pages 4363-4368, etc.

Unless the reaction is inhibited, the reaction solvent is not particularly limited, and includes, for example, aromatic hydrocarbons such as toluene or xylene; or amides such as N,N-dimethylformamide, N,N-dimethylacetamide, or 1-methyl-2-pyrrolidone. Otherwise, alcohols such as methanol, ethanol, tert-butanol, allylalcohol, benzylalcohol, or 2-trimethylsilylethanol can be used as a solvent or as a mixture with a solvent to synthesize Compound (7a) having a protected amino group.

The base includes organic amines such as triethylamine or diisopropylethylamine, and it is preferably triethylamine.

[Chemical Formula 105]

Step 77

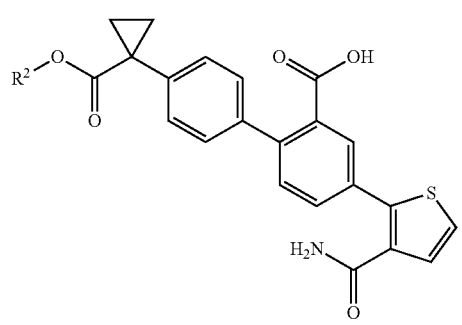

(35)

[Chemical Formula 106]

Step 78

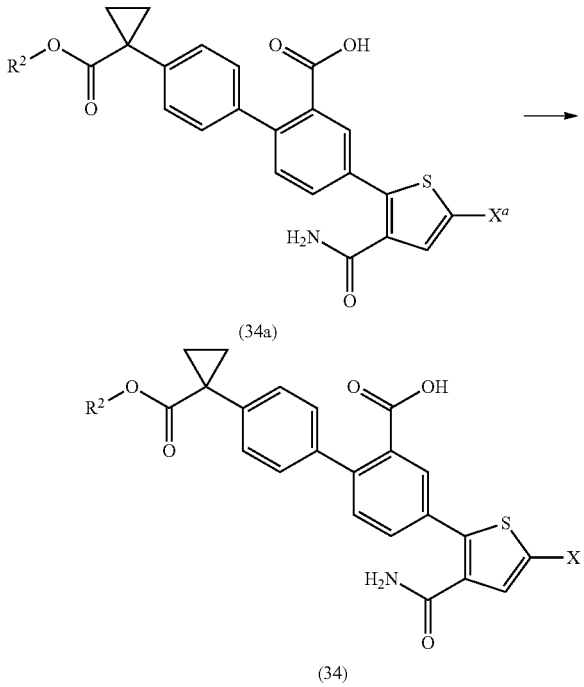

(34a)

(34)

Step 78: Compound (34a) can be treated in the similar manner to in Step 7 to synthesize Compound (34).

Step 79

[Chemical Formula 107]

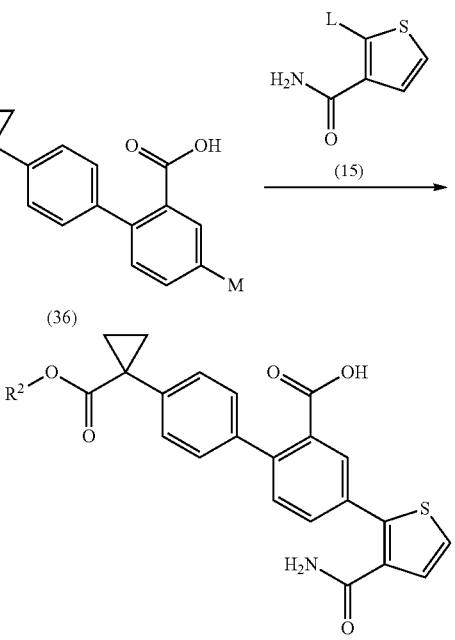

(36)

(15)

(35)

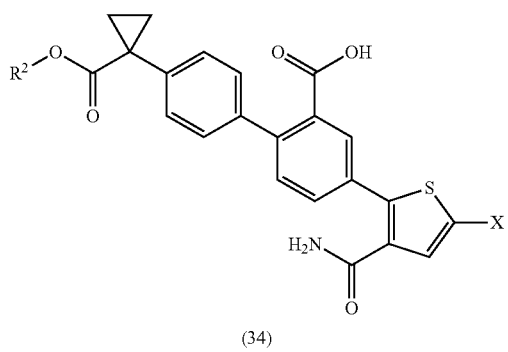

(34)

Step 77: Compound (35) can be treated in the similar manner to in Step 6 to synthesize Compound (34).

Step 79: Compound (36) and Compound (15) can be reacted in the similar manner to in Step 1 to synthesize Compound (35).

[Chemical Formula 108]

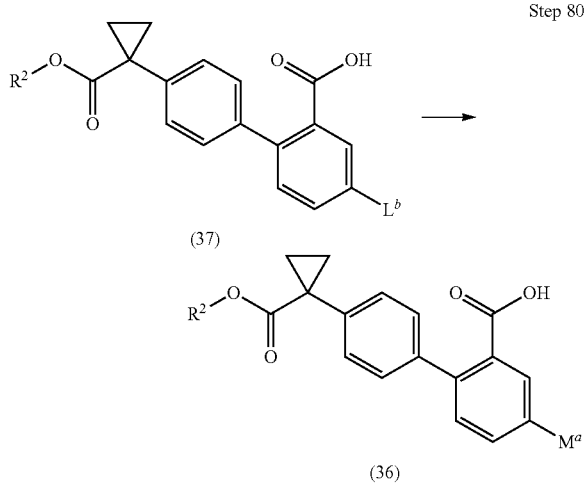

Step 80: Compound (36) can be treated in the similar manner to in Step 48 to synthesize Compound (35).

[Chemical Formula 109]

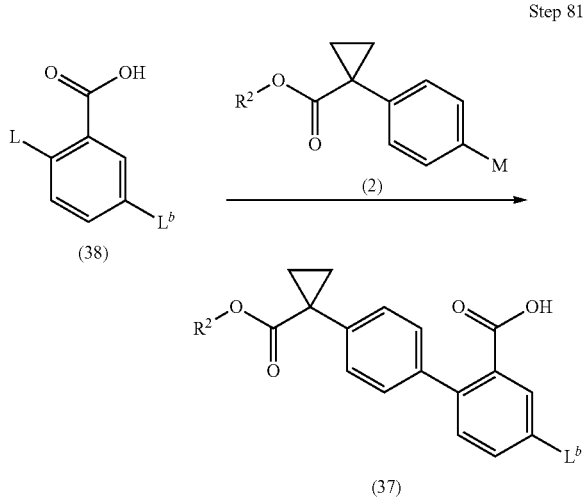

Step 81: Compound (38) and Compound (2) can be reacted in the similar manner to in Step 1 to synthesize Compound (37).

The objective compound produced in each reaction can be obtained from a reaction mixture according to an ordinary method. For example, it can be obtained by appropriately neutralizing the reaction mixture, removing insolubles by filtration if present, adding an organic solvent such as ethyl acetate, which is not miscible with water, washing with water to separate an organic layer which contains the objective compound, drying with a desiccating agent such as anhydrous magnesium sulfate or anhydrous sodium sulfate, and removing the solvent by evaporation.

If necessary, thus obtained objective compound can be separated and purified by appropriately combining an ordinary method, for example, recrystallization; reprecipitation; or a method commonly used for the separation and purification of organic compound (for example, an adsorption column chromatography method using a carrier such as silica gel or alumina; an ion exchange chromatography method; or a normal-phase or reverse-phase column chromatography method using silica gel or alkylated silica gel (preferably, high performance liquid chromatography); or a normal-phase or reverse-phase column chromatography method using a filler, wherein an optically active molecule is fixed on the filler, or coated on silica gel (preferably, high performance liquid chromatography)).

When the compound represented by the general formula (I) of the present invention, or a pharmacologically acceptable salt thereof is used as a medicament, it can be administered as such (as an ingredient), or can be orally or parenterally administered (such as intravenous administration, intramuscular administration, intraperitoneal administration, percutaneous administration, intratracheal administration, intracutaneous administration, or subcutaneous administration) in a form of tablet, capsule, powder, syrup, granule, fine granule, pill, suspension, emulsion, percutaneous absorption preparation, suppository, ointment, lotion, inhalant, or injection, etc., which is manufactured by mixing with an appropriate pharmacologically acceptable excipient, diluent, etc.

These preparations are manufactured, using additives such as excipient, lubricant, binder, disintegrant, emulsifier, stabilizer, flavoring agent, or diluent by a known method.

The excipient includes, for example, an organic excipient or an inorganic excipient. The organic excipient includes, for example, a sugar derivative such as lactose, sucrose, glucose, mannitol, or sorbitol; a starch derivative such as corn starch, potato starch, α-starch, or dextrin; a cellulose derivative such as crystalline cellulose; gum arabic; dextran; or pullulan, etc. The inorganic excipient includes, for example, light anhydrous silicic acid; a sulfate salt such as calcium sulfate, etc.

The lubricant includes, for example, stearic acid; a metal salt of stearic acid such as calcium stearate or magnesium stearate; talc; colloid silica; waxes such as bees wax or spermaceti wax; boric acid; adipinic acid; sulfate salt such as sodium sulfate; glycol; fumaric acid; sodium benzoate; D,L-leucine; sodium lauryl sulfate; silicic acids such as silicic anhydride or silicic acid hydrate; or a starch derivative as listed in the above excipient, etc.

The binder includes, for example, hydroxypropylcellulose, hydroxypropylmethylcellulose, polyvinylpyrrolidone, macrogol, or a compound as listed in the above excipient, etc.

The disintegrant includes, for example, cellulose derivative such as low substituted hydroxy-propylcellulose, carboxy methylcellulose, carboxy methylcellulose calcium, or internally-crosslinked carboxy methylcellulose calcium; crosslinked polyvinylpyrrolidone; or chemically modified starch or cellulose derivative such as carboxymethyl starch or sodium carboxymethyl starch.

The emulsifier includes, for example, colloidal clay such as bentonite or bee gum; anionic surfactant such as sodium lauryl sulfate; cationic surfactant such as benzalkonium chloride; or nonionic surfactant such as polyoxyethylene alkyl ether, polyoxyethylene sorbitan fatty acid ester, or sucrose fatty acid ester, etc.

The stabilizer includes, for example, p-hydroxybenzoic acid esters such as methylparaben or propylparaben; alcohols such as chlorobutanol, benzylalcohol, or phenylethyl alcohol; benzalkonium chloride; phenols such as phenol or cresol; thimerosal; acetic anhydride; or sorbic acid.

The flavoring agent includes, for example, sweetener such as saccharin sodium or aspartame; acidulant such as citric acid, malic acid, or tartaric acid; or flavoring agent such as menthol, lemon extract, or orange extract, etc.

The diluent is a compound which is usually used as a diluent, and includes, for example, lactose, mannitol, glucose, sucrose, calcium sulfate, hydroxypropyl cellulose, microcrystalline cellulose, water, ethanol, polyethyleneglycol, propyleneglycol, glycerol, starch, polyvinylpyrrolidone, or a mixture thereof, etc.

The dose of the compound represented by the general formula (I) of the present invention or a pharmacologically acceptable salt thereof may vary depending on the condition of the patient such as the symptom, the age, or the body weight, and if orally administered, 0.001 mg/kg (preferably 0.01 mg/kg) per administration at the minimum, or 20 mg/kg (preferably 10 mg/kg) per administration at the maximum, or if parenterally administered, 0.0001 mg/kg (preferably 0.0005 mg/kg) per administration at the minimum, or 10 mg/kg (preferably 5 mg/kg) per administration at the maximum can be administered to an adult 1 to 6 times per day, depending on the symptom.

EXAMPLES

The present invention is explained in detail below, by presenting examples (Examples 1 to 154), reference examples (Reference Examples 1 to 56), and test examples (Test Examples 1 to 7), and these examples are for the understanding better of the present invention, but they do not to limit the scope of the present invention.

Rf value in the physical properties in the examples and the reference examples was measured by using a thin layer chromatography (Merck Co., TLC Plate Silica Gel 60 $F_{254}$ (trade name)), and the note in the parentheses denotes a developing solvent (volume ratio).

COOH column in the silica gel column chromatography denote Chromatorex (registered trademark) Q-PACK COOH silica gel prepacked column by Fuji Silysia Chemical Ltd.

In a case where plural values of mass spectrum were observed due to the presence of isotope, the value of the smallest m/z only was described. DUIS in the ionization mode of the mass spectrum is a mixed mode of ESI and APCI.

Further, unless specifically described, Me represents a methyl group, Et represents an ethyl group, tBu represents a tert-butyl group, Bn represents a benzyl group, and Boc represents a tert-butoxycarbonyl group in the chemical structure.

Example 1

(RS)-1-{4'-[5-Bromo-3-({[1-(2-chlorophenyl) ethoxy]carbonyl}amino)thiophen-2-yl]-[1,1'-biphenyl]-4-yl}cyclopropanecarboxylic acid ethyl ester (Compound No. I-9)

[Chemical Formula 110]

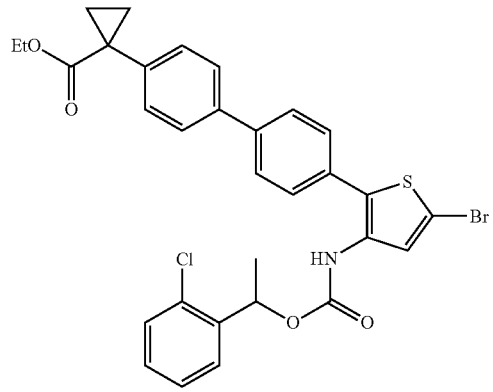

To a solution of 0.50 g (0.91 mmol) of (RS)-1-{4'-[3-({[1-(2-chlorophenyl)ethoxy]carbonyl}amino)thiophen-2-yl]-[1,1'-biphenyl]-4-yl}cyclopropanecarboxylic acid ethyl ester synthesized in analogy to Reference Example 14 in N,N-dimethylformamide (5 ml) was added portionwise 0.59 g (3.3 mmol) of N-bromosuccinimide under an argon atmosphere at 80° C., and the mixture was heated and stirred at the same temperature for 6 hours. After completion of the reaction, toluene was added, and the mixed solution was poured into a saturated aqueous sodium hydrogencarbonate solution, and extracted with toluene. The organic layer was dried over anhydrous magnesium sulfate, subsequently the residue obtained by concentration under reduced pressure was subjected to silica gel column chromatography (elution solvent; hexane:ethyl acetate=90:10 to 70:30 (V/V)), and the fractions containing the desired compound were concentrated under reduced pressure and dried under reduced pressure to obtain 0.31 g (0.49 mmol, yield 54%) of the title compound as a pale yellow oil (partially solidified).

Mass spectrum (CI, m/z): 623 [M]$^+$.

$^1$H-NMR spectrum (400 MHz, DMSO-$d_6$, 75° C.) δ: 9.18 (1H, brs), 7.71-7.67 (2H, m), 7.64-7.60 (2H, m), 7.56-7.52 (2H, m), 7.50-7.39 (4H, m), 7.38-7.34 (1H, m), 7.30 (1H, td, J=7.6, 1.8 Hz), 7.22 (1H, s), 5.99 (1H, q, J=6.4 Hz), 4.06 (2H, q, J=7.0 Hz), 1.52 (2H, dd, J=6.9, 3.9 Hz), 1.46 (3H, d, J=6.6 Hz), 1.22 (2H, dd, J=7.1, 4.1 Hz), 1.12 (3H, t, J=7.1 Hz).

The title compound was also synthesized as follows.

To a solution of 6.5 mg (0.014 mmol) of 5-bromo-2-{4'-[1-(ethoxycarbonyl)cyclopropyl]-[1,1'-biphenyl]-4-yl}thiophene-3-carboxylic acid synthesized in analogy to Reference Example 31 in dehydrated toluene (1 ml) were added 0.0030 ml (0.022 mmol) of triethylamine and 0.0035 ml (0.016 mmol) of diphenylphosphoryl azide under an argon atmosphere, and the mixture was stirred at room temperature for 5 minutes. Then, 0.090 ml (0.73 mmol) of (RS)-1-(2-chlorophenyl)ethanol (Tokyo Chemical Industry Co., Ltd.) was added, and the mixture was stirred under the heat-refluxing condition for 1.5 hours. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=98:2 to 69:31 (V/V)), and the fractions containing the desired compound were concentrated under reduced pressure to obtain 10.2 mg (0.095 mmol (purity 57% by weight), yield 69%) of the title compound as a yellow solid.

Example 2

(RS)-1-{4'-[5-Bromo-3-({[1-(2-chlorophenyl)ethoxy]carbonyl}amino)thiophen-2-yl]-[1,1'-biphenyl]-4-yl}cyclopropanecarboxylic acid (Compound No. I-11)

[Chemical Formula 111]

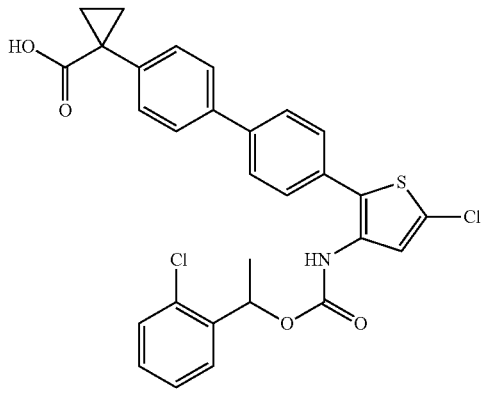

To a solution of 22.5 mg (0.036 mmol) of (RS)-(1-{4'-[5-bromo-3-({[1-(2-chlorophenyl)ethoxy]carbonyl}amino)thiophen-2-yl]-[1,1'-biphenyl]-4-yl}cyclopropanecarboxylic acid ethyl ester synthesized in analogy to Example 1 in isopropyl alcohol (1.8 ml) was added 0.030 ml (0.18 mmol) of a 6N aqueous sodium hydroxide solution, and the mixture was stirred under a nitrogen atmosphere at room temperature for 22 hours. After completion of the reaction, 0.18 ml (0.18 mmol) of 1N hydrochloric acid was added, and the mixture was concentrated under reduced pressure. The resulting residue was purified by preparative HPLC using a column of Xbridge Prep C18 OBD (trade name, Nihon Waters K.K.), 5.0 µm 19×150 mm (elution solvent; a 0.1% by volume formic acid aqueous solution (solution A)—a 0.1% by volume formic acid acetonitrile solution (solution B), gradient (% by volume of solution B): 80% (0.00 min.)—80% (0.80 min.)—95% (7.00 min.)—95% (12.00 min.)). To the fractions containing the desired compound was added water, and the mixture was lyophilized to obtain 7.1 mg (0.012 mmol, yield 33%) of the title compound as a white solid.

Mass spectrum (CI, m/z): 595 [M]$^+$.

$^1$H-NMR spectrum (500 MHz, DMSO-d$_6$, 75° C.) δ: 12.54 (1H, brs), 9.19 (1H, brs), 7.70-7.65 (2H, m), 7.60-7.56 (2H, m), 7.55-7.52 (2H, m), 7.51-7.44 (1H, m), 7.43-7.39 (3H, m), 7.39-7.34 (1H, m), 7.31 (1H, td, J=7.6, 1.7 Hz), 7.22 (1H, s), 5.99 (1H, q, J=6.5 Hz), 1.46 (3H, d, J=6.6 Hz), 1.44 (2H, dd, J=6.6, 3.6 Hz), 1.08 (2H, dd, J=6.5, 3.6 Hz).

Example 3

(RS)-1-{4'-[5-Chloro-3-({[1-(2-chlorophenyl)ethoxy]carbonyl}amino)thiophen-2-yl]-[1,1'-biphenyl]-4-yl}cyclopropanecarboxylic acid ethyl ester (Compound No. I-47)

[Chemical Formula 112]

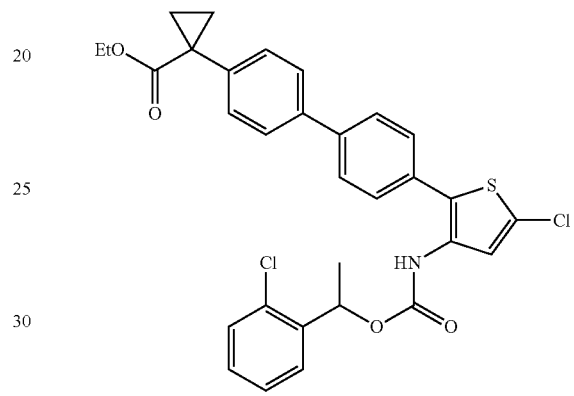

To a solution of 0.11 g (0.20 mmol) of (RS)-1-{4'-[3-({[1-(2-chlorophenyl)ethoxy]carbonyl}amino)thiophen-2-yl]-[1,1'-biphenyl]-4-yl}cyclopropanecarboxylic acid ethyl ester synthesized in analogy to Reference Example 14 in N,N-dimethylformamide (1.5 ml) was added portionwise 0.030 g (0.25 mmol) of N-chlorosuccinimide under an argon atmosphere at 80° C., and the mixture was heated and stirred at the same temperature for one hour. After completion of the reaction, to the reaction mixture were added toluene and water, and the mixture was extracted with toluene. The organic layer was dried over anhydrous magnesium sulfate, subsequently the residue obtained by concentration under reduced pressure was subjected to silica gel column chromatography (elution solvent; hexane:ethyl acetate=88:12 to 61:39 (V/V)), and the fractions containing the desired compound was concentrated under reduced pressure and dried under reduced pressure to obtain 0.11 g (0.18 mmol, yield 93%) of the title compound as a pale yellow oil.

Mass spectrum (CI, m/z): 579 [M]$^+$.

$^1$H-NMR spectrum (500 MHz, DMSO-d$_6$, 75° C.) δ: 9.19 (1H, brs), 7.71-7.67 (2H, m), 7.64-7.60 (2H, m), 7.57-7.53 (2H, m), 7.50-7.40 (4H, m), 7.38-7.34 (1H, m), 7.30 (1H, td, J=7.6, 1.7 Hz), 7.13 (1H, s), 5.99 (1H, q, J=6.5 Hz), 4.06 (2H, q, J=7.0 Hz), 1.52 (2H, dd, J=6.9, 3.9 Hz), 1.46 (3H, d, J=6.5 Hz), 1.22 (2H, dd, J=7.0, 4.0 Hz), 1.13 (3H, t, J=7.1 Hz).

Example 4

(RS)-1-{4'-[5-Chloro-3-({[1-(2-chlorophenyl)ethoxy]carbonyl}amino)thiophen-2-yl]-[1,1'-biphenyl]-4-yl}cyclopropanecarboxylic acid (Compound No. I-51)

[Chemical Formula 113]

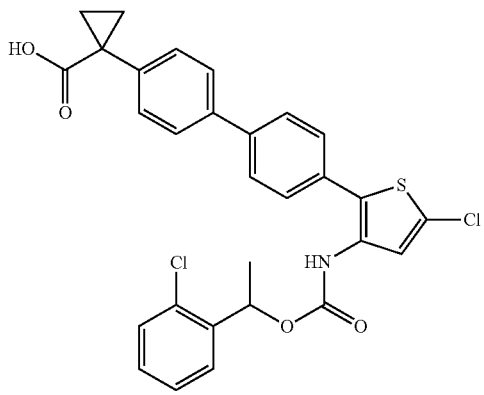

To a solution of 105.1 mg (0.181 mmol) of (RS)-1-{4'-[5-chloro-3-({[1-(2-chlorophenyl)ethoxy]carbonyl}amino)thiophen-2-yl]-[1,1'-biphenyl]-4-yl}cyclopropanecarboxylic acid ethyl ester synthesized in analogy to Example 3 in isopropyl alcohol (4 ml) was added 0.15 ml (0.90 mmol) of a 6N aqueous sodium hydroxide solution, and the mixture was stirred under a nitrogen atmosphere at room temperature for 17 hours. After completion of the reaction, 0.90 ml (0.90 mmol) of 1N hydrochloric acid was added, and the mixture was concentrated under reduced pressure. To the resulting residue was added water, the resulting solid was washed with water three times, acetonitrile was added, and the mixture was sonicated. Subsequently, the solid was collected by filtration and dried under reduced pressure to obtain 60.3 mg (0.11 mmol, yield 60%) of the title compound as a white solid.

Mass spectrum (EI, m/z): 551 [M]$^+$.

$^1$H-NMR spectrum (500 MHz, DMSO-d$_6$, 75° C.) δ: 12.08 (1H, brs), 9.22 (1H, brs), 7.73-7.68 (2H, m), 7.65-7.60 (2H, m), 7.59-7.54 (2H, m), 7.53-7.42 (4H, m), 7.42-7.36 (1H, m), 7.33 (1H, td, J=7.6, 1.7 Hz), 7.15 (1H, s), 6.02 (1H, q, J=6.5 Hz), 1.56-1.44 (5H, m), 1.18 (2H, dd, J=6.9, 4.0 Hz).

Example 5

(R)-1-{4'-[5-Chloro-3-({[1-(2-chlorophenyl)ethoxy]carbonyl}amino)thiophen-2-yl]-[1,1'-biphenyl]-4-yl}cyclopropanecarboxylic acid ethyl ester (Compound No. I-48)

[Chemical Formula 114]

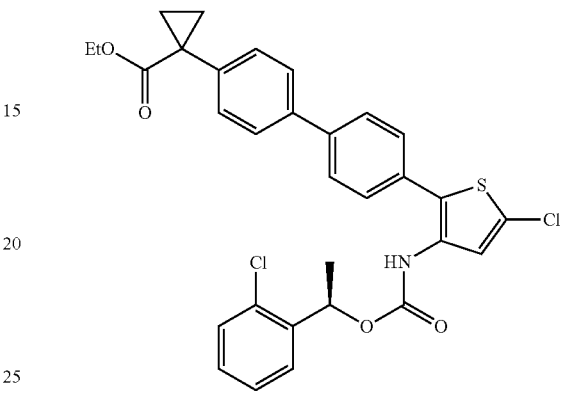

To a solution of 65.5 mg (0.153 mmol) of 5-chloro-2-{4'-[1-(ethoxycarbonyl)cyclopropyl]-[1,1'-biphenyl]-4-yl}thiophene-3-carboxylic acid synthesized in analogy to Reference Example 32 in dehydrated toluene (1 ml) was added 0.0030 ml (0.022 mmol) of triethylamine under an argon atmosphere, and the mixture was stirred at room temperature for 5 minutes. Then, 0.039 mL (0.18 mmol) of diphenylphosphoryl azide and 0.030 ml (0.21 mmol) of (R)-1-(2-chlorophenyl)ethanol (Shanghai AoBo Bio-pharm) were added, and the mixture was heated and stirred at 80° C. for one hour. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=100:0 to 69:31 (V/V)), and the fractions containing the desired compound were concentrated under reduced pressure to obtain 88.3 mg of a colorless oil containing the title compound. This was subjected to silica gel column chromatography again (elution solvent; hexane:ethyl acetate=93:7 to 72:28 (V/V)) to obtain 870 mg (0.10 mmol (purity 87% by weight), yield 68%) of the title compound as a colorless foam.

Mass spectrum (CI, m/z): 579 [M]$^+$.

$^1$H-NMR spectrum (500 MHz, DMSO-d$_6$, 75° C.) δ: 9.19 (1H, brs), 7.71-7.67 (2H, m), 7.64-7.59 (2H, m), 7.58-7.53 (2H, m), 7.51-7.40 (4H, m), 7.39-7.34 (1H, m), 7.30 (1H, td, J=7.6, 1.7 Hz), 7.14 (1H, s), 5.99 (1H, q, J=6.6 Hz), 4.06 (2H, q, J=7.1 Hz), 1.52 (2H, dd, J=6.9, 4.1 Hz), 1.46 (3H, d, J=6.5 Hz), 1.22 (2H, dd, J=7.1, 4.1 Hz), 1.13 (3H, t, J=7.0 Hz).

The title compound was also synthesized as follows.

To a solution of 81 mg (0.19 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 60 mg (0.38 mmol) of (R)-1-(2-chlorophenyl)ethanol (Shanghai AoBo Bio-pharm) and 0.050 ml (0.62 mmol) of pyridine in toluene (3 ml) was added 104 mg (0.24 mmol) of [bis(trifluoroacetoxy)iodo]

benzene under a nitrogen atmosphere at room temperature, and the mixture was heated and stirred at 80° C. for one hour. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography, and the fraction having Rf=0.2 (developing solvent; hexane:ethyl acetate=90:10 (V/V)) was concentrated under reduced pressure to obtain 0.13 g (0.16 mmol (purity 69% by weight), yield 84%) of the title compound as a pale orange oil.

Example 6

(R)-1-{4'-[5-Chloro-3-({[1-(2-chlorophenyl)ethoxy]carbonyl}amino)thiophen-2-yl]-[1,1'-biphenyl]-4-yl}cyclopropanecarboxylic acid (Compound No. I-52)

[Chemical Formula 115]

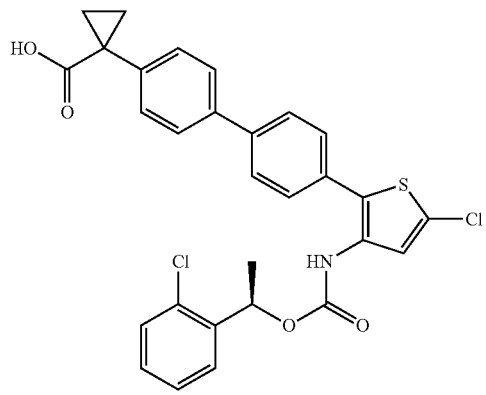

To a solution of 0.13 g (0.16 mmol (purity 69% by weight)) of (R)-1-{4'-[5-chloro-3-({[1-(2-chlorophenyl)ethoxy]carbonyl}amino)thiophen-2-yl]-[1,1'-biphenyl]-4-yl}cyclopropanecarboxylic acid ethyl ester synthesized in Example 5 in isopropyl alcohol (2 ml) was added 0.20 ml (0.80 mmol) of a 4N aqueous sodium hydroxide solution, and the mixture was stirred at room temperature for 64 hours. After completion of the reaction, the reaction mixture was acidified by adding 2N hydrochloric acid thereto, and the mixture was extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=75:25 to 0:100 (V/V)), and the fractions containing the desired compound were concentrated under reduced pressure to obtain 48 mg (0.088 mmol, yield 55%) of the title compound as a pale yellow solid.

Mass spectrum (EI, m/z): 551 [M]$^+$.

$^1$H-NMR spectrum (400 MHz, DMSO-d$_6$) δ: 12.38 (1H, brs), 9.53 (1H, brs), 7.74-7.69 (2H, m), 7.65-7.60 (2H, m), 7.58-7.53 (2H, m), 7.49-7.29 (6H, m), 7.17 (1H, s), 5.97 (1H, q, J=6.4 Hz), 1.54-1.42 (5H, m), 1.18 (2H, dd, J=6.9, 3.9 Hz).

Example 7

(R)-1-[4'-(5-Chloro-3-{[(1-phenylethoxy)carbonyl]amino}thiophen-2-yl)-[1,1'-biphenyl]-4-yl]cyclopropanecarboxylic acid ethyl ester (Compound No. I-22)

[Chemical Formula 116]

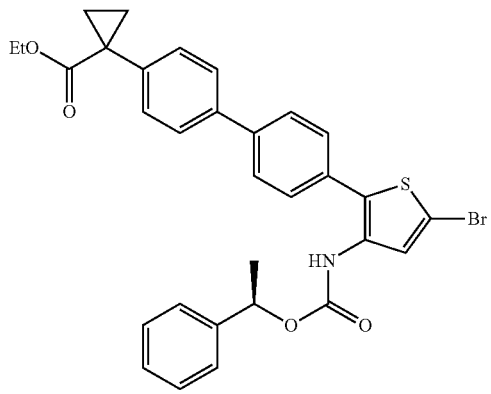

To a solution of 200 mg (0.47 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 0.090 ml (0.75 mmol) of (R)-1-phenylethanol (Tokyo Chemical Industry Co., Ltd.) and 0.10 ml (1.2 mmol) of pyridine in toluene (5 ml) was added 230 mg (0.54 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=87:13 to 66:34 (V/V)), and the fractions containing the desired compound were concentrated under reduced pressure to obtain 0.20 g (0.36 mmol, yield 78%) of the title compound as a pale yellow foam.

Mass spectrum (EI, m/z): 545 [M]$^+$.

$^1$H-NMR spectrum (400 MHz, DMSO-d$_6$) δ: 9.40 (1H, brs), 7.74-7.68 (2H, m), 7.66-7.62 (2H, m), 7.57-7.52 (2H, m), 7.46-7.41 (2H, m), 7.41-7.25 (5H, m), 7.17 (1H, s), 5.73 (1H, q, J=6.4 Hz), 4.05 (2H, q, J=7.1 Hz), 1.56-1.39 (5H, m), 1.24 (2H, dd, J=7.0, 4.0 Hz), 1.11 (3H, t, J=7.1 Hz).

Example 8

(R)-1-[4'-(5-Chloro-3-{[(1-phenylethoxy)carbonyl]amino}thiophen-2-yl)-[1,1'-biphenyl]-4-yl]cyclopropanecarboxylic acid (Compound No. I-24)

[Chemical Formula 117]

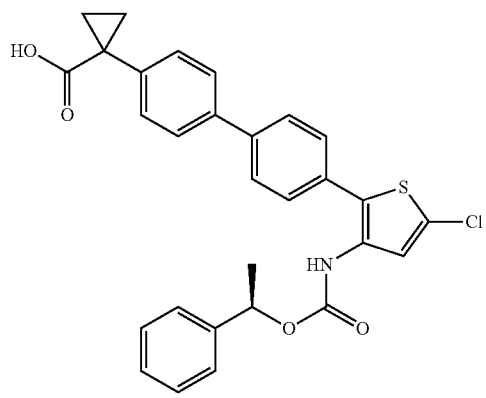

To a solution of 199 mg (0.364 mmol) of (R)-1-[4-(5-chloro-3-{[(1-phenylethoxy)carbonyl]amino}thiophen-2-yl)-[1,1'-biphenyl]-4-yl]cyclopropanecarboxylic acid ethyl ester synthesized in analogy to Example 7 in isopropyl alcohol (5 ml) was added 0.50 ml (2.0 mmol) of a 4N aqueous sodium hydroxide solution, and the mixture was stirred at room temperature for 67 hours. After completion of the reaction, the reaction mixture was acidified by adding 4N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=50:50 to 0:100 (V/V)), and the fractions containing the desired compound were concentrated under reduced pressure to obtain 120 mg (0.23 mmol, yield 64%) of the title compound as a white solid.

Mass spectrum (CI, m/z): 517 [M]$^+$.
$^1$H-NMR spectrum (400 MHz, DMSO-d$_6$) δ: 12.37 (1H, brs), 9.40 (1H, brs), 7.72-7.67 (2H, m), 7.64-7.60 (2H, m), 7.57-7.52 (2H, m), 7.45-7.41 (2H, m), 7.41-7.26 (5H, m), 7.17 (1H, s), 5.73 (1H, q, J=6.4 Hz), 1.56-1.40 (5H, m), 1.18 (2H, dd, J=7.1, 2.9 Hz).

Example 9

(R)-1-{4'-[5-Chloro-3-({[1-(2-fluorophenyl)ethoxy]carbonyl}amino)thiophen-2-yl]-[1,1'-biphenyl]-4-yl}cyclopropanecarboxylic acid ethyl ester (Compound No. I-26)

[Chemical Formula 118]

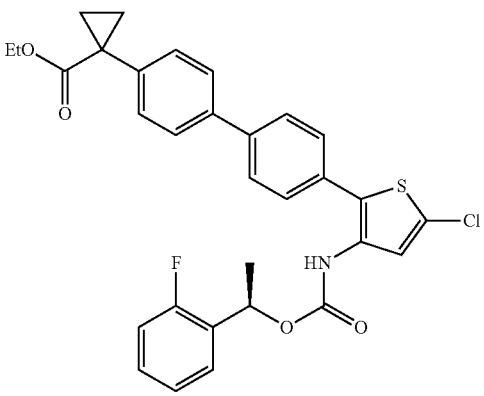

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 72 mg (0.51 mmol) of (R)-1-(2-fluorophenyl)ethanol (Apollo) and 0.10 ml (1.2 mmol) of pyridine in toluene (3 ml) was added 199 mg (0.46 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=87:13 to 66:34 (V/V)), and the fractions containing the desired compound were concentrated under reduced pressure to obtain 195 mg (0.30 mmol (purity 87% by weight), yield 80%) of the title compound as a brown oil.

Mass spectrum (CI, m/z): 563 [M]$^+$.
$^1$H-NMR spectrum (400 MHz, DMSO-d$_6$) δ: 9.47 (1H, brs), 7.74-7.69 (2H, m), 7.66-7.62 (2H, m), 7.59-7.32 (6H, m), 7.31-7.15 (3H, m), 5.93 (1H, q, J=6.1 Hz), 4.05 (2H, q, J=7.1 Hz), 1.56-1.43 (5H, m), 1.24 (2H, dd, J=7.1, 4.1 Hz), 1.12 (3H, t, J=7.1 Hz).

Example 10

(R)-1-{4'-[5-Chloro-3-({[1-(2-fluorophenyl)ethoxy]carbonyl}amino)thiophen-2-yl]-[1,1'-biphenyl]-4-yl}cyclopropanecarboxylic acid (Compound No. I-28)

[Chemical Formula 119]

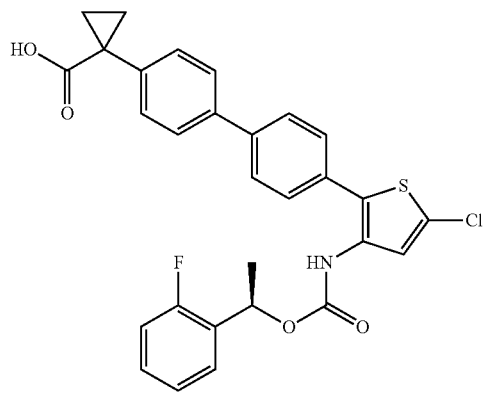

To a solution of 195 mg (0.30 mmol (purity 87% by weight)) of (R)-1-{4'-[5-chloro-3-({[1-(2-fluorophenyl)ethoxy]carbonyl}amino)thiophen-2-yl]-[1,1'-biphenyl]-4-yl}cyclopropanecarboxylic acid ethyl ester synthesized in Example 9 in isopropyl alcohol (5 ml) was added 1.0 ml (4.0 mmol) of a 4N aqueous sodium hydroxide solution, and the mixture was stirred at room temperature for 44 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=70:30 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 101 mg (0.19 mmol, yield 63%) of the title compound as a white solid.

Mass spectrum (EI, m/z): 535 [M]$^+$.

$^1$H-NMR spectrum (400 MHz, DMSO-d$_6$) δ: 12.39 (1H, brs), 9.48 (1H, brs), 7.73-7.67 (2H, m), 7.64-7.59 (2H, m), 7.57-7.33 (6H, m), 7.29-7.14 (3H, m), 5.93 (1H, q, J=6.1 Hz), 1.55-1.44 (5H, m), 1.17 (2H, dd, J=6.5, 3.9 Hz).

Example 11

(R)-1-{4'-[5-Chloro-3-({[1-(3-fluorophenyl)ethoxy]carbonyl}amino)thiophen-2-yl]-[1,1'-biphenyl]-4-yl}cyclopropanecarboxylic acid ethyl ester (Compound No. I-34)

[Chemical Formula 120]

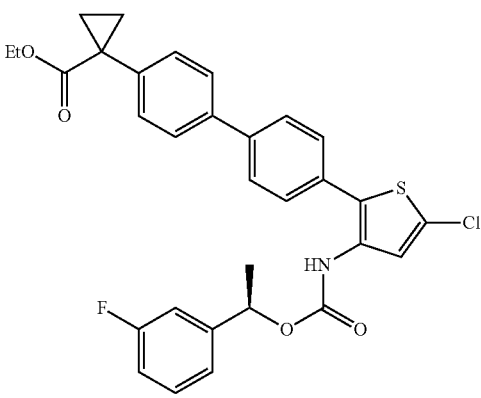

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 89 mg (0.64 mmol) of (R)-1-(3-fluorophenyl)ethanol (Apollo) and 0.10 ml (1.2 mmol) of pyridine in toluene (3 ml) was added 195 mg (0.45 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=87:13 to 66:34 (V/V)), and the fractions containing the desired compound were concentrated under reduced pressure to obtain 180 mg (0.32 mmol, yield 85%) of the title compound as a brown foam.

Mass spectrum (EI, m/z): 563 [M]$^+$.

$^1$H-NMR spectrum (400 MHz, DMSO-d$_6$) δ: 9.46 (1H, brs), 7.74-7.69 (2H, m), 7.66-7.61 (2H, m), 7.58-7.52 (2H, m), 7.46-7.35 (3H, m), 7.28-7.08 (4H, m), 5.74 (1H, q, J=6.1 Hz), 4.05 (2H, q, J=7.1 Hz), 1.55-1.41 (5H, m), 1.24 (2H, dd, J=7.1, 4.1 Hz), 1.12 (3H, t, J=7.0 Hz).

Example 12

(R)-1-{4'-[5-Chloro-3-({[1-(3-fluorophenyl)ethoxy]carbonyl}amino)thiophen-2-yl]-[1,1'-biphenyl]-4-yl}cyclopropanecarboxylic acid (Compound No. I-38)

[Chemical Formula 121]

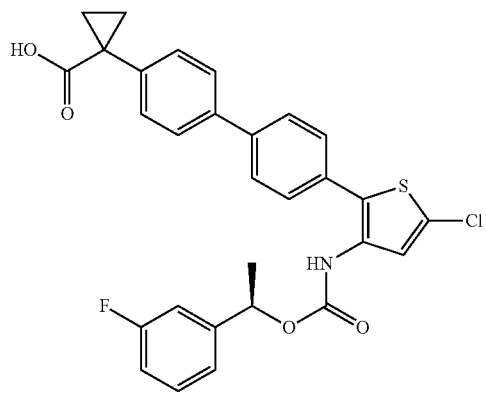

To a solution of 180 mg (0.32 mmol) of (R)-1-{4'-[5-chloro-3-({[1-(3-fluorophenyl)ethoxy]carbonyl}amino)thiophen-2-yl]-[1,1'-biphenyl]-4-yl}cyclopropanecarboxylic acid ethyl ester synthesized in analogy to Example 11 in isopropyl alcohol (5 ml) was added 1.0 ml (4.0 mmol) of a 4N aqueous sodium hydroxide solution, and the mixture was stirred at room temperature for 42 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=70:30 to 0:100 (V/V)), and the fractions containing the desired compound were concentrated under reduced pressure to obtain 115 mg (0.21 mmol, yield 67%) of the title compound as a pale yellow solid.

Mass spectrum (EI, m/z): 535 [M]$^+$.

$^1$H-NMR spectrum (400 MHz, DMSO-d$_6$) δ: 12.37 (1H, brs), 9.47 (1H, brs), 7.74-7.67 (2H, m), 7.65-7.59 (2H, m), 7.58-7.52 (2H, m), 7.48-7.35 (3H, m), 7.29-7.08 (4H, m), 5.74 (1H, q, J=6.4 Hz), 1.54-1.41 (5H, m), 1.18 (2H, dd, J=6.8, 3.9 Hz).

Example 13

(R)-1-{4'-[5-Chloro-3-({[1-(4-fluorophenyl)ethoxy]carbonyl}amino)thiophen-2-yl]-[1,1'-biphenyl]-4-yl}cyclopropanecarboxylic acid ethyl ester (Compound No. I-40)

[Chemical Formula 122]

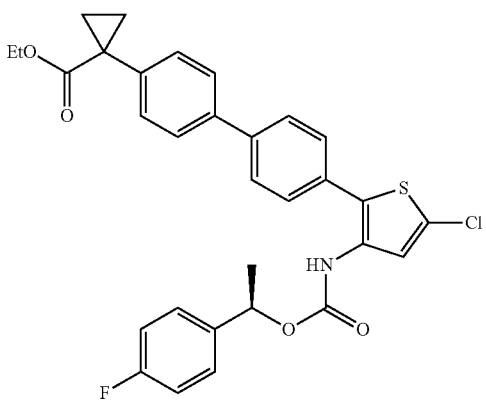

To a solution of 162 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 68 mg (0.49 mmol) of (R)-1-(4-fluorophenyl)ethanol (Acros Organics) and 0.10 ml (1.2 mmol) of pyridine in toluene (3 ml) was added 210 mg (0.49 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=87:13 to 66:34 (V/V)), and the fractions containing the desired compound were concentrated under reduced pressure to obtain 187 mg (0.33 mmol, yield 87%) of the title compound as an orange foam.

Mass spectrum (EI, m/z): 563 [M]$^+$.

$^1$H-NMR spectrum (400 MHz, DMSO-d$_6$) δ: 9.40 (1H, brs), 7.74-7.68 (2H, m), 7.66-7.62 (2H, m), 7.56-7.52 (2H, m), 7.46-7.34 (4H, m), 7.24-7.14 (3H, m), 5.73 (1H, q, J=6.4 Hz), 4.05 (2H, q, J=7.1 Hz), 1.55-1.40 (5H, m), 1.24 (2H, dd, J=7.0, 4.1 Hz), 1.11 (3H, t, J=7.1 Hz).

Example 14

(R)-1-{4'-[5-Chloro-3-({[1-(4-fluorophenyl)ethoxy]carbonyl}amino)thiophen-2-yl]-[1,1'-biphenyl]-4-yl}cyclopropanecarboxylic acid (Compound No. I-42)

[Chemical Formula 123]

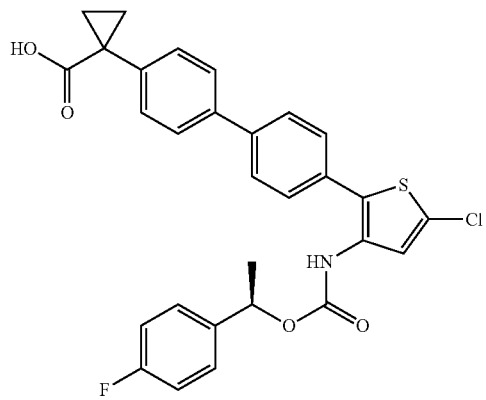

To a solution of 167 mg (0.30 mmol) of (R)-1-{4'-[5-chloro-3-({[1-(4-fluorophenyl)ethoxy]carbonyl}amino)thiophen-2-yl]-[1,1'-biphenyl]-4-yl}cyclopropanecarboxylic acid ethyl ester synthesized in analogy to Example 13 in isopropyl alcohol (5 ml) was added 0.5 ml (2.0 mmol) of a 4N aqueous sodium hydroxide solution, and the mixture was stirred at room temperature for 24 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=50:50 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 93 mg (0.17 mmol, yield 59%) of the title compound as a pale yellow solid.

Mass spectrum (EI, m/z): 535 [M]$^+$.

$^1$H-NMR spectrum (400 MHz, DMSO-$d_6$) δ: 12.38 (1H, brs), 9.41 (1H, brs), 7.72-7.68 (2H, m), 7.64-7.59 (2H, m), 7.56-7.51 (2H, m), 7.47-7.35 (4H, m), 7.25-7.14 (3H, m), 5.73 (1H, q, J=6.4 Hz), 1.55-1.40 (5H, m), 1.17 (2H, dd, J=6.8, 4.0 Hz).

Example 15

(R)-1-{4'-[5-Chloro-3-({[1-(4-chlorophenyl)ethoxy]carbonyl}amino)thiophen-2-yl]-[1,1'-biphenyl]-4-yl}cyclopropanecarboxylic acid ethyl ester (Compound No. I-54)

[Chemical Formula 124]

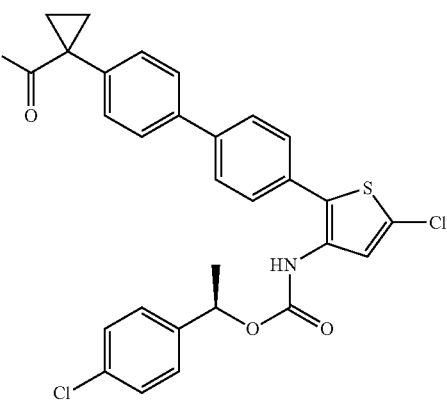

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 76 mg (0.49 mmol) of (R)-1-(4-chlorophenyl)ethanol (Aldrich) and 0.10 ml (1.2 mmol) of pyridine in toluene (3 ml) was added 200 mg (0.47 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=90:10 to 66:34 (V/V)), and the fractions containing the desired compound were concentrated under reduced pressure to obtain 178 mg (0.31 mmol, yield 82%) of the title compound as an orange foam.

Mass spectrum (EI, m/z): 579 [M]$^+$.

$^1$H-NMR spectrum (400 MHz, DMSO-$d_6$) δ: 9.44 (1H, brs), 7.74-7.68 (2H, m), 7.66-7.61 (2H, m), 7.57-7.51 (2H, m), 7.50-7.30 (6H, m), 7.16 (1H, s), 5.72 (1H, q, J=6.1 Hz), 4.05 (2H, q, J=7.1 Hz), 1.54-1.40 (5H, m), 1.24 (2H, dd, J=7.1, 4.1 Hz), 1.11 (3H, t, J=7.1 Hz).

Example 16

(R)-1-{4'-[5-Chloro-3-({[1-(4-chlorophenyl)ethoxy]carbonyl}amino)thiophen-2-yl]-[1,1'-biphenyl]-4-yl}cyclopropanecarboxylic acid (Compound No. I-56)

[Chemical Formula 125]

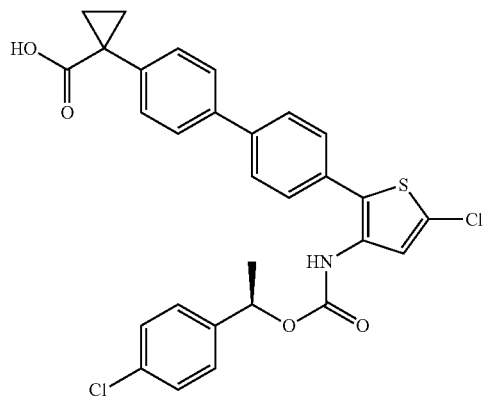

To a solution of 178 mg (0.31 mmol) of (R)-1-{4'-[5-chloro-3-({[1-(4-chlorophenyl)ethoxy]carbonyl}amino)thiophen-2-yl]-[1,1'-biphenyl]-4-yl}cyclopropanecarboxylic acid ethyl ester synthesized in analogy to Example 15 in isopropyl alcohol (4 ml) was added 1.0 ml (4.0 mmol) of a 4N aqueous sodium hydroxide solution, and the mixture was stirred at room temperature for 40 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=70:30 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 117 mg (0.21 mmol, yield 69%) of the title compound as a pale yellow solid.

Mass spectrum (EI, m/z): 551 [M]$^+$.

$^1$H-NMR spectrum (400 MHz, DMSO-d$_6$) δ: 12.37 (1H, brs), 9.43 (1H, brs), 7.72-7.67 (2H, m), 7.64-7.60 (2H, m), 7.56-7.50 (2H, m), 7.47-7.31 (6H, m), 7.17 (1H, s), 5.72 (1H, q, J=6.1 Hz), 1.56-1.37 (5H, m), 1.17 (2H, dd, J=6.6, 4.0 Hz).

Example 17

(R)-1-{4'-[5-Chloro-3-({[1-(o-tolyl)ethoxy]carbonyl}amino)thiophen-2-yl]-[1,1'-biphenyl]-4-yl}cyclopropanecarboxylic acid ethyl ester (Compound No. I-58)

[Chemical Formula 126]

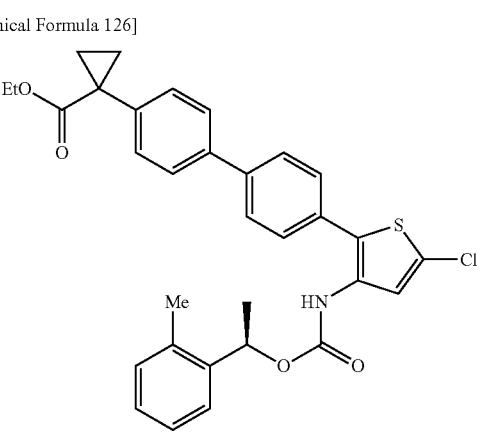

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 91 mg (0.67 mmol) of (R)-1-(o-tolyl)ethanol (Enamine Ltd) and 0.10 ml (1.2 mmol) of pyridine in toluene (3 ml) was added 195 mg (0.45 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=87:13 to 66:34 (V/V)), and the fractions containing the desired compound were concentrated under reduced pressure to obtain 177 mg (0.32 mmol, yield 84%) of the title compound as a pale brown foam.

Mass spectrum (EI, m/z): 559 [M]$^+$.

$^1$H-NMR spectrum (400 MHz, DMSO-d$_6$) δ: 9.40 (1H, brs), 7.73-7.68 (2H, m), 7.67-7.61 (2H, m), 7.56-7.50 (2H, m), 7.47-7.33 (3H, m), 7.28-7.12 (4H, m), 5.87 (1H, q, J=6.4 Hz), 4.05 (2H, q, J=7.1 Hz), 2.31 (3H, s), 1.52 (2H, dd, J=6.9, 3.9 Hz), 1.50-1.39 (3H, m), 1.24 (2H, dd, J=7.0, 4.0 Hz), 1.12 (3H, t, J=7.1 Hz).

Example 18

(R)-1-{4'-[5-Chloro-3-({[1-(o-tolyl)ethoxy]carbonyl}amino)thiophen-2-yl]-[1,1'-biphenyl]-4-yl}cyclopropanecarboxylic acid (Compound No. I-60)

[Chemical Formula 127]

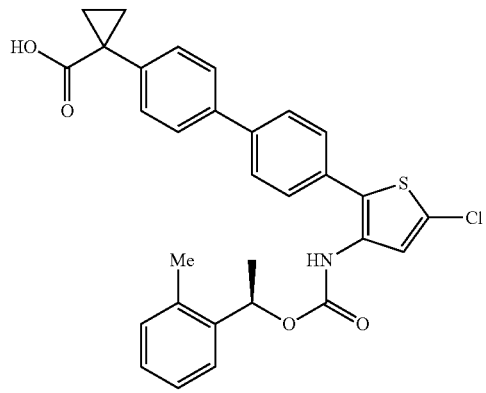

To a solution of 177 mg (0.32 mmol) of (R)-1-{4'-[5-chloro-3-({[1-(o-tolyl)ethoxy]carbonyl}amino)thiophen-2-yl]-[1,1'-biphenyl]-4-yl}cyclopropanecarboxylic acid ethyl ester synthesized in analogy to Example 17 in isopropyl alcohol (5 ml) was added 1.0 ml (4.0 mmol) of a 4N aqueous sodium hydroxide solution, and the mixture was stirred at room temperature for 44 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=70:30 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 119 mg (0.22 mmol, yield 71%) of the title compound as a white solid.

Mass spectrum (EI, m/z): 531 [M]$^+$.

$^1$H-NMR spectrum (400 MHz, DMSO-d$_6$) δ: 12.35 (1H, brs), 9.41 (1H, brs), 7.73-7.66 (2H, m), 7.65-7.59 (2H, m), 7.56-7.51 (2H, m), 7.46-7.33 (3H, m), 7.28-7.13 (4H, m), 5.87 (1H, q, J=6.2 Hz), 2.31 (3H, s), 1.51-1.39 (5H, m), 1.18 (2H, dd, J=7.0, 4.0 Hz).

Example 19

(R)-1-{4'-[5-Chloro-3-({[1-(2,4-difluorophenyl)ethoxy]carbonyl}amino)thiophen-2-yl]-[1,1'-biphenyl]-4-yl}cyclopropanecarboxylic acid ethyl ester (Compound No. I-62)

[Chemical Formula 128]

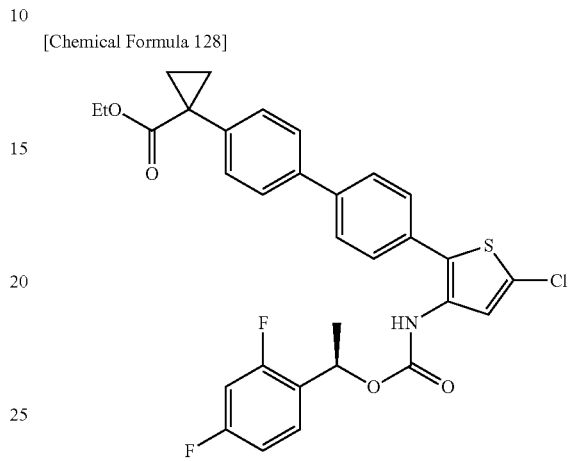

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 in toluene (2 ml) were added 0.10 ml (1.2 mmol) of pyridine and 204 mg (0.47 mmol) of [bis(trifluoroacetoxy)iodo]benzene under an argon atmosphere at room temperature, and the mixture was heated and stirred at 80° C. until dissolution. Then, 89 mg (0.56 mmol) of (R)-1-(2,4-difluorophenyl)ethanol (Enamine Ltd) was added at 80° C. while stirring, and the mixture was heated and stirred at the same temperature for 3 hours. After completion of the reaction, to the reaction mixture was added ethyl acetate, and the mixture was washed with 0.5N hydrochloric acid. The organic layer was dried over anhydrous magnesium sulfate, subsequently the residue obtained by concentration under reduced pressure was subjected to silica gel column chromatography (elution solvent; hexane:ethyl acetate=70:30 to 50:50 (V/V)), and the fractions containing the desired compound were concentrated under reduced pressure to obtain 210 mg (0.34 mmol (purity 94% by weight), yield 90%) of the title compound as a brown foam.

Mass spectrum (EI, m/z): 581 [M]$^+$.

$^1$H-NMR spectrum (400 MHz, DMSO-d$_6$) δ: 9.47 (1H, brs), 7.75-7.69 (2H, m), 7.67-7.61 (2H, m), 7.58-7.40 (5H, m), 7.30-7.22 (1H, m), 7.20-7.03 (2H, m), 5.89 (1H, q, J=6.3 Hz), 4.05 (2H, q, J=7.1 Hz), 1.60-1.42 (5H, m), 1.24 (2H, dd, J=7.0, 4.0 Hz), 1.11 (3H, t, J=7.1 Hz).

Example 20

(R)-1-{4'-[5-Chloro-3-({[1-(2,4-difluorophenyl)ethoxy]carbonyl}amino)thiophen-2-yl]-[1,1'-biphenyl]-4-yl}cyclopropanecarboxylic acid (Compound No. I-64)

[Chemical Formula 129]

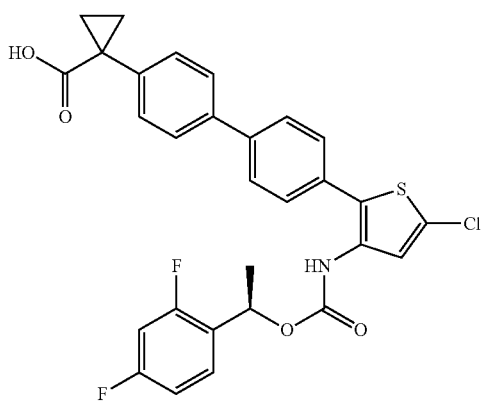

To a solution of 210 mg (0.34 mmol (purity 94% by weight)) of (R)-1-{4'-[5-chloro-3-({[1-(2,4-difluorophenyl)ethoxy]carbonyl}amino)thiophen-2-yl]-[1,1'-biphenyl]-4-yl}cyclopropanecarboxylic acid ethyl ester synthesized in Example 19 in isopropyl alcohol (5 ml) was added 0.90 ml (3.6 mmol) of a 4N aqueous sodium hydroxide solution, and the mixture was stirred at room temperature for 48 hours. After completion of the reaction, to the reaction mixture was added ethyl acetate, and the mixture was washed with 0.5N hydrochloric acid. The organic layer was dried over anhydrous magnesium sulfate, subsequently the residue obtained by concentration under reduced pressure was subjected to silica gel column chromatography (elution solvent; hexane:ethyl acetate=70:30 to 50:50 (V/V)), and the fractions containing the desired compound were concentrated under reduced pressure to obtain 147 mg (0.27 mmol, yield 79%) of the title compound as a white solid.

Mass spectrum (EI, m/z): 553 [M]$^+$.

$^1$H-NMR spectrum (400 MHz, DMSO-d$_6$, 75° C.) δ: 11.93 (1H, brs), 9.08 (1H, s), 7.70-7.64 (2H, m), 7.62-7.57 (2H, m), 7.55-7.50 (2H, m), 7.49-7.38 (3H, m), 7.17-7.10 (2H, m), 7.08-7.02 (1H, m), 5.90 (1H, q, J=6.6 Hz), 1.53-1.45 (5H, m), 1.16 (2H, dd, J=7.0, 3.6 Hz).

Example 21

(R)-1-{4'-[5-Chloro-3-({[1-(2,5-difluorophenyl)ethoxy]carbonyl}amino)thiophen-2-yl]-[1,1'-biphenyl]-4-yl}cyclopropanecarboxylic acid ethyl ester (Compound No. I-66)

[Chemical Formula 130]

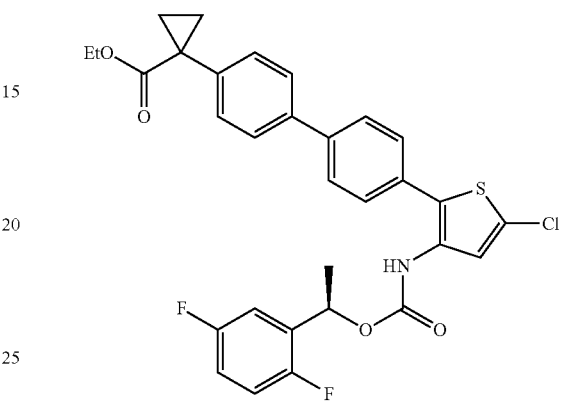

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 in toluene (2 ml) were added 0.10 ml (1.2 mmol) of pyridine and 202 mg (0.47 mmol) of [bis(trifluoroacetoxy)iodo]benzene under an argon atmosphere at room temperature, and the mixture was heated and stirred at 80° C. until dissolution. Then, 92 mg (0.58 mmol) of (R)-1-(2,5-difluorophenyl)ethanol (Enamine Ltd) was added at 80° C. while stirring, and the mixture was heated and stirred at the same temperature for 3 hours. After completion of the reaction, to the reaction mixture was added ethyl acetate, and the mixture was washed with 0.5N hydrochloric acid. The organic layer was dried over anhydrous magnesium sulfate, subsequently the residue obtained by concentration under reduced pressure was subjected to silica gel column chromatography (elution solvent; hexane:ethyl acetate=70:30 to 50:50 (V/V)), and the fractions containing the desired compound were concentrated under reduced pressure to obtain 220 mg (0.31 mmol (purity 83% by weight), yield 83%) of the title compound as a brown oil.

Mass spectrum (EI, m/z): 581 [M]$^+$.

$^1$H-NMR spectrum (400 MHz, DMSO-d$_6$) δ: 9.51 (1H, brs), 7.74-7.68 (2H, m), 7.66-7.61 (2H, m), 7.58-7.52 (2H, m), 7.46-7.41 (2H, m), 7.36-7.06 (4H, m), 5.88 (1H, q, J=6.4 Hz), 4.05 (2H, q, J=7.1 Hz), 1.57-1.44 (5H, m), 1.24 (2H, dd, J=7.1, 4.1 Hz), 1.12 (3H, t, J=7.0 Hz).

Example 22

(R)-1-{4'-[5-Chloro-3-({[1-(2,5-difluorophenyl)ethoxy]carbonyl}amino)thiophen-2-yl]-[1,1'-biphenyl]-4-yl}cyclopropanecarboxylic acid (Compound No. I-68)

[Chemical Formula 131]

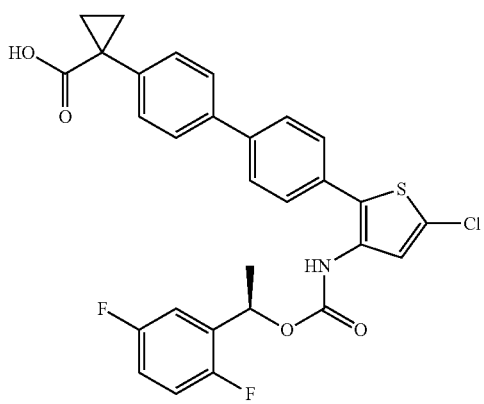

To a solution of 220 mg (0.31 mmol (purity 83% by weight)) of (R)-1-{4'-[5-chloro-3-({[1-(2,5-difluorophenyl)ethoxy]carbonyl}amino)thiophen-2-yl]-[1,1'-biphenyl]-4-yl}cyclopropanecarboxylic acid ethyl ester synthesized in Example 21 in isopropyl alcohol (5 ml) was added 0.95 ml (3.8 mmol) of a 4N aqueous sodium hydroxide solution, and the mixture was stirred at room temperature for 48 hours. After completion of the reaction, to the reaction mixture was added ethyl acetate, and the mixture was washed with 0.5N hydrochloric acid. The organic layer was dried over anhydrous magnesium sulfate, subsequently the residue obtained by concentration under reduced pressure was subjected to silica gel column chromatography (elution solvent; hexane:ethyl acetate=70:30 to 50:50 (V/V)), and the fractions containing the desired compound were concentrated under reduced pressure to obtain 107 mg (0.19 mmol, yield 62%) of the title compound as a white solid.

Mass spectrum (EI, m/z): 553 [M]$^+$.

$^1$H-NMR spectrum (400 MHz, DMSO-d$_6$, 75° C.) δ: 11.97 (1H, brs), 9.15 (1H, s), 7.70-7.64 (2H, m), 7.62-7.57 (2H, m), 7.56-7.50 (2H, m), 7.45-7.39 (2H, m), 7.26-7.11 (4H, m), 5.89 (1H, q, J=6.6 Hz), 1.52-1.45 (5H, m), 1.17 (2H, dd, J=6.8, 4.0 Hz).

Example 23

(R)-1-{4'-[5-Chloro-3-({[1-(3,4-difluorophenyl)ethoxy]carbonyl}amino)thiophen-2-yl]-[1,1'-biphenyl]-4-yl}cyclopropanecarboxylic acid ethyl ester (Compound No. I-70)

[Chemical Formula 132]

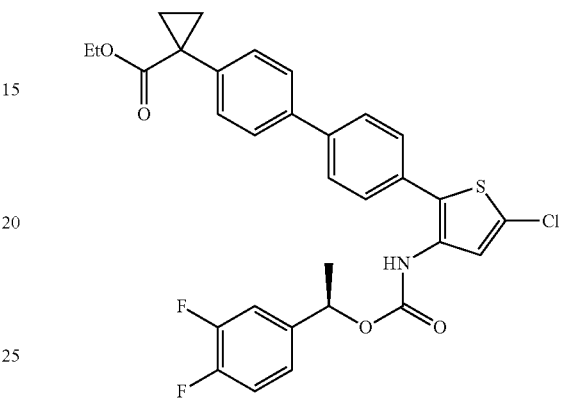

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 in toluene (2 ml) were added 0.10 ml (1.2 mmol) of pyridine and 198 mg (0.46 mmol) of [bis(trifluoroacetoxy)iodo]benzene under an argon atmosphere at room temperature, and the mixture was heated and stirred at 80° C. until dissolution. Then, 89 mg (0.56 mmol) of (R)-1-(3,4-difluorophenyl)ethanol (Enamine Ltd) was added at 80° C. while stirring, and the mixture was heated and stirred at the same temperature for 3 hours. After completion of the reaction, to the reaction mixture was added ethyl acetate, and the mixed solution was washed with 0.5N hydrochloric acid. The organic layer was dried over anhydrous magnesium sulfate, subsequently the residue obtained by concentration under reduced pressure was subjected to silica gel column chromatography (elution solvent; hexane:ethyl acetate=70:30 to 50:50 (V/V)), and the fractions containing the desired compound were concentrated under reduced pressure to obtain 168 mg (0.29 mmol, yield 77%) of the title compound as a brown oil.

Mass spectrum (EI, m/z): 581 [M]$^+$.

$^1$H-NMR spectrum (400 MHz, DMSO-d$_6$) δ: 9.45 (1H, brs), 7.74-7.69 (2H, m), 7.66-7.61 (2H, m), 7.57-7.52 (2H, m), 7.51-7.37 (4H, m), 7.30-7.15 (2H, m), 5.72 (1H, q, J=6.3 Hz), 4.05 (2H, q, J=7.1 Hz), 1.55-1.40 (5H, m), 1.24 (2H, dd, J=7.0, 4.1 Hz), 1.11 (3H, t, J=7.1 Hz).

Example 24

(R)-1-{4'-[5-Chloro-3-({[1-(3,4-difluorophenyl)ethoxy]carbonyl}amino)thiophen-2-yl]-[1,1'-biphenyl]-4-yl}cyclopropanecarboxylic acid (Compound No. I-72)

[Chemical Formula 133]

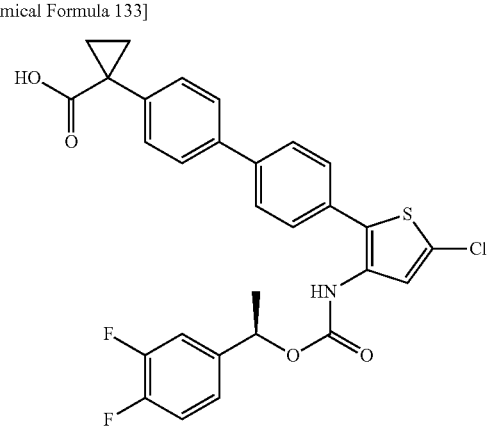

To a solution of 168 mg (0.29 mmol) of (R)-1-{4'-[5-chloro-3-({[1-(3,4-difluorophenyl)ethoxy]carbonyl}amino)thiophen-2-yl]-[1,1'-biphenyl]-4-yl}cyclopropanecarboxylic acid ethyl ester synthesized in analogy to Example 23 in isopropyl alcohol (4 ml) was added 0.725 ml (2.9 mmol) of a 4N aqueous sodium hydroxide solution, and the mixture was stirred at room temperature for 48 hours. After completion of the reaction, to the reaction mixture was added ethyl acetate, and the mixture was washed with 0.5N hydrochloric acid. The organic layer was dried over anhydrous magnesium sulfate and concentrated under reduced pressure, the resulting residue was subjected to silica gel column chromatography (elution solvent; hexane:ethyl acetate=70:30 to 50:50 (V/V)), and the fractions containing the desired compound were concentrated under reduced pressure to obtain 113 mg (0.20 mmol, yield 71%) of the title compound as a white solid.

Mass spectrum (EI, m/z): 553 [M]$^+$.

$^1$H-NMR spectrum (400 MHz, DMSO-d$_6$, 75° C.) δ: 11.98 (1H, brs), 9.08 (1H, s), 7.70-7.65 (2H, m), 7.62-7.57 (2H, m), 7.55-7.51 (2H, m), 7.44-7.40 (2H, m), 7.40-7.31 (2H, m), 7.21-7.16 (1H, m), 7.14 (1H, s), 5.72 (1H, q, J=6.6 Hz), 1.49 (2H, dd, J=6.8, 3.9 Hz), 1.45 (3H, d, J=6.5 Hz), 1.17 (2H, dd, J=7.0, 4.0 Hz).

Example 25

(R)-1-{4'-[5-Chloro-3-({[1-(2-chloro-4-fluorophenyl)ethoxy]carbonyl}amino)thiophen-2-yl]-[1,1'-biphenyl]-4-yl}cyclopropanecarboxylic acid ethyl ester (Compound No. I-74)

[Chemical Formula 134]

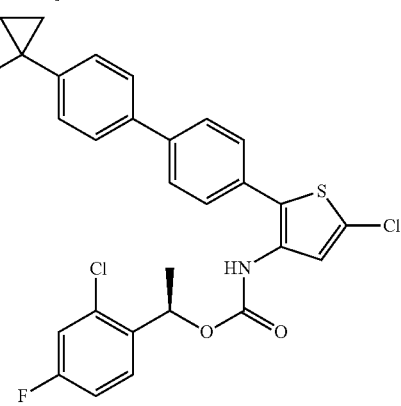

To a solution of 160 mg (0.38 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 103 mg (0.59 mmol) of (R)-1-(2-chloro-4-fluorophenyl)ethanol (Enamine Ltd), 0.10 ml (1.2 mmol) of pyridine in toluene (3 ml) was added 195 mg (0.45 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=90:10 to 69:31 (V/V)), and the fractions containing the desired compound were concentrated under reduced pressure to obtain 206 mg (0.34 mmol, yield 92%) of the title compound as a brown foam.

Mass spectrum (EI, m/z): 597 [M]$^+$.

$^1$H-NMR spectrum (400 MHz, DMSO-d$_6$) δ: 9.53 (1H, brs), 7.76-7.70 (2H, m), 7.67-7.62 (2H, m), 7.61-7.52 (3H, m), 7.49-7.40 (3H, m), 7.38-7.26 (1H, m), 7.17 (1H, s), 5.94 (1H, q, J=6.8 Hz), 4.05 (2H, q, J=7.1 Hz), 1.52 (2H, dd, J=6.9, 3.9 Hz), 1.50-1.43 (3H, m), 1.24 (2H, dd, J=7.1, 4.1 Hz), 1.12 (3H, t, J=7.1 Hz).

Example 26

(R)-1-{4'-[5-Chloro-3-({[1-(2-chloro-4-fluorophenyl)ethoxy]carbonyl}amino)thiophen-2-yl]-[1,1'-biphenyl]-4-yl}cyclopropanecarboxylic acid (Compound No. I-76)

[Chemical Formula 135]

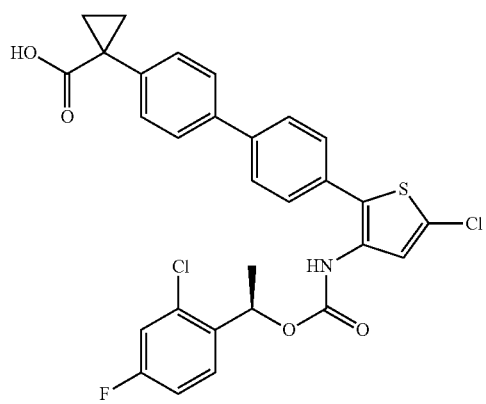

To a solution of 206 mg (0.34 mmol) of (R)-1-{4'-[5-chloro-3-({[1-(2-chloro-4-fluorophenyl)ethoxy]carbonyl}amino)thiophen-2-yl]-[1,1'-biphenyl]-4-yl}cyclopropanecarboxylic acid ethyl ester synthesized in analogy to Example 25 in isopropyl alcohol (5 ml) was added 1.0 ml (4.0 mmol) of a 4N aqueous sodium hydroxide solution, and the mixture was stirred at room temperature for 64 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=70:30 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 129 mg (0.23 mmol, yield 66%) of the title compound as a pale yellow solid.

Mass spectrum (EI, m/z): 569 [M]$^+$.

$^1$H-NMR spectrum (400 MHz, DMSO-d$_6$) δ: 12.37 (1H, brs), 9.53 (1H, brs), 7.75-7.68 (2H, m), 7.66-7.51 (5H, m), 7.50-7.40 (3H, m), 7.37-7.25 (1H, m), 7.17 (1H, s), 5.94 (1H, q, J=6.8 Hz), 1.53-1.43 (5H, m), 1.18 (2H, dd, J=6.8, 4.0 Hz).

Example 27

(R)-1-{4'-[5-(5-Chloro-3-{[(1-phenylethoxy)carbonyl]amino}thiophen-2-yl)pyridine-2-yl]phenyl}cyclopropanecarboxylic acid ethyl ester (Compound No. I-194)

[Chemical Formula 136]

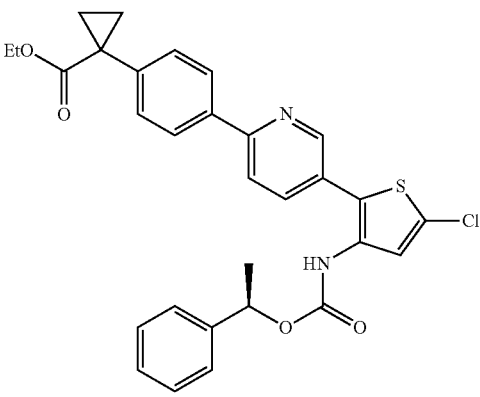

To 202.5 mg (0.474 mmol) of 1-{4-[5-(3-carbamoyl-5-chlorothiophen-2-yl)pyridine-2-yl]phenyl}cyclopropanecarboxylic acid ethyl ester synthesized in analogy to Reference Example 29 was added dehydrated toluene (2 ml). The mixture was subjected to azeotropic dehydration treatment, and subsequently the atmosphere was replaced with argon. Then, 4 ml of dehydrated toluene, 0.80 ml (9.9 mmol) of dehydrated pyridine and 249.0 mg (0.579 mmol) of [bis(trifluoroacetoxy)iodo]benzene were added sequentially, and the mixture was stirred at room temperature for 10 minutes. Subsequently, 0.086 mL (0.71 mmol) of (R)-1-phenylethanol (Tokyo Chemical Industry Co., Ltd.) was added, and the mixture was heated and stirred at 70° C. for 3 hours. After completion of the reaction, the reaction mixture was cooled, and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=96:4 to 75:25 (V/V)), and the fractions containing the desired compound were concentrated under reduced pressure to obtain 252.0 mg (0.368 mmol (purity 80% by weight), yield 78%) of the title compound as an orange oil.

Mass spectrum (EI, m/z): 546 [M]$^+$.

$^1$H-NMR spectrum (400 MHz, DMSO-d$_6$) δ: 9.56 (1H, brs), 8.75 (1H, dd, J=2.4, 0.6 Hz), 8.08-8.04 (2H, m), 8.00 (1H, dd, J=8.3, 0.6 Hz), 7.91 (1H, dd, J=8.4, 2.4 Hz), 7.49-7.44 (2H, m), 7.40-7.17 (6H, m), 5.73 (1H, q, J=6.7 Hz), 4.05 (2H, q, J=7.1 Hz), 1.53-1.42 (3H, m), 1.53 (2H, dd, J=6.9, 3.9 Hz), 1.26 (2H, dd, J=7.1, 4.1 Hz), 1.11 (3H, t, J=7.1 Hz).

Example 28

(R)-1-{4'-[5-(5-Chloro-3-{[(1-phenylethoxy)carbonyl]amino}thiophen-2-yl)pyridine-2-yl]phenyl}cyclopropanecarboxylic acid (Compound No. I-196)

[Chemical Formula 137]

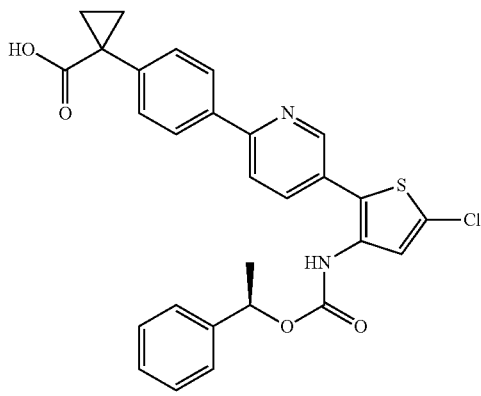

To a solution of 121.4 mg (0.177 mmol (purity 80% by weight)) of (R)-1-{4-[5-(5-chloro-3-{[(1-phenylethoxy)carbonyl]amino}thiophen-2-yl)pyridine-2-yl]phenyl}cyclopropanecarboxylic acid ethyl ester synthesized in Example 27 in ethanol (2.5 ml) was added 1.0 ml (2.0 mmol) of a 2N aqueous sodium hydroxide solution, and the mixture was stirred at room temperature for 12 hours. After completion of the reaction, the reaction mixture was neutralized by adding 2.0 ml of 1N hydrochloric acid thereto, and subsequently ethyl acetate and water were added to separate the layers. The organic layer was dried over anhydrous magnesium sulfate and subsequently concentrated under reduced pressure. The resulting residue was purified by preparative HPLC using a column of Xbridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B) gradient (% by volume of solution B): 70% (0.00 min.)—70% (0.80 min.)—90% (7.00 min.)—90% (12.00 min.)). To the fractions containing the desired compound was added water, and the mixture was lyophilized to obtain 70.7 mg (0.136 mmol, yield 77%) of the title compound as a pale yellow foam.

Mass spectrum (ESI+, m/z): 519 [M+1]+.
$^1$H-NMR spectrum (400 MHz, DMSO-d$_6$) δ: 12.38 (1H, brs), 9.56 (1H, brs), 8.74 (1H, dd, J=2.4, 0.6 Hz), 8.06-8.02 (2H, m), 7.99 (1H, dd, J=8.3, 0.6 Hz), 7.90 (1H, dd, J=8.4, 2.4 Hz), 7.48-7.43 (2H, m), 7.41-7.27 (5H, m), 7.25 (1H, s), 5.73 (1H, q, J=6.5 Hz), 1.51-1.43 (3H, m), 1.48 (2H, dd, J=6.7, 3.8 Hz), 1.19 (2H, dd, J=6.8, 4.0 Hz).

Example 29

(R)-1-[4'-(5-Fluoro-3-{[(1-phenylethoxy)carbonyl]amino}thiophen-2-yl)-[1,1'-biphenyl]-4-yl]cyclopropanecarboxylic acid ethyl ester (Compound No. I-98)

[Chemical Formula 138]

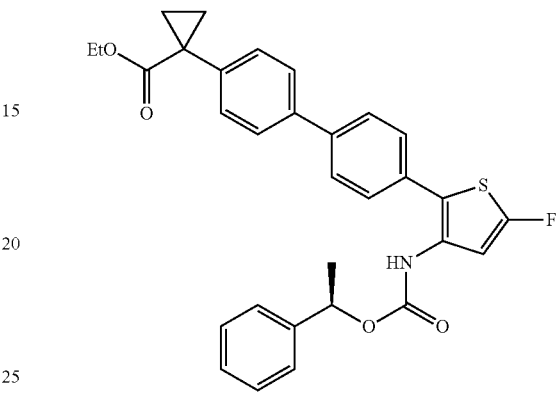

200.3 mg (0.488 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added, and dehydrated toluene (2 ml) was added. The mixture was subjected to azeotropic dehydration treatment, and subsequently the atmosphere was replaced with argon. Then, 4 ml of dehydrated toluene, 0.082 mL (0.59 mmol) of triethylamine and 0.127 mL (0.590 mmol) of diphenylphosphoryl azide were added, and the mixture was stirred at room temperature for one hour. Then, 0.090 ml (0.73 mmol) of (R)-1-phenylethanol (Tokyo Chemical Industry Co., Ltd.) was added, and the mixture was heated and stirred at 70° C. for 2 hours. After completion of the reaction, the reaction mixture was cooled, water and ethyl acetate were added to separate the layers. The organic layer was dried over anhydrous magnesium sulfate and subsequently concentrated under reduced pressure. The resulting residue was subjected to silica gel column chromatography (elution solvent; hexane:ethyl acetate=100:0 to 80:20 (V/V)), and the fractions containing the desired compound were concentrated under reduced pressure to obtain 228.5 mg (0.431 mmol, yield 88%) of the title compound as a colorless oil.

Mass spectrum (EI, m/z): 529 [M]+.
$^1$H-NMR spectrum (400 MHz, DMSO-d$_6$, 75° C.) δ: 8.99 (1H, brs), 7.68-7.64 (2H, m), 7.63-7.59 (2H, m), 7.55-7.50 (2H, m), 7.43-7.39 (2H, m), 7.36-7.31 (4H, m), 7.31-7.24 (1H, m), 6.76 (1H, d, J=2.8 Hz), 5.74 (1H, q, J=6.6 Hz), 4.06 (2H, q, J=7.1 Hz), 1.52 (2H, dd, J=7.0, 4.0 Hz), 1.47 (3H, d, J=6.7 Hz), 1.21 (2H, dd, J=7.1, 4.1 Hz), 1.13 (3H, t, J=7.1 Hz).

Example 30

(R)-1-[4'-(5-Fluoro-3-{[(1-phenylethoxy)carbonyl]amino}thiophen-2-yl)-[1,1'-biphenyl]-4-yl]cyclopropanecarboxylic acid (Compound No. I-100)

[Chemical Formula 139]

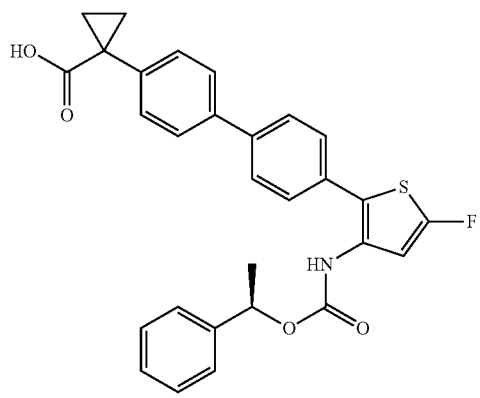

To a solution of 225.0 mg (0.425 mmol) of (R)-1-[4'-(5-fluoro-3-{[(1-phenylethoxy)carbonyl]amino}thiophen-2-yl)-[1,1'-biphenyl]-4-yl]cyclopropanecarboxylic acid ethyl ester synthesized in analogy to Example 29 in isopropyl alcohol (6 ml) was added 2.2 mL (8.8 mmol) of a 4N aqueous sodium hydroxide solution while stirring, and the mixture was stirred at room temperature for two days and then further heated and stirred at 40° C. for 8 hours. After completion of the reaction, the mixture was neutralized by adding 4.4 ml of 2N hydrochloric acid under ice cooling, and subsequently the precipitated solid was collected by filtration. To the resulting solid were added ethyl acetate and methylene chloride, insoluble matter was filtered, and the filtrate was concentrated under reduced pressure. The resulting residue was subjected to silica gel column chromatography (elution solvent; hexane:ethyl acetate=53:47 to 0:100 (V/V)), and the fractions containing the desired compound were concentrated under reduced pressure. To the residue was added ethanol-water, the mixture was sonicated, and subsequently the precipitated solid was collected by filtration and dried to obtain 83.7 mg (0.167 mmol, yield 39%) of the title compound as a white solid.

Mass spectrum (EI, m/z): 501 [M]$^+$.

$^1$H-NMR spectrum (400 MHz, DMSO-d$_6$, 75° C.) δ: 12.05 (1H, brs), 9.00 (1H, brs), 7.68-7.63 (2H, m), 7.61-7.57 (2H, m), 7.54-7.50 (2H, m), 7.44-7.39 (2H, m), 7.36-7.32 (4H, m), 7.31-7.24 (1H, m), 6.76 (1H, d, J=2.8 Hz), 5.74 (1H, q, J=6.6 Hz), 1.48 (2H, dd, J=6.8, 3.7 Hz), 1.47 (3H, d, J=6.7 Hz), 1.16 (2H, dd, J=6.9, 3.9 Hz).

Example 31

(R)-1-{4'-[5-Fluoro-3-({[1-(2-fluorophenyl)ethoxy]carbonyl}amino)thiophen-2-yl]-[1,1'-biphenyl]-4-yl}cyclopropanecarboxylic acid ethyl ester (Compound No. I-102)

[Chemical Formula 140]

201.9 mg (0.492 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added, and dehydrated toluene (2 ml) was added. The mixture was subjected to azeotropic dehydration treatment, and subsequently the atmosphere was replaced with argon. Then, 4 ml of dehydrated toluene, 0.083 mL of triethylamine (0.60 mmol) and 0.127 ml (0.590 mmol) of diphenylphosphoryl azide were added, and the mixture was stirred at room temperature for one hour. Then, 103.5 mg (0.738 mmol) of (R)-1-(2-fluorophenyl)ethanol (Apollo) was added, and the mixture was heated and stirred at 70° C. for 2 hours. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=100:0 to 76:24 (V/V)), and the fractions containing the desired compound were concentrated under reduced pressure to obtain 271.7 mg (0.413 mmol (purity 83% by weight), yield 84%) of the title compound as a colorless foam.

Mass spectrum (EI, m/z): 547 [M]$^+$.

$^1$H-NMR spectrum (400 MHz, DMSO-d$_6$, 75° C.) δ: 9.06 (1H, brs), 7.69-7.64 (2H, m), 7.63-7.59 (2H, m), 7.55-7.51 (2H, m), 7.45-7.39 (3H, m), 7.37-7.30 (1H, m), 7.23-7.11 (2H, m), 6.75 (1H, d, J=2.8 Hz), 5.94 (1H, q, J=6.6 Hz), 4.06 (2H, q, J=7.1 Hz), 1.52 (2H, dd, J=7.0, 4.0 Hz), 1.49 (3H, d, J=6.7 Hz), 1.22 (2H, dd, J=7.0, 4.1 Hz), 1.13 (3H, t, J=7.0 Hz).

Example 32

(R)-1-{4'-[5-Fluoro-3-({[1-(2-fluorophenyl)ethoxy]carbonyl}amino)thiophen-2-yl]-[1,1'-biphenyl]-4-yl}cyclopropanecarboxylic acid (Compound No. I-104)

[Chemical Formula 141]

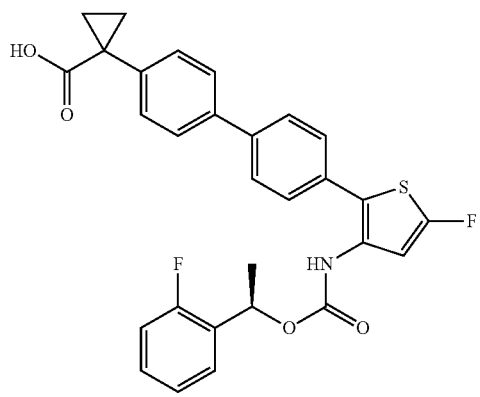

To a solution of 253.9 mg (0.386 mmol (purity 83% by weight)) of (R)-1-{4'-[5-fluoro-3-({[1-(2-fluorophenyl)ethoxy]carbonyl}amino)thiophen-2-yl]-[1,1'-biphenyl]-4-yl}cyclopropanecarboxylic acid ethyl ester synthesized in Example 31 in isopropyl alcohol (4 ml) was added 2.0 ml (8.0 mmol) of a 4N aqueous sodium hydroxide solution while stirring, and the mixture was stirred at room temperature for 37 hours. After completion of the reaction, the reaction mixture was neutralized by adding 4.0 ml of 2N hydrochloric acid under ice cooling, and subsequently ethyl acetate was added to separate the layers. The organic layer was dried over anhydrous magnesium sulfate and concentrated under reduced pressure. The resulting residue was subjected to silica gel column chromatography (elution solvent; hexane:ethyl acetate=60:40 to 0:100 (V/V)), and the fractions containing the desired compound were concentrated under reduced pressure. To the residue was added ethanol-water, the mixture was sonicated, and subsequently the precipitated solid was collected by filtration and dried to obtain 102.1 mg (0.197 mmol, yield 51%) of the title compound as a white solid.

Mass spectrum (EI, m/z): 519 [M]$^+$.

$^1$H-NMR spectrum (400 MHz, DMSO-d$_6$, 75° C.) δ: 11.99 (1H, brs), 9.06 (1H, brs), 7.68-7.63 (2H, m), 7.62-7.57 (2H, m), 7.54-7.49 (2H, m), 7.46-7.39 (3H, m), 7.37-7.30 (1H, m), 7.23-7.11 (2H, m), 6.75 (1H, d, J=2.6 Hz), 5.94 (1H, q, J=6.6 Hz), 1.49 (3H, d, J=6.5 Hz), 1.49 (2H, dd, J=6.9, 3.8 Hz), 1.16 (2H, dd, J=6.9, 3.9 Hz).

Example 33

(R)-1-{4'-[5-Fluoro-3-({[1-(4-fluorophenyl)ethoxy]carbonyl}amino)thiophen-2-yl]-[1,1'-biphenyl]-4-yl}cyclopropanecarboxylic acid ethyl ester (Compound No. I-110)

[Chemical Formula 142]

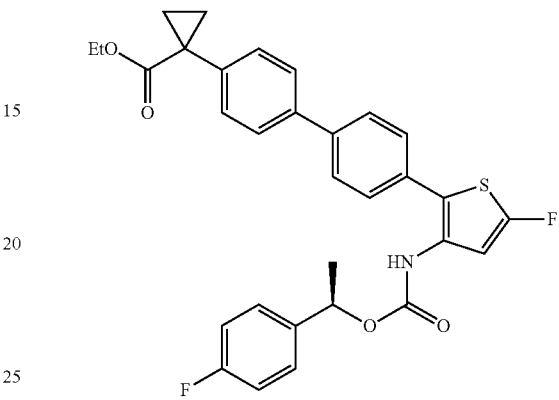

To 197.9 mg (0.482 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene (2 ml). The mixture was subjected to azeotropic dehydration treatment, and subsequently the atmosphere was replaced with argon. Then, 4 ml of dehydrated toluene, 0.082 mL (0.59 mmol) of triethylamine and 0.126 ml (0.585 mmol) of diphenylphosphoryl azide were added sequentially, and the mixture was stirred at room temperature for one hour. Then, 104.5 mg (0.708 mmol (purity 95% by weight)) of (R)-1-(4-fluorophenyl)ethanol (Acros Organics) was added, and the mixture was heated and stirred at 70° C. for 2 hours. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=100:0 to 84:16 (V/V)), and the fractions containing the desired compound were concentrated under reduced pressure to obtain 199.3 mg (0.364 mmol, yield 75%) of the title compound as a colorless foam.

Mass spectrum (EI, m/z): 547 [M]$^+$.

$^1$H-NMR spectrum (400 MHz, DMSO-d$_6$, 75° C.) δ: 9.00 (1H, brs), 7.69-7.65 (2H, m), 7.63-7.58 (2H, m), 7.54-7.49 (2H, m), 7.44-7.34 (4H, m), 7.17-7.09 (2H, m), 6.76 (1H, d, J=2.6 Hz), 5.73 (1H, q, J=6.6 Hz), 4.06 (2H, q, J=7.1 Hz), 1.52 (2H, dd, J=7.0, 4.0 Hz), 1.46 (3H, d, J=6.5 Hz), 1.21 (2H, dd, J=7.0, 4.1 Hz), 1.12 (3H, t, J=7.1 Hz).

Example 34

(R)-1-{4'-[5-Fluoro-3-({[1-(4-fluorophenyl)ethoxy]carbonyl}amino)thiophen-2-yl]-[1,1'-biphenyl]-4-yl}cyclopropanecarboxylic acid (Compound No. I-112)

[Chemical Formula 143]

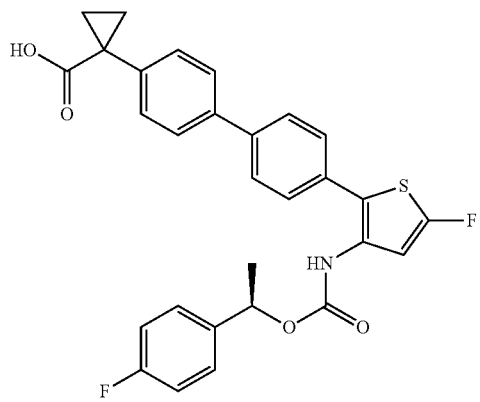

To a solution of 195.7 mg (0.357 mmol) of (R)-1-{4'-[5-fluoro-3-({[1-(4-fluorophenyl)ethoxy]carbonyl}amino)thiophen-2-yl]-[1,1'-biphenyl]-4-yl}cyclopropanecarboxylic acid ethyl ester synthesized in analogy to Example 33 in isopropyl alcohol (4 ml) were added 2.0 ml (8.0 mmol) of a 4N aqueous sodium hydroxide solution and 2 ml of isopropyl alcohol while stirring, and the mixture was stirred at room temperature for 12 hours. Then, 0.5 ml of tetrahydrofuran was added, and the mixture was stirred at room temperature for 32 hours. After completion of the reaction, the reaction mixture was neutralized by adding 4.0 ml of 2N hydrochloric acid under ice cooling, and subsequently water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=50:50 to 0:100 (V/V)), and the fractions containing the desired compound were concentrated under reduced pressure. To the residue was added ethanol-water, the mixture was sonicated, and subsequently the precipitated solid was collected by filtration and dried to obtain 138 mg (0.27 mmol, yield 76%) of the title compound as a white solid.

Mass spectrum (EI, m/z): 519 [M]$^+$.
$^1$H-NMR spectrum (400 MHz, DMSO-$d_6$) δ: 12.36 (1H, brs), 9.39 (1H, brs), 7.73-7.67 (2H, m), 7.64-7.59 (2H, m), 7.55-7.50 (2H, m), 7.49-7.31 (4H, m), 7.24-7.15 (2H, m), 6.81 (1H, d, J=1.9 Hz), 5.73 (1H, q, J=6.3 Hz), 1.54-1.39 (3H, m), 1.48 (2H, dd, J=6.7, 3.8 Hz), 1.18 (2H, dd, J=6.8, 3.9 Hz).

Example 35

(R)-1-{4'-[3-({[1-(2-Chlorophenyl)ethoxy]carbonyl}amino)-5-fluorothiophen-2-yl]-[1,1'-biphenyl]-4-yl}cyclopropanecarboxylic acid ethyl ester (Compound No. I-118)

[Chemical Formula 144]

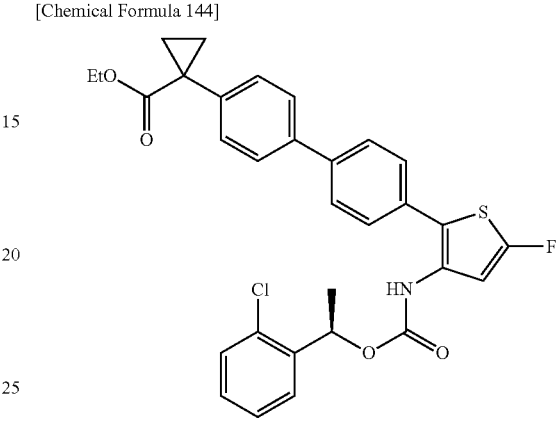

To 480.5 mg (1.171 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene (4 ml). The mixture was subjected to azeotropic dehydration treatment, and subsequently the atmosphere was replaced with argon. Then, 8 ml of dehydrated toluene, 0.196 mL (1.41 mmol) of triethylamine and 0.302 ml (1.40 mmol) of diphenylphosphoryl azide were added, and the mixture was stirred at room temperature for one hour. Then, 0.233 mL (1.75 mmol) of (R)-1-(2-chlorophenyl)ethanol (Shanghai AoBo Biopharm) was added, and the mixture was heated and stirred at 70° C. for 2 hours. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=99:1 to 74:26 (V/V)), and the fractions containing the desired compound were concentrated under reduced pressure to obtain 584 mg (0.873 mmol (purity 84% by weight), yield 75%) of the title compound as a colorless foam.

Mass spectrum (EI, m/z): 563 [M]$^+$.
$^1$H-NMR spectrum (400 MHz, DMSO-$d_6$, 75° C.) δ: 9.10 (1H, brs), 7.70-7.27 (12H, m), 6.76 (1H, d, J=2.6 Hz), 6.00 (1H, q, J=6.5 Hz), 4.06 (2H, q, J=7.1 Hz), 1.52 (2H, dd, J=7.0, 4.0 Hz), 1.47 (3H, d, J=6.7 Hz), 1.22 (2H, dd, J=7.0, 4.1 Hz), 1.13 (3H, t, J=7.1 Hz).

Example 36

(R)-1-{4'-[3-({[1-(2-Chlorophenyl)ethoxy]carbonyl}amino)-5-fluorothiophen-2-yl]-[1,1'-biphenyl]-4-yl}cyclopropanecarboxylic acid (Compound No. I-122)

[Chemical Formula 145]

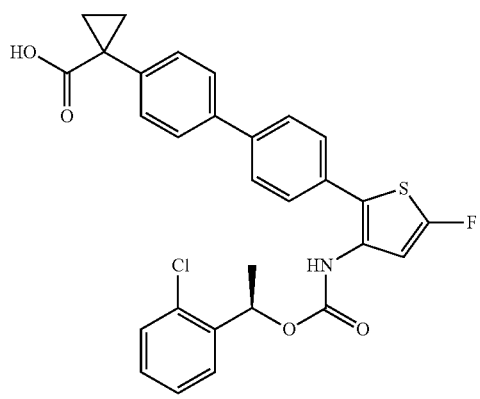

To a solution of 580.0 mg (0.867 mmol (purity 84% by weight)) of (R)-1-{4'-[3-({[1-(2-chlorophenyl)ethoxy]carbonyl}amino)-5-fluorothiophen-2-yl]-[1,1'-biphenyl]-4-yl}cyclopropanecarboxylic acid ethyl ester synthesized in Example 35 in isopropyl alcohol (6 ml) was added 3.0 ml (12 mmol) of a 4N aqueous sodium hydroxide solution while stirring, and the mixture was stirred at room temperature for 7 hours. Because the mixture was changed into a suspension, further isopropyl alcohol (4 ml) and 2.0 ml (8.0 mmol) of a 4N aqueous sodium hydroxide solution were added, and the mixture was heated and stirred at 40° C. for 9 hours. After completion of the reaction, the reaction mixture was neutralized with 2N hydrochloric acid (10.0 ml) under ice cooling, and subsequently the precipitated solid was collected by filtration. To the resulting solid were added ethyl acetate and methylene chloride, insoluble matter was filtered, and the filtrate was concentrated under reduced pressure. The resulting residue was subjected to silica gel column chromatography (elution solvent; hexane:ethyl acetate=53:47 to 0:100 (V/V)), and the fractions containing the desired compound were concentrated under reduced pressure. To the residue was added ethanol-water, the mixture was sonicated, and subsequently the precipitated solid was collected by filtration and dried to obtain 365 mg (0.682 mmol, yield 79%) of the title compound as a white solid.

Mass spectrum (EI, m/z): 535 [M]$^+$.

$^1$H-NMR spectrum (400 MHz, DMSO-d$_6$, 75° C.) δ: 12.35 (1H, brs), 9.50 (1H, brs), 7.74-7.30 (12H, m), 6.82 (1H, d, J=2.5 Hz), 5.98 (1H, q, J=6.7 Hz), 1.58-1.38 (5H, m), 1.17 (2H, dd, J=6.6, 3.8 Hz).

Example 37

(R)-1-{4'-[3-({[1-(4-Chlorophenyl)ethoxy]carbonyl}amino)-5-fluorothiophen-2-yl]-[1,1'-biphenyl]-4-yl}cyclopropanecarboxylic acid ethyl ester (Compound No. I-124)

[Chemical Formula 146]

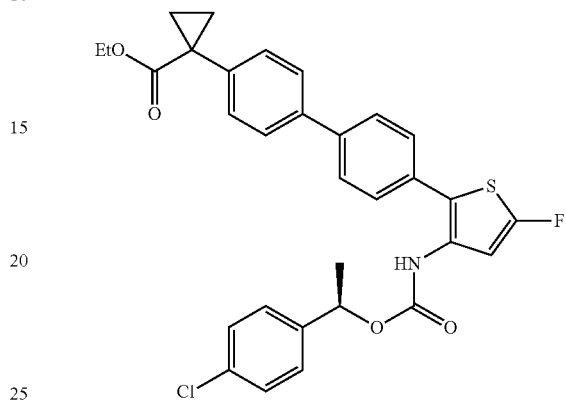

To 202.5 mg (0.493 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene. The mixture was subjected to azeotropic dehydration treatment, and subsequently the atmosphere was replaced with argon. Then, 4 ml of dehydrated toluene and 0.10 ml (0.72 mmol) of triethylamine were added, and the mixture was stirred at room temperature for 5 minutes. Then, 0.12 ml (0.56 mmol) of diphenylphosphoryl azide was added, and the mixture was stirred at room temperature for one hour. Then, 0.080 ml (0.59 mmol) of (R)-1-(4-chlorophenyl)ethanol (Aldrich) was added, and the mixture was heated and stirred at 70° C. for one hour. After completion of the reaction, the mixture was cooled, poured into a saturated aqueous ammonium chloride solution, and extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=86:14 to 59:41 (V/V)), and the fractions containing the desired compound were concentrated under reduced pressure to obtain 584 mg (0.873 mmol (purity 84% by weight), yield 75%) of the title compound as a colorless foam.

Mass spectrum (EI, m/z): 563 [M]$^+$.

$^1$H-NMR spectrum (400 MHz, DMSO-d$_6$) δ: 9.42 (1H, brs), 7.71-7.68 (2H, m), 7.65-7.62 (2H, m), 7.53-7.50 (2H, m), 7.49-7.26 (6H, m), 6.81 (1H, d, J=2.3 Hz), 5.71 (1H, m), 4.05 (2H, q, J=7.1 Hz), 1.56-1.35 (5H, m), 1.24 (2H, dd, J=7.0, 4.1 Hz), 1.11 (3H, t, J=7.1 Hz).

Example 38

(R)-1-{4'-[3-({[1-(4-Chlorophenyl)ethoxy]carbonyl}amino)-5-fluorothiophen-2-yl]-[1,1'-biphenyl]-4-yl}cyclopropanecarboxylic acid (Compound No. I-126)

[Chemical Formula 147]

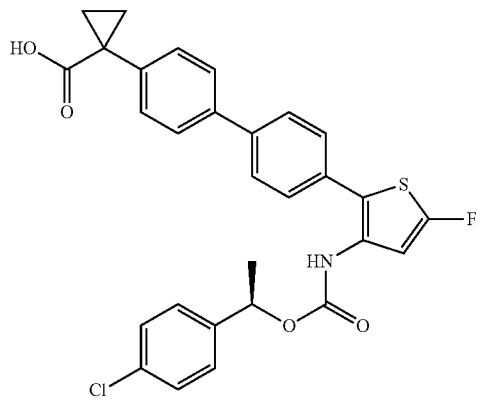

To a mixed solution of 215.4 mg (0.322 mmol (purity 84% by weight)) of (R)-1-{4'-[3-({[1-(4-chlorophenyl)ethoxy]carbonyl}amino)-5-fluorothiophen-2-yl]-[1,1'-biphenyl]-4-yl}cyclopropanecarboxylic acid ethyl ester synthesized in Example 37 in isopropyl alcohol (4 ml)-tetrahydrofuran (0.9 ml) was added 2.0 ml (8.0 mmol) of a 4N aqueous sodium hydroxide solution while stirring, and the mixture was stirred at room temperature for 14.5 hours. After completion of the reaction, the reaction mixture was neutralized by adding 8.0 ml of 1N hydrochloric acid, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane: ethyl acetate=60:40 to 0:100 (V/V)), and the fractions containing the desired compound were concentrated under reduced pressure. To the residue was added ethanol-water, the mixture was sonicated, and subsequently the precipitated solid was collected by filtration and dried to obtain 133 mg (0.25 mmol, yield 78%) of the title compound as a pale red solid.

Mass spectrum (CI, m/z): 535 [M]$^+$.

$^1$H-NMR spectrum (400 MHz, DMSO-d$_6$, 75° C.) δ: 12.01 (1H, brs), 9.03 (1H, brs), 7.68-7.63 (2H, m), 7.61-7.57 (2H, m), 7.53-7.49 (2H, m), 7.44-7.32 (6H, m), 6.76 (1H, d, J=2.6 Hz), 5.72 (1H, q, J=6.6 Hz), 1.48 (2H, dd, J=6.8, 3.8 Hz), 1.45 (3H, d, J=6.5 Hz), 1.15 (2H, dd, J=6.9, 3.9 Hz).

Example 39

(R)-1-{4'-[5-Fluoro-3-({[1-(o-tolyl)ethoxy]carbonyl}amino)thiophen-2-yl]-[1,1'-biphenyl]-4-yl}cyclopropanecarboxylic acid ethyl ester (Compound No. I-132)

[Chemical Formula 148]

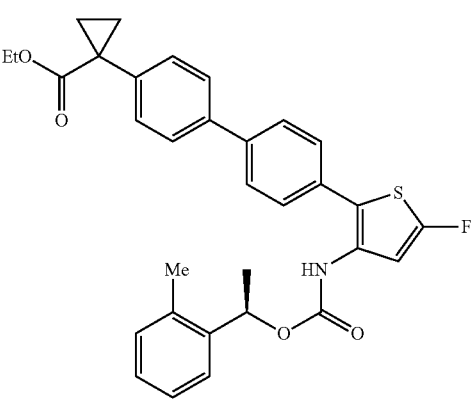

To a solution of 204 mg (0.50 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (4 ml) were added 0.10 ml (0.72 mmol) of triethylamine and 0.13 mL (0.62 mmol) of diphenylphosphoryl azide sequentially under a nitrogen atmosphere at room temperature, and the mixture was stirred at room temperature for 30 minutes. Then, 80 mg (0.59 mmol) of (R)-1-(o-tolyl)ethanol (Enamine Ltd) was added, and the mixture was heated and stirred at 70° C. for 2 hours. After completion of the reaction, to the reaction mixture was added a saturated aqueous ammonium chloride solution, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane: ethyl acetate=100:0 to 80:20 (V/V)), and the fractions containing the desired compound were concentrated under reduced pressure to obtain 194 mg (0.36 mmol, yield 72%) of the title compound as a white foam.

Mass spectrum (EI, m/z): 543 [M]$^+$.

$^1$H-NMR spectrum (400 MHz, DMSO-d$_6$, 75° C.) δ: 9.38 (1H, brs), 7.73-7.67 (2H, m), 7.66-7.61 (2H, m), 7.55-7.50 (2H, m), 7.47-7.30 (3H, m), 7.28-7.13 (3H, m), 6.80 (1H, d, J=2.4 Hz), 5.87 (1H, q, J=6.5 Hz), 4.05 (2H, q, J=7.1 Hz), 2.31 (3H, s), 1.52 (2H, dd, J=6.8, 4.1 Hz), 1.50-1.40 (3H, m), 1.24 (2H, dd, J=6.9, 4.1 Hz), 1.12 (3H, t, J=7.1 Hz).

Example 40

(R)-1-{4'-[5-Fluoro-3-({[1-(o-tolyl)ethoxy] carbonyl}amino)thiophen-2-yl]-[1,1'-biphenyl]-4-yl}cyclopropanecarboxylic acid (Compound No. I-136)

[Chemical Formula 149]

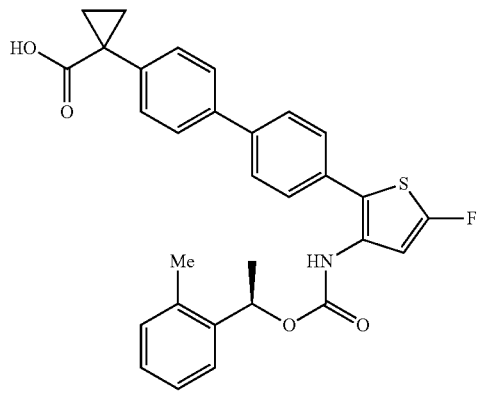

To a solution of 194 mg (0.36 mmol) of (R)-1-{4'-[5-fluoro-3-({[1-(o-tolyl)ethoxy]carbonyl}amino)thiophen-2-yl]-[1,1'-biphenyl]-4-yl}cyclopropanecarboxylic acid ethyl ester synthesized in analogy to Example 39 in isopropyl alcohol (4 ml) was added 1.5 ml (3.0 mmol) of a 2N aqueous sodium hydroxide solution, and the mixture was stirred at room temperature for 24 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=70:30 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 146 mg (0.28 mmol, yield 79%) of the title compound as a white solid.

Mass spectrum (EI, m/z): 515 [M]$^+$.

$^1$H-NMR spectrum (400 MHz, DMSO-$d_6$) δ: 12.36 (1H, brs), 9.38 (1H, brs), 7.72-7.66 (2H, m), 7.65-7.59 (2H, m), 7.56-7.49 (2H, m), 7.46-7.32 (3H, m), 7.29-7.13 (3H, m), 6.80 (1H, d, J=2.4 Hz), 5.87 (1H, q, J=6.6 Hz), 2.31 (3H, s), 1.50-1.40 (5H, m), 1.18 (2H, dd, J=6.8, 4.0 Hz).

Example 41

(R)-1-{4'-[3-({[1-(3,4-Difluorophenyl)ethoxy] carbonyl}amino)-5-fluorothiophen-2-yl]-[1,1'-biphenyl]-4-yl}cyclopropanecarboxylic acid ethyl ester (Compound No. I-146)

[Chemical Formula 150]

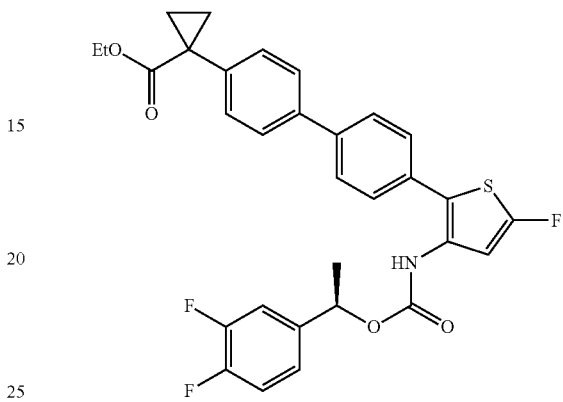

To 203.7 mg (0.496 mmol) of 2-{4'-[1-(ethoxycarbonyl) cyclopropyl]-[1,1'-biphenyl]-4-yl}-5-fluorothiophene-3-carboxylic acid synthesized in analogy to Reference Example 33 was added dehydrated toluene. The mixture was subjected to azeotropic dehydration treatment, and subsequently the atmosphere was replaced with argon. Then, 4 ml of dehydrated toluene and 0.110 ml (0.79 mmol) of triethylamine were added, and the mixture was stirred at room temperature for 5 minutes. Then, 0.13 mL (0.61 mmol) of diphenylphosphoryl azide was added, and the mixture was stirred at room temperature for one hour. Then, 99.3 mg (0.628 mmol) of (R)-1-(3,4-difluorophenyl)ethanol (Enamine Ltd) was added, and the mixture was heated and stirred at 70° C. for one hour. After completion of the reaction, the reaction mixture was cooled, poured into a saturated aqueous ammonium chloride solution, and extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 61:39 (V/V)), and the fractions containing the desired compound were concentrated under reduced pressure to obtain 202 mg (0.36 mmol, yield 72%) of the title compound as a white foam.

Mass spectrum (EI, m/z): 565 [M]$^+$.

$^1$H-NMR spectrum (400 MHz, DMSO-$d_6$, 75° C.) δ: 9.06 (1H, brs), 7.69-7.64 (2H, m), 7.62-7.58 (2H, m), 7.55-7.50 (2H, m), 7.44-7.31 (4H, m), 7.21-7.15 (1H, m), 6.77 (1H, d, J=2.8 Hz), 5.72 (1H, q, J=6.6 Hz), 4.06 (2H, q, J=7.1 Hz), 1.52 (2H, dd, J=6.8, 4.0 Hz), 1.46 (3H, d, J=6.7 Hz), 1.21 (2H, dd, J=7.0, 4.1 Hz), 1.12 (3H, t, J=7.1 Hz).

Example 42

(R)-1-{4'-[3-({[1-(3,4-Difluorophenyl)ethoxy]carbonyl}amino)-5-fluorothiophen-2-yl]-[1,1'-biphenyl]-4-yl}cyclopropanecarboxylic acid (Compound No. I-148)

[Chemical Formula 151]

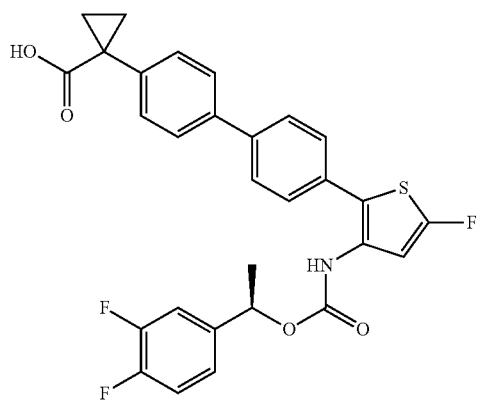

To a solution of 198.5 mg (0.351 mmol) of (R)-1-{4'-[3-({[1-(3,4-difluorophenyl)ethoxy]carbonyl}amino)-5-fluorothiophen-2-yl]-[1,1'-biphenyl]-4-yl}cyclopropanecarboxylic acid ethyl ester synthesized in analogy to Example 41 in isopropyl alcohol (3 ml) was added 1.8 ml (7.2 mmol) of a 4N aqueous sodium hydroxide solution, and the mixture was stirred at room temperature for 16 hours. After completion of the reaction, the reaction mixture was neutralized by adding 7.2 ml of 1N hydrochloric acid thereto, and extracted with ethyl acetate. The organic layer was dried over anhydrous magnesium sulfate and concentrated under reduced pressure. The resulting residue was subjected to silica gel column chromatography (elution solvent; hexane:ethyl acetate=60:40 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 122.5 mg (0.23 mmol, yield 65%) of the title compound as a white solid.

Mass spectrum (EI, m/z): 537 [M]$^+$.

$^1$H-NMR spectrum (400 MHz, DMSO-d$_6$, 75° C.) δ: 9.06 (1H, brs), 7.68-7.63 (2H, m), 7.61-7.56 (2H, m), 7.54-7.49 (2H, m), 7.44-7.31 (4H, m), 7.22-7.15 (1H, m), 6.77 (1H, d, J=2.8 Hz), 5.72 (1H, q, J=6.5 Hz), 1.51-1.42 (5H, m), 1.15 (2H, dd, J=6.9, 3.9 Hz).

Example 43

(R)-1-{4'-[3-({[1-(2,4-Difluorophenyl)ethoxy]carbonyl}amino)-5-fluorothiophen-2-yl]-[1,1'-biphenyl]-4-yl}cyclopropanecarboxylic acid ethyl ester (Compound No. I-138)

[Chemical Formula 152]

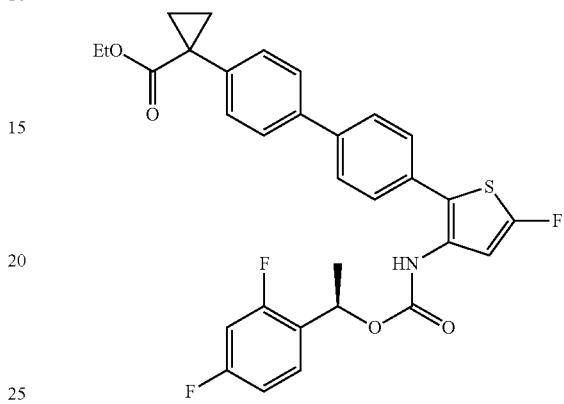

To 203.1 mg (0.496 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene. The mixture was subjected to azeotropic dehydration treatment, and subsequently the atmosphere was replaced with argon. Then, 4 ml of dehydrated toluene and 0.11 mL (0.79 mmol) of triethylamine were added, and the mixture was stirred at room temperature for 5 minutes. Then, 0.13 mL (0.61 mmol) of diphenylphosphoryl azide was added, and the mixture was stirred at room temperature for one hour. Then, 98.7 mg (0.624 mmol) of (R)-1-(2,4-difluorophenyl)ethanol (Enamine Ltd) was added, and the mixture was heated and stirred at 70° C. for one hour. After completion of the reaction, the reaction mixture was cooled and poured into a saturated aqueous ammonium chloride solution, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=84:16 to 63:37 (V/V)), and the fractions containing the desired compound were concentrated under reduced pressure to obtain 271 mg (0.41 mmol (purity 86% by weight), yield 83%) of the title compound as a white foam.

Mass spectrum (EI, m/z): 565 [M]$^+$.

$^1$H-NMR spectrum (400 MHz, DMSO-d$_6$) δ: 9.45 (1H, brs), 7.74-7.68 (2H, m), 7.66-7.61 (2H, m), 7.57-7.40 (4H, m), 7.37-7.31 (1H, m), 7.30-7.22 (1H, m), 7.18-7.10 (1H, m), 6.81 (1H, d, J=2.3 Hz), 5.89 (1H, q, J=6.4 Hz), 4.05 (2H, q, J=7.1 Hz), 1.58-1.43 (5H, m), 1.24 (2H, dd, J=7.1, 4.1 Hz), 1.11 (3H, t, J=7.1 Hz).

Example 44

(R)-1-{4'-[3-({[1-(2,4-Difluorophenyl)ethoxy]carbonyl}amino)-5-fluorothiophen-2-yl]-[1,1'-biphenyl]-4-yl}cyclopropanecarboxylic acid (Compound No. I-140)

[Chemical Formula 153]

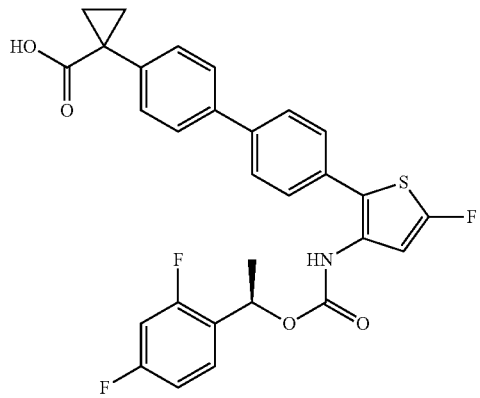

To a solution of 268.2 mg (0.405 mmol (purity 86% by weight)) of (R)-1-{4'-[3-({[1-(2,4-difluorophenyl)ethoxy]carbonyl}amino)-5-fluorothiophen-2-yl]-[1,1'-biphenyl]-4-yl}cyclopropanecarboxylic acid ethyl ester synthesized in Example 43 in isopropyl alcohol (3 ml) was added 2.37 mL (9.48 mmol) of a 4N aqueous sodium hydroxide solution, and the mixture was stirred at room temperature for 68 hours. After completion of the reaction, the reaction mixture was neutralized by adding 1N hydrochloric acid (9.5 ml) thereto, and extracted with ethyl acetate. The organic layer was dried over anhydrous magnesium sulfate and concentrated under reduced pressure. The resulting residue was subjected to silica gel column chromatography (elution solvent; hexane:ethyl acetate=60:40 to 0:100 (V/V)), and the fractions containing the desired compound were concentrated under reduced pressure. The resulting residue was dissolved in a small amount of ethanol, water was added to precipitate a solid, and the solid was collected by filtration and dried under reduced pressure to obtain 148 mg (0.28 mmol, yield 69%) of the title compound as a white solid.

Mass spectrum (EI, m/z): 537 [M]$^+$.

$^1$H-NMR spectrum (400 MHz, DMSO-d$_6$, 75° C.) δ: 11.91 (1H, brs), 9.08 (1H, brs), 7.70-7.64 (2H, m), 7.62-7.57 (2H, m), 7.57-7.52 (2H, m), 7.45-7.40 (2H, m), 7.36-7.23 (4H, m), 5.73 (1H, q, J=6.6 Hz), 1.52-1.43 (5H, m), 1.16 (2H, dd, J=6.9, 3.9 Hz).

Example 45

(R)-1-{4'-[3-({[1-(2-Cloro-4-fluorophenyl)ethoxy]carbonyl}amino)-5-fluorothiophen-2-yl]-[1,1'-biphenyl]-4-yl}cyclopropanecarboxylic acid ethyl ester (Compound No. I-150)

[Chemical Formula 154]

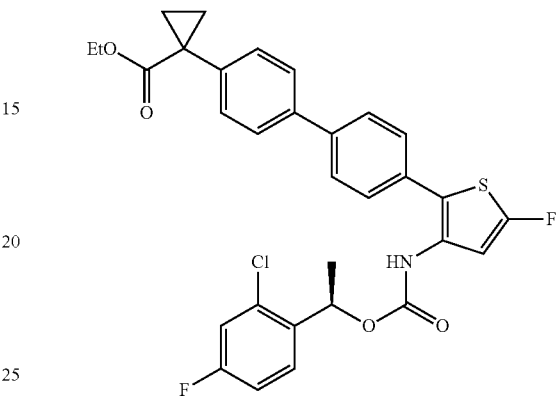

To 201.9 mg (0.492 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene (2 ml). The mixture was subjected to azeotropic dehydration treatment, and subsequently the atmosphere was replaced with argon. Then, 4 ml of dehydrated toluene, 0.082 ml (0.59 mmol) of triethylamine and 0.127 ml (0.590 mmol) of diphenylphosphoryl azide were added, and the mixture was stirred at room temperature for one hour. Then, 137.3 mg (0.747 mmol) of (R)-1-(2-chloro-4-fluorophenyl)ethanol (Enamine Ltd) was added, and the mixture was heated and stirred at 70° C. for 2 hours. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=100:0 to 76:24 (V/V)), and the fractions containing the desired compound were concentrated under reduced pressure to obtain 234 mg (0.402 mmol, yield 82%) of the title compound as a colorless foam.

Mass spectrum (EI, m/z): 581 [M]$^+$.

$^1$H-NMR spectrum (400 MHz, DMSO-d$_6$, 75° C.) δ: 9.10 (1H, brs), 7.70-7.66 (2H, m), 7.63-7.59 (2H, m), 7.55-7.48 (3H, m), 7.44-7.39 (2H, m), 7.35 (1H, dd, J=8.8, 2.6 Hz), 7.22 (1H, td, J=8.6, 2.6 Hz), 6.76 (1H, d, J=2.6 Hz), 5.96 (1H, q, J=6.5 Hz), 4.06 (2H, q, J=7.1 Hz), 1.52 (2H, dd, J=7.0, 4.0 Hz), 1.46 (3H, d, J=6.5 Hz), 1.21 (2H, dd, J=7.1, 4.1 Hz), 1.13 (3H, t, J=7.1 Hz).

Example 46

(R)-1-{4'-[3-({[1-(2-Chloro-4-fluorophenyl)ethoxy]carbonyl}amino)-5-fluorothiophen-2-yl]-[1,1'-biphenyl]-4-yl}cyclopropanecarboxylic acid (Compound No. I-152)

[Chemical Formula 155]

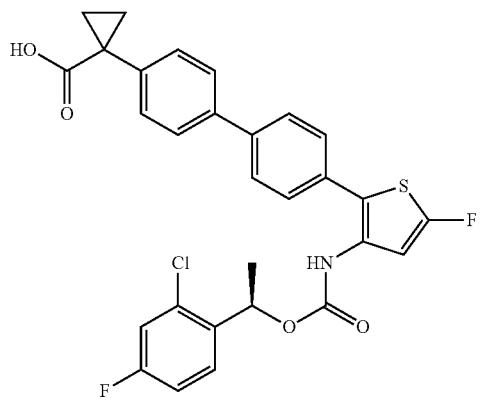

To a solution of 230.4 mg (0.396 mmol) of (R)-1-{4'-[3-({[1-(2-chloro-4-fluorophenyl)ethoxy]carbonyl}amino)-5-fluorothiophen-2-yl]-[1,1'-biphenyl]-4-yl}cyclopropanecarboxylic acid ethyl ester synthesized in analogy to Example 45 in isopropyl alcohol (4 ml) was added 2.0 ml (8.0 mmol) of a 4N aqueous sodium hydroxide solution while stirring, and the mixture was stirred at room temperature for 3 days. After completion of the reaction, the resulting mixture was neutralized by adding 4.0 ml of 2N hydrochloric acid under ice cooling. Further, water was then added to precipitate a solid and the solid was collected by filtration. The solid was dried under reduced pressure and dissolved in ethyl acetate, and the mixture was concentrated again under reduced pressure. The resulting residue was subjected to silica gel column chromatography (elution solvent; hexane:ethyl acetate=68:32 to 0:100 (V/V)), and the fractions containing the desired compound were concentrated under reduced pressure. To the resulting residue was added ethanol-water, and the mixture was sonicated, and subsequently the precipitated solid was collected by filtration and dried to obtain 131 mg (0.236 mmol, yield 60%) of the title compound as a white solid.

Mass spectrum (EI, m/z): 553 [M]$^+$.

$^1$H-NMR spectrum (400 MHz, DMSO-d$_6$, 75° C.) δ: 11.98 (1H, brs), 9.11 (1H, brs), 7.69-7.64 (2H, m), 7.62-7.57 (2H, m), 7.55-7.48 (3H, m), 7.44-7.39 (2H, m), 7.35 (1H, dd, J=8.8, 2.6 Hz), 7.22 (1H, td, J=8.5, 2.6 Hz), 6.76 (1H, d, J=2.8 Hz), 5.96 (1H, q, J=6.5 Hz), 1.49 (2H, dd, J=6.8, 3.9 Hz), 1.46 (3H, d, J=6.5 Hz), 1.16 (2H, dd, J=6.9, 4.0 Hz).

Example 47

(RS)-1-{4'-[3-({[1-(4-Chloro-2-fluorophenyl)ethoxy]carbonyl}amino)-5-fluorothiophen-2-yl]-[1,1'-biphenyl]-4-yl}cyclopropanecarboxylic acid ethyl ester (Compound No. I-157)

[Chemical Formula 156]

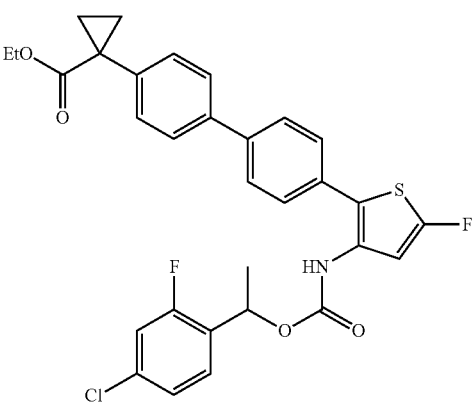

To a solution of 200 mg (0.49 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (4 ml) were added 0.10 ml (0.72 mmol) of triethylamine and 0.13 mL (0.61 mmol) of diphenylphosphoryl azide sequentially under a nitrogen atmosphere at room temperature, and the mixture was stirred at room temperature for 30 minutes. Then, 100 mg (0.57 mmol) of (RS)-1-(4-chloro-2-fluorophenyl)ethanol was added, and the mixture was heated and stirred at 70° C. for 3 hours. After completion of the reaction, to the reaction mixture was added a saturated aqueous ammonium chloride solution, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=100:0 to 80:20 (V/V)), and the fractions containing the desired compound were concentrated under reduced pressure to obtain 206 mg (0.35 mmol, yield 72%) of the title compound as a colorless oil.

Mass spectrum (CI, m/z): 581 [M]$^+$.

$^1$H-NMR spectrum (400 MHz, CDCl$_3$) δ: 7.69-7.64 (2H, m), 7.58-7.54 (2H, m), 7.47-7.42 (4H, m), 7.42-7.07 (4H, m), 6.80 (1H, brs), 6.06 (1H, q, J=6.7 Hz), 4.13 (2H, q, J=7.1 Hz), 1.65 (2H, dd, J=7.0, 4.0 Hz), 1.57 (3H, d, J=6.7 Hz), 1.23 (2H, dd, J=7.0, 4.0 Hz), 1.20 (3H, t, J=7.1 Hz).

Example 48

(RS)-1-{4'-[3-({[1-(4-Chloro-2-fluorophenyl)ethoxy]carbonyl}amino)-5-fluorothiophen-2-yl]-[1,1'-biphenyl]-4-yl}cyclopropanecarboxylic acid (Compound No. I-159)

[Chemical Formula 157]

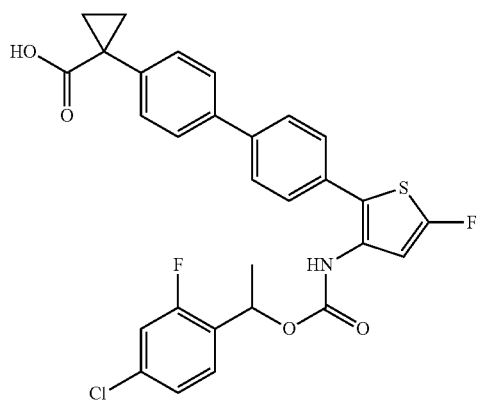

To a solution of 206 mg (0.35 mmol) of (RS)-1-{4'-[3-({[1-(4-chloro-2-fluorophenyl)ethoxy]carbonyl}amino)-5-fluorothiophen-2-yl]-[1,1'-biphenyl]-4-yl}cyclopropanecarboxylic acid ethyl ester synthesized in analogy to Example 47 in isopropyl alcohol (4 ml) was added 2.0 ml (4.0 mmol) of a 2N aqueous sodium hydroxide solution, and the mixture was stirred at room temperature for 26 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 109 mg (0.20 mmol, yield 56%) of the title compound as a white solid.

Mass spectrum (CI, m/z): 553 [M]$^+$.
$^1$H-NMR spectrum (400 MHz, DMSO-d$_6$) δ: 12.40 (1H, brs), 9.50 (1H, brs), 7.72-7.66 (2H, m), 7.64-7.59 (2H, m), 7.55-7.30 (7H, m), 6.81 (1H, d, J=2.4 Hz), 5.88 (1H, q, J=6.5 Hz), 1.53-1.44 (5H, m), 1.16 (2H, dd, J=6.6, 3.8 Hz).

Example 49

(RS)-1-{4'-[5-Fluoro-3-({[1-(2,4,5-trifluorophenyl)ethoxy]carbonyl}amino)thiophen-2-yl]-[1,1'-biphenyl]-4-yl}cyclopropanecarboxylic acid ethyl ester (Compound No. I-169)

[Chemical Formula 158]

To a solution of 208 mg (0.51 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (4 ml) were added 0.11 mL (0.75 mmol) of triethylamine and 0.13 mL (0.61 mmol) of diphenylphosphoryl azide sequentially under a nitrogen atmosphere at room temperature, and the mixture was stirred at room temperature for 30 minutes. Then, 110 mg (0.63 mmol) of (RS)-1-(2,4,5-trifluorophenyl)ethanol synthesized in analogy to Reference Example 47 was added, and the mixture was heated and stirred at 70° C. for 2 hours. After completion of the reaction, to the reaction mixture was added a saturated aqueous ammonium chloride solution, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 277 mg (0.39 mmol, purity 83% by weight), yield 77%) of the title compound as a colorless oil.

Mass spectrum (EI, m/z): 583 [M]$^+$.
$^1$H-NMR spectrum (400 MHz, CDCl$_3$) δ: 7.71-7.65 (2H, m), 7.59-7.54 (2H, m), 7.49-7.42 (4H, m), 7.23-7.08 (2H, m), 6.93 (1H, td, J=9.9, 6.7 Hz), 6.81 (1H, brs), 6.04 (1H, q, J=6.6 Hz), 4.13 (2H, q, J=7.1 Hz), 1.65 (2H, dd, J=6.9, 3.9 Hz), 1.55 (3H, d, J=6.7 Hz), 1.23 (2H, dd, J=7.0, 4.0 Hz), 1.20 (3H, t, J=7.1 Hz).

Example 50

(RS)-1-{4'-[5-Fluoro-3-({[1-(2,4,5-trifluorophenyl)ethoxy]carbonyl}amino)thiophen-2-yl]-[1,1'-biphenyl]-4-yl}cyclopropanecarboxylic acid (Compound No. I-171)

[Chemical Formula 159]

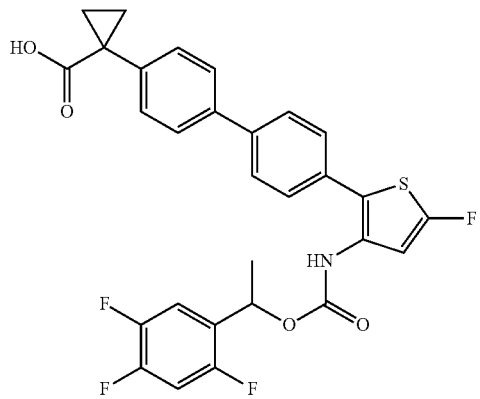

To a solution of 277 mg (0.39 mmol (purity 83% by weight)) of (RS)-1-{4'-[5-fluoro-3-({[1-(2,4,5-trifluorophenyl)ethoxy]carbonyl}amino)thiophen-2-yl]-[1,1'-biphenyl]-4-yl}cyclopropanecarboxylic acid ethyl ester synthesized in Example 49 in isopropyl alcohol (4 ml) was added 2.0 ml (4.0 mmol) of a 2N aqueous sodium hydroxide solution, and the mixture was stirred at room temperature for 67 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 43 mg (0.077 mmol, yield 20%) of the title compound as a white solid.

Mass spectrum (EI, m/z): 555 [M]$^+$.

$^1$H-NMR spectrum (400 MHz, DMSO-$d_6$) δ: 12.41 (1H, brs), 9.47 (1H, brs), 7.72-7.66 (2H, m), 7.64-7.50 (6H, m), 7.45-7.39 (2H, m), 6.84 (1H, d, J=2.3 Hz), 5.87 (1H, q, J=6.2 Hz), 1.56-1.40 (5H, m), 1.16-1.10 (2H, m).

Example 51

(R)-1-[4'-(5-Chloro-3-{[(1-phenylethoxy)carbonyl]amino}thiophen-2-yl)-2'-methoxy-[1,1'-biphenyl]-4-yl]cyclopropanecarboxylic acid ethyl ester (Compound No. I-346)

[Chemical Formula 160]

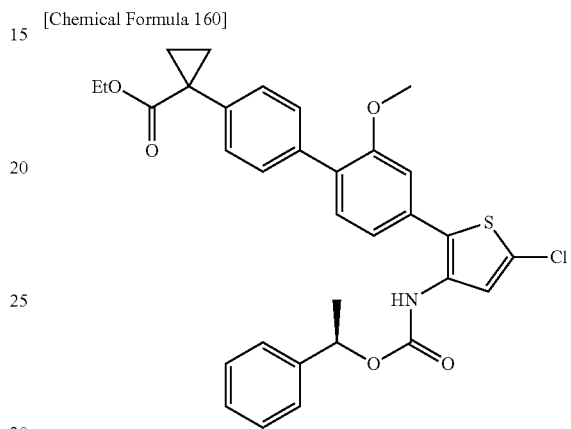

To a solution of 2.0 g (4.4 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 0.80 g (6.6 mmol) of (R)-1-phenylethanol (Tokyo Chemical Industry Co., Ltd.) and 1.2 ml (15 mmol) of pyridine in toluene (20 ml) was added 2.4 g (5.6 mmol) of [bis(trifluoroacetoxy)iodo]benzene under a nitrogen atmosphere at room temperature, and the mixture was heated and stirred at 60° C. for 1.5 hours. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 1.46 g (4.0 mmol (purity 72% by weight), yield 42%) of the title compound as an orange oil.

Mass spectrum (CI, m/z): 575 [M]$^+$.

$^1$H-NMR spectrum (400 MHz, DMSO-$d_6$) δ: 9.39 (1H, brs), 7.40-7.26 (10H, m), 7.23-7.16 (2H, m), 7.10 (1H, dd, J=7.8, 1.6 Hz), 5.75 (1H, q, J=6.4 Hz), 4.06 (2H, q, J=7.1 Hz), 3.73 (3H, s), 1.56-1.41 (5H, m), 1.23 (2H, dd, J=7.0, 4.0 Hz), 1.13 (3H, t, J=7.0 Hz).

Example 52

(R)-1-[4'-(5-Chloro-3-{[(1-phenylethoxy)carbonyl]amino}thiophen-2-yl)-2'-methoxy-[1,1'-biphenyl]-4-yl]cyclopropanecarboxylic acid (Compound No. I-350)

[Chemical Formula 161]

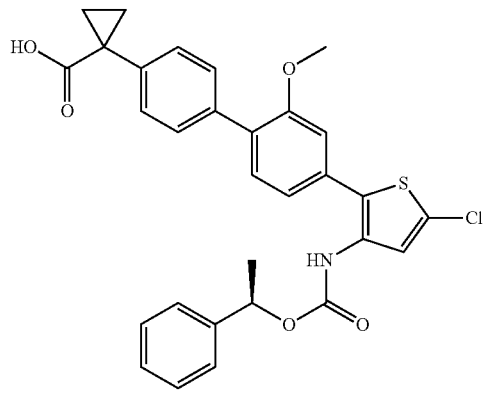

To a solution of 1.46 g (4.0 mmol (purity 72% by weight)) of (R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid ethyl ester synthesized in Example 51 in isopropyl alcohol (30 ml) was added 8.0 ml (16.0 mmol) of a 2N aqueous sodium hydroxide solution, and the mixture was stirred at room temperature for 110 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 588 mg (1.07 mmol, yield 58%) of the title compound as a pale red solid.

Mass spectrum (DUIS⁻, m/z): 546 [M−1]⁻

$^1$H-NMR spectrum (400 MHz, DMSO-$d_6$) δ: 12.34 (1H, brs), 9.40 (1H, brs), 7.45-7.25 (10H, m), 7.21-7.16 (2H, m), 7.09 (1H, dd, J=7.9, 1.6 Hz), 5.75 (1H, q, J=6.4 Hz), 3.73 (3H, s), 1.54-1.41 (5H, m), 1.18-1.12 (2H, m).

Example 53

(R)-1-{4'-[5-Chloro-3-({[1-(2-fluorophenyl)ethoxy]carbonyl}amino)thiophen-2-yl]-2'-methoxy-[1,1'-biphenyl]-4-yl}cyclopropanecarboxylic acid ethyl ester (Compound No. I-352)

[Chemical Formula 162]

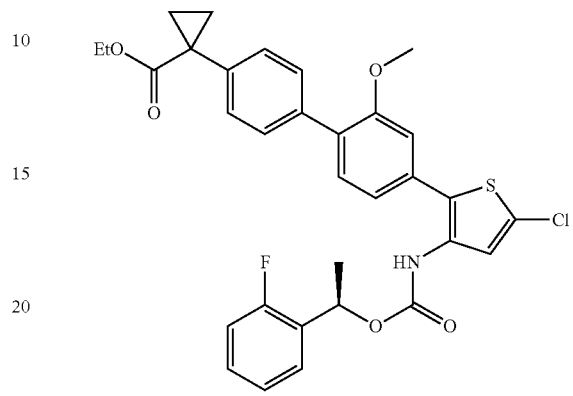

To a solution of 103 mg (0.23 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 41 mg (0.29 mmol) of (R)-1-(2-fluorophenyl)ethanol (Apollo) and 0.080 ml (0.99 mmol) of pyridine in toluene (4 ml) was added 120 mg (0.28 mmol) of [bis(trifluoroacetoxy)iodo]benzene under a nitrogen atmosphere at room temperature, and the mixture was heated and stirred at 80° C. for 1.5 hours. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 98 mg (0.16 mmol, yield 73%) of the title compound as an orange foam.

Mass spectrum (EI, m/z): 593 [M]⁺.

$^1$H-NMR spectrum (400 MHz, DMSO-$d_6$) δ: 9.47 (1H, brs), 7.48-7.31 (7H, m), 7.24-7.16 (4H, m), 7.13-7.07 (1H, m), 5.95 (1H, q, J=6.4 Hz), 4.06 (2H, q, J=7.1 Hz), 3.75 (3H, s), 1.54-1.43 (5H, m), 1.23 (2H, dd, J=7.0, 4.1 Hz), 1.13 (3H, t, J=7.1 Hz).

Example 54

(R)-1-{4'-[5-Chloro-3-({[1-(2-fluorophenyl)ethoxy]carbonyl}amino)thiophen-2-yl]-2'-methoxy-[1,1'-biphenyl]-4-yl}cyclopropanecarboxylic acid (Compound No. I-354)

[Chemical Formula 163]

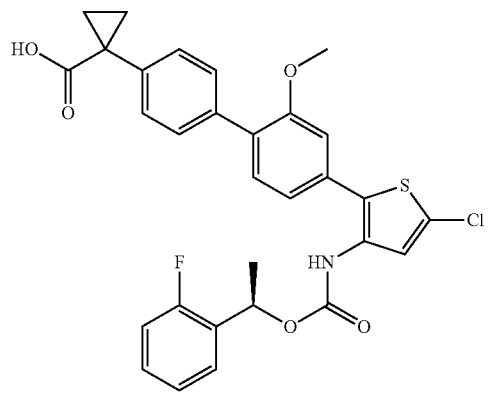

To a solution of 98 mg (0.16 mmol) of (R)-1-{4'-[5-chloro-3-({[1-(2-fluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 53 in isopropyl alcohol (4 ml) was added 0.80 ml (1.6 mmol) of a 2N aqueous sodium hydroxide solution, and the mixture was stirred at room temperature for 66 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane: ethyl acetate=80:20 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 53 mg (0.093 mmol, yield 57%) of the title compound as a white solid.

Mass spectrum (EI, m/z): 565 [M]+.

$^1$H-NMR spectrum (400 MHz, DMSO-d$_6$) δ: 12.38 (1H, brs), 9.47 (1H, brs), 7.52-7.30 (7H, m), 7.25-7.15 (4H, m), 7.09 (1H, dd, J=7.8, 1.6 Hz), 5.95 (1H, q, J=6.5 Hz), 3.75 (3H, s), 1.58-1.41 (5H, m), 1.17-1.09 (2H, m).

Example 55

(R)-1-{4'-[5-Chloro-3-({[1-(3-fluorophenyl)ethoxy]carbonyl}amino)thiophen-2-yl]-2'-methoxy-[1,1'-biphenyl]-4-yl}cyclopropanecarboxylic acid ethyl ester (Compound No. I-356)

[Chemical Formula 164]

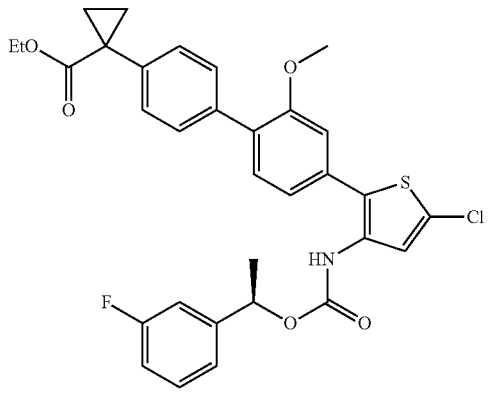

To a solution of 100 mg (0.22 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.18 ml (2.2 mmol) of pyridine in toluene (2 ml) was added 113 mg (0.26 mmol) of [bis(trifluoroacetoxy)iodo]benzene under an argon atmosphere, and the mixture was stirred at room temperature for 30 minutes. Then, 37 mg (0.26 mmol) of (R)-1-(3-fluorophenyl)ethanol (Enamine Ltd) was added under an argon atmosphere at room temperature, and the mixture was heated and stirred at 70° C. for 3 hours. After completion of the reaction, to the reaction mixture were added ethyl acetate and water to separate the layers. The resulting organic layer was washed with saturated brine, subsequently dried over anhydrous magnesium sulfate, and concentrated under reduced pressure. The resulting residue was subjected to silica gel column chromatography (elution solvent; hexane: ethyl acetate=80:20 to 30:70 (V/V)), and the fractions containing the desired compound were concentrated under reduced pressure to obtain 91 mg (0.15 mmol, yield 70%) of the title compound as a pale yellow oil.

Mass spectrum (EI, m/z): 593 [M]+.

$^1$H-NMR spectrum (400 MHz, CDCl$_3$) δ: 7.57-7.46 (3H, m), 7.44-7.38 (3H, m), 7.31 (1H, td, J=8.0, 5.9 Hz), 7.16-7.10 (1H, m), 7.09-6.93 (4H, m), 6.81 (I H, brs), 5.86 (1H, q, J=6.6 Hz), 4.13 (2H, q, J=7.1 Hz), 3.80 (3H, s), 1.63 (2H, dd, J=6.9, 3.9 Hz), 1.56 (3H, d, J=6.8 Hz), 1.24 (2H, dd, J=7.1, 4.1 Hz), 1.20 (3H, t, J=7.1 Hz).

Example 56

(R)-1-{4'-[5-Chloro-3-({[1-(3-fluorophenyl)ethoxy]carbonyl}amino)thiophen-2-yl]-2'-methoxy-[1,1'-biphenyl]-4-yl}cyclopropanecarboxylic acid (Compound No. I-358)

[Chemical Formula 165]

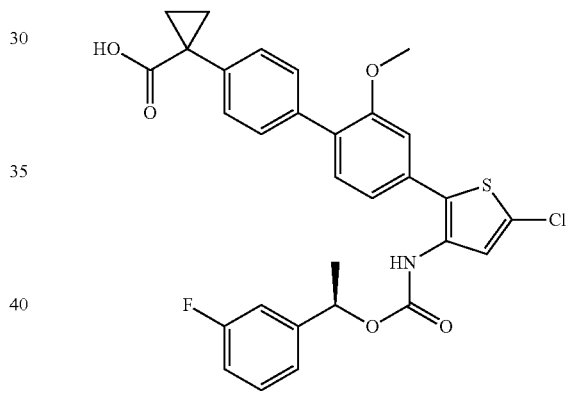

To a mixed solution of 86 mg (0.15 mmol) of (R)-1-{4'-[5-chloro-3-({[1-(3-fluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 55 in isopropyl alcohol (2 ml)-tetrahydrofuran (0.3 ml) was added 1.0 ml (2.0 mmol) of a 2N aqueous sodium hydroxide solution, and the mixture was stirred at room temperature for 16 hours. Further, 1.0 ml (2.0 mmol) of a 2N aqueous sodium hydroxide solution was added, and the mixture was stirred at room temperature for 6 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 20:80 (V/V)), and the fractions containing the desired compound were concentrated under reduced pressure to obtain 52 mg (0.092 mmol, yield 64%) of the title compound as a white solid.

Mass spectrum (DUIS$^-$, m/z): 564 [M-1]$^-$.

¹H-NMR spectrum (400 MHz, DMSO-d₆) δ: 12.33 (1H, brs), 9.47 (1H, brs), 7.59-7.44 (1H, m), 7.44-7.39 (1H, m), 7.39-7.31 (5H, m), 7.33 (1H, d, J=7.8 Hz), 7.30-7.21 (1H, m), 7.20-7.15 (1H, m), 7.15-7.06 (1H, m), 7.09 (1H, dd, J=7.8, 1.6 Hz), 5.91 (1H, q, J=6.6 Hz), 3.75 (3H, s), 1.55-1.42 (3H, m), 1.47 (2H, dd, J=6.7, 3.8 Hz), 1.21-1.13 (2H, m).

Example 57

(R)-1-{4'-[5-Chloro-3-({[1-(4-fluorophenyl)ethoxy]carbonyl}amino)thiophen-2-yl]-2'-methoxy-[1,1'-biphenyl]-4-yl}cyclopropanecarboxylic acid ethyl ester (Compound No. I-360)

[Chemical Formula 166]

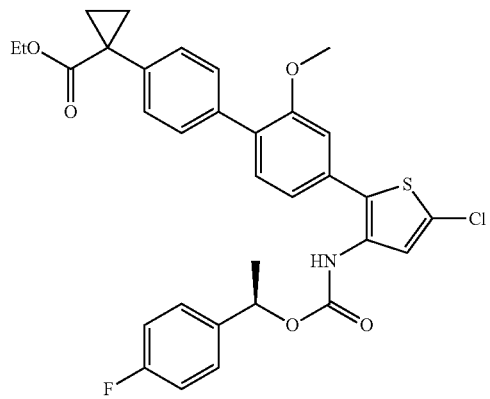

To a solution of 150 mg (0.33 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.30 ml (3.7 mmol) of pyridine in toluene (2 ml) was added 187 mg (0.44 mmol) of [bis(trifluoroacetoxy)iodo]benzene under an argon atmosphere, and the mixture was stirred at room temperature for 30 minutes. Then, 55 mg (0.39 mmol) of (R)-1-(4-fluorophenyl)ethanol (Acros Organics) was added under an argon atmosphere at room temperature, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure to obtain 74 mg (0.12 mmol, yield 38%) of the title compound as a pale yellow oil.

Mass spectrum (EI, m/z): 593 [M]⁺.

¹H-NMR spectrum (400 MHz, CDCl₃) δ: 7.56-7.46 (3H, m), 7.43-7.38 (3H, m), 7.37-7.31 (2H, m), 7.08-6.98 (3H, m), 6.94 (1H, d, J=1.6 Hz), 6.77 (1H, s), 5.86 (1H, q, J=6.7 Hz), 4.13 (2H, q, J=7.1 Hz), 3.79 (3H, s), 1.63 (2H, dd, J=6.9, 3.9 Hz), 1.57 (3H, d, J=6.7 Hz), 1.24 (2H, dd, J=7.0, 4.0 Hz), 1.20 (3H, t, J=7.1 Hz).

Example 58

(R)-1-{4'-[5-Chloro-3-({[1-(4-fluorophenyl)ethoxy]carbonyl}amino)thiophen-2-yl]-2'-methoxy-[1,1'-biphenyl]-4-yl}cyclopropanecarboxylic acid (Compound No. I-362)

[Chemical Formula 167]

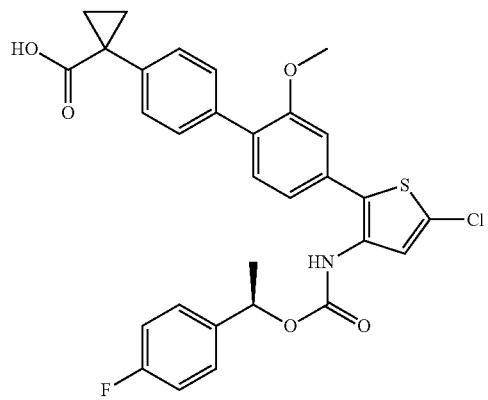

To a solution of 70 mg (0.12 mmol) of (R)-1-{4'-[5-chloro-3-({[1-(4-fluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 57 in isopropyl alcohol (2.0 ml) was added 0.60 ml (1.2 mmol) of a 2N aqueous sodium hydroxide solution, and the mixture was stirred at room temperature for 18 hours. Then, 2 ml of tetrahydrofuran and 1.0 ml (2.0 mmol) of a 2N aqueous sodium hydroxide solution were added, and the mixture was further stirred at room temperature for 47 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 20:80 (V/V)), and the fractions containing the desired compound were concentrated under reduced pressure to obtain 34 mg (0.060 mmol, yield 51%) of the title compound as a white solid.

Mass spectrum (DUIS⁻, m/z): 564 [M−1]⁻.

¹H-NMR spectrum (400 MHz, DMSO-d₆) δ: 12.33 (1H, brs), 9.41 (1H, brs), 7.45-7.30 (7H, m), 7.23-7.14 (4H, m), 7.09 (1H, dd, J=7.8, 1.5 Hz), 5.75 (1H, q, J=6.5 Hz), 3.74 (3H, s), 1.50-1.41 (5H, m), 1.20-1.12 (2H, m).

Example 59

(R)-1-{4'-[5-Chloro-3-({[1-(2-chlorophenyl)ethoxy]carbonyl}amino)thiophen-2-yl]-2'-methoxy-[1,1'-biphenyl]-4-yl}cyclopropanecarboxylic acid ethyl ester (Compound No. I-364)

[Chemical Formula 168]

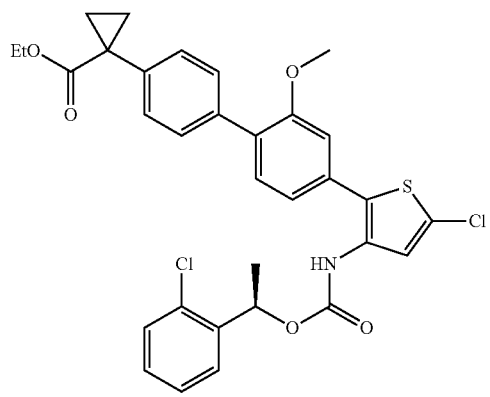

To a solution of 50 mg (0.11 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 26 mg (0.17 mmol) of (R)-1-(2-chlorophenyl)ethanol (Shanghai AoBo Bio-pharm) and 0.050 ml (0.62 mmol) of pyridine in toluene (2 ml) was added 70 mg (0.16 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 43 mg (0.046 mmol (purity 66% by weight), yield 42%) of the title compound as an orange oil.

Mass spectrum (EI, m/z): 609 [M]$^+$.

$^1$H-NMR spectrum (400 MHz, DMSO-d$_6$) δ: 9.53 (1H, brs), 7.57-7.29 (9H, m), 7.21-7.18 (2H, m), 7.11 (1H, dd, J=7.9, 1.5 Hz), 6.00 (1H, q, J=6.4 Hz), 4.06 (2H, q, J=7.1 Hz), 3.77 (3H, s), 1.54-1.42 (5H, m), 1.23 (2H, dd, J=7.0, 4.1 Hz), 1.13 (3H, t, J=7.1 Hz).

Example 60

(R)-1-{4'-[5-Chloro-3-({[1-(2-chlorophenyl)ethoxy]carbonyl}amino)thiophen-2-yl]-2'-methoxy-[1,1'-biphenyl]-4-yl}cyclopropanecarboxylic acid (Compound No. I-366)

[Chemical Formula 169]

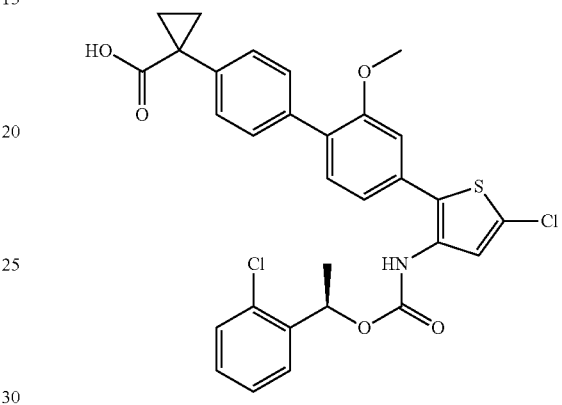

To a solution of 43 mg (0.043 mmol (purity 66% by weight)) of (R)-1-{4'-[5-chloro-3-({[1-(2-chlorophenyl)ethoxy]carbonyl}amino)thiophen-2-yl]-2'-methoxy-[1,1'-biphenyl]-4-yl}cyclopropanecarboxylic acid ethyl ester synthesized in Example 59 in isopropyl alcohol (2 ml) was added 0.30 ml (0.60 mmol) of a 2N aqueous sodium hydroxide solution, and the mixture was stirred at room temperature for 66 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure to obtain 8.5 mg (0.015 mmol, yield 35%) of the title compound as a pale yellow solid.

Mass spectrum (EI, m/z): 581 [M]$^+$.

$^1$H-NMR spectrum (400 MHz, DMSO-d$_6$) δ: 12.35 (1H, brs), 9.53 (1H, brs), 7.56-7.30 (9H, m), 7.20-7.17 (2H, m), 7.11 (1H, dd, J=7.8, 1.6 Hz), 6.00 (1H, q, J=6.2 Hz), 3.77 (3H, s), 1.57-1.41 (5H, m), 1.20-1.12 (2H, m).

Example 61

(R)-1-{4'-[5-Chloro-3-({[1-(4-chlorophenyl)ethoxy]carbonyl}amino)thiophen-2-yl]-2'-methoxy-[1,1'-biphenyl]-4-yl}cyclopropanecarboxylic acid ethyl ester (Compound No. I-368)

[Chemical Formula 170]

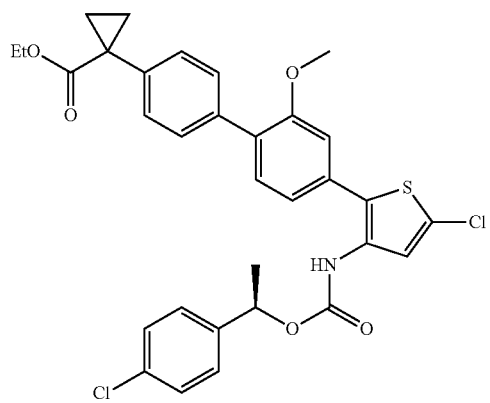

To a solution of 50 mg (0.11 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 25 mg (0.16 mmol) of (R)-1-(4-chlorophenyl)ethanol (Aldrich) and 0.050 ml (0.62 mmol) of pyridine in toluene (2 ml) was added 70 mg (0.16 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 52 mg (0.084 mmol, yield 77%) of the title compound as an orange oil.

Mass spectrum (EI, m/z): 609 [M]$^+$.

$^1$H-NMR spectrum (400 MHz, DMSO-d$_6$) δ: 9.43 (1H, brs), 7.46-7.31 (9H, m), 7.20-7.16 (2H, m), 7.10 (1H, dd, J=7.8, 1.6 Hz), 5.74 (1H, q, J=6.3 Hz), 4.06 (2H, q, J=7.1 Hz), 3.74 (3H, s), 1.51 (2H, dd, J=6.8, 4.0 Hz), 1.49-1.39 (3H, m), 1.23 (2H, dd, J=7.1, 4.1 Hz), 1.13 (3H, t, J=7.0 Hz).

Example 62

(R)-1-{4'-[5-Chloro-3-({[1-(4-chlorophenyl)ethoxy]carbonyl}amino)thiophen-2-yl]-2'-methoxy-[1,1'-biphenyl]-4-yl}cyclopropanecarboxylic acid (Compound No. I-370)

[Chemical Formula 171]

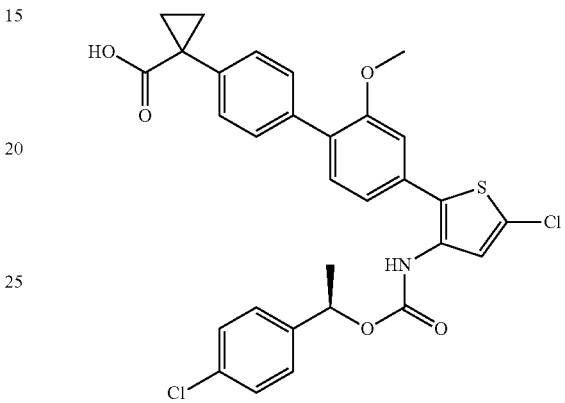

To a solution of 51 mg (0.084 mmol) of (R)-1-{4'-[5-chloro-3-({[1-(4-chlorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 61 in isopropyl alcohol (2 ml) was added 0.30 ml (0.60 mmol) of a 2N aqueous sodium hydroxide solution, further, 1 ml of tetrahydrofuran was added, and the mixture was stirred at room temperature for 66 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure to obtain 9.6 mg (0.016 mmol, yield 20%) of the title compound as a pale red solid.

Mass spectrum (EI, m/z): 581 [M]$^+$.

$^1$H-NMR spectrum (400 MHz, DMSO-d$_6$) δ: 12.35 (1H, brs), 9.43 (1H, brs), 7.45-7.30 (9H, m), 7.20-7.15 (2H, m), 7.09 (1H, dd, J=7.8, 1.6 Hz), 5.74 (1H, q, J=6.3 Hz), 3.74 (3H, s), 1.53-1.36 (5H, m), 1.17-1.00 (2H, m).

Example 63

(R)-1-{4'-[5-Chloro-3-({[1-(o-tolyl)ethoxy]carbonyl}amino)thiophen-2-yl]-2'-methoxy-[1,1'-biphenyl]-4-yl}cyclopropanecarboxylic acid ethyl ester (Compound No. I-372)

[Chemical Formula 172]

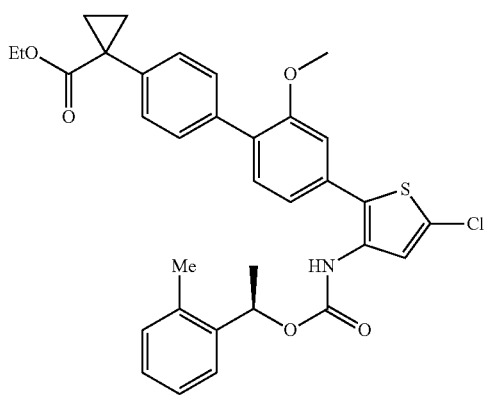

To a solution of 100 mg (0.22 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 40 mg (0.29 mmol) of (R)-1-(o-tolyl)ethanol (Enamine Ltd) and 0.080 ml (0.99 mmol) of pyridine in toluene (4 ml) was added 120 mg (0.28 mmol) of [bis(trifluoroacetoxy)iodo]benzene under a nitrogen atmosphere at room temperature, and the mixture was heated and stirred at 80° C. for 1.5 hours. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 73 mg (0.12 mmol, yield 56%) of the title compound as an orange foam.

Mass spectrum (EI, m/z): 589 [M]$^+$.

$^1$H-NMR spectrum (400 MHz, DMSO-$d_6$) δ: 9.40 (1H, brs), 7.46-7.42 (2H, m), 7.41-7.30 (4H, m), 7.23-7.13 (5H, m), 7.09 (1H, dd, J=7.9, 1.6 Hz), 5.89 (1H, q, J=6.3 Hz), 4.06 (2H, q, J=7.1 Hz), 3.74 (3H, s), 2.31 (3H, s), 1.51 (2H, dd, J=6.9, 4.0 Hz), 1.44 (3H, m), 1.23 (2H, dd, J=7.0, 4.0 Hz), 1.13 (3H, t, J=7.1 Hz).

Example 64

(R)-1-{4'-[5-Chloro-3-({[1-(o-tolyl)ethoxy]carbonyl}amino)thiophen-2-yl]-2'-methoxy-[1,1'-biphenyl]-4-yl}cyclopropanecarboxylic acid (Compound No. I-374)

[Chemical Formula 173]

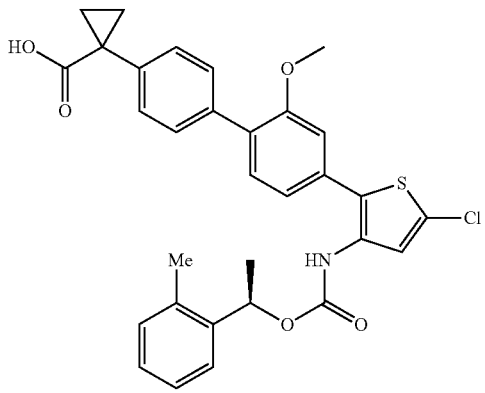

To a solution of 73 mg (0.12 mmol) of (R)-1-{4'-[5-chloro-3-({[1-(o-tolyl)ethoxy]carbonyl}amino)thiophen-2-yl]-2'-methoxy-[1,1'-biphenyl]-4-yl}cyclopropanecarboxylic acid ethyl ester synthesized in analogy to Example 63 in isopropyl alcohol (4 ml) was added 0.60 ml (1.2 mmol) of a 2N aqueous sodium hydroxide solution, and the mixture was stirred at room temperature for 66 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 51 mg (0.091 mmol, yield 74%) of the title compound as a white solid.

Mass spectrum (EI, m/z): 561 [M]$^+$.

$^1$H-NMR spectrum (400 MHz, DMSO-$d_6$) δ: 12.33 (1H, brs), 9.41 (1H, brs), 7.44-7.29 (6H, m), 7.23-7.13 (5H, m), 7.08 (1H, dd, J=7.8, 1.6 Hz), 5.89 (1H, q, J=6.4 Hz), 3.74 (3H, s), 2.31 (3H, s), 1.51-1.37 (5H, m), 1.16-1.06 (2H, m).

Example 65

(R)-1-{4'-[5-Chloro-3-({[1-(3,4-difluorophenyl)
ethoxy]carbonyl}amino)thiophen-2-yl]-2'-methoxy-
[1,1'-biphenyl]-4-yl}cyclopropanecarboxylic acid
ethyl ester (Compound No. I-390)

[Chemical Formula 174]

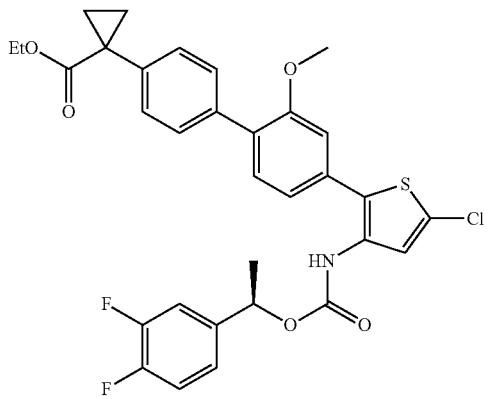

To a solution of 100 mg (0.22 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 67 mg (0.42 mmol) of (R)-1-(3,4-difluorophenyl)ethanol (Enamine Ltd) and 0.10 ml (1.2 mmol) of pyridine in toluene (4 ml) was added 120 mg (0.28 mmol) of [bis(trifluoroacetoxy)iodo]benzene under a nitrogen atmosphere at room temperature, and the mixture was heated and stirred at 80° C. for 1.5 hours. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 69 mg (0.11 mmol, yield 51%) of the title compound as a brown foam.

Mass spectrum (CI, m/z): 611 [M]$^+$.
$^1$H-NMR spectrum (400 MHz, DMSO-d$_6$) δ: 9.45 (1H, brs), 7.50-7.31 (7H, m), 7.27-7.16 (3H, m), 7.10 (1H, dd, J=7.9, 1.6 Hz), 5.74 (1H, q, J=6.3 Hz), 4.06 (2H, q, J=7.1 Hz), 3.75 (3H, s), 1.54-1.41 (5H, m), 1.23 (2H, dd, J=7.0, 4.0 Hz), 1.13 (3H, t, J=7.1 Hz).

Example 66

(R)-1-{4'-[5-Chloro-3-({[1-(3,4-difluorophenyl)
ethoxy]carbonyl}amino)thiophen-2-yl]-2'-methoxy-
[1,1'-biphenyl]-4-yl}cyclopropanecarboxylic acid
(Compound No. I-392)

[Chemical Formula 175]

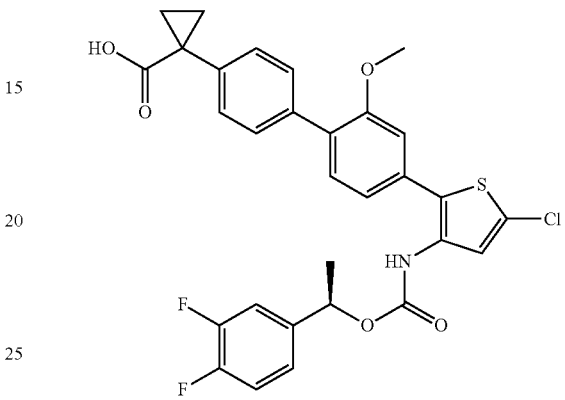

To a solution of 69 mg (0.11 mmol) of (R)-1-{4'-[5-chloro-3-({[1-(3,4-difluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 65 in isopropyl alcohol (4 ml) was added 0.60 ml (1.2 mmol) of a 2N aqueous sodium hydroxide solution, and the mixture was stirred at room temperature for 22 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane: ethyl acetate=80:20 to 0:100 (V/V)), and the fractions containing the desired compound were concentrated under reduced pressure. The resulting residue was dissolved in a small amount of ethanol, water was added to precipitate a solid and the solid was collected by filtration. The solid was washed with water and subsequently dried under reduced pressure to obtain 22 mg (0.037 mmol, yield 33%) of the title compound as a white solid.

Mass spectrum (EI, m/z): 583 [M]$^+$.
$^1$H-NMR spectrum (400 MHz, DMSO-d$_6$) δ: 12.31 (1H, brs), 9.45 (1H, brs), 7.50-7.30 (7H, m), 7.27-7.16 (3H, m), 7.09 (1H, dd, J=7.8, 1.6 Hz), 5.74 (1H, q, J=6.3 Hz), 3.75 (3H, s), 1.56-1.36 (5H, m), 1.15-1.04 (2H, m).

Example 67

(R)-1-{4'-[5-Chloro-3-({[1-(2,5-difluorophenyl)ethoxy]carbonyl}amino)thiophen-2-yl]-2'-methoxy-[1,1'-biphenyl]-4-yl}cyclopropanecarboxylic acid ethyl ester (Compound No. I-384)

[Chemical Formula 176]

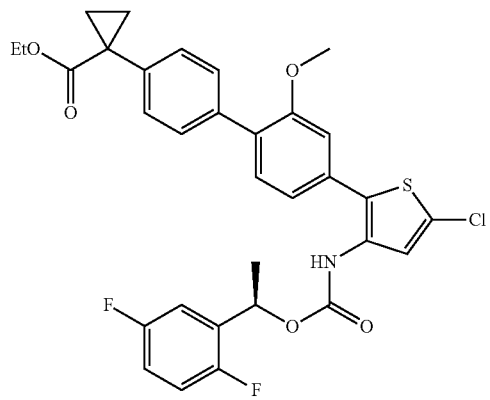

To a solution of 100 mg (0.219 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.18 ml (2.2 mmol) of pyridine in toluene (2 ml) was added 113 mg (0.263 mmol) of [bis(trifluoroacetoxy)iodo]benzene under an argon atmosphere, and the mixture was stirred at room temperature for 30 minutes. Then, 42 mg (0.27 mmol) of (R)-1-(2,5-difluorophenyl)ethanol (Enamine Ltd) was added under an argon atmosphere at room temperature, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure to obtain 84 mg (0.14 mmol (purity 65% by weight), yield 63%) of the title compound as a pale yellow oil.

Mass spectrum (EI, m/z): 611 [M]$^+$.

$^1$H-NMR spectrum (400 MHz, CDCl$_3$) δ: 7.54-7.47 (3H, m), 7.45-7.37 (3H, m), 7.07-6.88 (6H, m), 6.09 (1H, q, J=6.6 Hz), 4.13 (2H, q, J=7.1 Hz), 3.83 (3H, s), 1.63 (2H, dd, J=6.9, 3.9 Hz), 1.57 (3H, d, J=6.7 Hz), 1.24 (2H, dd, J=7.0, 4.0 Hz), 1.20 (3H, t, J=7.2 Hz).

Example 68

(R)-1-{4'-[5-Chloro-3-({[1-(2,5-difluorophenyl)ethoxy]carbonyl}amino)thiophen-2-yl]-2'-methoxy-[1,1'-biphenyl]-4-yl}cyclopropanecarboxylic acid (Compound No. I-388)

[Chemical Formula 177]

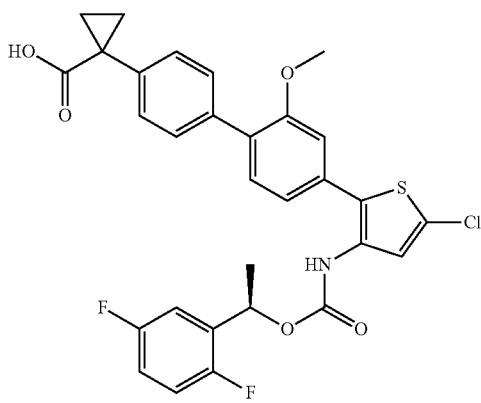

To a mixed solution of 82 mg (0.13 mmol (purity 65% by weight)) of (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid ethyl ester synthesized in Example 67 in isopropyl alcohol (2 ml)-tetrahydrofuran (0.3 ml) was added 1.0 ml (2.0 mmol) of a 2N aqueous sodium hydroxide solution, and the mixture was stirred at room temperature for 16.5 hours. Further, 1.0 ml (2.0 mmol) of a 2N aqueous sodium hydroxide solution was added, and the mixture was stirred at room temperature for 4 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 20:80 (V/V)), and the fractions containing the desired compound were concentrated under reduced pressure to obtain 18 mg (0.031 mmol, yield 24%) of the title compound as a pale yellow solid.

Mass spectrum (DUIS$^-$, m/z): 582 [M−1]$^-$.

$^1$H-NMR spectrum (400 MHz, DMSO-d$_6$) δ: 12.34 (1H, brs), 9.54 (1H, brs), 7.44-7.39 (2H, m), 7.39-7.34 (2H, m), 7.33 (1H, d, J=7.9 Hz), 7.32-7.21 (3H, m), 7.21 (1H, s), 7.18 (1H, d, J=1.5 Hz), 7.10 (1H, dd, J=7.8, 1.6 Hz), 5.91 (1H, q, J=6.4 Hz), 3.76 (3H, s), 1.54-1.45 (3H, m), 1.47 (2H, d, J=6.5, 3.8 Hz), 1.17 (2H, dd, J=6.8, 3.9 Hz).

Example 69

(R)-1-{4'-[5-Chloro-3-({[1-(2,4-difluorophenyl)ethoxy]carbonyl}amino)thiophen-2-yl]-2'-methoxy-[1,1'-biphenyl]-4-yl}cyclopropanecarboxylic acid ethyl ester (Compound No. I-376)

[Chemical Formula 178]

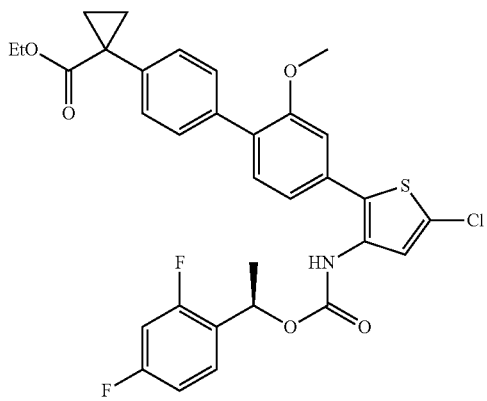

To a solution of 124 mg (0.272 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.25 ml (3.1 mmol) of pyridine in toluene (2 ml) was added 145 mg (0.337 mmol) of [bis(trifluoroacetoxy)iodo]benzene under an argon atmosphere, and the mixture was stirred at room temperature for 30 minutes. Then, 52 mg (0.33 mmol) of (R)-1-(2,4-difluorophenyl)ethanol (Enamine Ltd) was added under an argon atmosphere at room temperature, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure to obtain 103 mg (0.17 mmol, yield 62%) of the title compound as a pale yellow oil.

Mass spectrum (EI, m/z): 611 [M]$^+$.

$^1$H-NMR spectrum (400 MHz, CDCl$_3$) δ: 7.60-7.47 (3H, m), 7.44-7.38 (3H, m), 7.37-7.30 (1H, m), 7.05 (1H, dd, J=7.8, 1.6 Hz), 6.96 (1H, d, J=1.5 Hz), 6.90-6.74 (3H, m), 6.07 (1H, q, J=6.7 Hz), 4.13 (2H, q, J=7.1 Hz), 3.81 (3H, s), 1.63 (2H, dd, J=6.9, 3.9 Hz), 1.58 (3H, d, J=6.7 Hz), 1.24 (2H, dd, J=7.1, 4.1 Hz), 1.20 (3H, t, J=7.1 Hz).

Example 70

(R)-1-{4'-[5-Chloro-3-({[1-(2,4-difluorophenyl)ethoxy]carbonyl}amino)thiophen-2-yl]-2'-methoxy-[1,1'-biphenyl]-4-yl}cyclopropanecarboxylic acid (Compound No. I-378)

[Chemical Formula 179]

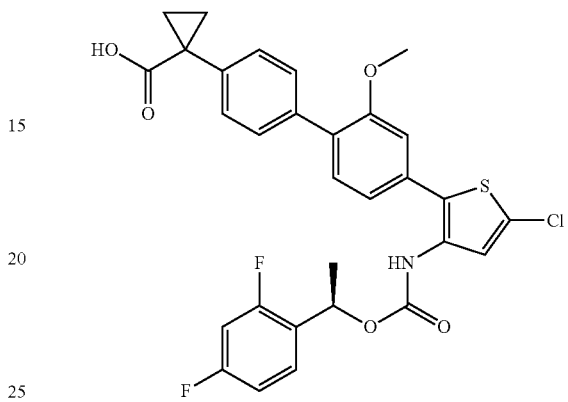

To a solution of 100 mg (0.163 mmol) of (R)-1-{4'-[5-chloro-3-({[1-(2,4-difluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 69 in isopropyl alcohol (2 ml) was added 1.0 ml (2.0 mmol) of a 2N aqueous sodium hydroxide solution, and the mixture was stirred at room temperature for 18 hours. 0.5 ml of tetrahydrofuran was added, and the mixture was further stirred at room temperature for 43 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 20:80 (V/V)), and the fractions containing the desired compound were concentrated under reduced pressure. The resulting residue was subjected to silica gel column chromatography again (elution solvent; hexane:ethyl acetate=90:10 to 40:60 (V/V)), and the fractions containing the desired compound were concentrated under reduced pressure to obtain 16 mg (0.027 mmol, yield 16%) of the title compound as a white solid.

Mass spectrum (DUIS$^-$, m/z): 582 [M−1]$^-$.

$^1$H-NMR spectrum (400 MHz, DMSO-d$_6$) δ: 12.35 (1H, brs), 9.47 (1H, brs), 7.60-7.44 (1H, m), 7.44-7.39 (2H, m), 7.38-7.34 (2H, m), 7.33 (1H, d, J=7.8 Hz), 7.30-7.21 (1H, m), 7.18 (1H, s), 7.17 (1H, d, J=1.6 Hz), 7.15-7.06 (1H, m), 7.09 (1H, dd, J=7.8, 1.6 Hz), 5.91 (1H, q, J=6.5 Hz), 3.75 (3H, s), 1.54-1.43 (3H, m), 1.46 (2H, dd, J=6.6, 3.8 Hz), 1.21-1.13 (2H, m).

Example 71

(RS)-1-{4'-[5-Chloro-3-({[1-(2-chloro-5-fluorophenyl)ethoxy]carbonyl}amino)thiophen-2-yl]-2'-methoxy-[1,1'-biphenyl]-4-yl}cyclopropanecarboxylic acid ethyl ester (Compound No. I-397)

[Chemical Formula 180]

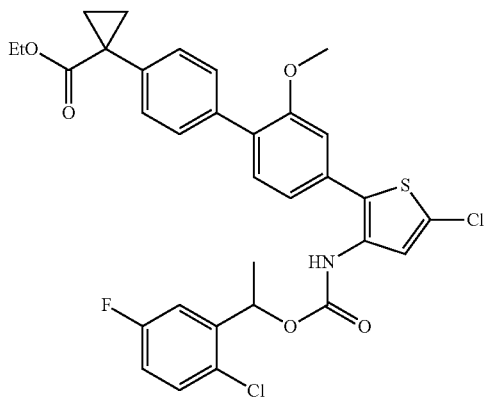

To a solution of 150 mg (0.329 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.27 mL (3.3 mmol) of pyridine in toluene (2 ml) was added 170 mg (0.395 mmol) of [bis(trifluoroacetoxy)iodo]benzene under an argon atmosphere, and the mixture was stirred at room temperature for 30 minutes. Then, 70 mg (0.40 mmol) of (RS)-1-(2-chloro-5-fluorophenyl)ethanol (synthesized according to a process described in Bioorganic and Medicinal Chemistry Letters, 23 (2013), pp. 4381-4387) was added under an argon atmosphere at room temperature, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 70:30 (V/V)), and the fractions containing the desired compound were concentrated under reduced pressure to obtain 182 mg (0.30 mmol, yield 88%) of the title compound as a pale yellow oil.

Mass spectrum (EI, m/z): 627 [M]$^+$.

$^1$H-NMR spectrum (400 MHz, CDCl$_3$) δ: 7.58-7.48 (3H, m), 7.45-7.38 (3H, m), 7.36-7.27 (1H, m), 7.14-7.04 (2H, m), 6.99-6.83 (3H, m), 6.16 (1H, q, J=6.5 Hz), 4.13 (2H, q, J=7.1 Hz), 3.83 (3H, s), 1.63 (2H, dd, J=6.9, 3.9 Hz), 1.54 (3H, d, J=6.7 Hz), 1.24 (2H, dd, J=7.0, 4.0 Hz), 1.20 (3H, t, J=7.2 Hz).

Example 72

(RS)-1-{4'-[5-Chloro-3-({[1-(2-chloro-5-fluorophenyl)ethoxy]carbonyl}amino)thiophen-2-yl]-2'-methoxy-[1,1'-biphenyl]-4-yl}cyclopropanecarboxylic acid (Compound No. I-399)

[Chemical Formula 181]

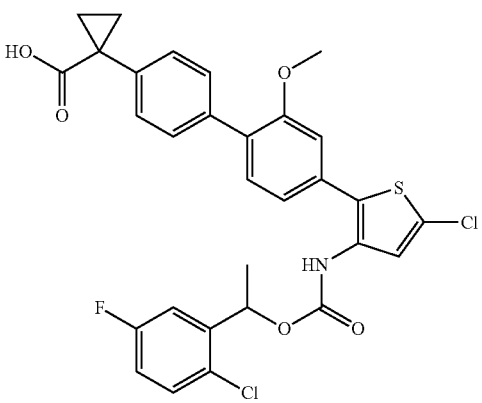

To a solution of 180 mg (0.286 mmol) of (RS)-1-{4'-[5-chloro-3-({[1-(2-chloro-5-fluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 71 in isopropyl alcohol (3 ml) was added 2.0 ml (4.0 mmol) of a 2N aqueous sodium hydroxide solution, and the mixture was stirred at room temperature for 89 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. To the resulting residue were added 3 ml of isopropyl alcohol and 2.0 ml (4.0 mmol) of a 2N aqueous sodium hydroxide solution, further, tetrahydrofuran was added until the solution became homogeneous, and the mixture was stirred at room temperature for 67 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 50:50 (V/V)), and the fractions containing the desired compound were concentrated under reduced pressure. Hexane was added, and the mixture was concentrated under reduced pressure to obtain 35 mg (0.058 mmol, yield 20%) of the title compound as a pale yellow solid.

Mass spectrum (DUIS$^-$, m/z): 598 [M−1]$^-$.

$^1$H-NMR spectrum (400 MHz, DMSO-d$_6$) δ: 12.36 (1H, brs), 9.60 (1H, brs), 7.53 (1H, dd, J=8.7, 5.3 Hz), 7.45-7.29 (6H, m), 7.27-7.15 (3H, m), 7.11 (1H, dd, J=7.9, 1.5 Hz), 5.99-5.91 (1H, m), 3.77 (3H, s), 1.54-1.37 (5H, m), 1.22-1.05 (2H, m).

Example 73

(R)-1-{4'-[5-Chloro-3-({[1-(2-chloro-4-fluorophenyl)ethoxy]carbonyl}amino)thiophen-2-yl]-2'-methoxy-[1,1'-biphenyl]-4-yl}cyclopropanecarboxylic acid ethyl ester (Compound No. I-394)

[Chemical Formula 182]

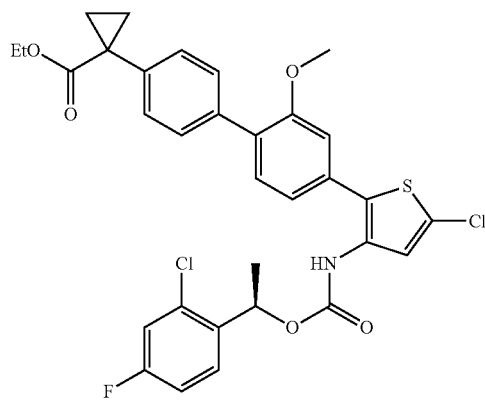

To a solution of 150 mg (0.329 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.30 ml (3.7 mmol) of pyridine in toluene (2 ml) was added 170 mg (0.395 mmol) of [bis(trifluoroacetoxy)iodo]benzene under an argon atmosphere, and the mixture was stirred at room temperature for 30 minutes. Then, 69 mg (0.344 mmol) of (R)-1-(2-chloro-4-fluorophenyl)ethanol (Enamine Ltd) was added under an argon atmosphere at room temperature, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 30:70 (V/V)), and the fractions containing the desired compound were concentrated under reduced pressure to obtain 178 mg (0.22 mmol (purity 76% by weight), yield 86%) of the title compound as a pale yellow oil.

Mass spectrum (CI, m/z): 627 [M]$^+$.

$^1$H-NMR spectrum (400 MHz, CDCl$_3$) δ: 7.62-7.47 (3H, m), 7.45-7.35 (4H, m), 7.15-6.93 (4H, m), 6.84 (1H, brs), 6.18 (1H, q, J=6.6 Hz), 4.13 (2H, q, J=7.1 Hz), 3.82 (3H, s), 1.63 (2H, dd, J=6.9, 3.9 Hz), 1.55 (3H, d, J=6.4 Hz), 1.24 (2H, dd, J=7.0, 4.0 Hz), 1.20 (3H, t, J=7.1 Hz).

Example 74

(R)-1-{4'-[5-Chloro-3-({[1-(2-chloro-4-fluorophenyl)ethoxy]carbonyl}amino)thiophen-2-yl]-2'-methoxy-[1,1'-biphenyl]-4-yl}cyclopropanecarboxylic acid (Compound No. I-396)

[Chemical Formula 183]

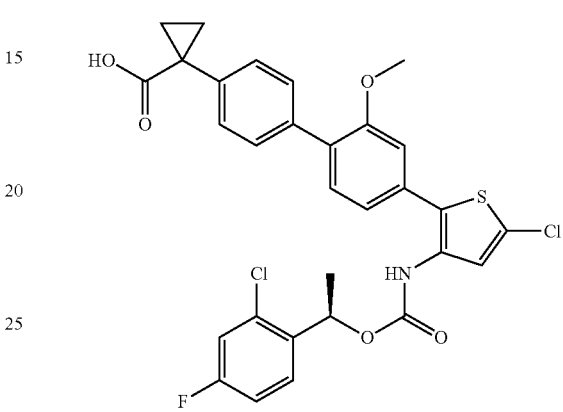

To a solution of 177 mg (0.215 mmol (purity 76% by weight)) of (R)-1-{4'-[5-chloro-3-({[1-(2-chloro-4-fluorophenyl)ethoxy]carbonyl}amino)thiophen-2-yl]-2'-methoxy-[1,1'-biphenyl]-4-yl}cyclopropanecarboxylic acid ethyl ester synthesized in Example 73 in isopropyl alcohol (3.0 ml) was added 2.0 ml (4.0 mmol) of a 2N aqueous sodium hydroxide solution, and the mixture was stirred at room temperature for 41 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 20:80 (V/V)), and the fractions containing the desired compound were concentrated under reduced pressure. Hexane was added, and the mixture was concentrated under reduced pressure to obtain 40 mg (0.067 mmol, yield 26%) of the title compound as a white solid.

Mass spectrum (DUIS$^-$, m/z): 598 [M−1]$^-$.

$^1$H-NMR spectrum (400 MHz, DMSO-d$_6$) δ: 12.36 (1H, brs), 9.54 (1H, brs), 7.63-7.50 (1H, m), 7.46 (1H, dd, J=8.8, 2.1 Hz), 7.44-7.39 (2H, m), 7.38-7.34 (2H, m), 7.34 (1H, d, J=7.8 Hz), 7.32-7.23 (1H, m), 7.19 (1H, s), 7.18 (1H, d, J=1.6 Hz), 7.10 (1H, dd, J=7.8, 1.6 Hz), 5.97 (1H, q, J=6.3 Hz), 3.77 (3H, s), 1.51-1.43 (5H, m), 1.20-1.12 (2H, m).

Example 75

(RS)-1-{4'-[5-Chloro-3-({[1-(5-fluoro-2-methylphenyl)ethoxy]carbonyl}amino)thiophen-2-yl]-2'-methoxy-[1,1'-biphenyl]-4-yl}cyclopropanecarboxylic acid (Compound No. I-411)

[Chemical Formula 184]

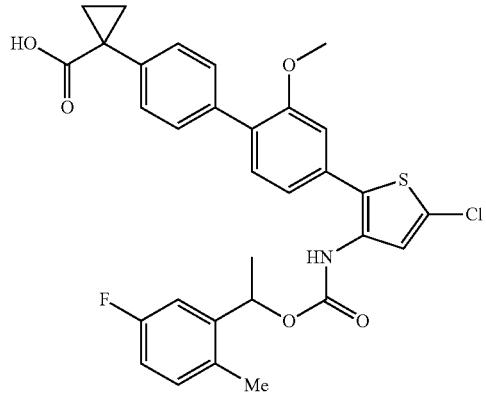

To a solution of 120 mg (0.26 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 70 mg (0.45 mmol) of (RS)-1-(5-fluoro-2-methylphenyl)ethanol synthesized in analogy to Reference Example 48 and 0.10 ml (1.2 mmol) of pyridine in toluene (5 ml) was added 140 mg (0.33 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography, and the fraction having around Rf=0.2 (developing solvent; hexane:ethyl acetate=80:20 (V/V)) was concentrated under reduced pressure to obtain 57 mg of a brown oil. This was dissolved in isopropyl alcohol (3 ml), 0.50 ml (1.0 mmol) of a 2N aqueous sodium hydroxide solution was added, and the mixture was stirred at room temperature for 44 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure to obtain 32 mg (0.055 mmol, yield 21%) of the title compound as a pale red solid.

Mass spectrum (EI, m/z): 579 [M]$^+$.

$^1$H-NMR spectrum (400 MHz, DMSO-$d_6$) δ: 12.32 (1H, brs), 9.49 (1H, brs), 7.43-7.39 (2H, m), 7.38-7.34 (2H, m), 7.34-7.30 (1H, m), 7.24-7.11 (4H, m), 7.09 (1H, dd, J=7.9, 1.6 Hz), 7.02 (1H, td, J=8.5, 2.7 Hz), 5.85 (1H, q, J=6.1 Hz), 3.75 (3H, s), 2.27 (3H, s), 1.52-1.38 (5H, m), 1.20-1.13 (2H, m).

Example 76

(RS)-1-{4'-[5-Chloro-3-({[1-(4-fluoro-2-methylphenyl)ethoxy]carbonyl}amino)thiophen-2-yl]-2'-methoxy-[1,1'-biphenyl]-4-yl}cyclopropanecarboxylic acid (Compound No. I-407)

[Chemical Formula 185]

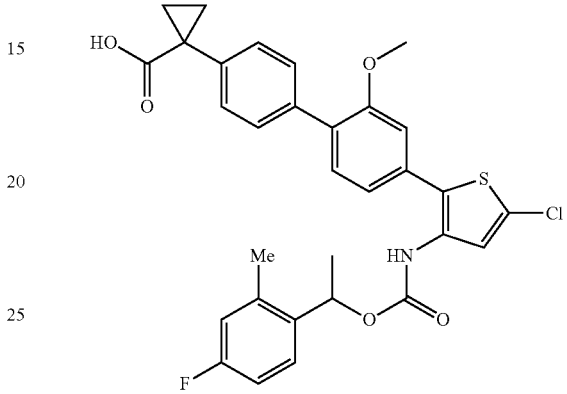

To a solution of 120 mg (0.26 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 70 mg (0.45 mmol) of (RS)-1-(4-fluoro-2-methylphenyl)ethanol synthesized in analogy to Reference Example 49 and 0.10 ml (1.2 mmol) of pyridine in toluene (5 ml) was added 140 mg (0.33 mmol) of [bis(trifluoroacetoxy)iodo]benzene under a nitrogen atmosphere at room temperature, and the mixture was heated and stirred at 80° C. for one hour. After completion of the reaction, the reaction mixture was concentrated under reduced pressure, the resulting residue was subjected to silica gel column chromatography, and the fraction having around Rf=0.2 (developing solvent; hexane:ethyl acetate=80:20 (V/V)) was concentrated under reduced pressure to obtain 56 mg of a brown oil. This was dissolved in isopropyl alcohol (3 ml), 0.5 ml (1.0 mmol) of a 2N aqueous sodium hydroxide solution was added, and the mixture was stirred at room temperature for 44 hours. After completion of the reaction, the reaction mixture was acidified by adding 2N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 0:100 (V/V)), and the fractions containing the desired compound were concentrated under reduced pressure to obtain 26 mg (0.044 mmol, yield 17%) of the title compound as a pale red solid.

Mass spectrum (EI, m/z): 579 [M]$^+$.

$^1$H-NMR spectrum (400 MHz, DMSO-$d_6$) δ: 12.34 (1H, brs), 9.42 (1H, brs), 7.44-7.30 (6H, m), 7.20-7.14 (2H, m), 7.08 (1H, dd, J=7.9, 1.6 Hz), 7.06-6.98 (2H, m), 5.86 (1H, q, J=6.3 Hz), 3.75 (3H, s), 2.32 (3H, s), 1.52-1.38 (5H, m), 1.20-1.12 (2H, m).

Example 77

(R)-1-[4'-(5-Chloro-3-{[(1-phenylethoxy)carbonyl]amino}thiophen-2-yl)-2'-nitro-[1,1'-biphenyl]-4-yl]cyclopropanecarboxylic acid ethyl ester (Compound No. I-488)

[Chemical Formula 186]

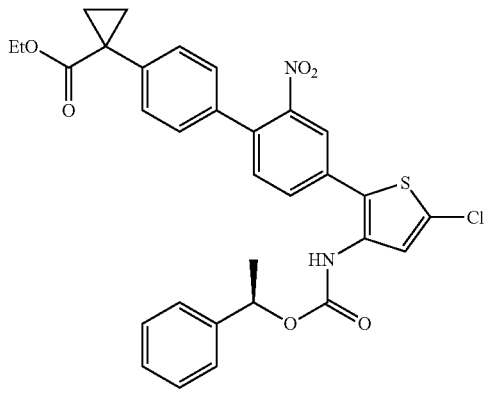

To 155 mg (0.329 mmol) of 1-[4'-(3-carbamoyl-5-chlorothiophen-2-yl)-2'-nitro-[1,1'-biphenyl]-4-yl]cyclopropanecarboxylic acid ethyl ester synthesized in analogy to Reference Example 25 was added toluene (3 ml), and the mixture was subjected to azeotropic dehydration treatment. After the mixture was dried under reduced pressure, 3 ml of toluene, 0.080 ml (0.99 mmol) of pyridine and 178 mg (0.414 mmol) of [bis(trifluoroacetoxy)iodo]benzene were added sequentially under an argon atmosphere. Then, 82 mg (0.67 mmol) of (R)-1-phenylethanol (Tokyo Chemical Industry Co., Ltd.) was added, and the mixture was heated and stirred at 80° C. for 2 hours. After completion of the reaction, the reaction mixture was allowed to cool and was subjected to silica gel column chromatography (elution solvent; hexane:ethyl acetate=88:12 to 45:55 (V/V)), and the fractions containing the desired compound were concentrated under reduced pressure to obtain 146 mg (0.247 mmol, yield 75%) of the title compound as a yellow foam.

Mass spectrum (CI, m/z): 590 [M]$^+$.

1H-NMR spectrum (400 MHz, $CD_2CJ_2$) δ: 7.88 (1H, d, J=1.8 Hz), 7.66 (1H, dd, J 8.0, 1.9 Hz), 7.54 (1H, d, J=7.9 Hz), 7.48-7.23 (10H, m), 6.72 (1H, brs), 5.84 (1H, q, J=6.7 Hz), 4.10 (2H, q, J=7.1 Hz), 1.62 (2H, dd, J=7.0, 4.0 Hz), 1.57 (3H, d, J=6.5 Hz), 1.24 (2H, dd, J=7.0, 4.0 Hz), 1.19 (3H, t, J=7.1 Hz).

Example 78

(R)-1-[4'-(5-Chloro-3-{[(1-phenylethoxy)carbonyl]amino}thiophen-2-yl)-2'-nitro-[1,1'-biphenyl]-4-yl]cyclopropanecarboxylic acid (Compound No. I-490)

[Chemical Formula 187]

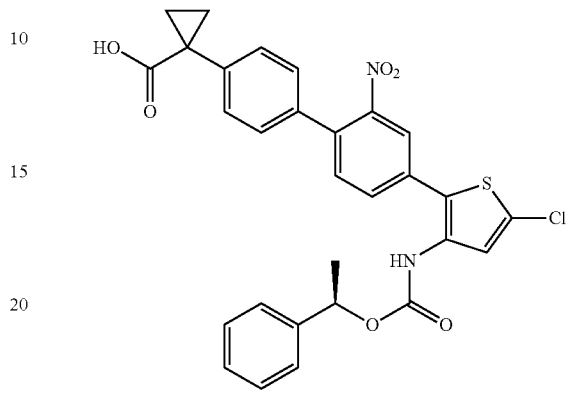

To a solution of 140 mg (0.238 mmol) of (R)-1-[4'-(5-chloro-3-{[(1-phenylethoxy)carbonyl]amino}thiophen-2-yl)-2'-nitro-[1,1'-biphenyl]-4-yl]cyclopropanecarboxylic acid ethyl ester synthesized in analogy to Example 77 in isopropyl alcohol (4 ml) was added 2 ml (8 mmol) of a 4N aqueous sodium hydroxide solution, and the mixture was stirred at room temperature for 93 hours. After completion of the reaction, the reaction mixture was acidified by adding 1N hydrochloric acid thereto, and extracted with ethyl acetate. The organic layer was washed with saturated brine, and the mixture was concentrated under reduced pressure. The resulting residue was subjected to silica gel column chromatography (elution solvent; hexane:ethyl acetate=72:28 to 25:75 (V/V)), and the fractions containing the desired compound were concentrated under reduced pressure to obtain 67.6 mg (0.120 mmol, yield 51%) of the title compound as a yellow solid.

1H-NMR spectrum (400 MHz, $CD_2Cl_2$) δ: 7.88 (1H, d, J=1.9 Hz), 7.66 (1H, dd, J=8.0, 1.9 Hz), 7.52 (1H, d, J=7.9 Hz), 7.49-7.27 (10H, m), 6.76 (1H, brs), 5.84 (1H, q, J=6.6 Hz), 1.71 (2H, dd, J=7.0, 4.0 Hz), 1.56 (3H, d, J=6.7 Hz), 1.35 (2H, dd, J=7.3, 4.1 Hz).

Example 79

(R)-1-{4'-[5-Chloro-3-({[1-(4-fluorophenyl)ethoxy]carbonyl}amino)thiophen-2-yl]-2'-nitro-[1,1'-biphenyl]-4-yl}cyclopropanecarboxylic acid ethyl ester (Compound No. I-496)

[Chemical Formula 188]

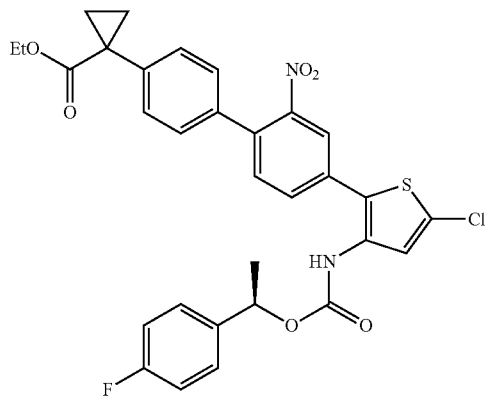

To 100 mg (0.212 mmol) of 1-[4'-(3-carbamoyl-5-chlorothiophen-2-yl)-2'-nitro-[1,1'-biphenyl]-4-yl]cyclopropanecarboxylic acid ethyl ester synthesized in analogy to Reference Example 25 was added toluene (2 ml), and the mixture was subjected to azeotropic dehydration treatment. After the mixture was dried under reduced pressure, 2 ml of toluene, 0.055 ml (0.68 mmol) of pyridine and 124 mg (0.288 mmol) of [bis(trifluoroacetoxy)iodo]benzene were added under an argon atmosphere. Then, 59 mg (0.42 mmol) of (R)-1-(4-fluorophenyl)ethanol (Acros Organics) was added, and the mixture was heated and stirred at 80° C. for 3.5 hours. After completion of the reaction, the reaction mixture was allowed to cool and was subjected to silica gel column chromatography (elution solvent; hexane:ethyl acetate=88:12 to 45:55 (V/V)), and the fractions containing the desired compound were concentrated under reduced pressure to obtain 71.3 mg (0.064 mmol (purity 55% by weight), yield 30%) of the title compound as a yellow foam.

Mass spectrum (CI, m/z): 608 [M]$^+$.

1H-NMR spectrum (400 MHz, CD$_2$Cl$_2$) δ: 7.88 (1H, d, J=1.8 Hz), 7.66 (1H, dd, J=8.0, 1.9 Hz), 7.54 (1H, d, J=8.0 Hz), 7.46-7.27 (7H, m), 7.09-7.00 (2H, m), 6.71 (1H, brs), 5.83 (1H, q, J=6.7 Hz), 4.10 (2H, q, J=7.2 Hz), 1.62 (2H, dd, J=7.0, 4.0 Hz), 1.56 (3H, d, J=6.7 Hz), 1.24 (2H, dd, J=7.0, 4.0 Hz), 1.19 (3H, t, J=7.2 Hz).

Example 80

(R)-1-{4'-[5-Chloro-3-({[1-(4-fluorophenyl)ethoxy]carbonyl}amino)thiophen-2-yl]-2'-nitro-[1,1'-biphenyl]-4-yl}cyclopropanecarboxylic acid (Compound No. I-498)

[Chemical Formula 189]

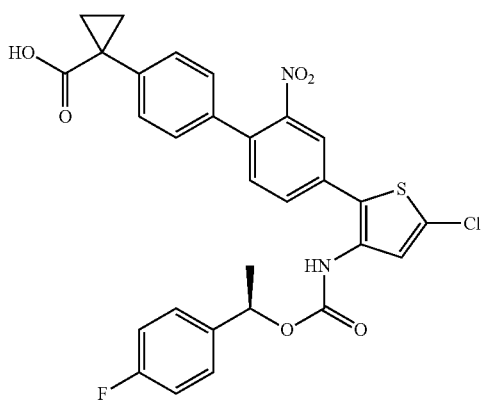

To a solution of 70 mg (0.063 mmol (purity 55% by weight)) of (R)-1-{4-[5-chloro-3-({[1-(4-fluorophenyl)ethoxy]carbonyl}amino)thiophen-2-yl]-2'-nitro-[1,1'-biphenyl]-4-yl}cyclopropanecarboxylic acid ethyl ester synthesized in Example 79 in isopropyl alcohol (2 ml), 1 ml (4 mmol) of a 4N aqueous sodium hydroxide solution was added, and the mixture was stirred at room temperature for 94 hours. After completion of the reaction, the reaction mixture was acidified by adding 1N hydrochloric acid thereto, and extracted with ethyl acetate. The organic layer was washed with saturated brine, and concentrated under reduced pressure. The resulting residue was purified by preparative HPLC using a column of Xbridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B), gradient (% by volume of solution B): 70% (0.00 min.)—90% (6.00 min.)). To the fractions containing the desired compound was added water, and the mixture was lyophilized to obtain 37 mg (0.063 mmol, yield: quantitative) of the title compound as a yellow solid.

Mass spectrum (DUIS', m/z): 579 [M−1]$^-$.

$^1$H-NMR spectrum (400 MHz, DMSO-d$_6$) δ: 12.48 (1H, brs), 9.63 (1H, brs), 8.01 (1H, d, J=1.9 Hz), 7.76 (1H, dd, J=8.0, 1.9 Hz), 7.61 (1H, d, J=8.2 Hz), 7.47-7.37 (4H, m), 7.30-7.23 (3H, m), 7.22-7.14 (2H, m), 5.74 (1H, q, J=6.5 Hz), 1.55-1.42 (5H, m), 1.19-1.12 (2H, m).

Example 81

(R)-1-{4'-[5-Chloro-3-({[1-(2-chlorophenyl)ethoxy]carbonyl}amino)thiophen-2-yl]-2'-nitro-[1,1'-biphenyl]-4-yl}cyclopropanecarboxylic acid ethyl ester (Compound No. I-500)

[Chemical Formula 190]

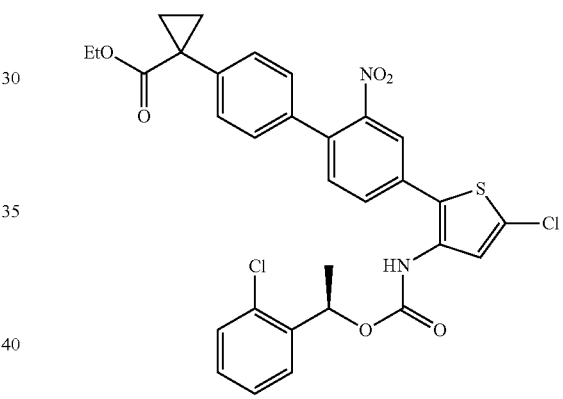

To 100 mg (0.212 mmol) of 1-[4'-(3-carbamoyl-5-chlorothiophen-2-yl)-2'-nitro-[1,1'-biphenyl]-4-yl]cyclopropanecarboxylic acid ethyl ester synthesized in analogy to Reference Example 25 was added toluene (2 ml), and the mixture was subjected to azeotropic dehydration treatment. After the mixture was dried under reduced pressure, toluene (2 ml), 0.055 ml of pyridine (0.68 mmol) and 124 mg (0.288 mmol) of [bis(trifluoroacetoxy)iodo]benzene were added under an argon atmosphere. Then, 66 mg (0.42 mmol) of (R)-1-(2-chlorophenyl)ethanol (Shanghai AoBo Bio-pharm) was added, and the mixture was heated and stirred at 80° C. for 2 hours. After completion of the reaction, the reaction mixture was allowed to cool and was subjected to silica gel column chromatography (elution solvent; hexane:ethyl acetate=88:12 to 45:55 (V/V)), and the fractions containing the desired compound were concentrated under reduced pressure to obtain 65.4 mg (0.100 mmol (purity 95% by weight), yield 47%) of the title compound as a yellow oil.

Mass spectrum (CI, m/z): 624 [M]$^+$.

$^1$H-NMR spectrum (400 MHz, CD$_2$Cl$_2$) δ: 7.90 (1H, d, J=1.8 Hz), 7.68 (1H, dd, J=8.0, 1.8 Hz), 7.56 (1H, d, J=8.0 Hz), 7.51-7.41 (4H, m), 7.38 (1H, dd, J=7.8, 1.4 Hz), 7.35-7.23 (4H, m), 6.78 (1H, brs), 6.17 (1H, q, J=6.6 Hz), 4.10 (2H, q, J=7.1 Hz), 1.63 (2H, dd, J=7.0, 4.0 Hz), 1.56 (3H, d, J=6.5 Hz), 1.24 (2H, dd, J=7.1, 4.1 Hz), 1.19 (3H, t, J=7.1 Hz).

Example 82

(R)-1-{4'-[5-Chloro-3-({[1-(2-chlorophenyl)ethoxy]carbonyl}amino)thiophen-2-yl]-2'-nitro-[1,1'-biphenyl]-4-yl}cyclopropanecarboxylic acid (Compound No. I-502)

[Chemical Formula 191]

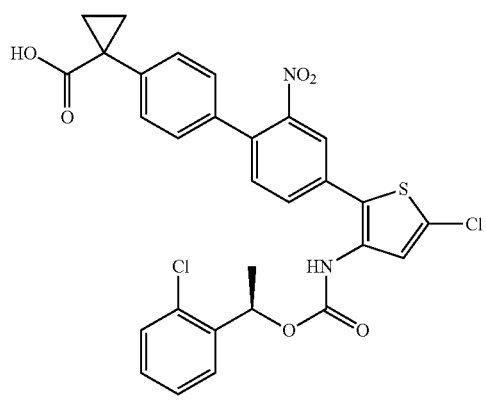

To a solution of 62.2 mg (0.0947 mmol (purity 95% by weight)) of (R)-1-{4'-[5-chloro-3-({[1-(2-chlorophenyl)ethoxy]carbonyl}amino)thiophen-2-yl]-2'-nitro-[1,1'-biphenyl]-4-yl}cyclopropanecarboxylic acid ethyl ester synthesized in Example 81 in isopropyl alcohol (2 ml) was added 1 ml (4 mmol) of a 4N aqueous sodium hydroxide solution, and the mixture was stirred at room temperature for 95 hours. After completion of the reaction, the reaction mixture was acidified by adding 1N hydrochloric acid thereto, and extracted with ethyl acetate. The organic layer was washed with saturated brine, and the mixture was concentrated under reduced pressure. The resulting residue was purified by preparative HPLC using a column of Xbridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B), gradient (% by volume of solution B): 70% (0.00 min.)—90% (6.00 min.)). To the fractions containing the desired compound was added water, and the mixture was lyophilized to obtain 28.6 mg (0.048 mmol, yield 51%) of the title compound as a yellow solid.

Mass spectrum (DUIS⁻, m/z): 595 [M−1]⁻.

¹H-NMR spectrum (400 MHz, DMSO-d₆) δ: 12.49 (1H, brs), 9.75 (1H, brs), 8.03 (1H, d, J=1.9 Hz), 7.78 (1H, dd, J=8.1, 1.8 Hz), 7.62 (1H, d, J=8.2 Hz), 7.57-7.24 (9H, m), 5.98 (1H, q, J=6.6 Hz), 1.56-1.40 (5H, m), 1.19-1.13 (2H, m).

Example 83

(R)-1-{2'-Amino-4'-(5-chloro-3-{[(1-phenylethoxy)carbonyl]amino}thiophen-2-yl)-[1,1'-biphenyl]-4-yl}cyclopropanecarboxylic acid (Compound No. I-534)

[Chemical Formula 192]

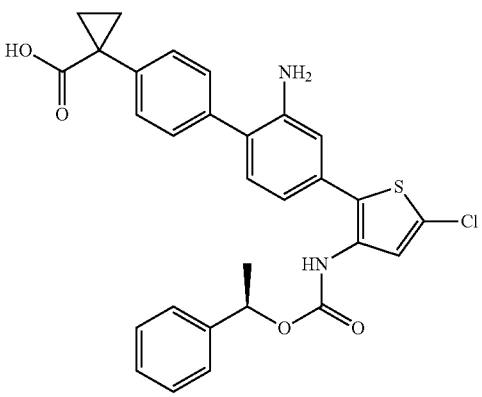

To a solution of 39.8 mg (0.0629 mmol) of (R)-1-{2'-[(tert-butoxycarbonyl)amino]-4'-(5-chloro-3-{[(1-phenylethoxy)carbonyl]-amino}thiophen-2-yl)-[1,1'-biphenyl]-4-yl}cyclopropanecarboxylic acid synthesized in analogy to Reference Example 56 in isopropyl alcohol (2 ml) was added 0.40 ml (1.6 mmol) of a 4N hydrogen chloride/1,4-dioxane solution, and the mixture was stirred at room temperature for 16.5 hours. After completion of the reaction, to the reaction mixture was added 1 ml of water, and the mixture was concentrated under reduced pressure. The resulting residue was purified by preparative HPLC using a column of abridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B), gradient (% by volume of solution B): 70% (0.00-4.50 min.)—90% (4.50-5.00 min.)). The fractions containing the desired compound was lyophilized to obtain 17.8 mg (0.033 mmol, yield 53%) of the title compound as a white solid.

Mass spectrum (CI, m/z): 533 [M+1]⁺.

1H-NMR spectrum (500 MHz, DMSO-d₆, 75° C.) δ: 11.86 (1H, brs), 8.92 (1H, s), 7.44-7.24 (914, m), 7.11 (1H, s), 7.02 (1H, d, J=7.9 Hz), 6.86 (1H, d, J=1.7 Hz), 6.77 (1H, dd, J=7.8, 1.8 Hz), 5.75 (1H, q, J=6.6 Hz), 4.75 (2H, br s), 1.50-1.45 (5H, m), 1.15-1.12 (2H, m).

Example 84

(R)-1-[4'-(5-Fluoro-3-{[(1-phenylethoxy)carbonyl]amino}thiophen-2-yl)-2'-methoxy-[1,1'-biphenyl]-4-yl]cyclopropanecarboxylic acid ethyl ester (Compound No. I-418)

[Chemical Formula 193]

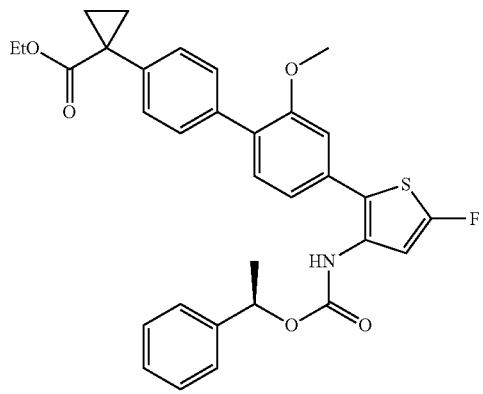

To a solution of 105 mg (0.238 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4 ml) were added 0.050 ml (0.36 mmol) of triethylamine and 0.060 ml (0.28 mmol) of diphenylphosphoryl azide under an argon atmosphere, and the mixture was stirred at room temperature for 30 minutes. Then, 33 mg (0.27 mmol) of (R)-1-phenylethanol (Tokyo Chemical Industry Co., Ltd.) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 98 mg (0.18 mmol, yield 73%) of the title compound as a colorless oil.

Mass spectrum (EI, m/z): 559 [M]$^+$.

$^1$H-NMR spectrum (400 MHz, CDCl$_3$) δ: 7.53-7.45 (2H, m), 7.43-7.24 (8H, m), 7.15 (1H, brs), 7.04 (1H, dd, J=7.8, 1.8 Hz), 6.95 (1H, d, J=1.6 Hz), 6.81 (1H, brs), 5.88 (1H, q, J=6.7 Hz), 4.13 (2H, q, J=7.1 Hz), 3.79 (3H, s), 1.62 (2H, dd, J=6.9, 4.0 Hz), 1.58 (3H, d, J=6.7 Hz), 1.24 (2H, dd, J=6.9, 3.9 Hz), 1.20 (3H, t, J=7.1 Hz).

Example 85

(R)-1-[4'-(5-Fluoro-3-{[(1-phenylethoxy)carbonyl]amino}thiophen-2-yl)-2'-methoxy-[1,1'-biphenyl]-4-yl]cyclopropanecarboxylic acid (Compound No. I-420)

[Chemical Formula 194]

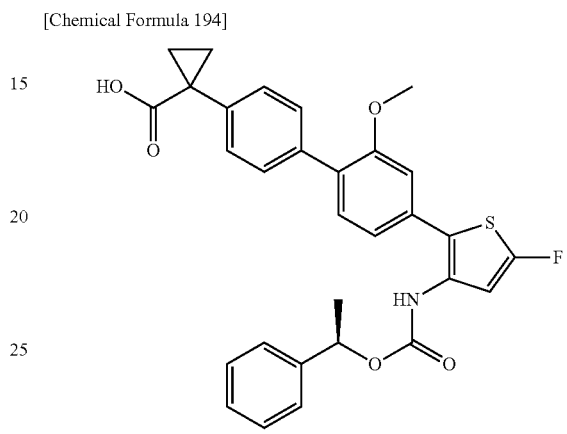

To a mixed solution of 98 mg (0.17 mmol) of (R)-1-[4'-(5-fluoro-3-{[(1-phenylethoxy)carbonyl]amino}thiophen-2-yl)-2'-methoxy-[1,1'-biphenyl]-4-yl]cyclopropanecarboxylic acid ethyl ester synthesized in analogy to Example 84 in isopropyl alcohol (3.0 ml)-tetrahydrofuran (0.5 ml) was added 1.5 ml (3.0 mmol) of a 2N aqueous sodium hydroxide solution, and the mixture was stirred at room temperature for 42.5 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure to obtain 69 mg (0.13 mmol, yield 75%) of the title compound as a white solid.

Mass spectrum (DUIS$^-$, m/z): 530 [M−1]$^-$.

$^1$H-NMR spectrum (400 MHz, DMSO-d$_6$) δ: 12.37 (1H, brs), 9.39 (1H, brs), 7.45-7.24 (10H, m), 7.18 (1H, d, J=1.4 Hz), 7.07 (1H, dd, J=7.8, 1.4 Hz), 6.83 (1H, d, J=2.1 Hz), 5.75 (1H, q, J=6.5 Hz), 3.73 (3H, s), 1.50-1.44 (5H, m), 1.17 (2H, dd, J=6.5, 3.8 Hz).

Example 86

(R)-1-{4'-[5-Fluoro-3-({[1-(2-fluorophenyl)ethoxy]carbonyl}amino)thiophen-2-yl]-2'-methoxy-[1,1'-biphenyl]-4-yl}cyclopropanecarboxylic acid ethyl ester (Compound No. I-422)

[Chemical Formula 195]

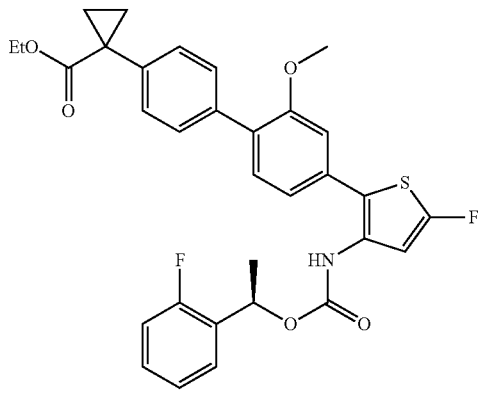

To a solution of 72 mg (0.16 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4 ml) was added 0.045 ml (0.32 mmol) of triethylamine and 0.045 ml (0.21 mmol) of diphenylphosphoryl azide under an argon atmosphere, and the mixture was stirred at room temperature for 30 minutes. Then, 35 mg (0.25 mmol) of (R)-1-(2-fluorophenyl)ethanol (Apollo) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 67 mg (0.081 mmol (purity 73% by weight, yield 52%) of the title compound as a colorless oil.

Mass spectrum (EI, m/z): 577 [M]$^+$.

$^1$H-NMR spectrum (400 MHz, CDCl$_3$) δ: 7.53-7.46 (2H, m), 7.43-7.33 (4H, m), 7.31-7.26 (1H, m), 7.18-7.10 (2H, m), 7.08-6.98 (2H, m), 6.97 (1H, d, J=1.6 Hz), 6.84 (1H, brs), 6.13 (1H, q, J=6.7 Hz), 4.13 (2H, q, J=7.1 Hz), 3.81 (3H, s), 1.62 (2H, dd, J=7.0, 4.0 Hz), 1.60 (3H, d, J=6.7 Hz), 1.24 (2H, dd, J=6.9, 3.9 Hz), 1.20 (3H, t, J=7.2 Hz).

Example 87

(R)-1-{4'-[5-Fluoro-3-({[1-(2-fluorophenyl)ethoxy]carbonyl}amino)thiophen-2-yl]-2'-methoxy-[1,1'-biphenyl]-4-yl}cyclopropanecarboxylic acid (Compound No. I-424)

[Chemical Formula 196]

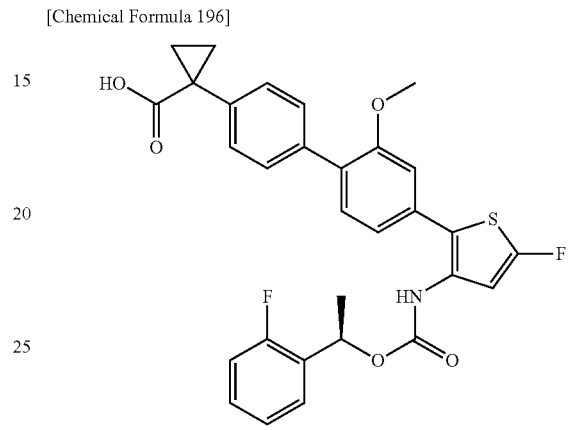

To a solution of 64 mg (0.081 mmol (purity 73% by weight)) of (R)-1-{4'-[5-fluoro-3-({[1-(2-fluorophenyl)ethoxy]carbonyl}amino)thiophen-2-yl]-2'-methoxy-[1,1'-biphenyl]-4-yl}cyclopropanecarboxylic acid ethyl ester synthesized in Example 86 in isopropyl alcohol (3 ml) was added 1.5 ml (3.0 mmol) of a 2N aqueous sodium hydroxide solution, and the mixture was stirred at room temperature for 18.5 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure to obtain 28 mg (0.051 mmol, yield 62%) of the title compound as a white solid.

Mass spectrum (DUIS$^-$, m/z): 548 [M−1]$^-$.

$^1$H-NMR spectrum (400 MHz, DMSO-d$_6$) δ: 12.38 (1H, brs), 9.47 (1H, brs), 7.53-7.28 (7H, m), 7.26-7.14 (3H, m), 7.07 (1H, dd, J=7.9, 1.5 Hz), 6.83 (1H, d, J=2.3 Hz), 5.95 (1H, q, J=6.5 Hz), 3.75 (3H, s), 1.55-1.44 (3H, m), 1.47 (2H, dd, J=6.7, 3.8 Hz), 1.17 (2H, dd, J=6.7, 3.8 Hz).

Example 88

(R)-1-{4'-[5-Fluoro-3-({[1-(3-fluorophenyl)ethoxy] carbonyl}amino)thiophen-2-yl]-2'-methoxy-[1,1'-biphenyl]-4-yl}cyclopropanecarboxylic acid ethyl ester (Compound No. I-426)

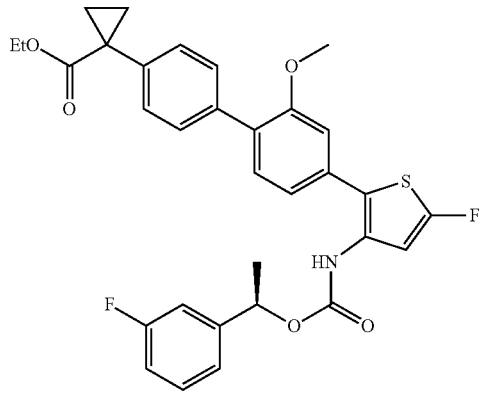

[Chemical Formula 197]

To a solution of 72 mg (0.16 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4 ml) were added 0.040 ml (0.29 mmol) of triethylamine and 0.045 ml (0.21 mmol) of diphenylphosphoryl azide under an argon atmosphere, and the mixture was stirred at room temperature for 30 minutes. Then, 35 mg (0.25 mmol) of (R)-1-(3-fluorophenyl)ethanol (Apollo) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 59 mg (0.10 mmol, yield 62%) of the title compound as a colorless oil.

Mass spectrum (EI, m/z): 577 [M]$^+$.

$^1$H-NMR spectrum (400 MHz, CDCl$_3$) δ: 7.53-7.47 (2H, m), 7.43-7.37 (3H, m), 7.35-7.27 (1H, m), 7.16-6.94 (6H, m), 6.83 (1H, brs), 5.86 (1H, q, J=6.6 Hz), 4.13 (2H, q, J=7.1 Hz), 3.81 (3H, s), 1.62 (2H, dd, J=6.9, 3.9 Hz), 1.56 (3H, d, J=6.7 Hz), 1.24 (2H, dd, J=6.9, 3.9 Hz), 1.20 (3H, t, J=7.1 Hz).

Example 89

(R)-1-{4'-[5-Fluoro-3-({[1-(3-fluorophenyl)ethoxy] carbonyl}amino)thiophen-2-yl]-2'-methoxy-[1,1'-biphenyl]-4-yl}cyclopropanecarboxylic acid (Compound No. I-428)

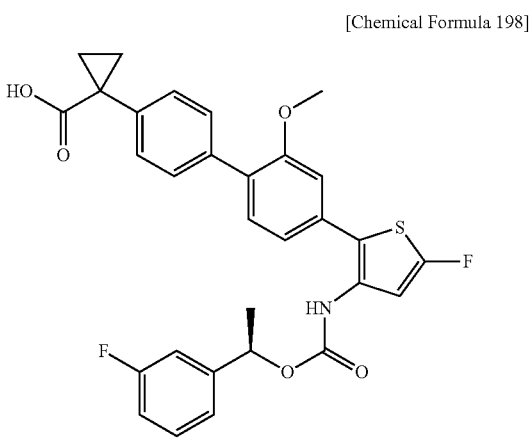

[Chemical Formula 198]

To a solution of 56 mg (0.097 mmol) of (R)-1-{4'-[5-fluoro-3-({[1-(3-fluorophenyl)ethoxy]carbonyl}amino) thiophen-2-yl]-2'-methoxy-[1,1'-biphenyl]-4-yl}cyclopropanecarboxylic acid ethyl ester synthesized in analogy to Example 88 in isopropyl alcohol (3 ml) was added 1.5 ml (3.0 mmol) of a 2N aqueous sodium hydroxide solution, and the mixture was stirred at room temperature for 20.5 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure.

The resulting residue was subjected to silica gel column chromatography (a COOH column, elution solvent; hexane:ethyl acetate=80:20 to 20:80 (V/V)), and the fractions containing the desired compound were concentrated under reduced pressure to obtain 29 mg (0.053 mmol, yield 54%) of the title compound as a white solid.

Mass spectrum (DUIS$^-$, m/z): 548 [M−1]$^-$.

$^1$H-NMR spectrum (400 MHz, DMSO-d$_6$) δ: 12.38 (1H, brs), 9.46 (1H, brs), 7.45-7.34 (5H, m), 7.32 (1H, d, J=7.8 Hz), 7.24-7.16 (2H, m), 7.18 (1H, d, J=1.6 Hz), 7.15-7.08 (1H, m), 7.08 (1H, dd, J=7.9, 1.6 Hz), 6.85 (1H, d, J=2.4 Hz), 5.76 (1H, q, J=6.4 Hz), 3.75 (3H, s), 1.52-1.41 (3H, m), 1.47 (2H, dd, J=6.5, 3.6 Hz), 1.17 (2H, dd, J=6.8, 3.9 Hz).

Example 90

(R)-1-{4'-[5-Fluoro-3-({[1-(4-fluorophenyl)ethoxy]carbonyl}amino)thiophen-2-yl]-2'-methoxy-[1,1'-biphenyl]-4-yl}cyclopropanecarboxylic acid ethyl ester (Compound No. I-430)

[Chemical Formula 199]

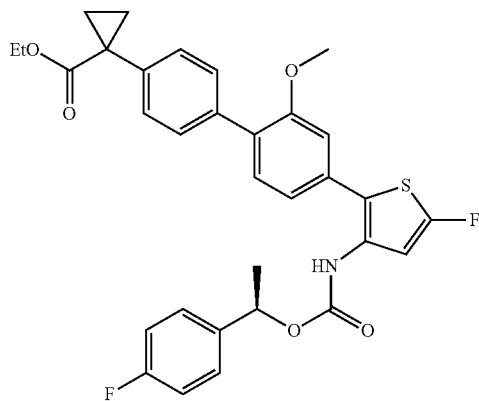

To a solution of 72 mg (0.16 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4.0 ml) were added 0.040 ml (0.29 mmol) of triethylamine and 0.045 ml (0.21 mmol) of diphenylphosphoryl azide under an argon atmosphere, and the mixture was stirred at room temperature for 30 minutes. Then, 35 mg (0.25 mmol) of (R)-1-(4-fluorophenyl)ethanol (Acros Organics) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 58 mg (0.10 mmol, yield 71%) of the title compound as a colorless oil.

Mass spectrum (CI, m/z): 577 $[M]^+$.

$^1$H-NMR spectrum (400 MHz, CDCl$_3$) δ: 7.52-7.47 (2H, m), 7.43-7.37 (3H, m), 7.37-7.31 (2H, m), 7.14 (1H, brs), 7.06-7.00 (3H, m), 6.94 (1H, d, J=1.6 Hz), 6.79 (1H, brs), 5.86 (1H, q, J=6.7 Hz), 4.13 (2H, q, J=7.1 Hz), 3.79 (3H, s), 1.62 (2H, dd, J 6.9, 3.9 Hz), 1.56 (3H, d, J=6.7 Hz), 1.24 (2H, dd, J=7.0, 4.0 Hz), 1.20 (3H, t, J=7.2 Hz).

Example 91

(R)-1-{4'-[5-Fluoro-3-({[1-(4-fluorophenyl)ethoxy]carbonyl}amino)thiophen-2-yl]-2'-methoxy-[1,1'-biphenyl]-4-yl}cyclopropanecarboxylic acid (Compound No. I-432)

[Chemical Formula 200]

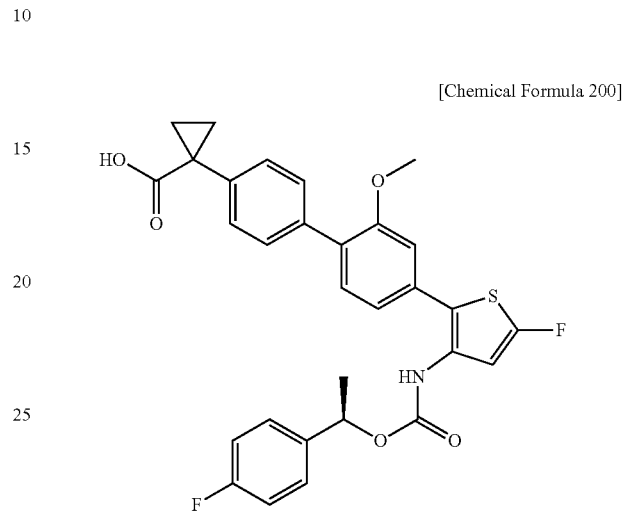

To a solution of 56 mg (0.097 mmol) of (R)-1-{4'-[5-fluoro-3-({[1-(4-fluorophenyl)ethoxy]carbonyl}amino)thiophen-2-yl]-2'-methoxy-[1,1'-biphenyl]-4-yl}cyclopropanecarboxylic acid ethyl ester synthesized in analogy to Example 90 in isopropyl alcohol (3.0 ml) was added 1.5 ml (3.0 mmol) of a 2N aqueous sodium hydroxide solution, and the mixture was stirred at room temperature for 20.5 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure to obtain 34 mg (0.062 mmol, yield 63%) of the title compound as a white solid.

Mass spectrum (DUIS$^-$, m/z): 548 $[M-1]^-$.

$^1$H-NMR spectrum (400 MHz, DMSO-d$_6$) 12.37 (1H, brs), 9.39 (1H, brs), 7.46-7.33 (6H, m), 7.32 (1H, d, J=7.9 Hz), 7.23-7.14 (3H, m), 7.07 (1H, dd, J=7.8, 1.6 Hz), 6.83 (1H, d, J=2.4 Hz), 5.75 (1H, q, J=6.3 Hz), 3.73 (3H, s), 1.55-1.37 (5H, m), 1.21-1.13 (2H, m).

Example 92

(R)-1-{4'-[3-({[1-(2-Chlorophenyl)ethoxy]carbonyl}amino)-5-fluorothiophen-2-yl]-2'-methoxy-[1,1'-biphenyl]-4-yl}cyclopropanecarboxylic acid ethyl ester (Compound No. I-438)

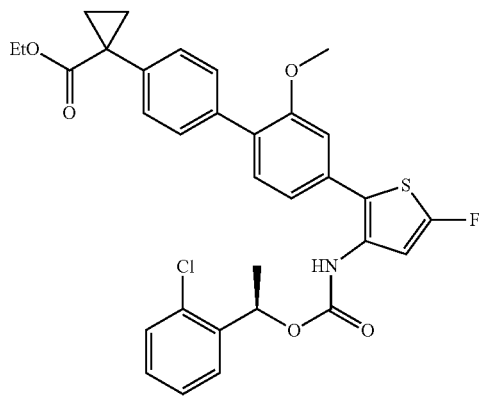

[Chemical Formula 201]

To a solution of 72 mg (0.16 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4.0 ml) were added 0.040 ml (0.29 mmol) of triethylamine and 0.045 ml (0.21 mmol) of diphenylphosphoryl azide under an argon atmosphere, and the mixture was stirred at room temperature for 30 minutes. Then, 35 mg (0.22 mmol) of (R)-1-(2-chlorophenyl)ethanol (Shanghai AoBo Bio-pharm) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 84 mg (0.061 mmol (purity 43% by weight), yield 37%) of the title compound as a colorless oil.

Mass spectrum (EI, m/z): 593 [M]+.

$^1$H-NMR spectrum (400 MHz, CDCl$_3$) δ: 7.52-7.48 (2H, m), 7.43-7.17 (9H, m), 7.06 (1H, dd, J=7.8, 1.6 Hz), 6.97 (1H, d, J=1.6 Hz), 6.23 (1H, q, J=6.7 Hz), 4.13 (2H, q, J=7.1 Hz), 3.82 (3H, s), 1.63 (2H, dd, J=6.9, 3.9 Hz), 1.57 (3H, d, J=6.7 Hz), 1.24 (2H, dd, J=7.0, 4.0 Hz), 1.20 (3H, t, J=7.2 Hz).

Example 93

(R)-1-{4'-[3-({[1-(2-Chlorophenyl)ethoxy]carbonyl}amino)-5-fluorothiophen-2-yl]-2'-methoxy-[1,1'-biphenyl]-4-yl}cyclopropanecarboxylic acid (Compound No. I-442)

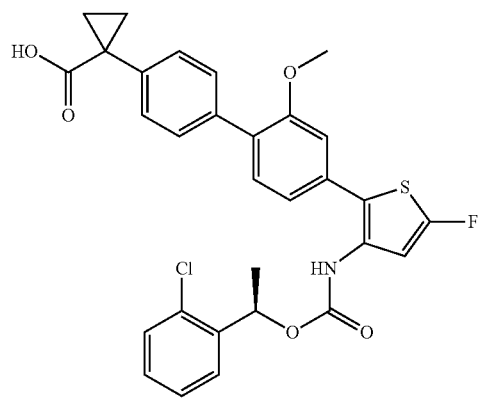

[Chemical Formula 202]

To a solution of 80 mg (0.058 mmol (purity 43% by weight)) of (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid ethyl ester synthesized in Example 92 in isopropyl alcohol (3.0 ml) was added 1.5 ml (3.0 mmol) of a 2N aqueous sodium hydroxide solution, and the mixture was stirred at room temperature for 23 hours. After completion of the reaction, the reaction mixture was acidified by adding 2N hydrochloric acid thereto, and extracted with methylene chloride. The resulting organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure to obtain 13 mg (0.023 mmol, yield 40%) of the title compound as a white solid.

Mass spectrum (DUIS−, m/z): 564 [M−1]−.

$^1$H-NMR spectrum (400 MHz, DMSO-d$_6$) δ: 12.35 (1H, brs), 9.55 (1H, brs), 7.60-7.28 (9H, m), 7.18 (1H, d, J=1.5 Hz), 7.09 (1H, dd, J=7.8, 1.4 Hz), 6.84 (1H, d, J=2.5 Hz), 6.00 (1H, q, J=6.1 Hz), 3.77 (3H, s), 1.55-1.39 (5H, m), 1.21-1.10 (2H, m).

Example 94

(R)-1-{4'-[3-({[1-(4-Chlorophenyl)ethoxy]carbonyl}amino)-5-fluorothiophen-2-yl]-2'-methoxy-[1,1'-biphenyl]-4-yl}cyclopropanecarboxylic acid ethyl ester (Compound No. I-444)

[Chemical Formula 203]

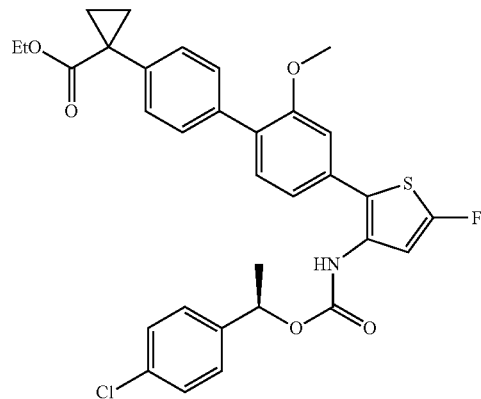

To a solution of 106 mg (0.241 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (3.0 ml) were added 0.050 ml (0.36 mmol) of triethylamine and 0.060 ml (0.28 mmol) of diphenylphosphoryl azide under an argon atmosphere, and the mixture was stirred at room temperature for 30 minutes. Then, 55 mg (0.35 mmol) of (R)-1-(4-chlorophenyl)ethanol (Aldrich) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 70:30 (V/V)), and the fractions containing the desired compound were concentrated under reduced pressure to obtain 116 mg (0.20 mmol, yield 81%) of the title compound as a colorless oil.

Mass spectrum (DUIS⁻, m/z): 592 [M−1]⁻.

H-NMR spectrum (400 MHz, CDCl$_3$) δ: 7.51-7.47 (2H, m), 7.42-7.38 (3H, m), 7.36-7.27 (4H, m), 7.13 (1H, brs), 7.04 (1H, dd, J=7.8, 1.6 Hz), 6.94 (1H, d, J=1.6 Hz), 6.80 (1H, brs), 5.84 (1H, q, J=6.6 Hz), 4.13 (2H, q, J=7.1 Hz), 3.79 (3H, s), 1.63 (2H, dd, J=7.0, 4.0 Hz), 1.56 (3H, d, J=6.7 Hz), 1.24 (2H, dd, J=7.0, 4.2 Hz), 1.20 (3H, t, J=7.1 Hz).

Example 95

(R)-1-{4'-[3-({[1-(4-Chlorophenyl)ethoxy]carbonyl}amino)-5-fluorothiophen-2-yl]-2'-methoxy-[1,1'-biphenyl]-4-yl}cyclopropanecarboxylic acid (Compound No. I-446)

[Chemical Formula 204]

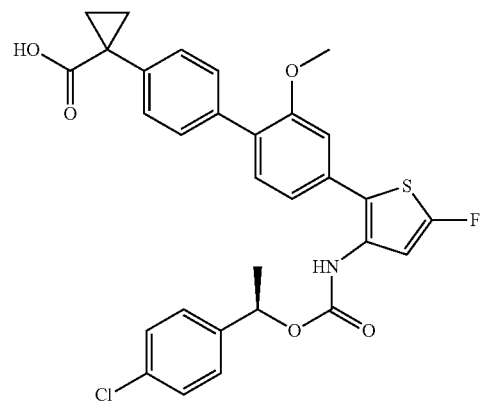

To a solution of 114 mg (0.192 mmol) of 1-{4'-[3-({[1-(4-chlorophenyl)ethoxy]carbonyl}amino)-5-fluorothiophen-2-yl]-2'-methoxy-[1,1'-biphenyl]-4-yl}cyclopropanecarboxylic acid ethyl ester synthesized in analogy to Example 94 in isopropyl alcohol (2.0 ml) was added 1.0 ml (2.0 mmol) of a 2N aqueous sodium hydroxide solution, and the mixture was stirred at room temperature for 15.5 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure. To the resulting residue was added hexane, and the mixture was ultrasonically washed and subsequently concentrated under reduced pressure to obtain 62 mg (0.11 mmol, yield 57%) of the title compound as a white solid.

Mass spectrum (DUIS⁻, m/z): 564 [M−1]⁻.

$^1$H-NMR spectrum (400 MHz, DMSO-d$_6$) δ: 12.35 (1H, brs), 9.43 (1H, brs), 7.46-7.29 (9H, m), 7.16 (1H, d, J=1.6 Hz), 7.07 (1H, dd, J=7.9, 1.5 Hz), 6.83 (1H, d, J=2.4 Hz), 5.74 (1H, q, J=6.6 Hz), 3.74 (3H, s), 1.52-1.39 (5H, m), 1.19-1.12 (2H, m).

Example 96

(R)-1-{4'-[5-Fluoro-3-({[1-(o-tolyl)ethoxy]carbonyl}amino)thiophen-2-yl]-2'-methoxy-[1,1'-biphenyl]-4-yl}cyclopropanecarboxylic acid ethyl ester (Compound No. I-448)

[Chemical Formula 205]

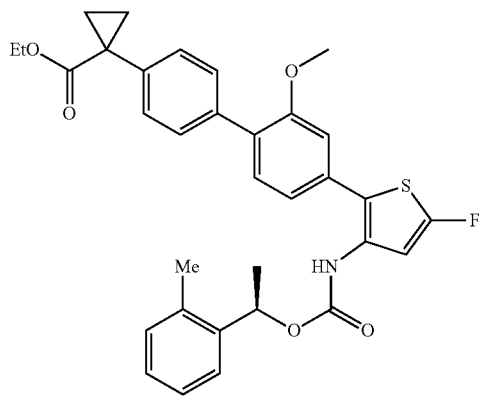

To a solution of 80 mg (0.18 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4.0 ml) were added 0.040 ml (0.29 mmol) of triethylamine and 0.050 ml (0.23 mmol) of diphenylphosphoryl azide under an argon atmosphere, and the mixture was stirred at room temperature for 30 minutes. Then, 30 mg (0.22 mmol) of (R)-1-(o-tolyl)ethanol (Enamine Ltd) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 81 mg (0.13 mmol (purity 92% by weight), yield 71%) of the title compound as a colorless oil.

Mass spectrum (EI, m/z): 573 [M]$^+$.

$^1$H-NMR spectrum (400 MHz, CDCl$_3$) δ: 7.54-7.46 (2H, m), 7.43-7.33 (5H, m), 7.29-7.11 (3H, m), 7.04 (1H, dd, J=7.8, 1.6 Hz), 6.95 (1H, d, J=1.6 Hz), 6.82 (1H, brs), 6.09 (1H, q, J=6.6 Hz), 4.13 (2H, q, J=7.1 Hz), 3.80 (3H, s), 2.40 (3H, s), 1.62 (2H, dd, J=6.9, 3.9 Hz), 1.55-1.54 (3H, m), 1.24 (2H, dd, J=6.9, 3.9 Hz), 1.20 (3H, t, J=7.1 Hz).

Example 97

(R)-1-{4'-[5-Fluoro-3-({[1-(o-tolyl)ethoxy]carbonyl}amino)thiophen-2-yl]-2'-methoxy-[1,1'-biphenyl]-4-yl}cyclopropanecarboxylic acid (Compound No. I-450)

[Chemical Formula 206]

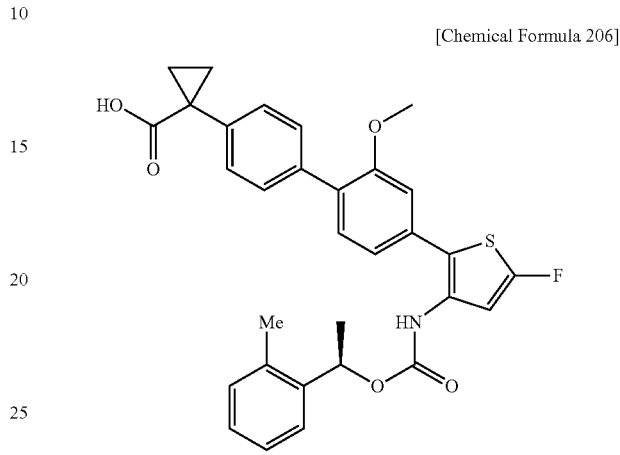

To a mixed solution of 79 mg (0.13 mmol (purity 92% by weight)) of (R)-1-{4'-[5-fluoro-3-({[1-(o-tolyl)ethoxy]carbonyl}amino)thiophen-2-yl]-2'-methoxy-[1,1'-biphenyl]-4-yl}cyclopropanecarboxylic acid ethyl ester synthesized in Example 96 in isopropyl alcohol (3 ml)-tetrahydrofuran (0.5 ml) was added 1.5 ml (3.0 mmol) of a 2N aqueous sodium hydroxide solution, and the mixture was stirred at room temperature for 66 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 41 mg (0.075 mmol, yield 60%) of the title compound as a white solid.

Mass spectrum (DUIS$^-$, m/z): 544 [M−1]$^-$.

$^1$H-NMR spectrum (400 MHz, DMSO-d$_6$) δ: 12.33 (1H, brs), 9.40 (1H, brs), 7.44-7.34 (5H, m), 7.31 (1H, d, J=7.9 Hz), 7.22-7.13 (4H, m), 7.07 (1H, dd, J=7.8, 1.6 Hz), 6.82 (1H, d, J=2.4 Hz), 5.90 (1H, q, J=6.5 Hz), 3.74 (3H, s), 2.31 (3H, s), 1.50-1.40 (3H, m), 1.47 (2H, dd, J=6.8, 3.8 Hz), 1.17 (2H, dd, J=6.8, 3.9 Hz).

Example 98

(R)-1-{4'-[3-({[1-(3,4-Difluorophenyl)ethoxy]carbonyl}amino)-5-fluorothiophen-2-yl]-2'-methoxy-[1,1'-biphenyl]-4-yl}cyclopropanecarboxylic acid (Compound No. I-462)

[Chemical Formula 207]

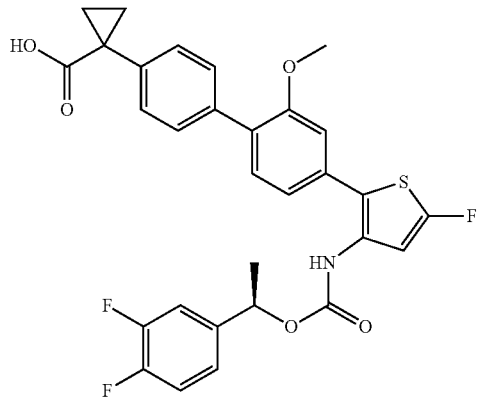

To a solution of 73 mg (0.17 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4.0 ml) were added 0.040 ml (0.29 mmol) of triethylamine and 0.045 ml (0.21 mmol) of diphenylphosphoryl azide under an argon atmosphere, and the mixture was stirred at room temperature for 30 minutes. Then, 35 mg (0.22 mmol) of (R)-1-(3,4-difluorophenyl)ethanol (Enamine Ltd) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fraction having around Rf=0.3 (developing solvent; hexane:ethyl acetate=80:20 (V/V)) was concentrated under reduced pressure to obtain 66 mg of a colorless oil. This was dissolved in isopropyl alcohol (3.0 ml), 1.5 ml (3.0 mmol) of a 2N aqueous sodium hydroxide solution was added, and the mixture was stirred at room temperature for 21 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 32 mg (0.056 mmol, yield 52%) of the title compound as a white solid.

Mass spectrum (DUIS−, m/z): 566 [M−1]−.

1H-NMR spectrum (400 MHz, DMSO-d6) δ: 12.35 (1H, brs), 9.46 (1H, brs), 7.50-7.30 (7H, m), 7.27-7.15 (2H, m), 7.08 (1H, dd, J=7.8, 1.6 Hz), 6.85 (1H, d, J=2.3 Hz), 5.74 (1H, q, J=6.3 Hz), 3.75 (3H, s), 1.52-1.40 (5H, m), 1.20-1.11 (2H, m).

Example 99

(R)-1-{4'-[3-({[1-(2,5-Difluorophenyl)ethoxy]carbonyl}amino)-5-fluorothiophen-2-yl]-2'-methoxy-[1,1'-biphenyl]-4-yl}cyclopropanecarboxylic acid ethyl ester (Compound No. I-456)

[Chemical Formula 208]

To a solution of 100 mg (0.227 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4 ml) were added 0.050 ml (0.36 mmol) of triethylamine and 0.060 ml (0.28 mmol) of diphenylphosphoryl azide under an argon atmosphere, and the mixture was stirred at room temperature for 30 minutes. Then, 43 mg (0.27 mmol) of (R)-1-(2,5-difluorophenyl)ethanol (Enamine Ltd) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 101 mg (0.12 mmol (purity 71% by weight), yield 53%) of the title compound as a colorless oil.

Mass spectrum (EI, m/z): 595 [M]+.

1H-NMR spectrum (400 MHz, CDCl3) δ: 7.52-7.47 (2H, m), 7.43-7.35 (3H, m), 7.25-6.76 (7H, m), 6.09 (1H, q, J=6.6 Hz), 4.13 (2H, q, J=7.1 Hz), 3.83 (3H, s), 1.62 (2H, dd, J=6.9, 3.9 Hz), 1.57 (3H, d, J=6.7 Hz), 1.24 (2H, dd, J=7.0, 4.0 Hz), 1.20 (3H, t, J=7.1 Hz).

Example 100

(R)-1-{4'-[3-({[1-(2,5-Difluorophenyl)ethoxy]carbonyl}amino)-5-fluorothiophen-2-yl]-2'-methoxy-[1,1'-biphenyl]-4-yl}cyclopropanecarboxylic acid (Compound No. I-458)

[Chemical Formula 209]

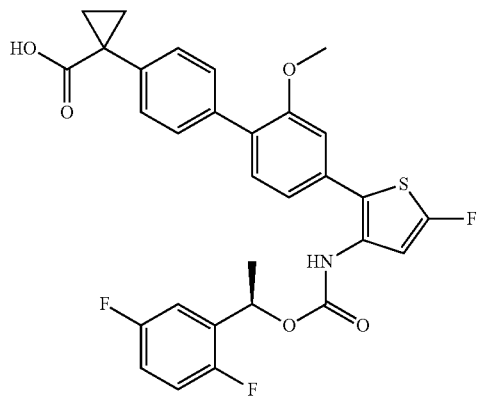

To a solution of 99 mg (0.12 mmol (purity 71% by weight)) of (R)-1-{4'-[3-({[1-(2,5-difluorophenyl)ethoxy]carbonyl}amino)-5-fluorothiophen-2-yl]-2'-methoxy-[1,1'-biphenyl]-4-yl}cyclopropanecarboxylic acid ethyl ester synthesized in Example 99 in isopropyl alcohol (3.0 ml) was added 1.5 ml (3.0 mmol) of a 2N aqueous sodium hydroxide solution, and the mixture was stirred at room temperature for 21.5 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 60:40 (V/V)), and the fractions containing the desired compound were concentrated under reduced pressure. The residue was subjected to silica gel column chromatography again (a COOH column, elution solvent; hexane:ethyl acetate=80:20 to 30:70 (V/V)), and the fractions containing the desired compound were concentrated under reduced pressure. To the resulting residue were added hexane and ethyl acetate, and the precipitated solid was filtered to obtain 15 mg (0.026 mmol, yield 22%) of the title compound as a white solid.

Mass spectrum (DUIS$^-$, m/z): 566 [M−1]$^-$.

$^1$H-NMR spectrum (400 MHz, DMSO-d$_6$) δ: 12.35 (1H, brs), 9.51 (1H, brs), 7.44-7.38 (2H, m), 7.38-7.34 (2H, m), 7.32 (1H, d, J=7.8 Hz), 7.30-7.18 (3H, m), 7.18 (1H, d, J=1.6 Hz), 7.07 (1H, dd, J=7.9, 1.6 Hz), 6.85 (1H, d, J=2.3 Hz), 5.91 (1H, q, J=6.4 Hz), 3.76 (3H, s), 1.55-1.40 (5H, m), 1.20-1.08 (2H, m).

Example 101

(R)-1-{4'-[3({[1-(2,4-Difluorophenyl)ethoxy]carbonyl}amino)-5-fluorothiophen-2-yl]-2'-methoxy-[1,1'-biphenyl]-4-yl}cyclopropanecarboxylic acid (Compound No. I-454)

[Chemical Formula 210]

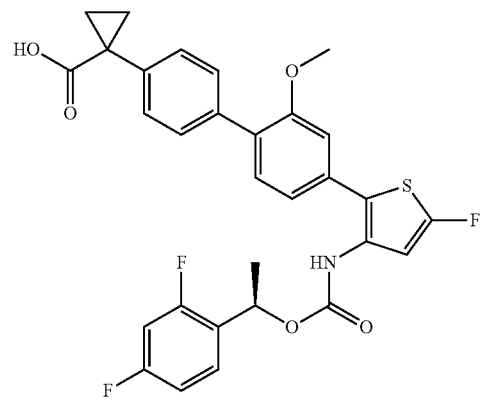

To a solution of 100 mg (0.227 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (3.0 ml) were added 0.050 ml (0.36 mmol) of triethylamine and 0.060 ml (0.28 mmol) of diphenylphosphoryl azide under an argon atmosphere, and the mixture was stirred at room temperature for 30 minutes. Then, 55 mg (0.34 mmol) of (R)-1-(2,4-difluorophenyl)ethanol (Enamine Ltd) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fraction having around Rf=0.3 (developing solvent; hexane:ethyl acetate=80:20 (V/V)) was concentrated under reduced pressure to obtain 148 mg of a colorless oil. This was dissolved in isopropyl alcohol (2.0 ml), 1.0 ml (2.0 mmol) of a 2N aqueous sodium hydroxide solution was added, and the mixture was stirred at room temperature for 40.5 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 59 mg (0.11 mmol, yield 44%) of the title compound as a white solid.

Mass spectrum (DUIS$^-$, m/z): 566 [M−1]$^-$.

$^1$H-NMR spectrum (400 MHz, DMSO-d$_6$) δ: 12.37 (1H, brs), 9.47 (1H, brs), 7.51 (1H, brs), 7.43-7.37 (2H, m), 7.37-7.33 (2H, m), 7.32 (1H, d, J=7.8 Hz), 7.29-7.21 (1H, m), 7.16 (1H, d, J=1.5 Hz), 7.15-7.08 (1H, m), 7.07 (1H, dd, J=7.9, 1.5 Hz), 6.83 (1H, d, J=2.3 Hz), 5.91 (1H, d, J=6.3 Hz), 3.75 (3H, s), 1.57-1.38 (5H, m), 1.20-1.03 (2H, m).

Example 102

(RS)-1-{4'-[3-({[1-(2-Chloro-5-fluorophenyl)ethoxy]carbonyl}amino)-5-fluorothiophen-2-yl]-2'-methoxy-[1,1'-biphenyl]-4-yl}cyclopropanecarboxylic acid ethyl ester (Compound No. I-467)

[Chemical Formula 211]

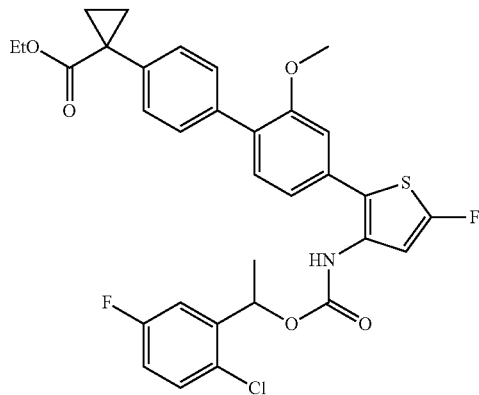

To a solution of 100 mg (0.227 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (2.0 ml) were added 0.050 ml (0.36 mmol) of triethylamine and 0.073 ml (0.34 mmol) of diphenylphosphoryl azide under an argon atmosphere, and the mixture was stirred at room temperature for 30 minutes. Then, a solution of 50 mg (0.29 mmol) of (RS)-1-(2-chloro-5-fluorophenyl)ethanol (synthesized according to a process described in Bioorganic and Medicinal Chemistry Letters, 23 (2013) pp. 4381-4387) in toluene (1.0 ml) dried over Molecular Sieves 4A (powder) (trade name, NACALAI TESQUE, INC.) (0.1 g) was added, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:5 to 70:30 (V/V)), and the fractions containing the desired compound were concentrated under reduced pressure to obtain 106 mg (0.14 mmol (purity 75% by weight), yield 60%) of the title compound as a colorless oil.

Mass spectrum (DUB$^-$, m/z): 610 [M−1]$^-$.

$^1$H-NMR spectrum (400 MHz, CDCl$_3$) 7.54-7.48 (2H, m), 7.45-7.36 (4H, m), 7.36-7.28 (1H, m), 7.19-7.04 (2H, m), 7.00-6.85 (3H, m), 6.16 (1H, q, J=6.8 Hz), 4.13 (2H, q, J=7.1 Hz), 3.84 (3H, s), 1.63 (2H, dd, J=6.9, 4.0 Hz), 1.54 (3H, d, J=6.8 Hz), 1.24 (2H, dd, J=7.0, 4.0 Hz), 1.20 (3H, t, J=7.2 Hz).

Example 103

(RS)-1-{4'-[3-({[1-(2-Chloro-5-fluorophenyl)ethoxy]carbonyl}amino)-5-fluorothiophen-2-yl]-2'-methoxy-[1,1'-biphenyl]-4-yl}cyclopropanecarboxylic acid (Compound No. I-469)

[Chemical Formula 212]

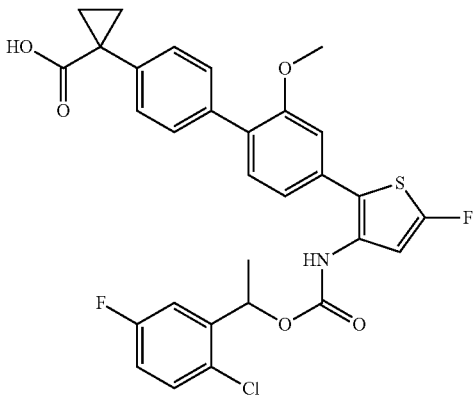

To a solution of 104 mg (0.127 mmol (purity 75% by weight)) of (RS)-1-{4'-[3-({[1-(2-chloro-5-fluorophenyl)ethoxy]carbonyl}amino)-5-fluorothiophen-2-yl]-2'-methoxy-[1,1'-biphenyl]-4-yl}cyclopropanecarboxylic acid ethyl ester synthesized in Example 102 in isopropyl alcohol (3.0 ml) was added 2.0 ml (4.0 mmol) of a 2N aqueous sodium hydroxide solution. Then, tetrahydrofuran was added until the reaction mixture became homogeneous, and the mixture was stirred at room temperature for 15.5 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 13 mg (0.022 mmol, yield 17%) of the title compound as a white solid.

Mass spectrum (DUIS$^-$, m/z): 582 [M−1]$^-$.

$^1$H-NMR spectrum (400 MHz, DMSO-d$_6$) δ: 12.41 (1H, brs), 9.59 (1H, brs), 7.52 (1H, dd, J=8.8, 5.1 Hz), 7.45-7.38 (2H, m), 7.38-7.30 (4H, m), 7.23 (1H, td, J=8.5, 3.1 Hz), 7.18 (1H, d, J=1.6 Hz), 7.09 (1H, dd, J=7.8, 1.6 Hz), 6.87 (1H, d, J=2.6 Hz), 5.95 (1H, q, J=6.4 Hz), 3.77 (3H, s), 1.52-1.42 (5H, m), 1.20-1.12 (2H, m).

Example 104

(R)-1-{4'-[3-({[1-(2-Chloro-4-fluorophenyl)ethoxy]carbonyl}amino)-5-fluorothiophen-2-yl]-2'-methoxy-[1,1'-biphenyl]-4-yl}cyclopropanecarboxylic acid (Compound No. I-466)

[Chemical Formula 213]

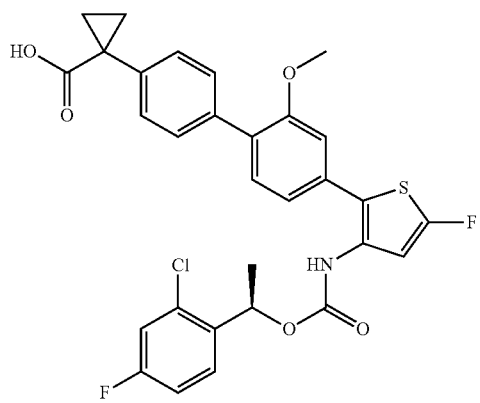

To a solution of 100 mg (0.227 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (2.0 ml) were added 0.050 ml (0.36 mmol) of triethylamine and 0.073 ml (0.34 mmol) of diphenylphosphoryl azide under an argon atmosphere, and the mixture was stirred at room temperature for 30 minutes. Then, a solution of 50 mg (0.29 mmol) of (R)-1-(2-chloro-4-fluorophenyl)ethanol (Enamine Ltd) in toluene (1.0 ml) dried over Molecular Sieves 4A (powder) (trade name, NACALAI TESQUE, INC.) (0.1 g) was added, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 72:30 (V/V)), and the fraction having around Rf=0.3 (developing solvent; hexane:ethyl acetate=80:20 (V/V)) was concentrated under reduced pressure to obtain 178 mg of a colorless oil. This was dissolved in isopropyl alcohol (2.0 ml), 2.0 ml (4.0 mmol) of a 2N aqueous sodium hydroxide solution was added, and the mixture was stirred at room temperature for 41 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 40 mg (0.068 mmol, yield 31%) of the title compound as a white solid.

Mass spectrum (DUIS$^-$, m/z): 582 [M−1]$^-$.

$^1$H-NMR spectrum (400 MHz, DMSO-d$_6$) δ: 12.41 (1H, brs), 9.54 (1H, brs), 7.55 (1H, brs), 7.47 (1H, dd, J=8.8, 2.4 Hz), 7.44-7.39 (2H, m), 7.38-7.34 (2H, m), 7.33 (1H, d, J=7.9 Hz), 7.31-7.23 (1H, m), 7.17 (1H, d, J=1.6 Hz), 7.08 (1H, dd, J=7.8, 1.4 Hz), 6.84 (1H, d, J=2.4 Hz), 5.97 (1H, q, J=6.2 Hz), 3.77 (3H, s), 1.54-1.41 (5H, m), 1.20-1.11 (2H, m).

Example 105

(RS)-1-{4'-[5-Fluoro-3-({[1-(5-fluoro-2-methylphenyl)ethoxy]carbonyl}amino)thiophen-2-yl]-2'-methoxy-[1,1'-biphenyl]-4-yl}cyclopropaneearboxylic acid ethyl ester (Compound No. I-479)

[Chemical Formula 214]

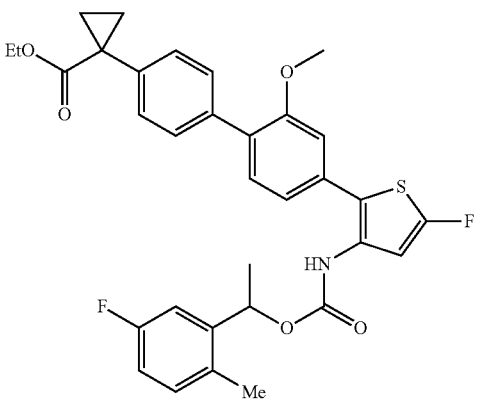

To a solution of 100 mg (0.227 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (3.0 ml) were added 0.050 ml (0.36 mmol) of triethylamine and 0.060 ml (0.28 mmol) of diphenylphosphoryl azide under an argon atmosphere, and the mixture was stirred at room temperature for 30 minutes. Then, 55 mg (0.36 mmol) of (RS)-1-(5-fluoro-2-methylphenyl)ethanol synthesized in analogy to Reference Example 48 was added, and the mixture was heated and stirred at 70° C. for 4 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 70:30 (V/V)), and the fractions containing the desired compound were concentrated under reduced pressure to obtain 134 mg (0.20 mmol (purity 90% by weight), yield 90%) of the title compound as a colorless oil.

Mass spectrum (CI, m/z): 591 [M]$^+$.

$^1$H-NMR spectrum (400 MHz, CDCl$_3$) δ: 7.53-7.48 (2H, m), 7.44-7.37 (3H, m), 7.14-7.02 (4H, m), 6.96 (1H, d, J=1.6 Hz), 6.92-6.79 (2H, m), 6.06-5.97 (1H, m), 4.13 (2H, q, J=7.1 Hz), 3.82 (3H, s), 2.35 (3H, s), 1.62 (2H, dd, J=6.9, 4.0 Hz), 1.51 (3H, d, J=6.7 Hz), 1.24 (2H, dd, J=7.0, 4.0 Hz), 1.20 (3H, t, J=7.1 Hz).

Example 106

(RS)-1-{4'-[5-Fluoro-3-({[1-(5-fluoro-2-methylphenyl)ethoxy]carbonyl}amino)thiophen-2-yl]-2'-methoxy-[1,1'-biphenyl]-4-yl}cyclopropanecarboxylic acid (Compound No. I-481)

[Chemical Formula 215]

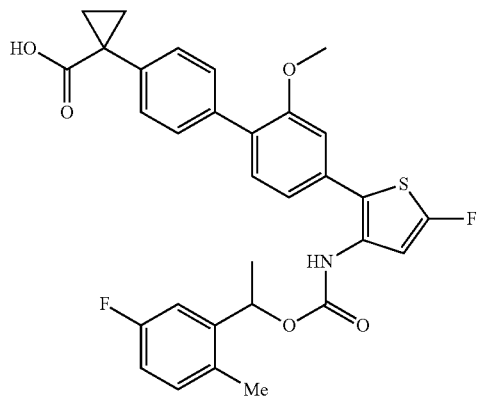

To a solution of 114 mg (0.173 mmol (purity 90% by weight)) of (RS)-1-{4'-[5-fluoro-3-({[1-(5-fluoro-2-methylphenyl)ethoxy]carbonyl}amino)thiophen-2-yl]-2'-methoxy-[1,1'-biphenyl]-4-yl}cyclopropanecarboxylic acid ethyl ester synthesized in Example 105 in isopropyl alcohol (2.0 ml) was added 1.1 ml (2.2 mmol) of a 2N aqueous sodium hydroxide solution, and the mixture was stirred at room temperature for 41.5 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 46 mg (0.082 mmol, yield 47%) of the title compound as a white solid.

Mass spectrum (DUIS$^-$, m/z): 562 [M−1]$^-$.

$^1$H-NMR spectrum (400 MHz, DMSO-d$_6$) δ: 12.35 (1H, brs), 9.49 (1H, brs), 7.43-7.38 (2H, m), 7.38-7.33 (2H, m), 7.31 (1H, d, J=7.9 Hz), 7.24-7.11 (3H, m), 7.07 (1H, dd, J=7.8, 1.6 Hz), 7.02 (1H, td, J=8.5, 2.8 Hz), 6.84 (1H, d, J=2.4 Hz), 5.85 (1H, q, J=6.5 Hz), 3.75 (3H, s), 2.28 (3H, s), 1.50-1.38 (5H, m), 1.18-1.09 (2H, m).

Example 107

(RS)-1-{4'-[5-Fluoro-3-({[1-(4-fluoro-2-methylphenyl)ethoxy]carbonyl}amino)thiophen-2-yl]-2'-methoxy-[1,1'-biphenyl]-4-yl}cyclopropanecarboxylic acid ethyl ester (Compound No. I-475)

[Chemical Formula 216]

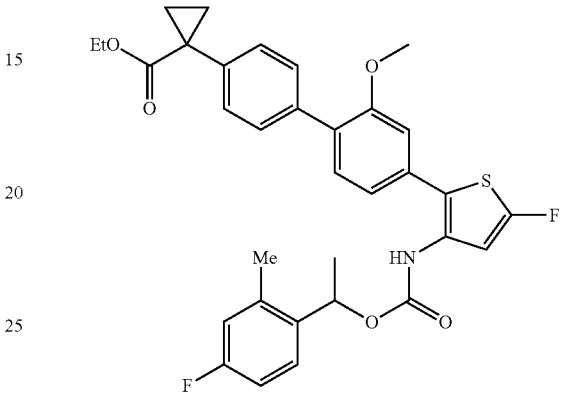

To a solution of 100 mg (0.227 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (3.0 ml) were added 0.050 ml (0.36 mmol) of triethylamine and 0.060 ml (0.28 mmol) of diphenylphosphoryl azide under an argon atmosphere, and the mixture was stirred at room temperature for 30 minutes. Then, 55 mg (0.36 mmol) of (RS)-1-(4-fluoro-2-methylphenyl)ethanol synthesized in analogy to Reference Example 49 was added, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 70:30 (V/V)), and the fractions containing the desired compound were concentrated under reduced pressure to obtain 124 mg (0.21 mmol, yield 92%) of the title compound as a colorless oil.

Mass spectrum (CI, m/z): 591 [M]$^+$.

$^1$H-NMR spectrum (400 MHz, CDCl$_3$) δ: 7.52-7.47 (2H, m), 7.42-7.37 (3H, m), 7.32 (1H, dd, J=8.4, 5.9 Hz), 7.13 (1H, brs), 7.04 (1H, dd, J=7.8, 1.6 Hz), 6.95 (1H, d, J=1.5 Hz), 6.92-6.71 (3H, m), 6.03 (1H, q, J=6.6 Hz), 4.13 (2H, q, J=7.1 Hz), 3.80 (3H, s), 2.40 (3H, s), 1.63 (2H, dd, J=6.9, 4.0 Hz), 1.53 (3H, d, J=6.5 Hz), 1.24 (2H, dd, J=7.1, 4.1 Hz), 1.20 (3H, t, J=7.1 Hz).

Example 108

(RS)-1-{4'-[5-Fluoro-3-({[1-(4-fluoro-2-methylphenyl)ethoxy]carbonyl}amino)thiophen-2-yl]-2'-methoxy-[1,1'-biphenyl]-4-yl}cyclopropanecarboxylic acid (Compound No. I-477)

[Chemical Formula 217]

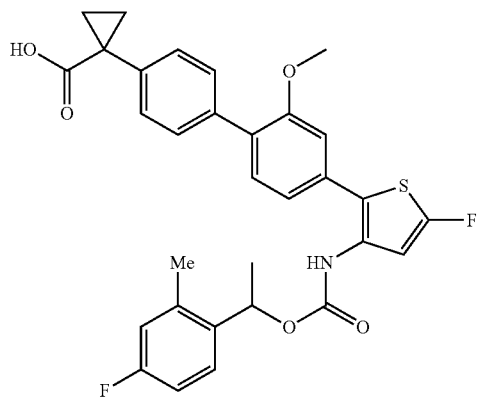

To a solution of 114 mg (0.193 mmol) of (RS)-1-{4'-[5-fluoro-3-({[1-(4-fluoro-2-methylphenyl)ethoxy]carbonyl}amino)thiophen-2-yl]-2'-methoxy-[1,1'-biphenyl]-4-yl}cyclopropanecarboxylic acid ethyl ester synthesized in analogy to Example 107 in isopropyl alcohol (2.0 ml) was added 1.0 ml (2.0 mmol) of a 2N aqueous sodium hydroxide solution, and the mixture was stirred at room temperature for 42.5 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure. To the resulting residue was added hexane, and the mixture was ultrasonically washed and subsequently concentrated under reduced pressure to obtain 58 mg (0.10 mmol, yield 53%) of the title compound as a white solid.

Mass spectrum (DUIS⁻, m/z): 562 [M−1]⁻.

$^1$H-NMR spectrum (400 MHz, DMSO-$d_6$) δ: 12.39 (1H, brs), 9.40 (1H, brs), 7.43-7.34 (5H, m), 7.31 (1H, d, J=7.9 Hz), 7.16 (1H, d, J=1.6 Hz), 7.09-6.98 (3H, m), 6.82 (1H, d, J=2.3 Hz), 5.86 (1H, q, J=6.4 Hz), 3.75 (3H, s), 2.32 (3H, s), 1.49-1.39 (5H, m), 1.18-1.12 (2H, m).

Example 109

(RS)-1-{4'-[5-Chloro-3-({[1-(thiophen-3-yl)ethoxy]carbonyl}amino)thiophen-2-yl]-[1,1'-biphenyl]-4-yl}cyclopropanecarboxylic acid ethyl ester (Compound No. I-591)

[Chemical Formula 218]

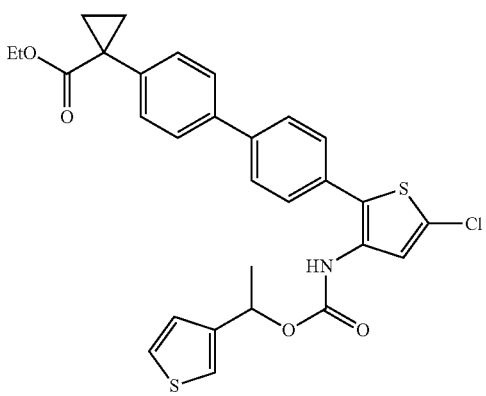

To 198.7 mg (0.467 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 was added dehydrated toluene (2 ml). The mixture was subjected to azeotropic dehydration treatment, and subsequently the atmosphere was replaced with argon. Then, 3 ml of dehydrated toluene, 0.115 ml (1.43 mmol) of dehydrated pyridine and 245.0 mg (0.570 mmol) of [bis(trifluoroacetoxy)iodo]benzene were added, and the mixture was stirred at room temperature for 5 minutes. Then, a solution of 94.1 mg (0.734 mmol) of (RS)-1-(thiophen-3-yl)ethanol synthesized in analogy to Reference Example 50 in dehydrated toluene (1 ml), dried over Molecular Sieves 4A (powder) (trade name, NACALAI TESQUE, INC.) (50 mg) was added, and the mixture was washed with dehydrated toluene (1 ml), and subsequently heated and stirred at 70° C. for 3 hours. After completion of the reaction, the reaction mixture was cooled, insoluble matter was filtered, and subsequently ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=99:1 to 88:12 (V/V)), and the fractions containing the desired compound were concentrated under reduced pressure to obtain 216.1 mg (0.391 mmol, yield 84%) of the title compound as a brown foam.

Mass spectrum (ESI⁻, m/z): 550 [M−1]⁻.

$^1$H-NMR spectrum (400 MHz, DMSO-$d_6$) δ: 9.33 (1H, brs), 7.76-7.70 (2H, m), 7.67-7.62 (2H, m), 7.59-7.50 (3H, m), 7.48-7.40 (3H, m), 7.19 (1H, s), 7.12 (1H, brs), 5.82 (1H, q, J=6.5 Hz), 4.05 (2H, q, J=7.1 Hz), 1.59-1.42 (3H, m), 1.51 (2H, dd, J=6.8, 4.0 Hz), 1.24 (2H, dd, J=7.1, 4.1 Hz), 1.11 (3H, t, J=7.1 Hz).

Example 110

(RS)-1-{4'-[5-Chloro-3-({[1-(thiophen-3-yl)ethoxy]carbonyl}amino)thiophen-2-yl]-[1,1'-biphenyl]-4-yl}cyclopropanecarboxylic acid (Compound No. I-595)

[Chemical Formula 219]

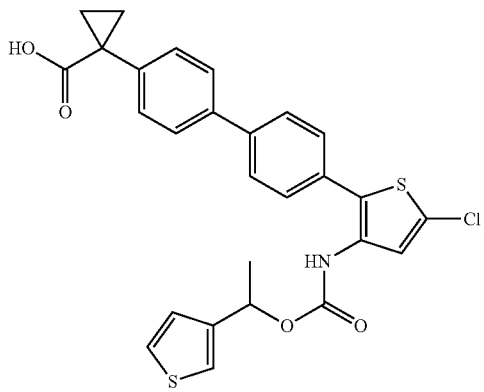

To a mixed solution of 214.1 mg (0.388 mmol) of (RS)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid ethyl ester synthesized in analogy to Example 109 in tetrahydrofuran (2 ml)-isopropyl alcohol (2 ml) was added 2.0 ml (4.0 mmol) of a 2N aqueous sodium hydroxide solution at room temperature, and the mixture was stirred at room temperature for 4 days. After completion of the reaction, the mixture was neutralized by adding 1N hydrochloric acid (4 ml), and subsequently ethyl acetate and water were added to separate the layers. The organic layer was dried over anhydrous magnesium sulfate and concentrated under reduced pressure. The resulting residue was subjected to silica gel column chromatography (a COOH column, elution solvent; hexane:ethyl acetate=62:38 to 10:90 (V/V)), and the fractions containing the desired compound were concentrated under reduced pressure. To the resulting residue was added hexane, and the mixture was sonicated and concentrated to dryness to obtain 145.6 mg (0.278 mmol, yield 72%) of the title compound as a white solid.

Mass spectrum (ESI$^-$, m/z): 522 [M−1]$^-$.

$^1$H-NMR spectrum (400 MHz, DMSO-d$_6$) δ: 12.40 (1H, brs), 9.33 (1H, brs), 7.75-7.68 (2H, m), 7.65-7.60 (2H, m), 7.58-7.51 (3H, m), 7.48-7.39 (3H, m), 7.19 (1H, s), 7.12 (1H, brs), 5.82 (1H, q, J=6.5 Hz), 1.57-1.43 (3H, m), 1.47 (2H, dd, J=6.8, 3.8 Hz), 1.17 (2H, dd, J=6.8, 3.9 Hz).

Example 111

(R)-1-{4'-[5-Chloro-3-({[1-(thiophen-3-yl)ethoxy]carbonyl}amino)thiophen-2-yl]-[1,1'-biphenyl]-4-yl}cyclopropanecarboxylic acid ethyl ester (Compound No. I-592)

[Chemical Formula 220]

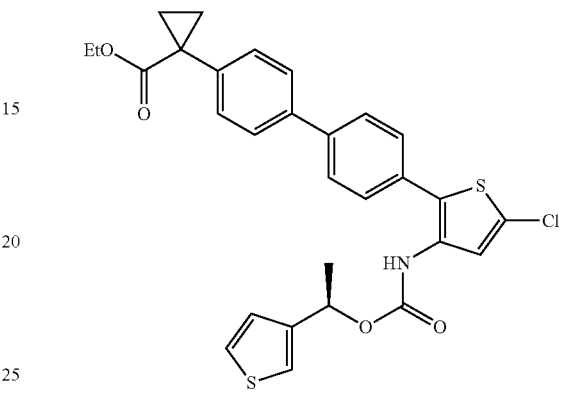

To a solution of 300 mg (0.704 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 and 0.53 ml (6.6 mmol) of pyridine in toluene (6 ml) was added 340 mg (0.791 mmol) of [bis(trifluoroacetoxy)iodo]benzene under an argon atmosphere, and the mixture was stirred at room temperature for 30 minutes. Then, 105 mg (0.819 mmol) of (R)-1-(thiophen-3-yl)ethanol synthesized in analogy to Reference Example 53 was added under a nitrogen atmosphere at room temperature, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20~30:70(V/V)), and the fractions containing the desired compound were concentrated under reduced pressure to obtain 306 mg (0.55 mmol, yield 79%) of the title compound as a brown oil.

Mass spectrum (DUIS$^-$, m/z): 550 [M−1]$^-$.

$^1$H-NMR spectrum (400 MHz, CDCl$_3$) δ: 7.69-7.63 (2H, m), 7.63-7.51 (3H, m), 7.48-7.40 (4H, m), 7.31 (1H, dd, J=5.0, 2.9 Hz), 7.28-7.26 (1H, m), 7.11 (1H, dd, J=5.0, 1.3 Hz), 6.72 (1H, s), 5.99 (1H, q, J=6.6 Hz), 4.13 (2H, q, J=7.1 Hz), 1.64 (2H, dd, J=7.0, 4.0 Hz), 1.62 (3H, d, J=6.5 Hz), 1.23 (2H, dd, J=7.0, 4.0 Hz), 1.19 (3H, t, J=7.1 Hz).

Example 112

(R)-1-{4'-[5-Chloro-3-({[1-(thiophen-3-yl)ethoxy]carbonyl}amino)thiophen-2-yl]-[1,1'-biphenyl]-4-yl}cyclopropanecarboxylic acid (Compound No. I-596)

Example 113

(RS)-1-{4'-[5-Chloro-3-({[1-(thiophen-3-yl)ethoxy]carbonyl}amino)thiophen-2-yl]-2'-methoxy-[1,1'-biphenyl]-4-yl}cyclopropanecarboxylic acid (Compound No. I-779)

[Chemical Formula 221]

[Chemical Formula 222]

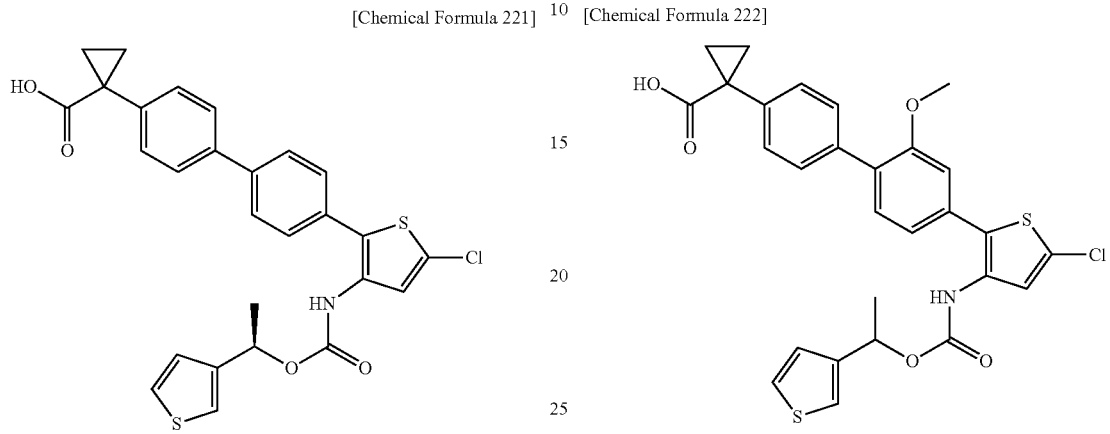

To a solution of 304 mg (0.551 mmol) of (R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid ethyl ester synthesized in analogy to Example 111 in isopropyl alcohol (4 ml) was added 2.0 ml (4.0 mmol) of a 2N aqueous sodium hydroxide solution, and the mixture was stirred at room temperature for 42.5 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=70:30 to 10:90 (V/V)), and the fractions containing the desired compound were concentrated under reduced pressure. To the resulting residue were added hexane (10 ml) and ethyl acetate (3 ml), and the precipitated white solid was filtered and washed with a mixed solution of hexane-ethyl acetate (3:1 (V/V)). The mother liquid and the washings were concentrated under reduced pressure to obtain 65 mg (0.55 mmol, yield 23%, optical purity 92% ee) of the title compound as a white solid.

Optical Purity Analysis Conditions

Column: CHIRALCEL OJ-H (trade name, Daicel Corporation)

Size: 0.46 cmI.D.×25 cmL.

Mobile phase: methanol/acetonitrile/acetic acid=90/10/0.1 (V/V/V)

Flow rate: 1.0 mL/min.

Temperature: 40° C.

Wavelength: 254 nm

Mass spectrum (DUIS$^-$, m/z): 522 [M−1]$^-$.

$^1$H-NMR spectrum (400 MHz, DMSO-d$_6$) δ: 12.37 (1H, brs), 9.33 (1H, brs), 7.74-7.68 (2H, m), 7.65-7.60 (2H, m), 7.58-7.50 (3H, m), 7.48-7.37 (3H, m), 7.25-7.07 (2H, m), 5.82 (1H, q, J=6.4 Hz), 1.56-1.44 (3H, m), 1.48 (2H, dd, J=6.7, 3.8 Hz), 1.19-1.16 (2H, m).

To a solution of 300 mg (0.658 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.532 ml (6.58 mmol) of pyridine in toluene (6.0 ml) was added 340 mg (0.791 mmol) of [bis(trifluoroacetoxy)iodo]benzene under an argon atmosphere, and the mixture was stirred at room temperature for 30 minutes. Then, 105 mg (0.819 mmol) of (RS)-1-(thiophen-3-yl)ethanol synthesized in analogy to Reference Example 50 was added, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fraction having around Rf=0.3 (developing solvent; hexane:ethyl acetate=80:20 (V/V)) was concentrated under reduced pressure to obtain 199 mg of a pale yellow oil. To this were added isopropyl alcohol (4.0 ml) and 1.0 ml (2.0 mmol) of a 2N aqueous sodium hydroxide solution, further, tetrahydrofuran was added until the reaction mixture became homogeneous, and the mixture was stirred at room temperature for 47 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure. To the resulting residue was added hexane, and the mixture was concentrated under reduced pressure to obtain 66 mg (0.12 mmol, yield 35%) of the title compound as a white solid.

Mass spectrum (DUN$^-$, m/z): 552 [M−1]$^-$.

$^1$H-NMR spectrum (400 MHz, DMSO-d$_6$) δ: 12.41 (1H, brs), 9.35 (1H, brs), 7.52 (1H, dd, J=4.8, 2.9 Hz), 7.45-7.39 (3H, m), 7.38-7.34 (2H, m), 7.33 (1H, d, J=7.9 Hz), 7.20 (1H, brs), 7.18 (1H, d, J=1.6 Hz), 7.14-7.10 (1H, m), 7.10 (1H, dd, J=7.8, 1.7 Hz), 5.83 (1H, q, J=6.4 Hz), 3.74 (3H, s), 1.55-1.46 (3H, m), 1.46 (2H, dd, J=6.7, 3.8 Hz), 1.17 (2H, dd, J=6.7, 3.9 Hz).

Example 114

(R)-1-{4'-[5-Chloro-3-({[1-(thiophen-3-yl)ethoxy]
carbonyl}amino)thiophen-2-yl]-2'-methoxy-[1,1'-
biphenyl]-4-yl}cyclopropanecarboxylic acid ethyl
ester (Compound No. I-776)

[Chemical Formula 223]

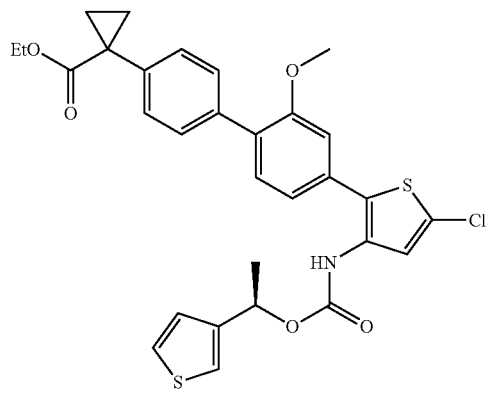

To 499.7 mg (1.096 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 was added dehydrated toluene (5 ml), the mixture was subjected to azeotropic dehydration treatment, and subsequently the atmosphere was replaced with argon. Then, 10 ml of dehydrated toluene, 0.442 ml (5.49 mmol) of dehydrated pyridine and 577.0 mg (1.342 mmol) of [bis(trifluoroacetoxy)iodo]benzene were added sequentially, and the mixture was stirred at room temperature for 5 minutes. Subsequently, 222.0 mg (1.732 mmol) of (R)-1-(thiophen-3-yl)ethanol synthesized in analogy to Reference Example 53 was added, and the mixture was heated and stirred at 70° C. for 3 hours. After completion of the reaction, the reaction mixture was cooled, and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=98:2 to 78:22 (V/V)), and the fractions containing the desired compound were concentrated under reduced pressure to obtain 438.9 mg (0.754 mmol, yield 69%) of the title compound as a pale yellow foam.

Mass spectrum (DUIS$^-$, m/z): 580 [M–1]$^-$.

$^1$H-NMR spectrum (400 MHz, DMSO-d$_6$) δ: 9.36 (1H, brs), 7.52 (1H, dd, J=4.8, 2.9 Hz), 7.47-7.42 (3H, m), 7.39-7.35 (2H, m), 7.35 (1H, d, J=7.8 Hz), 7.20 (1H, brs), 7.18 (1H, d, J=1.6 Hz), 7.14-7.09 (1H, m), 7.11 (1H, dd, J=7.8, 1.7 Hz), 5.83 (1H, q, J 6.3 Hz), 4.05 (2H, q, J=7.1 Hz), 3.74 (3H, s), 1.55-1.45 (3H, m), 1.51 (2H, dd, J=6.8, 3.9 Hz), 1.23 (2H, dd, J=7.0, 4.1 Hz), 1.12 (3H, t, J=7.0 Hz).

Example 115

(R)-1-{4'-[5-Chloro-3-({[1-(thiophen-3-yl)ethoxy]
carbonyl}amino)thiophen-2-yl]-2'-methoxy-[1,1'-
biphenyl]-4-yl}cyclopropanecarboxylic acid (Compound No. I-780)

[Chemical Formula 224]

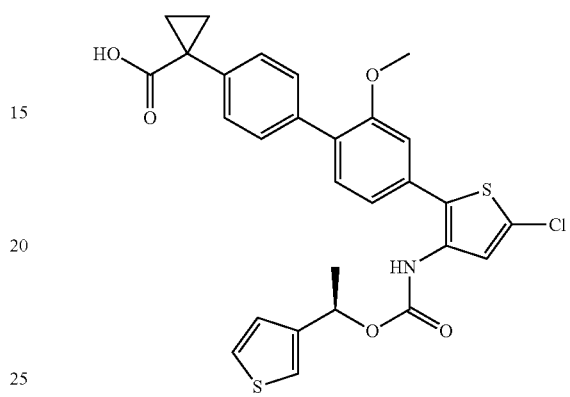

To a mixed solution of 435.9 mg (0.749 mmol) of (R)-1-{4'-[5-chloro-3-({[1-(thiophen-3-yl)ethoxy]carbonyl}amino)thiophen-2-yl]-2'-methoxy-[1,1'-biphenyl]-4-yl}cyclopropanecarboxylic acid ethyl ester synthesized in analogy to Example 114 in tetrahydrofuran (4 ml)-isopropyl alcohol (5 ml) was added 4.0 ml (8.0 mmol) of a 2N aqueous sodium hydroxide solution, and the mixture was stirred at room temperature for one hour. Additionally, tetrahydrofuran (2 ml) was then added, and the mixture was stirred at room temperature for 24 hours. Additionally, 2.0 ml (4.0 mmol) of a 2N aqueous sodium hydroxide solution and isopropyl alcohol (2 ml) were added, and the mixture was stirred at room temperature for 24 hours and then heated and stirred at 40° C. for 2 hours. After completion of the reaction, the mixture was neutralized by adding 12 ml of 1N hydrochloric acid under ice cooling, and subsequently ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=72:28 to 10:90 (V/V)), and the fractions containing the desired compound were concentrated under reduced pressure. To the resulting residue was added hexane, and the mixture was sonicated. A precipitated solid was collected by filtration, washed with hexane, and dried to obtain 280.9 mg (0.507 mmol, yield 68%, optical purity 85.2% ee) of the title compound as a white solid.

Optical Purity Analysis Conditions

Column: CHIRALCEL OJ-H (trade name, Daicel Corporation)

Size: 0.46 cmI.D.×25 cmL.

Mobile phase: methanol/acetonitrile/acetic acid=90/10/0.1 (V/V/V)

Flow rate: 1.0 mL/min.

Temperature: 40° C.

Wavelength: 254 nm

Mass spectrum (DUIS$^-$, m/z): 552 [M–1]$^-$.

$^1$H-NMR spectrum (400 MHz, DMSO-d$_6$) δ: 12.35 (1H, brs), 9.35 (1H, brs), 7.52 (1H, dd, J=4.8, 2.9 Hz), 7.47-7.40

(3H, m), 7.38-7.34 (2H, m), 7.33 (1H, d, J=7.9 Hz), 7.20 (1H, brs), 7.18 (1H, d, J=1.6 Hz), 7.14-7.08 (1H, m), 7.10 (1H, dd, J=7.9, 1.6 Hz), 5.83 (1H, q, J=6.4 Hz), 3.74 (3H, s), 1.56-1.44 (3H, m), 1.47 (2H, dd, J=6.7, 3.8 Hz), 1.17 (2H, dd, J=6.8, 4.0 Hz).

Example 116

(RS)-1-{4'-[5-Chloro-3-({[1-(4-methylthiophen-3-yl)ethoxy]carbonyl}amino)thiophen-2-yl]-[1,1'-biphenyl]-4-yl}cyclopropanecarboxylic acid ethyl ester (Compound No. I-601)

[Chemical Formula 225]

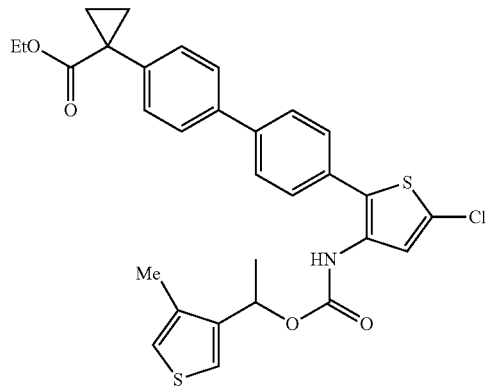

To 200.0 mg (0.470 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 was added dehydrated toluene (2 ml). The mixture was subjected to azeotropic dehydration treatment, and subsequently the atmosphere was replaced with argon. Then, 3 ml of dehydrated toluene, 0.115 ml (1.43 mmol) of dehydrated pyridine and 242.0 mg (0.563 mmol) of [bis(trifluoroacetoxy)iodo]benzene were added, and the mixture was stirred at room temperature for 5 minutes. Subsequently, a solution of 100.4 mg (0.706 mmol) of (RS)-1-(4-methylthiophen-3-yl)ethanol synthesized in analogy to Reference Example 39 in dehydrated toluene (1 ml), dried over Molecular Sieves 4A (powder) (trade name, NACALAI TESQUE, INC.) (100 mg) was added. The mixture was washed with dehydrated toluene (1 ml), and heated and stirred at 70° C. for 3 hours. After completion of the reaction, the mixture was cooled, insoluble matter was filtered, and subsequently ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=99:1 to 88:12 (V/V)), and the fractions containing the desired compound were concentrated under reduced pressure to obtain 229.7 mg (0.406 mmol, yield 86%) of the title compound as a brown foam.

Mass spectrum (ESI⁻, m/z): 564 [M−1]⁻.

¹H-NMR spectrum (400 MHz, DMSO-$d_6$) δ: 9.34 (1H, brs), 7.75-7.69 (2H, m), 7.67-7.61 (2H, m), 7.58-7.52 (2H, m), 7.49-7.39 (3H, m), 7.18 (1H, s), 7.15 (1H, d, J=1.8 Hz), 5.74 (1H, q, J=6.5 Hz), 4.05 (2H, q, J=7.1 Hz), 2.17 (3H, s), 1.58-1.46 (3H, m), 1.52 (2H, dd, J=6.9, 3.9 Hz), 1.24 (2H, dd, J=7.0, 4.1 Hz), 1.11 (3H, t, J=7.1 Hz).

Example 117

(RS)-1-{4'-[5-Chloro-3-({[1-(4-methylthiophen-3-yl)ethoxy]carbonyl}amino)thiophen-2-yl]-[1,1'-biphenyl]-4-yl}cyclopropanecarboxylic acid (Compound No. I-605)

[Chemical Formula 226]

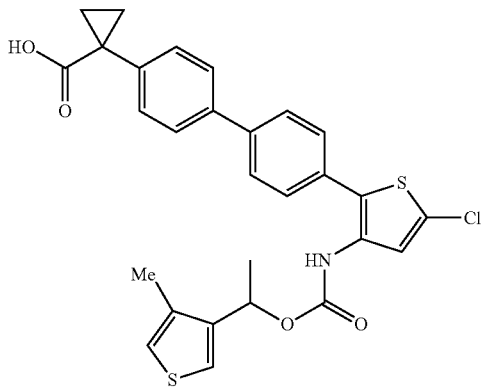

To a mixed solution of 226.7 mg (0.400 mmol) of (RS)-1-{4'-[5-chloro-3-({[1-(4-methylthiophen-3-yl)ethoxy]carbonyl}amino)thiophen-2-yl]-[1,1'-biphenyl]-4-yl}cyclopropanecarboxylic acid ethyl ester synthesized in analogy to Example 116 in tetrahydrofuran (2 ml)-isopropyl alcohol (2 ml) was added 2.0 ml (4.0 mmol) of a 2N aqueous sodium hydroxide solution at room temperature, and the mixture was stirred at room temperature for 4 days. After completion of the reaction, the mixture was neutralized by adding 4 ml of 1N hydrochloric acid, and subsequently ethyl acetate and water were added to separate the layers. The organic layer was dried over anhydrous magnesium sulfate and concentrated under reduced pressure. The resulting residue was subjected to silica gel column chromatography (a COOH column, elution solvent; hexane:ethyl acetate=62:38 to 10:90 (V/V)), and the fractions containing the desired compound were concentrated under reduced pressure to obtain 154.1 mg (0.286 mmol, yield 72%) of the title compound as a pale red solid.

Mass spectrum (ESI⁻, m/z): 536 [M−1]⁻.

¹H-NMR spectrum (400 MHz, DMSO-$d_6$) δ: 12.44 (1H, brs), 9.34 (1H, brs), 7.74-7.68 (2H, m), 7.65-7.60 (2H, m), 7.57-7.52 (2H, m), 7.48-7.39 (3H, m), 7.18 (1H, brs), 7.17-7.14 (1H, m), 5.74 (1H, q, J=6.5 Hz), 2.17 (3H, s), 1.58-1.45 (3H, m), 1.48 (2H, dd, J=6.7, 3.8 Hz), 1.17 (2H, dd, J=6.8, 4.0 Hz).

Example 118

(R)-1-{4'-[5-Chloro-3-({[1-(4-methylthiophen-3-yl)ethoxy]carbonyl}amino)thiophen-2-yl]-[1,1'-biphenyl]-4-yl}cyclopropanecarboxylic acid ethyl ester (Compound No. I-602)

[Chemical Formula 227]

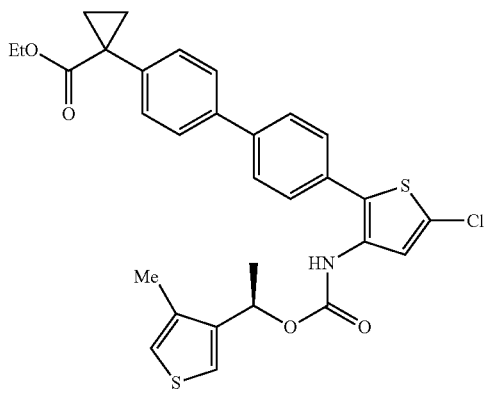

To a solution of 550 mg (1.29 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24 and 0.55 ml (6.8 mmol) of pyridine in toluene (10 ml) was added 670 mg (1.56 mmol) of [bis(trifluoroacetoxy)iodo]benzene under an argon atmosphere, and the mixture was stirred at room temperature for 30 minutes. Then, a toluene solution (1 ml) of 220 mg (1.55 mmol) of (R)-1-(4-methylthiophen-3-yl)ethanol synthesized in analogy to Reference Example 54, dried over Molecular Sieves 4A (powder) (trade name, NACALAI TESQUE, INC.) (0.3 g) was added, and the mixture was heated and stirred at 70° C. for 2.5 hours. After completion of the reaction, to the reaction mixture were added ethyl acetate and 2N hydrochloric acid to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 (V/V)), and the fractions containing the desired compound were concentrated under reduced pressure to obtain 644 mg (1.14 mmol, yield 88%) of the title compound as an orange foam.

Mass spectrum (DUIS−, m/z): 564 [M−1]−.

$^1$H-NMR spectrum (400 MHz, DMSO-$d_6$) δ: 9.34 (1H, brs), 7.75-7.69 (2H, m), 7.67-7.62 (2H, m), 7.58-7.52 (2H, m), 7.49-7.40 (3H, m), 7.21-7.12 (2H, m), 5.74 (1H, q, J=6.5 Hz), 4.05 (2H, q, J=7.1 Hz), 2.17 (3H, s), 1.61-1.42 (3H, m), 1.52 (2H, dd, J=6.8, 4.0 Hz), 1.24 (2H, dd, J=7.1, 4.1 Hz), 1.11 (3H, t, J=7.1 Hz).

Example 119

(R)-1-{4'-[5-Chloro-3-({[1-(4-methylthiophen-3-yl)ethoxy]carbonyl}amino)thiophen-2-yl]-[1,1'-biphenyl]-4-yl}cyclopropanecarboxylic acid (Compound No. I-606)

[Chemical Formula 228]

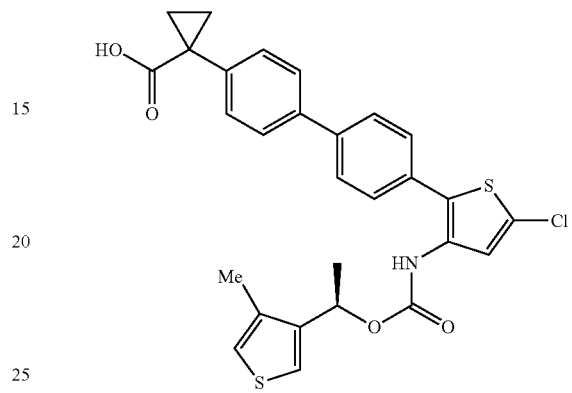

To a solution of 644 mg (1.14 mmol) of (R)-1-{4'-[5-chloro-3-({[1-(4-methylthiophen-3-yl)ethoxy]carbonyl}amino)thiophen-2-yl]-[1,1'-biphenyl]-4-yl}cyclopropanecarboxylic acid ethyl ester synthesized in analogy to Example 118 in isopropyl alcohol (10 ml) was added 5.0 ml (10 mmol) of a 2N aqueous sodium hydroxide solution, and the mixture was stirred at room temperature for 18 hours. Then, the mixture was stirred at 40° C. for 8 hours and futhrer at room temperature for 15 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=50:50 (V/V)), and the fractions containing the desired compound were concentrated under reduced pressure. To the resulting residue were added 10 ml of hexane and 6 mL of ethyl acetate, and the precipitated solid was filtered and washed with a mixed solution of hexane-ethyl acetate (5:3 (V/V)). The mother liquid and the washings were concentrated under reduced pressure, to the resulting residue were added 8 ml of acetonitrile, 4 ml of water and 3 ml of tetrahydrofuran, and the mixture was lyophilized to obtain 125 mg (0.23 mmol, yield 20%, optical purity 87% ee) of the title compound as a white foam.

Optical Purity Analysis Conditions

Column: CHIRALCEL OJ-H (trade name, Daicel Corporation)

Size: 0.46 cmI.D.×25 cmL.

Mobile phase: methanol/acetonitrile/acetic acid=90/10/0.1 (V/V/V)

Flow rate: 1.0 mL/min.

Temperature: 40° C.

Wavelength: 254 nm

Mass spectrum (DUIS−, m/z): 536 [M−1]−.

$^1$H-NMR spectrum (400 MHz, DMSO-$d_6$) δ: 12.37 (1H, brs), 9.34 (1H, brs), 7.74-7.68 (2H, m), 7.66-7.60 (2H, m), 7.58-7.51 (2H, m), 7.48-7.38 (3H, m), 7.22-7.11 (2H, m), 5.74 (1H, q, J=6.5 Hz), 2.17 (3H, s), 1.61-1.46 (3H, m), 1.48 (2H, dd, J=6.7, 3.8 Hz), 1.18 (2H, dd, J=6.8, 3.9 Hz).

Example 120

(RS)-1-{4'-[5-Chloro-3-({[1-(4-methylthiophen-3-yl)ethoxy]carbonyl}amino)thiophen-2-yl]-2'-methoxy-[1,1'-biphenyl]-4-yl}cyclopropanecarboxylic acid ethyl ester (Compound No. I-781)

[Chemical Formula 229]

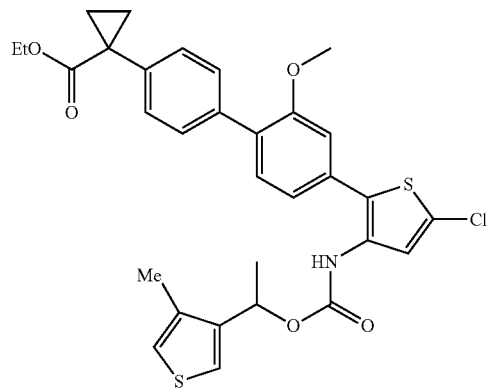

To 101.8 mg (0.223 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 was added dehydrated toluene (1 ml). The mixture was subjected to azeotropic dehydration treatment, and subsequently the atmosphere was replaced with argon. Then, 1 ml of dehydrated toluene, 0.090 ml (1.1 mmol) of dehydrated pyridine and 117.0 mg (0.272 mmol) of [bis(trifluoroacetoxy)iodo]benzene were added sequentially, and the mixture was stirred at room temperature for 5 minutes. Subsequently, a solution of 49.0 mg (0.35 mmol) of (RS)-1-(4-methylthiophen-3-yl)ethanol synthesized in analogy to Reference Example 39 in dehydrated toluene (1 ml), dried over Molecular Sieves 4A (powder) (trade name, NACALAI TESQUE, INC.) (50 mg) was added, and the mixture was washed with dehydrated toluene (1 ml) and heated and stirred at 70° C. for 3 hours. After completion of the reaction, the reaction mixture was cooled, insoluble matter was filtered, and subsequently ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=99:1 to 84:16 (V/V)), and the fractions containing the desired compound were concentrated under reduced pressure to obtain 57.2 mg (0.096 mmol, yield 43%) of the title compound as a pale yellow foam.

Mass spectrum (ESI⁻, m/z): 594 [M−1]⁻.

$^1$H-NMR spectrum (400 MHz, DMSO-$d_6$) δ: 9.35 (1H, brs), 7.47-7.41 (3H, m), 7.39-7.35 (2H, m), 7.34 (1H, d, J=7.9 Hz), 7.19 (1H, brs), 7.18 (1H, d, J=1.6 Hz), 7.14 (1H, d, J=2.3 Hz), 7.11 (1H, dd, J=7.9, 1.6 Hz), 5.76 (1H, q, J=6.5 Hz), 4.05 (2H, q, J=7.1 Hz), 3.75 (3H, s), 2.16 (3H, brs), 1.62-1.40 (3H, m), 1.51 (2H, dd, J=6.8, 4.0 Hz), 1.23 (2H, dd, J=7.0, 4.1 Hz), 1.12 (3H, t, J=7.1 Hz).

Example 121

(RS)-1-{4'-[5-Chloro-3-({[1-(4-methylthiophen-3-yl)ethoxy]carbonyl}amino)thiophen-2-yl]-2'-methoxy-[1,1'-biphenyl]-4-yl}cyclopropanecarboxylic acid (Compound No. I-783)

[Chemical Formula 230]

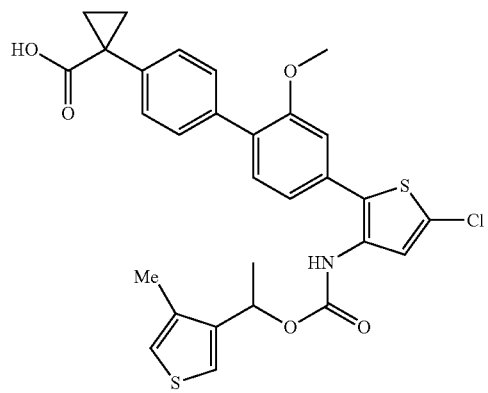

To a mixed solution of 55.8 mg (0.400 mmol) of (RS)-1-{4'-[5-chloro-3-({[1-(4-methylthiophen-3-yl)ethoxy]carbonyl}amino)thiophen-2-yl]-2'-methoxy-[1,1'-biphenyl]-4-yl}cyclopropanecarboxylic acid ethyl ester synthesized in analogy to Example 120 in tetrahydrofuran (2 ml)-isopropyl alcohol (2 ml) was added 1.0 ml (2.0 mmol) of a 2N aqueous sodium hydroxide solution, and the mixture was stirred at room temperature for 3 days. After completion of the reaction, the mixture was neutralized by adding 2 ml of 1N hydrochloric acid, and subsequently ethyl acetate and water were added to separate the layers. The organic layer was dried over anhydrous magnesium sulfate and concentrated under reduced pressure. The resulting residue was purified by preparative HPLC using a column of Xbridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B), gradient (% by volume of solution B): 80% (0.00 min.)—80% (0.80 min.)—90% (7.00 min.)—90% (12.00 min.)). To the fractions containing the desired compound was added water, and the mixture was lyophilized to obtain 36.9 mg (0.065 mmol, yield 69%) of the title compound as a white foam.

Mass spectrum (ESI⁻, m/z): 566 [M−1]⁻.

$^1$H-NMR spectrum (400 MHz, DMSO-$d_6$) δ: 12.44 (1H, brs), 9.36 (1H, brs), 7.47-7.39 (3H, m), 7.38-7.34 (2H, m), 7.33 (1H, d, J=7.9 Hz), 7.19 (1H, s), 7.17 (1H, d, J=1.5 Hz), 7.15 (1H, d, J=2.4 Hz), 7.10 (1H, dd, J=7.8, 1.6 Hz), 5.76 (1H, q, J=6.5 Hz), 3.75 (3H, s), 2.16 (3H, brs), 1.57-1.43 (3H, m), 1.45 (2H, dd, J=6.5, 3.8 Hz), 1.15 (2H, dd, J=6.0, 3.8 Hz).

Example 122

(RS)-1-{4'-[5-Chloro-3-({[1-(4-chlorothiophen-3-yl)ethoxy]carbonyl}amino)thiophen-2-yl]-2'-methoxy-[1,1'-biphenyl]-4-yl}cyclopropanecarboxylic acid ethyl ester (Compound No. I-789)

[Chemical Formula 231]

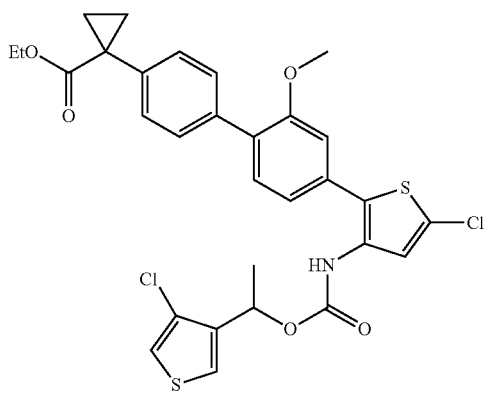

To a solution of 150 mg (0.22 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30 and 0.27 mL (3.34 mmol) of pyridine in toluene (2 ml) was added 170 mg (0.40 mmol) of [bis(trifluoroacetoxy)iodo]benzene under an argon atmosphere, and the mixture was stirred at room temperature for 30 minutes. Then, a toluene solution (1 ml) of 54 mg (0.33 mmol) of (RS)-1-(4-chlorothiophen-3-yl)ethanol synthesized in analogy to Reference Example 40, dried over Molecular Sieves 4A (powder) (trade name, NACALAI TESQUE, INC.) (0.1 g) was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 70:30 (V/V)), and the fractions containing the desired compound were concentrated under reduced pressure to obtain 186 mg (0.26 mmol (purity 86% by weight), yield 79%) of the title compound as a pale yellow oil.

$^1$H-NMR spectrum (400 MHz, CDCl$_3$) δ: 7.58 (1H, brs), 7.52-7.46 (2H, m), 7.42-7.37 (3H, m), 7.28-7.25 (1H, m), 7.17-7.14 (1H, m), 7.05 (1H, dd, J=7.7, 1.7 Hz), 6.96 (1H, d, J=1.6 Hz), 6.80 (1H, brs), 5.98 (1H, q, J=6.6 Hz), 4.13 (2H, q, J=7.1 Hz), 3.81 (3H, s), 1.66-1.60 (5H, m), 1.23 (2H, dd, J=6.8, 3.8 Hz), 1.20 (3H, t, J=7.1 Hz).

Example 123

(RS)-1-{4'-[5-Chloro-3-({[1-(4-chlorothiophen-3-yl)ethoxy]carbonyl}amino)thiophen-2-yl]-2'-methoxy-[1,1'-biphenyl]-4-yl}cyclopropanecarboxylic acid (Compound No. I-791)

[Chemical Formula 232]

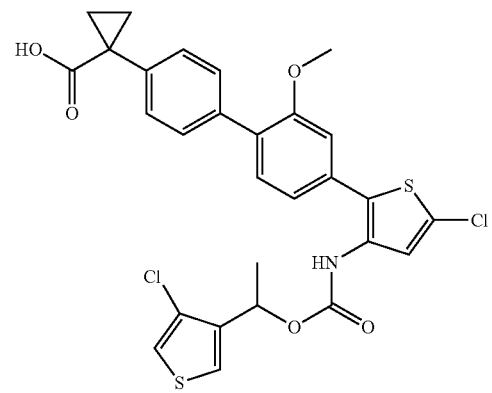

To a solution of 182 mg (0.25 mmol (purity 86% by weight)) of (RS)-1-{4'-[5-chloro-3-({[1-(4-chlorothiophen-3-yl)ethoxy]carbonyl}amino)thiophen-2-yl]-2'-methoxy-[1,1'-biphenyl]-4-yl}cyclopropanecarboxylic acid ethyl ester synthesized in Example 122 in isopropyl alcohol (3 ml) was added 2.0 ml (4.0 mmol) of a 2N aqueous sodium hydroxide solution, further tetrahydrofuran was added until the reaction mixture became homogeneous, and the mixture was stirred at room temperature for 67 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure. To the resulting residue was added hexane, and the mixture was concentrated under reduced pressure to obtain 22 mg (0.037 mmol, yield 15%) of the title compound as a white solid.

Mass spectrum (DUIS$^-$, m/z): 586 [M−1]$^-$.

$^1$H-NMR spectrum (400 MHz, DMSO-d$_6$) δ: 12.42 (1H, brs), 9.41 (1H, brs), 7.75-7.56 (2H, m), 7.46-7.39 (2H, m), 7.38-7.33 (2H, m), 7.33 (1H, d, J=8.0 Hz), 7.24-7.15 (1H, m), 7.18 (1H, d, J=1.6 Hz), 7.11 (1H, dd, J=7.8, 1.6 Hz), 5.76 (1H, q, J=6.4 Hz), 3.77 (3H, s), 1.62-1.38 (5H, m), 1.20-1.07 (2H, m).

Example 124

(RS)-1-{4'-[5-Chloro-3-({[(1-(isothiazol-3-yl)ethoxy]carbonyl}amino)thiophen-2-yl]-[1,1'-biphenyl]-4-yl}cyclopropanecarboxylic acid (Compound. No. I-621)

[Chemical Formula 233]

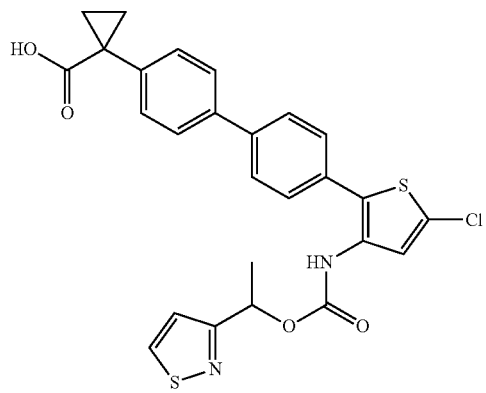

To a solution of 89 mg (0.22 mmol) of 1-[4'-(3-carbamoyl-5-chlorothiophen-2-yl)-[1,1'-biphenyl]-4-yl]cyclopropanecarboxylic acid synthesized in analogy to Reference Example 37 and 0.18 ml (2.2 mmol) of pyridine in toluene (2 ml) was added 115 mg (0.267 mmol) of [bis(trifluoroacetoxy)iodo]benzene under an argon atmosphere, and the mixture was stirred at room temperature for 30 minutes. Then, 29 mg (0.22 mmol) of (RS)-1-(isothiazol-3-yl)ethanol synthesized in analogy to Reference Example 51 was added, and the mixture was heated and stirred at 70° C. for 2.0 hours. After completion of the reaction, to the reaction mixture were added ethyl acetate and 2N hydrochloric acid to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure. The residue was dissolved in ethanol, subsequently water was added, and the precipitated solid was collected by filtration, washed with water and subsequently dried under reduced pressure to obtain 6.7 mg (0.013 mmol, yield 5.7%) of the title compound as a white solid.

Mass spectrum (DUIS$^-$, m/z): 523 [M−1]$^-$.

$^1$H-NMR spectrum (400 MHz, DMSO-d$_6$) δ: 12.33 (1H, brs), 9.45 (1H, brs), 9.06 (1H, d, J=4.6 Hz), 7.75-7.69 (2H, m), 7.67-7.60 (2H, m), 7.60-7.54 (2H, m), 7.47-7.40 (2H, m), 7.35 (1H, brs), 7.20 (1H, s), 5.88 (1H, q, J=6.6 Hz), 1.62-1.51 (3H, m), 1.48 (2H, dd, J=6.7, 3.8 Hz), 1.18 (2H, dd, J=6.7, 4.0 Hz).

Example 125

(RS)-1-{4'-[5-Chloro-3-({[1-(isothiazol-4-yl)ethoxy]carbonyl}amino)thiophen-2-yl]-[1,1'-biphenyl]-4-yl}cyclopropanecarboxylic acid (Compound No. I-625)

[Chemical Formula 234]

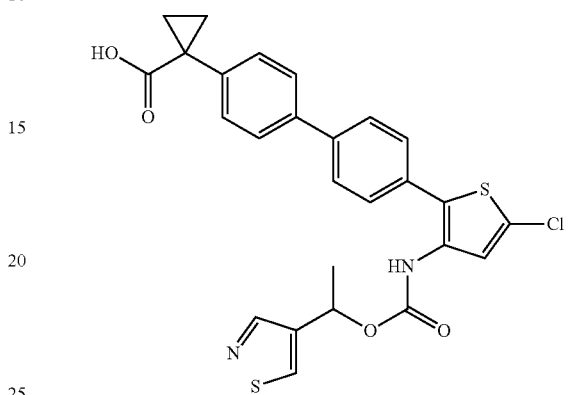

105 mg (0.27 mmol) of 1-[4'-(3-carbamoyl-5-chlorothiophen-2-yl)-[1,1'-biphenyl]-4-yl]cyclopropanecarboxylic acid synthesized in analogy to Reference Example 37 was subjected to azeotropic dehydration treatment with dehydrated toluene, and the atmosphere was replaced with argon. Then, 0.22 ml (2.7 mmol) of pyridine and 5 ml of toluene were added, subsequently 137.5 mg (0.32 mmol) of [bis(trifluoroacetoxy)iodo]benzene was added, and the mixture was stirred at room temperature for 30 minutes. Then, 45.1 mg (0.35 mmol) of (RS)-1-(isothiazol-4-yl)ethanol synthesized in analogy to Reference Example 41 was added, and the mixture was heated and stirred at 70° C. for 2 hours. After completion of the reaction, the reaction mixture was concentrated under reduced pressure, the resulting residue was subjected to silica gel column chromatography (elution solvent; hexane:ethyl acetate=90:10 to 0:100 (V/V)), and the fractions containing the desired compound were concentrated under reduced pressure. The resulting residue was subjected to silica gel column chromatography again (elution solvent; hexane:ethyl acetate=75:25 to 0:100 (V/V)), and the fractions containing the desired compound were concentrated under reduced pressure. The resulting residue was dissolved in tetrahydrofuran, insoluble matter was filtered, subsequently diethyl ether was added, and the precipitated solid was collected by filtration and dried under reduced pressure to obtain 40 mg (0.076 mmol, yield 29%) of the title compound as a white solid.

Mass spectrum (CI, m/z): 525 [M+1]$^+$.

$^1$H-NMR spectrum (400 MHz, DMSO-d$_6$) δ: 12.38 (1H, brs), 9.41 (1H, brs), 8.97 (1H, brs), 8.60 (1H, brs), 7.73-7.68 (2H, m), 7.65-7.60 (2H, m), 7.56-7.51 (2H, m), 7.45-7.39 (2H, m), 7.20 (1H, s), 5.94 (1H, q, J=5.9 Hz), 1.66-1.50 (3H, m), 1.47 (2H, dd, J=6.6, 3.8 Hz), 1.17 (2H, dd, J=6.6, 3.8 Hz).

Example 126

(RS)-1-(4-{5-[5-Chloro-3-({[1-(thiophen-3-yl)ethoxy]carbonyl}amino)thiophen-2-yl]-pyridine-2-yl}phenyl)cyclopropanecarboxylic acid ethyl ester (Compound No. I-691)

[Chemical Formula 235]

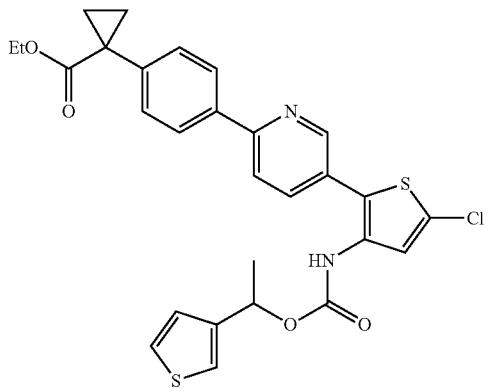

To 202.5 mg (0.474 mmol) of 1-{4-[5-(3-carbamoyl-5-chlorothiophen-2-yl)pyridine-2-yl]phenyl}cyclopropanecarboxylic acid ethyl ester synthesized in analogy to Reference Example 29 was added dehydrated toluene (2 ml). The mixture was subjected to azeotropic dehydration treatment, and subsequently the atmosphere was replaced with argon. Then, 3 ml of dehydrated toluene, 0.38 ml (4.7 mmol) of dehydrated pyridine and 255.0 mg (0.593 mmol) of [bis(trifluoroacetoxy)iodo]benzene were added sequentially, and the mixture was stirred at room temperature for 20 minutes. Subsequently, a solution of 91.0 mg (0.71 mmol) of (RS)-1-(thiophen-3-yl)ethanol synthesized in analogy to Reference Example 50 in dehydrated toluene (1 ml), dried over Molecular Sieves 4A (powder) (trade name, NACALAI TESQUE, INC.) (100 mg) was added, and the mixture was washed with dehydrated toluene (1 ml) and then heated and stirred at 70° C. for 4 hours. After completion of the reaction, the reaction mixture was cooled and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=99:1 to 80:20 (V/V)), and the fractions containing the desired compound were concentrated under reduced pressure to obtain 223.4 mg (0.366 mmol (purity 91% by weight), yield 77%) of the title compound as an orange oil.

Mass spectrum (ESI⁻, m/z): 551 [M−1]⁻.

$^1$H-NMR spectrum (400 MHz, DMSO-$d_6$) δ: 9.52 (1H, brs), 8.75 (1H, dd, J=2.4, 0.8 Hz), 8.09-8.04 (2H, m), 8.02 (1H, dd, J=8.4, 0.6 Hz), 7.92 (1H, dd, J=8.3, 2.4 Hz), 7.52 (1H, dd, J=4.8, 3.0 Hz), 7.49-7.43 (3H, m), 7.27 (1H, brs), 7.16-7.08 (1H, m), 5.82 (1H, q, J=6.4 Hz), 4.05 (2H, q, J=7.1 Hz), 1.57-1.46 (3H, m), 1.52 (2H, dd, J 6.9, 3.9 Hz), 1.25 (2H, dd, J=7.1, 4.1 Hz), 1.11 (3H, t, J=7.1 Hz).

Example 127

(RS)-1-(4-{5-[5-Chloro-3-({[1-(thiophen-3-yl)ethoxy]carbonyl}amino)thiophen-2-yl]-pyridine-2-yl}phenyl)cyclopropanecarboxylic acid (Compound No. I-693)

[Chemical Formula 236]

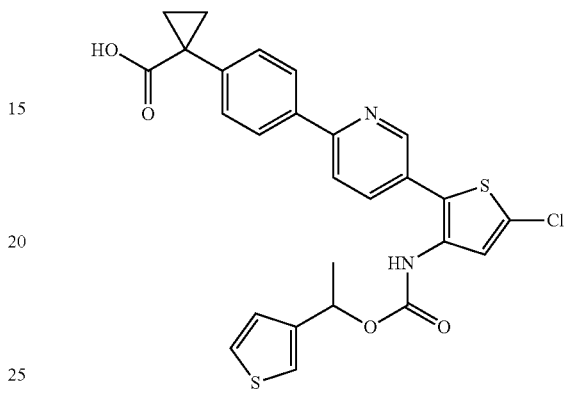

To a mixed solution of 218.8 mg (0.359 mmol (purity 91% by weight)) of (RS)-1-(4-{5-[5-chloro-3-({[1-(thiophen-3-yl)ethoxy]carbonyl}amino)thiophen-2-yl]-pyridine-2-yl}phenyl)cyclopropanecarboxylic acid ethyl ester synthesized in Example 126 in isopropyl alcohol (4.0 ml)-tetrahydrofuran (4.0 ml) was added 2.0 ml (4.0 mmol) of a 2N aqueous sodium hydroxide solution, and the mixture was stirred at room temperature for 3 days and then heated and stirred at 35° C. for 6 hours. After completion of the reaction, the mixture was neutralized by adding 1N hydrochloric acid (4.0 ml), and subsequently ethyl acetate and water were added to separate the layers. The organic layer was dried over anhydrous magnesium sulfate and concentrated under reduced pressure. The resulting residue was purified by preparative HPLC using a column of Xbridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B), gradient (% by volume of solution B): 70% (0.00 min.)—70% (0.80 min.)—90% (7.00 min.)—90% (12.00 min.)). To the fractions containing the desired compound was added water, and the mixture was lyophilized to obtain 132.4 mg (0.252 mmol, yield 70%) of the title compound as a white foam.

Mass spectrum (ESI⁺, m/z): 525 [M+1]⁺.

$^1$H-NMR spectrum (400 MHz, DMSO-$d_6$) δ: 12.44 (1H, brs), 9.50 (1H, brs), 8.75 (1H, dd, J=2.4, 0.8 Hz), 8.06-8.02 (2H, m), 8.00 (1H, dd, J=8.4, 0.8 Hz), 7.91 (1 H, dd, J=8.4, 2.4 Hz), 7.52 (1H, dd, J=4.9, 3.0 Hz), 7.48-7.41 (3H, m), 7.27 (1H, brs), 7.12 (1H, d, J=3.1 Hz), 5.82 (1H, q, J=6.5 Hz), 1.59-1.44 (3H, m), 1.47 (2H, dd, J=6.7, 3.8 Hz), 1.17 (2H, dd, J=6.5, 3.9 Hz).

Example 128

(RS)-1-(4-{5-[5-Chloro-3-({[1-(4-methylthiophen-3-yl)ethoxy]carbonyl}amino)thiophen-2-yl]pyridine-2-yl}phenyl)cyclopropanecarboxylic acid ethyl ester (Compound No. I-695)

[Chemical Formula 237]

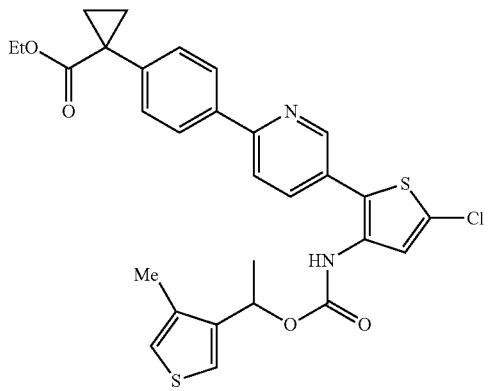

To 200.8 mg (0.470 mmol) of 1-{4-[5-(3-carbamoyl-5-chlorothiophen-2-yl)pyridine-2-yl]phenyl}cyclopropanecarboxylic acid ethyl ester synthesized in analogy to Reference Example 29 was added dehydrated toluene (2 ml). The mixture was subjected to azeotropic dehydration treatment, and subsequently the atmosphere was replaced with argon. Then, 6 mL of dehydrated toluene, 0.38 ml (4.7 mmol) of dehydrated pyridine and 265.0 mg (0.616 mmol) of [bis(trifluoroacetoxy)iodo]benzene were added, and the mixture was stirred at room temperature for 10 minutes. Subsequently, a solution of 100.0 mg (0.703 mmol) of (RS)-1-(4-methylthiophen-3-yl)ethanol synthesized in analogy to Reference Example 39 in dehydrated toluene (1 ml), dried over Molecular Sieves 4A (powder) (trade name, NACALAI TESQUE, INC.) (100 mg) was added, and the mixture was washed with dehydrated toluene (1 ml) and then heated and stirred at 70° C. for 4 hours. After completion of the reaction, the reaction mixture was cooled and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=99:1 to 80:20 (V/V)), and the fractions containing the desired compound were concentrated under reduced pressure to obtain 234.9 mg (0.358 mmol, purity 86% by weight), yield 76%) of the title compound as an orange oil.

Mass spectrum (ESI⁻, m/z): 565 [M−1]⁻.

$^1$H-NMR spectrum (400 MHz, DMSO-$d_6$) δ: 9.52 (1H, brs), 8.74 (1H, dd, J=2.4, 0.8 Hz), 8.08-8.04 (2H, m), 8.02 (1H, dd, J=8.4, 0.6 Hz), 7.91 (1H, dd, J=8.4, 2.4 Hz), 7.50-7.41 (3H, m), 7.27 (1H, brs), 7.15 (1H, d, J=2.1 Hz), 5.74 (1H, q, J=6.5 Hz), 4.05 (2H, q, J=7.1 Hz), 2.18-2.13 (3H, m), 1.59-1.44 (3H, m), 1.52 (2H, dd, J=6.8, 4.0 Hz), 1.25 (2H, dd, J=7.1, 4.1 Hz), 1.11 (3H, t, J=7.1 Hz).

Example 129

(RS)-1-(4-{5-[5-Chloro-3-({[1-(4-methylthiophen-3-yl)ethoxy]carbonyl}amino)thiophen-2-yl]pyridine-2-yl}phenyl)cyclopropanecarboxylic acid (Compound No. I-697)

[Chemical Formula 238]

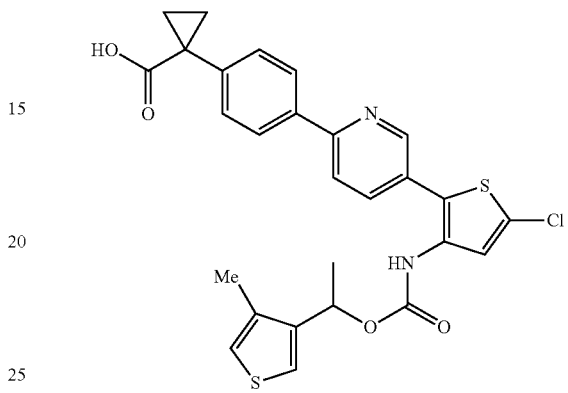

To a solution of 230.3 mg (0.351 mmol (purity 86% by weight)) of (RS)-1-(4-{5-[5-chloro-3-({[1-(4-methylthiophen-3-yl)ethoxy]carbonyl}amino)thiophen-2-yl]pyridine-2-yl}phenyl)cyclopropanecarboxylic acid ethyl ester synthesized in Example 128 in tetrahydrofuran (2.0 ml) were added 2.0 ml (4.0 mmol) of a 2N aqueous sodium hydroxide solution and isopropyl alcohol (4.0 ml), and the mixture was stirred at room temperature for 2 days. After completion of the reaction, the mixture was neutralized by adding 4.0 ml of 1N hydrochloric acid, and subsequently ethyl acetate and water were added to separate the layers. The organic layer was dried over anhydrous magnesium sulfate and concentrated under reduced pressure. The resulting residue was purified by preparative HPLC using a column of Xbridge Prep C18 OBD (trade name, Nihon Waters K.K.) 5.0 μm 19×150 mm (elution solvent; a 0.1% by volume formic acid aqueous solution (solution A)—a 0.1% by volume formic acid acetonitrile solution (solution B), gradient (% by volume of solution B): 70% (0.00 min.)—70% (0.80 min.)—90% (7.00 min.)—90% (12.00 min.)). To the fractions containing the desired compound was added water, and the mixture was lyophilized to obtain 151.5 mg (0.281 mmol, yield 80%) of the title compound as a white foam.

Mass spectrum (ESI⁺, m/z): 539 [M+1]⁺.

$^1$H-NMR spectrum (400 MHz, DMSO-$d_6$) δ: 12.42 (1H, brs), 9.51 (1H, brs), 8.74 (1H, dd, J=2.4, 0.6 Hz), 8.06-8.02 (2H, m), 8.00 (1H, dd, J=8.4, 0.6 Hz), 7.90 (1H, dd, J=8.3, 2.4 Hz), 7.48-7.42 (3H, m), 7.26 (1H, m), 7.15 (1H, d, J=2.1 Hz), 5.74 (1H, q, J 6.4 Hz), 2.16 (3H, s), 1.57-1.45 (3H, m), 1.48 (2H, dd, J=6.7, 3.8 Hz), 1.18 (2H, dd, J=6.7, 3.8 Hz).

Example 130

(RS)-1-{4'-[5-Fluoro-3-({[1-(thiophen-3-yl)ethoxy]carbonyl}amino)thiophen-2-yl]-[1,1'-biphenyl]-4-yl}cyclopropanecarboxylic acid ethyl ester (Compound No. I-635)

[Chemical Formula 239]

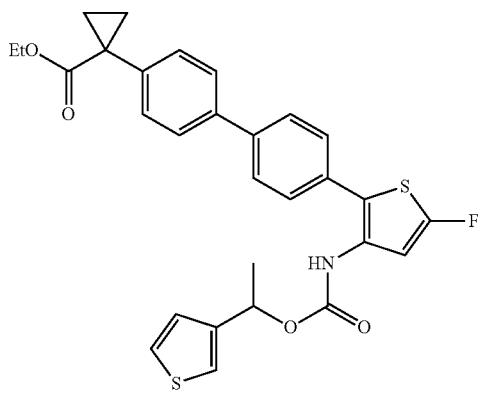

To 201.9 mg (0.492 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene (2 ml), the mixture was subjected to azeotropic dehydration treatment, and subsequently the atmosphere was replaced with argon. Then, 4 ml of dehydrated toluene, 0.081 ml (0.58 mmol) of triethylamine and 0.126 mL (0.590 mmol) of diphenylphosphoryl azide were added sequentially, and the mixture was stirred at room temperature for one hour. Then, 94.0 mg (0.73 mmol) of (RS)-1-(thiophen-3-yl)ethanol synthesized in analogy to Reference Example 50 was added, and the mixture was heated and stirred at 70° C. for 1.5 hours. After completion of the reaction, the reaction mixture was cooled, and water and ethyl acetate were added to separate the layers. The organic layer was dried over anhydrous magnesium sulfate and concentrated under reduced pressure. The resulting residue was subjected to silica gel column chromatography (elution solvent; hexane:ethyl acetate=95:5 to 74:26 (V/V)), and the fractions containing the desired compound were concentrated under reduced pressure to obtain 155.7 mg (0.291 mmol, yield 59%) of the title compound as a pale yellow oil.

Mass spectrum (ESI⁻, m/z): 534 [M−1]⁻.

$^1$H-NMR spectrum (400 MHz, DMSO-$d_6$) δ: 9.29 (1H, brs), 7.73-7.69 (2H, m), 7.66-7.62 (2H, m), 7.57-7.51 (3H, m), 7.45-7.40 (3H, m), 7.15-7.09 (1H, m), 6.83 (1H, brs), 5.82 (1H, q, J=6.5 Hz), 4.05 (2H, q, J=7.1 Hz), 1.53-1.47 (3H, m), 1.51 (2H, dd, J=6.9, 3.9 Hz), 1.23 (2H, dd, J=7.1, 4.1 Hz), 1.11 (3H, t, J=7.1 Hz).

Example 131

(RS)-1-{4'-[5-Fluoro-3-({[1-(thiophen-3-yl)ethoxy]carbonyl}amino)thiophen-2-yl]-[1,1'-biphenyl]-4-yl}cyclopropanecarboxylic acid (Compound No. I-639)

[Chemical Formula 240]

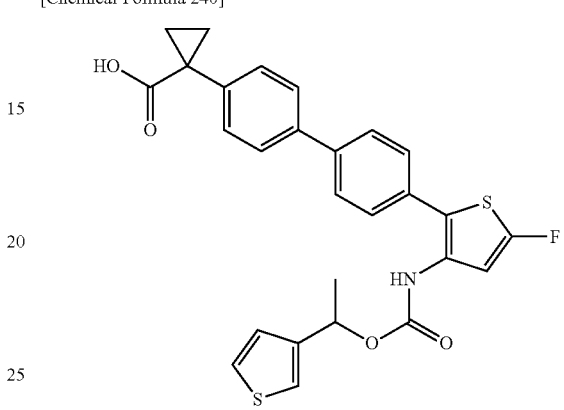

To a solution of 153.9 mg (0.287 mmol) of (RS)-1-{4'-[5-fluoro-3-({[1-(thiophen-3-yl)ethoxy]carbonyl}amino)thiophen-2-yl]-[1,1'-biphenyl]-4-yl}cyclopropanecarboxylic acid ethyl ester synthesized in analogy to Example 130 in isopropyl alcohol (5.0 ml) was added 2.0 ml (4.0 mmol) of a 2N aqueous sodium hydroxide solution while stirring, and the mixture was stirred at room temperature for 27 hours. After completion of the reaction, the mixture was neutralized by adding 4.0 ml of 1N hydrochloric acid, and subsequently ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=72:28 to 0:100 (V/V)), and the fractions containing the desired compound were concentrated under reduced pressure. To the resulting residue were added a small amount of ethanol and water, and the mixture was sonicated. The precipitated solid was collected by filtration, washed with water, and subsequently dried under reduced pressure to obtain 102.7 mg (0.202 mmol, yield 70%) of the title compound as a white solid.

Mass spectrum (ESI⁻, m/z): 506 [M−1]⁻.

$^1$H-NMR spectrum (400 MHz, DMSO-$d_6$) δ: 12.36 (1H, brs), 9.30 (1H, brs), 7.74-7.67 (2H, m), 7.65-7.59 (2H, m), 7.56-7.51 (3H, m), 7.48-7.38 (3H, m), 7.17-7.07 (1H, m), 6.83 (1H, brs), 5.82 (1H, q, J=6.5 Hz), 1.60-1.41 (5H, m), 1.17 (2H, dd, J=7.0, 3.8 Hz).

Example 132

(R)-1-{4'-[5-Fluoro-3-({[1-(thiophen-3-yl)ethoxy]carbonyl}amino)thiophen-2-yl]-[1,1'-biphenyl]-4-yl}cyclopropanecarboxylic acid ethyl ester (Compound No. I-636)

[Chemical Formula 241]

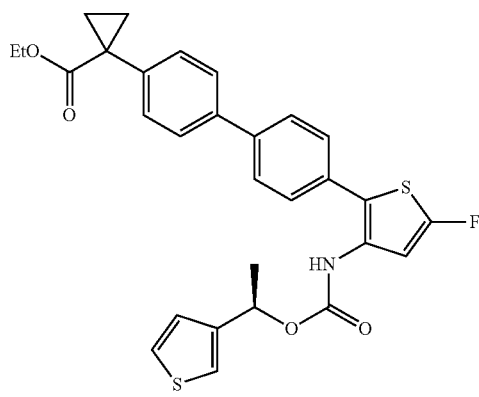

To 513.9 mg (1.252 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene (5 ml), the mixture was subjected to azeotropic dehydration treatment, and subsequently the atmosphere was replaced with argon. Then, 8 ml of dehydrated toluene, 0.203 ml (1.46 mmol) of triethylamine and 0.315 ml (1.46 mmol) of diphenylphosphoryl azide were added sequentially, and the mixture was stirred at room temperature for 50 minutes. Then, a solution of 249.5 mg (1.946 mmol) of (R)-1-(thiophen-3-yl)ethanol synthesized in analogy to Reference Example 53 in dehydrated toluene (1 ml), dried over Molecular Sieves 4A (powder) (trade name, NACALAI TESQUE, INC.) (250 mg) was added, and the mixture was washed with dehydrated toluene (1 ml) and then heated and stirred at 70° C. for 2.2 hours. After completion of the reaction, the reaction mixture was cooled, insoluble matter was filtered, and water, ethyl acetate and a small amount of saturated brine were added to separate the layers. The organic layer was dried over anhydrous magnesium sulfate and concentrated under reduced pressure. The resulting residue was subjected to silica gel column chromatography (elution solvent; hexane:ethyl acetate=95:5 to 74:26 (V/V)), and the fractions containing the desired compound were concentrated under reduced pressure to obtain 648.3 mg (1.210 mmol, yield 97%) of the title compound as a white oil.

Mass spectrum (DUIS$^-$, m/z): 534 [M−1]$^-$.

$^1$H-NMR spectrum (400 MHz, DMSO-$d_6$) δ: 9.31 (1H, brs), 7.73-7.69 (2H, m), 7.66-7.62 (2H, m), 7.57-7.51 (3H, m), 7.46-7.40 (3H, m), 7.16-7.09 (1H, m), 6.84 (1H, brs), 5.82 (1H, q, J=6.4 Hz), 4.05 (2H, q, J=7.2 Hz), 1.58-1.45 (3H, m), 1.51 (2H, dd, J=6.9, 3.9 Hz), 1.23 (2H, dd, J=7.1, 4.1 Hz), 1.11 (3H, t, J=7.1 Hz).

Example 133

(R)-1-{4'-[5-Fluoro-3-({[1-(thiophen-3-yl)ethoxy]carbonyl}amino)thiophen-2-yl]-[1,1'-biphenyl]-4-yl}cyclopropanecarboxylic acid (Compound No. I-640)

[Chemical Formula 242]

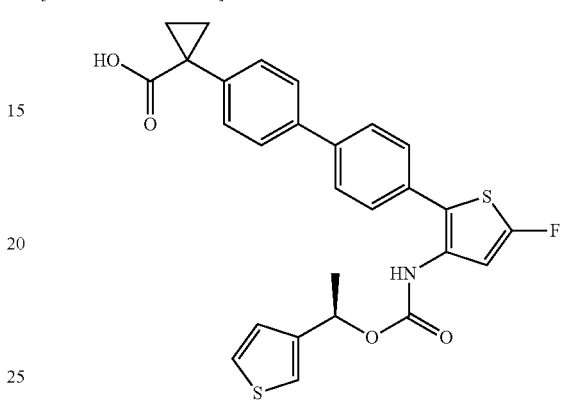

To a solution of 645.3 mg (1.205 mmol) of (R)-1-{4'-[5-fluoro-3-({[1-(thiophen-3-yl)ethoxy]carbonyl}amino)thiophen-2-yl]-[1,1'-biphenyl]-4-yl}cyclopropanecarboxylic acid ethyl ester synthesized in analogy to Example 132 in tetrahydrofuran (2.0 ml) was added 5.0 ml of isopropyl alcohol while stirring, then 6.0 ml (12 mmol) of a 2N aqueous sodium hydroxide solution was added, and the mixture was stirred at room temperature for 27 hours. After completion of the reaction, the mixture was neutralized by adding 12 ml of 1N hydrochloric acid, and subsequently ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=72:28 to 10:90 (V/V)), and the fractions containing the desired compound were concentrated under reduced pressure. To the resulting residue was added hexane, and the mixture was sonicated. The precipitated solid was collected by filtration, washed with hexane and dried to obtain 455.0 mg (0.896 mmol, yield 74%, optical purity 86.0% ee) of the title compound as a white solid.

Optical Purity Analysis Conditions

Column: CHIRALCEL OJ-H (trade name, Daicel Corporation)

Size: 0.46 cmI.D.×25 cmL.

Mobile phase: methanol/acetonitrile/acetic acid=90/10/0.1 (V/V/V)

Flow rate: 1.0 mL/min.

Temperature: 40° C.

Wavelength: 254 nm

Mass spectrum (DUIS$^-$, m/z): 506 [M−1]$^-$.

$^1$H-NMR spectrum (400 MHz, DMSO-$d_6$) δ: 12.37 (1H, brs), 9.32 (1H, brs), 7.72-7.68 (2H, m), 7.64-7.60 (2H, m), 7.56-7.51 (3H, m), 7.47-7.40 (3H, m), 7.17-7.08 (1H, m), 6.84 (1H, brs), 5.82 (1H, q, J=6.5 Hz), 1.54-1.46 (3H, m), 1.48 (2H, dd, J=6.8, 3.8 Hz), 1.18 (2H, dd, J=6.8, 3.9 Hz).

Example 134

(RS)-1-{4'-[5-Fluoro-3-({[1-(thiophen-3-yl)ethoxy]carbonyl}amino)thiophen-2-yl]-2'-methoxy-[1,1'-biphenyl]-4-yl}cyclopropanecarboxylic acid (Compound No. I-811)

[Chemical Formula 243]

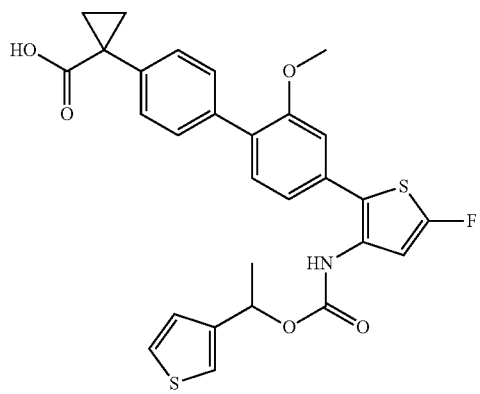

To a solution of 74 mg (0.17 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4 ml) were added 0.040 ml (0.29 mmol) of triethylamine and 0.050 ml (0.28 mmol) of diphenylphosphoryl azide under an argon atmosphere, and the mixture was stirred at room temperature for 30 minutes. Then, 40 mg (0.28 mmol) of (RS)-1-(thiophen-3-yl)ethanol synthesized in analogy to Reference Example 50 was added, and the mixture was heated and stirred at 70° C. for 2 hours After completion of the reaction, to the reaction mixture were added ethyl acetate and water to separate the organic layer. The resulting organic layer was washed with saturated brine, subsequently dried over anhydrous magnesium sulfate and concentrated under reduced pressure. The resulting residue was subjected to silica gel column chromatography (elution solvent; hexane:ethyl acetate=93:7 to 72:28 (V/V)), and the fraction having around Rf=0.3 (developing solvent; hexane:ethyl acetate=80:20 (V/V)) was concentrated under reduced pressure to obtain 97 mg of a colorless oil. This was dissolved in isopropyl alcohol (3 ml), 1.0 ml (2.0 mmol) of a 2N aqueous sodium hydroxide solution was added, and the mixture was stirred at room temperature for 66 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure. To the resulting residue was added hexane, the precipitated solid was filtered and washed with hexane to obtain 26 mg (0.048 mmol, yield 27%) of the title compound as a white solid.

Mass spectrum (DUIS$^+$, m/z): 538 [M+1]$^+$.

$^1$H-NMR spectrum (400 MHz, DMSO-d$_6$) δ: 12.38 (1H, brs), 9.31 (1H, brs), 7.52 (1H, dd, J=5.0, 2.9 Hz), 7.46-7.39 (3H, m), 7.38-7.34 (2H, m), 7.32 (1H, d, J=7.8 Hz), 7.17 (1H, d, J=1.6 Hz), 7.14-7.10 (1H, m), 7.08 (1H, dd, J=8.0, 1.7 Hz), 6.84 (1H, d, J=1.4 Hz), 5.84 (1H, q, J=6.4 Hz), 3.74 (3H, s), 1.54-1.44 (3H, m), 1.46 (2H, dd, J 6.7, 3.8 Hz), 1.17 (2H, dd, J=6.7, 3.8 Hz).

Example 135

(RS)-1-{4'-[5-Fluoro-3-({[1-(4-methylthiophen-3-yl)ethoxy]carbonyl}amino)thiophen-2-yl]-[1,1'-biphenyl]-4-yl}cyclopropanecarboxylic acid ethyl ester (Compound No. I-645)

[Chemical Formula 244]

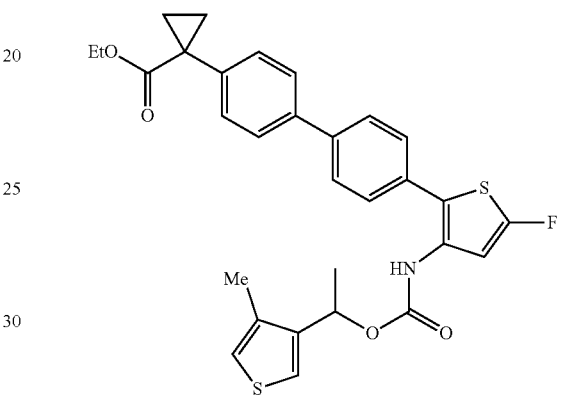

To a solution of 208 mg (0.507 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (4 ml) were added 0.105 ml (0.753 mmol) of triethylamine and 0.13 ml (0.61 mmol) of diphenylphosphoryl azide under an argon atmosphere, and the mixture was stirred at room temperature for 30 minutes. Then, 86 mg (0.61 mmol) of (RS)-1-(4-methylthiophen-3-yl)ethanol synthesized in analogy to Reference Example 39 was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 212 mg (0.39 mmol, yield 76%) of the title compound as a colorless oil.

Mass spectrum (EI, m/z): 549 [M]$^+$.

$^1$H-NMR spectrum (400 MHz, CDCl$_3$) δ: 7.68-7.61 (2H, m), 7.59-7.52 (2H, m), 7.47-7.40 (4H, m), 7.29-7.11 (2H, m), 6.94 (1H, dq, J=3.3, 0.9 Hz), 6.75 (1H, brs), 5.93 (1H, q, J=6.5 Hz), 4.12 (2H, q, J=7.1 Hz), 2.25 (3H, d, J=0.9 Hz), 1.64 (2H, dd, J=7.2, 4.1 Hz), 1.62 (3H, d, J=6.5 Hz), 1.23 (2H, dd, J=7.2, 4.2 Hz), 1.19 (3H, t, J=7.1 Hz).

Example 136

(RS)-1-{4'-[5-Fluoro-3-({[1-(4-methylthiophen-3-yl)ethoxy]carbonyl}amino)thiophen-2-yl]-[1,1'-biphenyl]-4-yl}cyclopropanecarboxylic acid (Compound No. I-649)

[Chemical Formula 245]

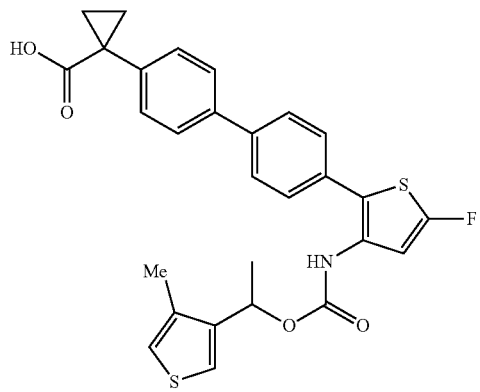

To a solution of 210 mg (0.382 mmol) of (RS)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid ethyl ester synthesized in analogy to Example 135 in isopropyl alcohol (5 ml) was added 2.0 ml (4.0 mmol) of a 2N aqueous sodium hydroxide solution, and the mixture was stirred at room temperature for 62 hours. After completion of the reaction, the reaction mixture was acidified by adding 1N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 30:70 (V/V)), and the fractions containing the desired compound were concentrated under reduced pressure. The resulting residue was suspended in ethanol, and the solid obtained by pouring the suspension into water was filtered, washed with water, and subsequently dried under reduced pressure to obtain 121 mg (0.23 mmol, yield 60%) of the title compound as a white solid.

Mass spectrum (DUIS$^-$, m/z): 520 [M−1]$^-$.

$^1$H-NMR spectrum (400 MHz, DMSO-d$_6$) δ: 12.37 (1H, brs), 9.33 (1H, s), 7.73-7.66 (2H, m), 7.65-7.58 (2H, m), 7.57-7.50 (2H, m), 7.49-7.37 (3H, m), 7.17-7.13 (1H, m), 6.83 (1H, brs), 5.74 (1H, q, J=6.5 Hz), 2.17 (3H, brs), 1.57-1.43 (3H, m), 1.48 (2H, dd, J=6.7, 3.8 Hz), 1.17 (2H, dd, J=6.7, 3.9 Hz).

Example 137

(R)-1-{4'-[5-Fluoro-3-({[1-(4-methylthiophen-3-yl)ethoxy]carbonyl}amino)thiophen-2-yl]-[1,1'-biphenyl]-4-yl}cyclopropanecarboxylic acid ethyl ester (Compound No. I-646)

[Chemical Formula 246]

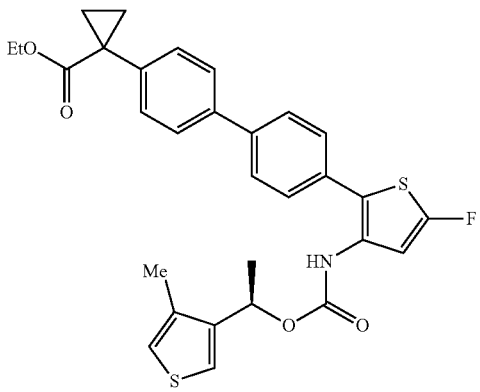

To a solution of 456 mg (1.11 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (10 ml) were added 0.24 ml (1.7 mmol) of triethylamine and 0.29 mL (1.4 mmol) of diphenylphosphoryl azide under an argon atmosphere, and the mixture was stirred at room temperature for 30 minutes. Then, a solution of 190 mg (1.34 mmol) of (R)-1-(4-methylthiophen-3-yl)ethanol synthesized in analogy to Reference Example 54 in toluene (1 ml), dried over Molecular Sieves 4A (powder) (trade name, NACALAI TESQUE, INC.) (0.3 g) was added, and the mixture was heated and stirred at 70° C. for 2 hours. After completion of the reaction, to the reaction mixture were added ethyl acetate and a saturated aqueous ammonium chloride solution to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 (V/V)), and the fractions containing the desired compound were concentrated under reduced pressure to obtain 570 mg (1.04 mmol, yield 93%) of the title compound as a colorless oil.

Mass spectrum (DUIS$^-$, m/z): 548 [M−1]$^-$.

$^1$H-NMR spectrum (400 MHz, DMSO-d$_6$) δ: 9.31 (1H, brs), 7.74-7.68 (2H, m), 7.66-7.61 (2H, m), 7.57-7.40 (5H, m), 7.17-7.13 (1H, m), 6.83 (1H, brs), 5.74 (1H, q, J=6.5 Hz), 4.05 (2H, q, J=7.2 Hz), 2.17 (3H, brs), 1.60-1.43 (3H, m), 1.51 (2H, dd, J=6.8, 4.0 Hz), 1.23 (2H, dd, J=7.1, 4.1 Hz), 1.11 (3H, t, J=7.1 Hz).

Example 138

(R)-1-{4'-[5-Fluoro-3-({[1-(4-methylthiophen-3-yl)ethoxy]carbonyl}amino)thiophen-2-yl]-[1,1'-biphenyl]-4-yl}cyclopropanecarboxylic acid (Compound No. I-650)

[Chemical Formula 247]

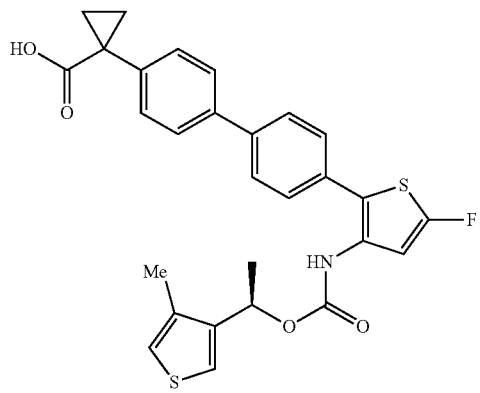

To a solution of 565 mg (1.03 mmol) of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid ethyl ester synthesized in analogy to Example 137 in isopropyl alcohol (12 ml) was added 4.0 ml (8.0 mmol) of a 2N aqueous sodium hydroxide solution, and the mixture was stirred at room temperature for 91 hours. After completion of the reaction, the reaction mixture was acidified by adding 1N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=50:50 (V/V)), and the fractions containing the desired compound were concentrated under reduced pressure. Then, 6 ml of hexane and 12 ml of ethyl acetate were added, and the mixture was warmed at 50° C. Subsequently, a solid precipitated by cooling was filtered and washed with a mixed solution of hexane-ethyl acetate (50:50 (V/V)). The mother liquid and the washings were concentrated under reduced pressure, to the resulting residue were added 8 ml of acetonitrile, 4 ml of water and 3 ml of tetrahydrofuran, and the mixture was lyophilized to obtain 193 mg (0.37 mmol, yield 36%, optical purity 87% ee) of the title compound as a white solid.

Optical Purity Analysis Conditions
Column: CHIRALCEL OJ-H (trade name, Daicel Corporation)
Size: 0.46 cmI.D.×25 cmL.
Mobile phase: methanol/acetonitrile/acetic acid=90/10/0.1 (V/V/V)
Flow rate: 1.0 mL/min.
Temperature: 40° C.
Wavelength: 254 nm
Mass spectrum (DUIS$^-$, m/z): 520 [M−1]$^-$.
$^1$H-NMR spectrum (400 MHz, DMSO-d$_6$) δ: 12.38 (1H, brs), 9.33 (1H, brs), 7.73-7.67 (2H, m), 7.65-7.59 (2H, m), 7.57-7.50 (2H, m), 7.49-7.38 (3H, m), 7.19-7.12 (1H, m), 6.83 (1H, brs), 5.74 (1H, q, J=6.4 Hz), 2.17 (3H, brs), 1.59-1.44 (3H, m), 1.48 (2H, dd, J=6.7, 3.8 Hz), 1.18 (2H, dd, J=6.9, 3.9 Hz).

The title compound was also synthesized as follows.

Using 94.0 mg (0.180 mmol) of (RS)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid synthesized in analogy to Example 136, the fraction having 7.39 minutes of the retention time under the following separating conditions was concentrated under reduced pressure, water (5 ml) and acetonitrile (5 ml) were added, and the mixture was lyophilized to otain 38.0 mg of a white foam (0.0729 mmol, recovery 81%, optical purity 100% ee). Similarly, 39.1 mg of a white foam (0.0750 mmol, recovery 83%, optical purity 99.7% ee) was obtained from the fraction having 11.1 minutes of the retention time.

Compared to the authentic preparation of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid, the fraction having 7.39 minutes of the retention time was identified as the R form and the fraction having 11.1 minutes was identified as the S form.

Optical Purity Analysis Conditions
Column: CHIRALCEL OJ-H (trade name, Daicel Corporation)
Size: 0.46 cmI.D.×25 cmL.
Mobile phase: methanol/acetonitrile/acetic acid=90/10/0.1 (V/V/V)
Flow rate: 1.0 mL/min.
Temperature: 40° C.
Wavelength: 305 nm

Example 139

(RS)-1-{4'-[5-Fluoro-3-({[1-(2-methylthiophen-3-yl)ethoxy]carbonyl}amino)thiophen-2-yl]-[1,1'-biphenyl]-4-yl}cyclopropanecarboxylic acid ethyl ester (Compound No. I-659)

[Chemical Formula 248]

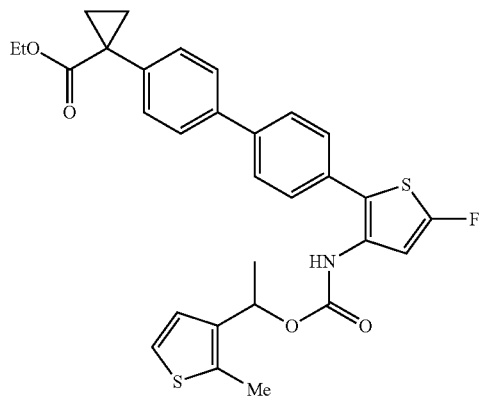

To a solution of 208 mg (0.507 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (4 ml) were added 0.105 ml (0.753 mmol) of triethylamine and 0.130 ml (0.61 mmol) of diphenylphosphoryl azide under an argon atmosphere, and the mixture was stirred at room temperature for 30 minutes. Then, 86 mg (0.61 mmol) of (RS)-1-(2-methylth-iophen-3-yl)ethanol synthesized in analogy to Reference Example 52 was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 146 mg (0.27 mmol, yield 52%) of the title compound as a colorless oil.

Mass spectrum (EI, m/z): 549 [M]$^+$.

$^1$H-NMR spectrum (400 MHz, CDCl$_3$) δ: 7.69-7.61 (2H, m), 7.59-7.50 (2H, m), 7.49-7.40 (4H, m), 7.16 (1H, brs), 7.05 (1H, d, J=5.3 Hz), 6.99 (1H, d, J=5.4 Hz), 6.70 (1H, brs), 5.97 (1H, q, J=6.6 Hz), 4.13 (2H, q, J=7.1 Hz), 1.64 (2H, dd, J=6.9, 3.9 Hz), 1.56 (3H, d, J=5.8 Hz), 1.23 (2H, dd, J=6.7, 3.8 Hz), 1.20 (3H, t, J=7.1 Hz).

Example 140

(RS)-1-{4'-[5-Fluoro-3-({[1-(2-methylthiophen-3-yl)ethoxy]carbonyl}amino)thiophen-2-yl]-[1,1'-biphenyl]-4-yl}cyclopropanecarboxylic acid (Compound No. I-661)

[Chemical Formula 249]

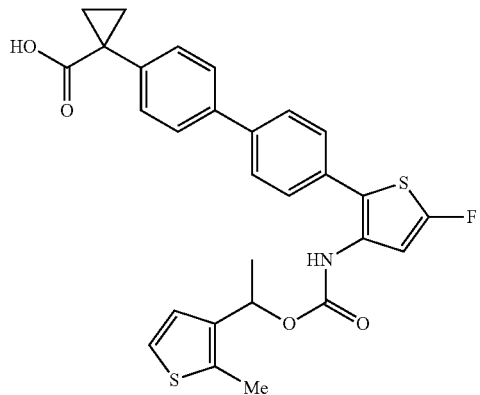

To a solution of 142 mg (0.258 mmol) of (RS)-1-{4'-[5-fluoro-3-({[1-(2-methylthiophen-3-yl)ethoxy]carbonyl}amino)thiophen-2-yl]-[1,1'-biphenyl]-4-yl}cyclopropanecarboxylic acid ethyl ester synthesized in analogy to Example 139 in isopropyl alcohol (5 ml) was added 1.5 ml (3.0 mmol) of a 2N aqueous sodium hydroxide solution, and the mixture was stirred at room temperature for 66 hours. After completion of the reaction, the reaction mixture was acidified by adding 1N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 30:70 (V/V)), and the fractions containing the desired compound were concentrated under reduced pressure. To the resulting residue were added methylene chloride and methanol, and the precipitated solid was filtered to obtain 76 mg (0.15 mmol, yield 56%) of the title compound as a white solid.

Mass spectrum (DUIS$^-$, m/z): 520 [M−1]$^-$.

$^1$H-NMR spectrum (400 MHz, DMSO-d$_6$) δ: 12.36 (1H, brs), 9.27 (1H, brs), 7.71-7.65 (2H, m), 7.65-7.59 (2H, m), 7.53-7.47 (2H, m), 7.46-7.39 (2H, m), 7.27 (1H, d, J=5.1 Hz), 7.08-6.96 (1H, m), 6.84-6.76 (1H, m), 5.80 (1H, q, J=6.6 Hz), 2.39 (3H, s), 1.53-1.39 (3H, m), 1.47 (2H, dd, J=6.7, 3.8 Hz), 1.17 (2H, dd, J=6.8, 3.9 Hz).

Example 141

(RS)-1-{4'-[5-Fluoro-3-({[1-(4-methylthiophen-3-yl)ethoxy]carbonyl}amino)thiophen-2-yl]-2'-methoxy-[1,1'-biphenyl]-4-yl}cyclopropanecarboxylic acid ethyl ester (Compound No. I-813)

[Chemical Formula 250]

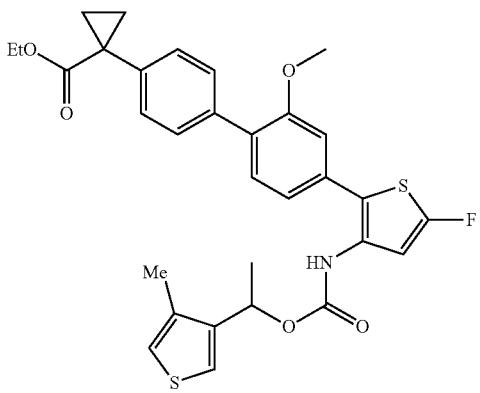

To a solution of 74 mg (0.17 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (4 ml) were added 0.040 ml (0.29 mmol) of triethylamine and 0.050 ml (0.28 mmol) of diphenylphosphoryl azide under an argon atmosphere, and the mixture was stirred at room temperature for 30 minutes. Then, 40 mg (0.28 mmol) of (RS)-1-(4-methylthiophen-3-yl)ethanol synthesized in analogy to Reference Example 39 was added, and the mixture was heated and stirred at 70° C. for 2 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=93:7 to 72:28 (V/V)), and the fractions containing the desired compound were concentrated under reduced pressure to obtain 97 mg (0.17 mmol, yield: quantitative) of the title compound as a colorless oil.

Mass spectrum (EI, m/z): 579 [M]$^+$.

$^1$H-NMR spectrum (400 MHz, CDCl$_3$) δ: 7.50-7.46 (2H, m), 7.42-7.35 (3H, m), 7.25-7.12 (2H, m), 7.04 (1H, dd, J=7.8, 1.6 Hz), 6.96-6.90 (2H, m), 6.79 (1H, brs), 5.93 (1H, q, J=6.6 Hz), 4.12 (2H, q, J=7.1 Hz), 3.80 (3H, s), 2.25 (3H, d, J=0.9 Hz), 1.65-1.59 (5H, m), 1.28-1.21 (2H, m), 1.20 (3H, t, J=7.2 Hz).

Example 142

(RS)-1-{4'-[5-Fluoro-3-({[1-(4-methylthiophen-3-yl)ethoxy]carbonyl}amino)thiophen-2-yl]-2'-methoxy-[1,1'-biphenyl]-4-yl}cyclopropanecarboxylic acid (Compound No. I-815)

[Chemical Formula 251]

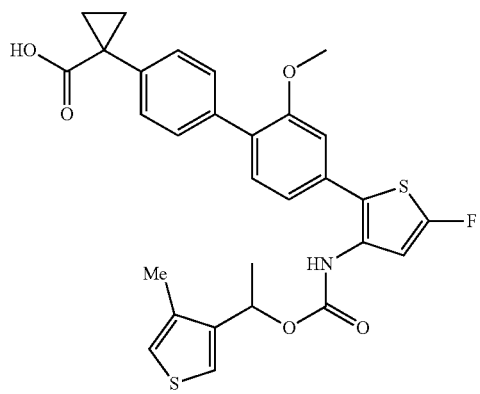

To a solution of 95 mg (0.16 mmol) of (RS)-1-{4'-[5-fluoro-3-({[1-(4-methylthiophen-3-yl)ethoxy]carbonyl}amino)thiophen-2-yl]-2'-methoxy-[1,1'-biphenyl]-4-yl}cyclopropanecarboxylic acid ethyl ester synthesized in analogy to Example 141 in isopropyl alcohol (3 ml) was added 1.5 ml (3.0 mmol) of a 2N aqueous sodium hydroxide solution, and the mixture was stirred at room temperature for 24 hours. Then, tetrahydrofuran was added until the reaction mixture became homogeneous, and the mixture was further stirred at room temperature for 72 hours. After completion of the reaction, the reaction mixture was acidified by adding 2N hydrochloric acid thereto, and extracted with methylene chloride. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=80:20 to 20:80 (V/V)), and the fractions containing the desired compound were concentrated under reduced pressure to obtain 49 mg (0.089 mmol, yield 54%) of the title compound as a white solid.

Mass spectrum (DUIS$^-$, m/z): 550 [M−1]$^-$.

$^1$H-NMR spectrum (400 MHz, DMSO-d$_6$) δ: 12.35 (1H, brs), 9.33 (1H, brs), 7.44-7.39 (3H, m), 7.38-7.34 (2H, m), 7.32 (1H, d, J=7.9 Hz), 7.16 (1H, d, J=1.5 Hz), 7.16-7.13 (1H, m), 7.08 (1H, dd, J=7.8, 1.6 Hz), 6.84 (1H, brs), 5.76 (1H, q, J=6.4 Hz), 3.75 (3H, s), 2.16 (3H, brs), 1.54-1.43 (3H, m), 1.46 (2H, dd, J=6.5, 3.7 Hz), 1.18-1.11 (2H, m).

Example 143

(RS)-1-{4'-[3-({[1-(4-Chlorothiophen-3-yl)ethoxy]carbonyl}amino)-5-fluorothiophen-2-yl]-[1,1'-biphenyl]-4-yl}cyclopropanecarboxylic acid ethyl ester (Compound No. I-655)

[Chemical Formula 252]

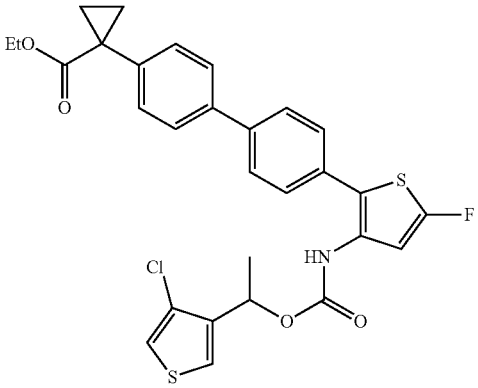

To a solution of 208 mg (0.51 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 in toluene (4 ml) were added 0.11 ml (0.75 mmol) of triethylamine and 0.13 ml (0.61 mmol) of diphenylphosphoryl azide under an argon atmosphere, and the mixture was stirred at room temperature for 30 minutes. Then, 86 mg (0.53 mmol) of (RS)-1-(4-chlorothiophen-3-yl)ethanol synthesized in analogy to Reference Example 40 was added, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=90:10 to 60:40 (V/V)), and the fractions containing the desired compound were concentrated under reduced pressure to obtain 159 mg (0.18 mmol, yield 55%) of the title compound as a colorless oil.

Mass spectrum (EI, m/z): 569 [M]$^+$.

$^1$H-NMR spectrum (400 MHz, CDCl$_3$) δ: 7.69-7.61 (2H, m), 7.58-7.51 (2H, m), 7.49-7.41 (4H, m), 7.29-7.26 (1H, m), 7.22-7.12 (2H, m), 6.76 (1H, brs), 5.97 (1H, q, J=6.5 Hz), 4.13 (2H, q, J=7.1 Hz), 1.64 (2H, dd, J=6.9, 3.9 Hz), 1.62 (3H, d, J=6.5 Hz), 1.23 (2H, dd, J=6.9, 3.9 Hz), 1.19 (3H, t, J=7.1 Hz).

Example 144

(RS)-1-{4'-[3-({[1-(4-Chlorothiophen-3-yl)ethoxy]carbonyl}amino)-5-fluorothiophen-2-yl]-[1,1'-biphenyl]-4-yl}cyclopropanecarboxylic acid (Compound No. I-657)

[Chemical Formula 253]

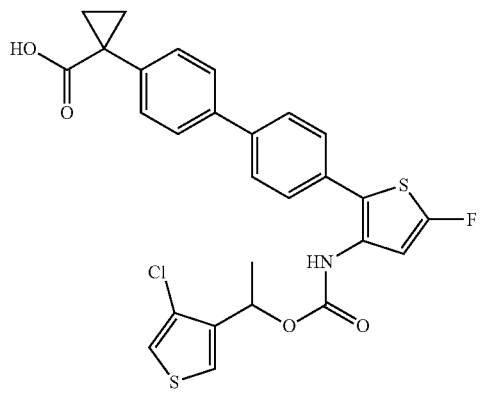

To a solution of 159 mg (0.28 mmol) of (RS)-1-{4'-[3-({[1-(4-chlorothiophen-3-yl)ethoxy]carbonyl}amino)-5-fluorothiophen-2-yl]-[1,1'-biphenyl]-4-yl cyclopropanecarboxylic acid ethyl ester synthesized in analogy to Example 143 in isopropyl alcohol (5 ml) was added 1.5 ml (3.0 mmol) of a 2N aqueous sodium hydroxide solution, and the mixture was stirred at room temperature for 67 hours. After completion of the reaction, the reaction mixture was acidified by adding 1N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 30:70 (V/V)), and the fractions containing the desired compound were concentrated under reduced pressure. To the resulting residue was added ethanol, the suspended solution was added to water, and the precipitated solid was filtered and washed with water. The resulting solid was subjected to silica gel column chromatography (elution solvent; hexane:ethyl acetate=90:10 to 30:70 (V/V)), and the fractions containing the desired compound were concentrated under reduced pressure. The resulting residue was dissolved in a 2N aqueous sodium hydroxide solution, and the mixture was washed with ethyl acetate. The aqueous layer was acidified with 2N hydrochloric acid, and extracted with methylene chloride. The organic layer was dried over anhydrous magnesium sulfate and concentrated under reduced pressure. To the resulting residue were added hexane and methylene chloride, and the mixture was sonicated, and subsequently concentrated under reduced pressure to obtain 8 mg (0.02 mmol, yield 6%) of the title compound as a white solid.

Mass spectrum (DUIS$^-$, m/z): 540 [M−1]$^-$.

$^1$H-NMR spectrum (400 MHz, DMSO-$d_6$) δ: 12.33 (1H, brs), 9.36 (1H, brs), 7.73-7.68 (2H, m), 7.66-7.61 (4H, m), 7.57-7.52 (2H, m), 7.47-7.37 (2H, m), 6.82 (1H, brs), 5.75 (1H, q, J=6.5 Hz), 1.60-1.46 (3H, m), 1.48 (2H, dd, J=6.7, 3.8 Hz), 1.18 (2H, dd, J=6.8, 4.0 Hz).

Example 145

(RS)-1-{4'-[3-({[1-(4-Chlorothiophen-3-yl)ethoxy]carbonyl}amino)-5-fluorothiophen-2-yl]-2'-methoxy-[1,1'-biphenyl]-4-yl}cyclopropanecarboxylic acid ethyl ester (Compound No. I-821)

[Chemical Formula 254]

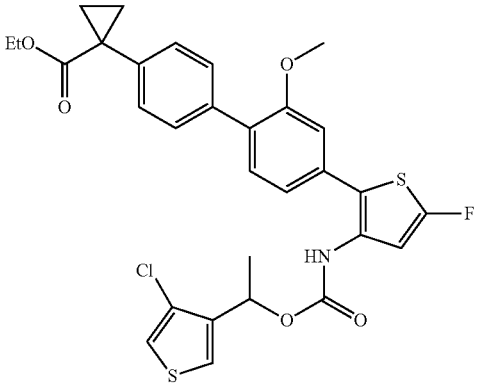

To a solution of 140 mg (0.32 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 in toluene (3 ml) were added 0.070 ml (0.50 mmol) of triethylamine and 0.090 ml (0.42 mmol) of diphenylphosphoryl azide under an argon atmosphere, and the mixture was stirred at room temperature for 30 minutes. Then, 51 mg (0.31 mmol) of (RS)-1-(4-chlorothiophen-3-yl)ethanol synthesized in analogy to Reference Example 40 was added, and the mixture was heated and stirred at 70° C. for 3 hours. After completion of the reaction, to the reaction mixture were added ethyl acetate and water to separate the organic layer. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 70:30 (V/V)), and the fractions containing the desired compound were concentrated under reduced pressure to obtain 181 mg (0.28 mmol (purity 93% by weight), yield 87%) of the title compound as a colorless oil.

Mass spectrum (CI, m/z): 599 [M]$^+$.

$^1$H-NMR spectrum (400 MHz, CDCl$_3$) δ: 7.52-7.47 (2H, m), 7.42-7.35 (3H, m), 7.29-7.24 (1H, m), 7.23-7.13 (2H, m), 7.05 (1H, dd, J=7.8, 1.6 Hz), 6.96 (1H, d, J=1.6 Hz), 6.82 (1H, brs), 5.98 (1H, q, J=6.5 Hz), 4.13 (2H, q, J=7.1 Hz), 3.81 (3H, s), 1.66-1.60 (5H, m), 1.23 (2H, dd, J=7.0, 4.0 Hz), 1.20 (3H, t, J=7.2 Hz).

Example 146

(RS)-1-{4'-[3-({[1-(4-Chlorothiophen-3-yl)ethoxy]carbonyl}amino)-5-fluorothiophen-2-yl]-2'-methoxy-[1,1'-biphenyl]-4-yl}cyclopropanecarboxylic acid (Compound No. I-823)

[Chemical Formula 255]

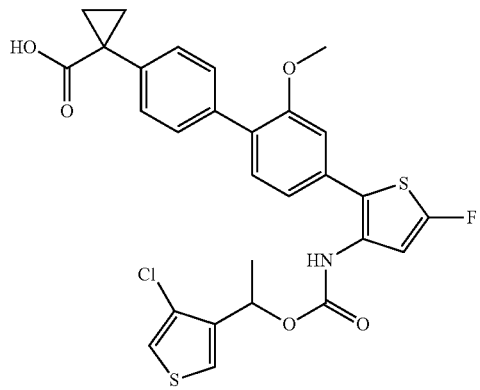

To a solution of 179 mg (0.28 mmol (purity 93% by weight)) of (RS)-1-{4'-[3-({[1-(4-chlorothiophen-3-yl)ethoxy]carbonyl}amino)-5-fluorothiophen-2-yl]-2'-methoxy-[1,1'-biphenyl]-4-yl}cyclopropanecarboxylic acid ethyl ester synthesized in Example 145 in isopropyl alcohol (3 ml) was added 2.0 ml (4.0 mmol) of a 2N aqueous sodium hydroxide solution, and the mixture was stirred at room temperature for 51 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=80:20 to 30:70 (V/V)), and the fractions containing the desired compound were concentrated under reduced pressure. To the resulting residue was added hexane, and the mixture was concentrated under reduced pressure to obtain 70 mg (0.12 mmol, yield 44%) of the title compound as a white solid.

Mass spectrum (DUIS$^-$, m/z): 570 [M−1]$^-$.

$^1$H-NMR spectrum (400 MHz, DMSO-d$_6$) δ: 12.38 (1H, brs), 9.40 (1H, brs), 7.74-7.57 (2H, m), 7.45-7.39 (2H, m), 7.39-7.34 (2H, m), 7.32 (1H, d, J=7.9 Hz), 7.17 (1H, d, J=1.6 Hz), 7.09 (1H, dd, J=7.8, 1.7 Hz), 6.84 (1H, brs), 5.77 (1H, q, J=6.4 Hz), 3.77 (3H, s), 1.61-1.44 (3H, m), 1.47 (2H, dd, J=6.8, 3.8 Hz), 1.19-1.16 (2H, m).

Example 147

(R)-1-{4'-[5-Chloro-3-({[1-(thiophen-2-yl)ethoxy]carbonyl}amino)thiophen-2-yl]-[1,1'-biphenyl]-4-yl}cyclopropanecarboxylic acid ethyl ester (Compound No. I-628)

[Chemical Formula 256]

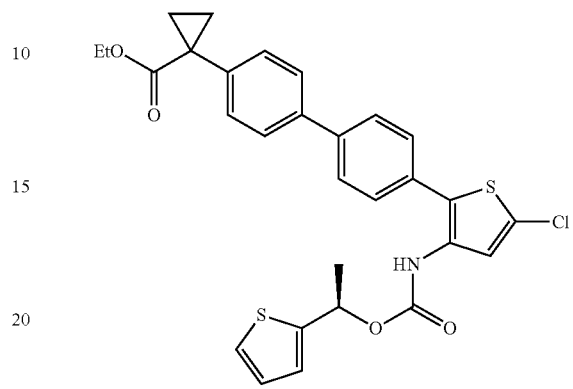

To a solution of 100 mg (0.24 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 24, 50 mg (0.39 mmol) of (R)-1-(thiophen-2-yl)ethanol (Alfa Aeser) and 0.060 ml (0.74 mmol) of pyridine in toluene (2 ml) were added 130 mg (0.30 mmol) of [bis(trifluoroacetoxy)iodo]benzene under a nitrogen atmosphere at room temperature, and the mixture was heated and stirred at 70° C. for one hour. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 106 mg (0.177 mmol (purity 92% by weight), yield 75%) of the title compound as a brown oil.

Mass spectrum (DUIS$^-$, m/z): 550 [M−1]$^-$.

$^1$H-NMR spectrum (400 MHz, DMSO-d$_6$) δ: 9.38 (1H, brs), 7.74-7.68 (2H, m), 7.66-7.61 (2H, m), 7.57-7.49 (3H, m), 7.46-7.40 (2H, m), 7.22-7.07 (2H, m), 7.04-6.98 (1H, m), 6.00 (1H, q, J=6.3 Hz), 4.05 (2H, q, J=7.2 Hz), 1.66-1.53 (3H, m), 1.51 (2H, dd, J=6.8, 4.0 Hz), 1.23 (2H, dd, J=7.0, 4.0 Hz), 1.11 (3H, t, J=7.1 Hz).

Example 148

(R)-1-{4'-[5-Chloro-3-({[1-(thiophen-2-yl)ethoxy]carbonyl}amino)thiophen-2-yl]-[1,1'-biphenyl]-4-yl}cyclopropanecarboxylic acid (Compound No. I-630)

[Chemical Formula 257]

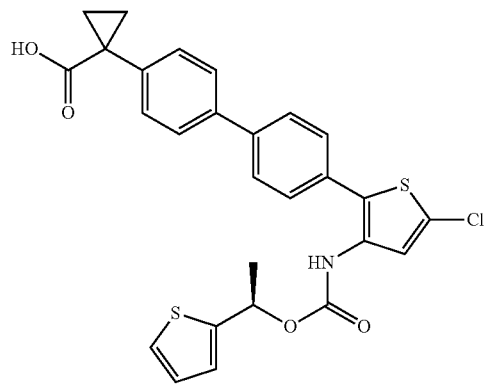

To a mixed solution of 106 mg (0.177 mmol (purity 92% by weight)) of (R)-1-{4'-[5-chloro-3-({[1-(thiophen-2-yl)ethoxy]carbonyl}amino)thiophen-2-yl]-[1,1'-biphenyl]-4-yl}cyclopropanecarboxylic acid ethyl ester synthesized in Example 147 in isopropyl alcohol (1.5 ml)-tetrahydrofuran (0.5 ml) was added 1.0 ml (2.0 mmol) of a 2N aqueous sodium hydroxide solution, and the mixture was stirred at room temperature for 13 hours and then heated and stirred at 40° C. for 8 hours. After completion of the reaction, the reaction mixture was acidified by adding 1N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (a COOH column, elution solvent; hexane:ethyl acetate=66:34 to 20:80 (V/V)), and the fractions containing the desired compound were concentrated under reduced pressure. The resulting residue was dissolved by adding 2 ml of acetonitrile, 1 ml of water and 1 ml of tetrahydrofuran, and the mixture was lyophilized to obtain 38 mg (0.073 mmol, yield 41%) of the title compound as a white foam.

Mass spectrum (DUIS$^-$, m/z): 522 [M−1]$^-$.

$^1$H-NMR spectrum (400 MHz, DMSO-d$_6$) δ: 12.40 (1H, brs), 9.38 (1H, brs), 7.74-7.66 (2H, m), 7.66-7.58 (2H, m), 7.58-7.48 (3H, m), 7.46-7.39 (2H, m), 7.22-7.07 (2H, m), 7.05-6.97 (1H, m), 6.00 (1H, q, J=6.5 Hz), 1.71-1.52 (3H, m), 1.47 (2H, dd, J=6.7, 3.8 Hz), 1.17 (2H, dd, J=6.6, 3.8 Hz).

Example 149

(R)-1-{4'-[5-Chloro-3-({[1-(thiophen-2-yl)ethoxy]carbonyl}amino)thiophen-2-yl]-2'-methoxy-[1,1'-biphenyl]-4-yl}cyclopropanecarboxylic acid ethyl ester (Compound No. I-806)

[Chemical Formula 258]

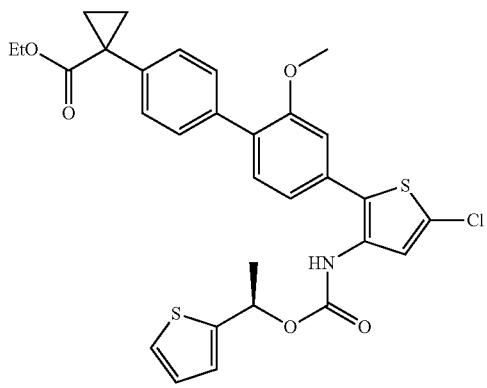

To a solution of 100 mg (0.22 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 30, 50 mg (0.39 mmol) of (R)-1-(thiophen-2-yl)ethanol (Alfa Aesar) and 0.060 ml (0.74 mmol) of pyridine in toluene (2 ml) was added 120 mg (0.28 mmol) of [bis(trifluoroacetoxy)iodo]benzene under a nitrogen atmosphere at room temperature, and the mixture was heated and stirred at 70° C. for one hour. After completion of the reaction, the reaction mixture was concentrated under reduced pressure, the resulting residue was subjected to silica gel column chromatography (elution solvent; hexane:ethyl acetate=99:1 to 80:20 (V/V)), and the fractions containing the desired compound were concentrated under reduced pressure to obtain 137 mg (0.15 mmol (purity 65% by weight), yield 69%) of the title compound as a brown oil.

Mass spectrum (DUIS$^-$, m/z): 580 [M−1]$^-$.

$^1$H-NMR spectrum (400 MHz, DMSO-d$_6$) δ: 9.41 (1H, brs), 7.50 (1H, dd, J=5.0, 0.9 Hz), 7.46-7.41 (2H, m), 7.39-7.31 (3H, m), 7.20-7.15 (2H, m), 7.13-7.07 (2H, m), 7.00 (1H, dd, J=4.9, 3.6 Hz), 6.02 (1H, q, J=6.4 Hz), 4.05 (2H, q, J=7.1 Hz), 3.72 (3H, s), 1.64-1.53 (3H, m), 1.51 (2H, dd, J=6.9, 3.9 Hz), 1.23 (2H, dd, J=7.0, 4.0 Hz), 1.12 (3H, t, J=7.1 Hz).

Example 150

(R)-1-{4'-[5-Chloro-3-({[1-(thiophen-2-yl)ethoxy]carbonyl}amino)thiophen-2-yl]-2'methoxy-[1,1'-biphenyl]-4-yl}cyclopropanecarboxylic acid (Compound No. I-808)

[Chemical Formula 259]

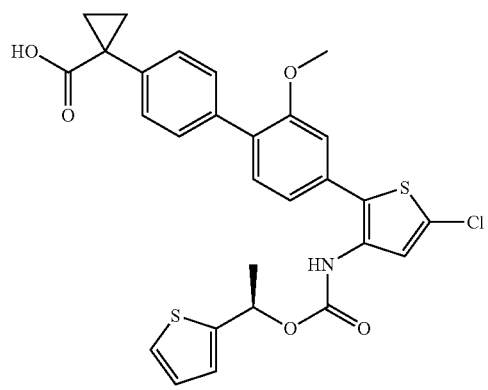

To a mixed solution of 137 mg (0.15 mmol (purity 65% by weight)) of (R)-1-{4'-[5-chloro-3-({[1-(thiophen-2-yl)ethoxy]carbonyl}amino)thiophen-2-yl]-2'-methoxy-[1,1'-biphenyl]-4-yl}cyclopropanecarboxylic acid ethyl ester synthesized in Example 149 in isopropyl alcohol (1.5 ml)-tetrahydrofuran (0.5 ml) was added 1.00 ml (2.0 mmol) of a 2N aqueous sodium hydroxide solution, and the mixture was stirred at room temperature for 13 hours and then heated and stirred at 40° C. for 8 hours. After completion of the reaction, the reaction mixture was acidified by adding 1N hydrochloric acid thereto, and extracted with methylene chloride. The organic layer was washed with saturated brine, subsequently dried over anhydrous magnesium sulfate, and concentrated under reduced pressure. The resulting residue was subjected to silica gel column chromatography (a COOH column, elution solvent; hexane:ethyl acetate=66:34 to 17:83 (V/V)), and the fractions containing the desired compound were concentrated under reduced pressure. The resulting residue was dissolved by adding 2 ml of acetonitrile, 1 ml of water and 1 ml of tetrahydrofuran, and the mixture was lyophilized to obtain 38 mg (0.069 mmol, yield 46%) of the title compound as a white foam.

Mass spectrum (DUIS$^-$, m/z): 552 [M−1]$^-$.

$^1$H-NMR spectrum (400 MHz, DMSO-d$_6$) δ: 12.38 (1H, brs), 9.41 (1H, brs), 7.50 (1H, dd, J=5.1, 0.9 Hz), 7.45-7.39

(2H, m), 7.38-7.34 (2H, m), 7.32 (1H, d, J=7.9 Hz), 7.22-7.14 (2H, m), 7.13-7.07 (2H, m), 7.00 (1H, dd, J=5.0, 3.7 Hz), 6.02 (1H, q, J=6.3 Hz), 3.72 (3H, s), 1.63-1.52 (3H, m), 1.46 (2H, dd, J=6.5, 3.8 Hz), 1.21-1.12 (2H, m).

Example 151

(R)-1-{4'-[5-Fluoro-3-({[1-(thiophen-2-yl)ethoxy]carbonyl}amino)thiophen-2-yl]-[1,1'-biphenyl]-4-yl}cyclopropanecarboxylic acid ethyl ester (Compound No. I-672)

[Chemical Formula 260]

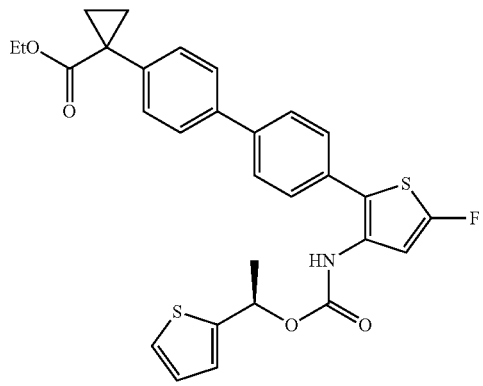

To 100 mg (0.24 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 33 was added dehydrated toluene (10 ml). The mixture was subjected to azeotropic dehydration treatment, and subsequently the atmosphere was replaced with argon. Then, 3 ml of dehydrated toluene, 0.050 ml (0.36 mmol) of triethylamine and 0.060 ml (0.29 mmol) of diphenylphosphoryl azide were added sequentially, and the mixture was stirred at room temperature for 30 minutes. Then, a solution of 50 mg (0.39 mmol) of (R)-1-(thiophen-2-yl)ethanol (Alfa Aesar) in toluene (1 ml), dried over Molecular Sieves 4A (powder) (trade name, NACALAI TESQUE, INC.) (0.1 g) was added, and the mixture was heated and stirred at 70° C. for 3 hours. After completion of the reaction, to the reaction mixture were added ethyl acetate and a saturated aqueous ammonium chloride solution to separate the layers. The organic layer was washed with saturated brine, subsequently dried over anhydrous magnesium sulfate, and concentrated under reduced pressure. The resulting residue was subjected to silica gel column chromatography (elution solvent; hexane:ethyl acetate=87:13 to 66:34 (V/V)), and the fractions containing the desired compound were concentrated under reduced pressure to obtain 141 mg (0.24 mmol (purity 92%), yield: quantitative) of the title compound as a colorless oil.

Mass spectrum (DUIS$^-$, m/z): 534 [M−1]$^-$.

$^1$H-NMR spectrum (400 MHz, DMSO-d$_6$) δ: 9.37 (1H, brs), 7.73-7.67 (2H, m), 7.66-7.61 (2H, m), 7.56-7.50 (3H, m), 7.46-7.40 (2H, m), 7.15-7.09 (1H, m), 7.04-6.99 (1H, m), 6.81 (1H, brs), 6.01 (114, q, J=6.4 Hz), 4.05 (2H, q, J=7.2 Hz), 1.66-1.54 (3H, m), 1.51 (2H, dd, J=7.0, 4.0 Hz), 1.23 (2H, dd, J=7.1, 4.1 Hz), 1.11 (3H, t, J=7.1 Hz).

Example 152

(R)-1-{4'-[5-Fluoro-3-({[1-(thiophen-2-yl)ethoxy]carbonyl}amino)thiophen-2-yl]-[1,1'-biphenyl]-4-yl}cyclopropanecarboxylic acid (Compound No. I-674)

[Chemical Formula 261]

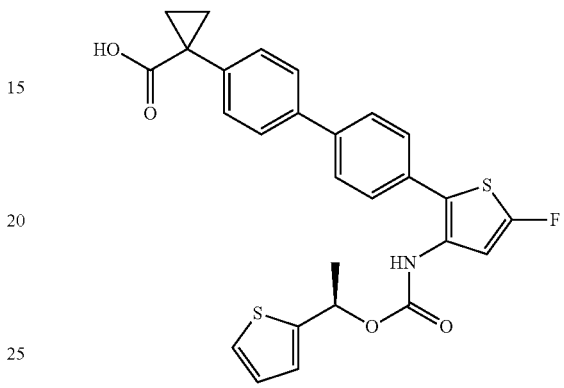

To a solution of 135 mg (0.23 mmol (purity 92%)) of (R)-1-{4'-[5-fluoro-3-({[1-(thiophen-2-yl)ethoxy]carbonyl}amino)thiophen-2-yl]-[1,1'-biphenyl]-4-yl}cyclopropanecarboxylic acid ethyl ester synthesized in Example 151 in isopropyl alcohol (3 ml) was added 1.0 ml (2.0 mmol) of a 2N aqueous sodium hydroxide solution, and the mixture was stirred at room temperature for 41 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=67:33 to 17:83 (V/V)), and the fractions containing the desired compound were concentrated under reduced pressure. The resulting residue was dissolved by adding 2 ml of acetonitrile, 1 ml of water and 0.5 ml of tetrahydrofuran, and the mixture was lyophilized to obtain 71 mg (0.14 mmol, yield 60%) of the title compound as a white foam.

Mass spectrum (DUIS$^-$, m/z): 506 [M−1]$^-$.

$^1$H-NMR spectrum (400 MHz, DMSO-d$_6$) δ: 12.40 (1H, brs), 9.37 (1H, brs), 7.73-7.65 (2H, m), 7.64-7.59 (2H, m), 7.57-7.49 (3H, m), 7.46-7.37 (2H, m), 7.16-7.09 (1H, m), 7.05-6.99 (1H, m), 6.81 (1H, brs), 6.01 (1H, q, J=6.4 Hz), 1.65-1.52 (3H, m), 1.48 (2H, dd, J=6.7, 3.8 Hz), 1.17 (2H, dd, J=6.8, 3.9 Hz).

Example 153

(R)-1-{4'-[5-Fluoro-3-({[1-(thiophen-2-yl)ethoxy]carbonyl}amino)thiophen-2-yl]-2'-methoxy-[1,1'-biphenyl]-4-yl}cyclopropanecarboxylic acid ethyl ester (Compound No. I-838)

[Chemical Formula 262]

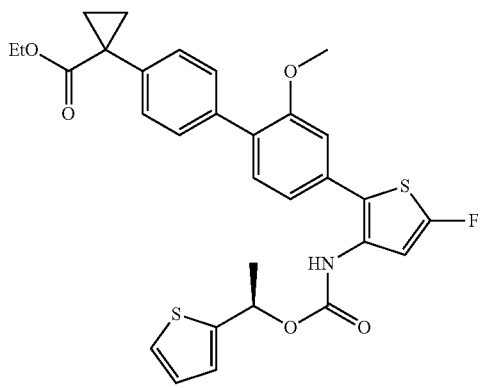

To 102 mg (0.23 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 34 was added dehydrated toluene (10 ml). The mixture was subjected to azeotropic dehydration treatment, and subsequently the atmosphere was replaced with argon. Then, 3 ml of dehydrated toluene, 0.050 ml (0.36 mmol) of triethylamine and 0.060 ml (0.28 mmol) of diphenylphosphoryl azide were added sequentially, and the mixture was stirred at room temperature for 30 minutes. Then, a solution of 45 mg (0.35 mmol) of (R)-1-(thiophen-2-yl)ethanol (Alfa Aesar) in toluene (1 ml), dried over Molecular Sieves 4A (powder) (trade name, NACALAI TESQUE, INC.) (0.1 g) was added, and the mixture was heated and stirred at 70° C. for 2 hours. After completion of the reaction, to the reaction mixture were added ethyl acetate and a saturated aqueous ammonium chloride solution to separate the layers. The organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 75:25 (V/V)), and the fractions containing the desired compound were concentrated under reduced pressure to obtain 107 mg (0.19 mmol, yield 82%) of the title compound as a colorless oil.

Mass spectrum (DUIS$^-$, m/z): 564 [M−1]$^-$.

$^1$H-NMR spectrum (400 MHz, DMSO-d$_6$) δ: 9.40 (1H, brs), 7.50 (1H, dd, J=5.0, 1.0 Hz), 7.46-7.41 (2H, m), 7.39-7.34 (2H, m), 7.32 (1H, d, J=7.9 Hz), 7.16 (1H, d, J=1.5 Hz), 7.14-7.09 (1H, m), 7.07 (1H, dd, J=7.9, 1.6 Hz), 7.00 (1H, dd, J=5.0, 3.6 Hz), 6.82 (1H, brs), 6.02 (1H, q, J=6.5 Hz), 4.05 (2H, q, J=7.1 Hz), 3.72 (3H, s), 1.65-1.53 (3H, m), 1.51 (2H, dd, J=6.8, 4.0 Hz), 1.23 (2H, dd, J=7.0, 4.0 Hz), 1.12 (3H, t, J=7.0 Hz).

Example 154

(R)-1-{4'-[5-Fluoro-3-({[1-(thiophen-2-yl)ethoxy]carbonyl}amino)thiophen-2-yl]-2'-methoxy-[1,1'-biphenyl]-4-yl}cyclopropanecarboxylic acid (Compound No. I-840)

[Chemical Formula 263]

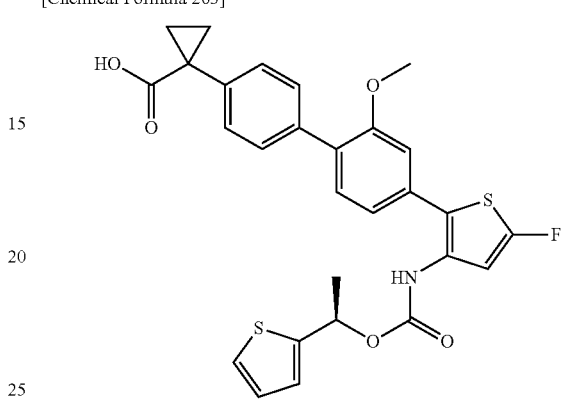

To a solution of 105 mg (0.19 mmol) of (R)-1-{4'-[5-fluoro-3-({[1-(thiophen-2-yl)ethoxy]carbonyl}amino)thiophen-2-yl]-2'-methoxy-[1,1'-biphenyl]-4-yl}cyclopropanecarboxylic acid ethyl ester synthesized in analogy to Example 153 in isopropyl alcohol (3 ml) was added 1.0 ml (2.0 mmol) of a 2N aqueous sodium hydroxide solution, and the mixture was stirred at room temperature for 50 hours. After completion of the reaction, the reaction mixture was acidified by adding 2N hydrochloric acid thereto, and extracted with ethyl acetate. The organic layer was washed sequentially with water and saturated brine, subsequently dried over anhydrous magnesium sulfate, and concentrated under reduced pressure. The resulting residue was subjected to silica gel column chromatography (a COOH column, elution solvent; hexane:ethyl acetate=67:33 to 17:83 (V/V)), and the fractions containing the desired compound were concentrated under reduced pressure. The resulting residue was dissolved by adding 3 ml of acetonitrile, 1.5 ml of water and 1 ml of tetrahydrofuran, and the mixture was lyophilized to obtain 15 mg (0.028 mmol, yield 15%) of the title compound as a white foam.

Mass spectrum (DUIS$^-$, m/z): 536 [M−1]$^-$.

$^1$H-NMR spectrum (400 MHz, DMSO-d$_6$) δ: 12.31 (1H, brs), 9.40 (1H, brs), 7.50 (1H, dd, J=5.1, 1.1 Hz), 7.45-7.39 (2H, m), 7.39-7.33 (2H, m), 7.31 (1H, d, J=7.9 Hz), 7.16 (1H, d, J=1.6 Hz), 7.14-7.09 (1H, m), 7.07 (1H, dd, J=7.8, 1.6 Hz), 7.00 (1H, dd, J=5.0, 3.6 Hz), 6.82 (1H, brs), 6.02 (1H, q, J=6.5 Hz), 3.72 (3H, s), 1.66-1.53 (3H, m), 1.47 (2H, dd, J=6.8, 3.8 Hz), 1.17 (2H, dd, J=6.9, 3.9 Hz).

Reference Example

Reference Example 1

(RS)-1-(2-Chlorophenyl)ethyl (2-bromothiophen-3-yl)carbamate

[Chemical Formula 264]

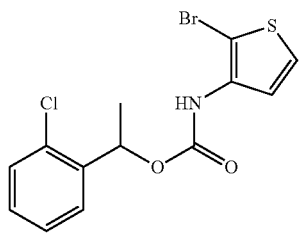

To a solution of 4.44 g (21.4 mmol) of 2-bromothiophene-3-carboxylic acid (Aldrich) in toluene (5 ml) was added dropwise 4.61 ml (33.1 mmol) of triethylamine under an argon atmosphere at room temperature while stirring, and the mixture was stirred at the same temperature for 5 minutes. Then, 3.4 ml (24 mmol) of (RS)-1-(2-chlorophenyl)ethanol (Tokyo Chemical Industry Co., Ltd.) and 5.30 ml (24.7 mmol) of diphenyiphosphoryl azide were added, and the mixture was stirred for one hour under the heat-refluxing conditions. After completion of the reaction, to the reaction mixture was added water, and the mixture was extracted with toluene. The organic layer was washed with saturated brine, subsequently dried over anhydrous magnesium sulfate, and concentrated under reduced pressure. The resulting residue was subjected to silica gel column chromatography (elution solvent; hexane:ethyl acetate=100:0 to 75:25 (V/V)), and the fractions containing the desired compound were concentrated under reduced pressure to obtain 6.80 g (18.9 mmol, yield 88%) of the title compound as a white solid.

Mass spectrum (CI, m/z): 359 [M]$^+$.

$^1$H-NMR spectrum (400 MHz, DMSO-d$_6$, 75° C.) δ: 8.97 (1H, brs), 7.55 (1H, dd, J=7.7, 1.6 Hz), 7.50 (1H, d, J=5.8 Hz), 7.43 (1H, dd, J=7.8, 1.4 Hz), 7.38 (1H, td, J=7.5, 1.4 Hz), 7.32 (1H, td, J=7.6, 1.8 Hz), 7.10 (1H, d, J=5.9 Hz), 6.05 (1H, q, J=6.5 Hz), 1.52 (3H, d, J=6.5 Hz).

Reference Example 2

2-Bromothiophene-3-carboxylic acid benzyl ester

[Chemical Formula 265]

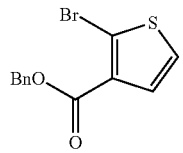

To a solution of 5.80 g (28.0 mmol) of 2-bromothiophene-3-carboxylic acid (Aldrich) and 0.86 g (7.0 mmol) of N,N-dimethylaminopyridine-4-amine in methylene chloride (112 ml) were added 4.4 ml (42 mmol) of benzyl alcohol and 4.7 mL (34 mmol) of triethylamine under ice cooling, then 6.45 g (33.6 mmol) of 1-ethyl-3-(3-dimethylaminopropyl)carbodiimide hydrochloride was added, and the mixture was stirred at room temperature for 13 hours. After completion of the reaction, the reaction mixture was poured into water to separate the organic layer. The resulting organic layer was washed with a saturated aqueous ammonium chloride solution, subsequently dried over anhydrous magnesium sulfate, concentrated under reduced pressure, subsequently subjected to silica gel column chromatography (elution solvent; hexane:ethyl acetate=99:1 to 78:22 (V/V)), and the fractions containing the desired compound were concentrated under reduced pressure to obtain 7.44 g (25.0 mmol, yield 89%) of the title compound as a colorless oil.

Mass spectrum (CI, m/z): 296 [M]$^+$.

$^1$H-NMR spectrum (400 MHz, DMSO-d$_6$) δ: 7.68 (1H, d, J=5.8 Hz), 7.49-7.44 (2H, m), 7.43-7.32 (4H, m), 5.32 (2H, s).

Reference Example 3

2-Bromothiophene-3-carboxylic acid tert-butyl ester

[Chemical Formula 266]

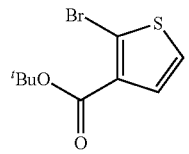

To a solution of 15 g (72 mmol) of 2-bromothiophene-3-carboxylic acid (Aldrich) and 0.60 ml (7.8 mmol) of N,N-dimethylformamide in methylene chloride (70 ml) was added dropwise 7.6 ml (87 mmol) of oxalyl chloride under a nitrogen atmosphere at room temperature while stirring, and the mixture was stirred at the same temperature for 15 hours. After completion of the reaction, the reaction mixture was concentrated under reduced pressure, to the resulting residue were added sequentially tert-butanol (70 ml), 65 ml (372 mmol) of N,N-diisopropylethylamine and 0.90 g (7.4 mmol) of N,N-dimethylaminopyridine-4-amine, and the mixture was heated and stirred under a nitrogen atmosphere at 80° C. for 2 hours. After completion of the reaction, the reaction mixture was concentrated under reduced pressure, to the residue was added water, and the mixture was extracted with toluene. The organic layer was washed with saturated brine, subsequently dried over anhydrous magnesium sulfate, and concentrated under reduced pressure. The resulting residue was subjected to silica gel column chromatography (elution solvent; hexane:ethyl acetate=100:0 to 90:10 (V/V)), and the fractions containing the desired compound were concentrated under reduced pressure to obtain 12 g (32 mmol, (purity 71% by weight), yield 45%) of the title compound as a pale yellow oil.

Mass spectrum (EI, m/z): 262 [M]$^+$.

$^1$H-NMR spectrum (400 MHz, CDCl$_3$) δ: 7.32 (1H, d, J=5.8 Hz), 7.18 (1H, d, J=5.8 Hz), 1.59 (9H, s).

The title compound was also synthesized as follows.

To a solution of 1.005 g (4.85 mmol) of 2-bromothiophene-3-carboxylic acid (Aldrich) in pyridine (9.6 ml) was added portionwise 1.80 g (9.70 mmol) of p-toluenesulfonyl chloride under an argon atmosphere under ice cooling while stirring, 0.46 ml (4.8 mmol) of tert-butanol was then added, and the mixture was stirred under ice cooling for 2 hours.

After the mixture was further stirred at room temperature for one hour, 0.47 mL (5.0 mmol) of tert-butanol was added, and the mixture was stirred at room temperature for 27 hours. After completion of the reaction, the reaction mixture was concentrated under reduced pressure, and ethyl acetate and a saturated aqueous sodium hydrogencarbonate solution were added to separate the layers. The organic layer was washed with a saturated aqueous sodium hydrogencarbonate solution and subsequently washed with saturated brine. Further, the organic layer was washed with a 5% by weight aqueous potassium hydrogensulfate solution, and washed with saturated brine again. The organic layer was dried over anhydrous magnesium sulfate and concentrated under reduced pressure. The resulting residue was subjected to silica gel column chromatography (elution solvent; hexane:ethyl acetate=99:1 to 94:6 (V/V)), and the fractions containing the desired compound were concentrated under reduced pressure to obtain 1.22 g (4.64 mmol, yield 96%) of the title compound as a pale yellow oil.

$^1$H-NMR spectrum (400 MHz, DMSO-$d_6$) δ: 7.63 (1H, d, J=5.8 Hz), 7.28 (1H, d, J=5.8 Hz), 1.53 (9H, s).

Reference Example 4

2-(4-Chloro-3-nitrophenyl)thiophene-3-carboxamide

[Chemical Formula 267]

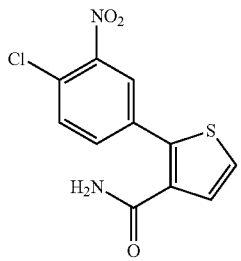

A solution of 493 mg (2.39 mmol) of 2-bromothiophene-3-carboxamide (synthesized according to WO 10/036497) and 645 mg (3.20 mmol) of 4-chloro-3-nitrophenyl boronic acid in 1,4-dioxane (7 ml) was degassed, a suspension of 1.26 g (11.9 mmol) of sodium carbonate in 2 ml of water was added, then 0.196 g (0.240 mmol) of [1,1'-bis(diphenylphosphino)ferrocene]palladium(II) dichloride methylene chloride adduct was added, and the mixture was heated and stirred under an argon atmosphere at 95° C. for 1.5 hours. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=63:37 to 42:58 (V/V)), and the fractions containing the desired compound were concentrated under reduced pressure to obtain 382 mg (1.35 mmol, yield 57%) of the title compound as a white solid.

Mass spectrum (CI, m/z): 283 [M+1]$^+$.

1H-NMR spectrum (400 MHz, CD$_2$Cl$_2$) δ: 8.08 (1H, d, J=2.1 Hz), 7.73 (1H, dd, J=8.3, 2.2 Hz), 7.61 (1H, d, J=8.4 Hz), 7.43 (1H, d, J=5.3 Hz), 7.34 (1H, d, J=5.3 Hz), 5.63 (2H, brs).

Reference Example 5

4-Bromo-1-iodo-2-methoxybenzene

[Chemical Formula 268]

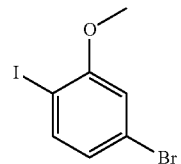

To a mixed solution of 2.0 g (9.0 mmol) of 4-bromo-2-methoxy aniline (Tokyo Chemical Industry Co., Ltd.) in acetic acid (15 ml)-concentrated hydrochloric acid (1 ml) was added 0.75 g (11 mmol) of sodium nitrite under ice cooling while stirring so that the internal temperature did not exceed 10° C., and the mixture was stirred at room temperature for 30 minutes. Then, the reaction mixture was added dropwise to a solution of 1.0 g (30 mmol) of potassium iodide in a 48% by weight aqueous hydrobromic acid solution (30 ml) at room temperature while stirring, and the mixture was stirred at the same temperature for one hour. After completion of the reaction, to a mixture of an aqueous sodium carbonate solution and methylene chloride was added the reaction mixture portionwise, the basicity of the aqueous layer was confirmed, and an extraction with methylene chloride from the mixed solution was subsequently conducted. The organic layer was washed sequentially with a 10% by weight aqueous sodium hydrogen sulfite solution, a saturated aqueous sodium hydrogencarbonate solution and saturated brine, dried over anhydrous magnesium sulfate, and concentrated under reduced pressure. The resulting residue was subjected to silica gel column chromatography (elution solvent; hexane:ethyl acetate=100:0 to 91:9 (V/V)), and the fractions containing the desired compound were concentrated under reduced pressure to obtain 2.2 g (7.2 mmol, yield 73%) of the title compound as an orange solid.

Mass spectrum (EI, m/z): 312 [M]$^+$.

$^1$H-NMR spectrum (400 MHz, CDCl$_3$) δ: 7.61 (1H, d, J=8.3 Hz), 6.94 (1H, d, J=2.1 Hz), 6.87 (1H, dd, J=8.2, 2.1 Hz), 3.88 (3H, s).

Reference Example 6

5-Bromo-2-iodobenzoic acid tert-butyl ester

[Chemical Formula 269]

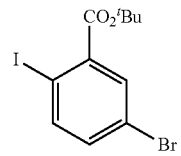

To a solution of 2.0 g (6.1 mmol) of 5-bromo-2-iodobenzoic acid (Aldrich) and 0.10 g (0.82 mmol) of N,N-dimethylaminopyridine-4-amine in tetrahydrofuran (20 ml) was added 2.8 ml (12 mmol) of di-tert-butyl dicarbonate under a nitrogen atmosphere while stirring, and the mixture was stirred at room temperature for 3 hours. After completion of the reaction, to the reaction mixture was added a saturated aqueous sodium hydrogencarbonate solution, and an extraction with ethyl acetate from the mixed solution was conducted. The organic layer was washed with saturated brine, subsequently dried over anhydrous magnesium sulfate, and concentrated under reduced pressure. The resulting residue was subjected to silica gel column chromatography (elution solvent; hexane:ethyl acetate=80:20 to 50:50 (V/V)), and the fractions containing the desired compound were concentrated under reduced pressure to obtain 1.5 g (2.9 mmol (purity 74% by weight), yield 35%) of the title compound as a colorless oil.

$^1$H-NMR spectrum (400 MHz, CDCl$_3$) δ: 7.80-7.77 (2H, m), 7.23 (1H, dd, J=8.4, 2.4 Hz), 1.62 (9H, s).

Reference Example 7

1-[4-(5-Bromopyridine-2-yl)phenyl]cyclopropanecarboxylic acid ethyl ester

[Chemical Formula 270]

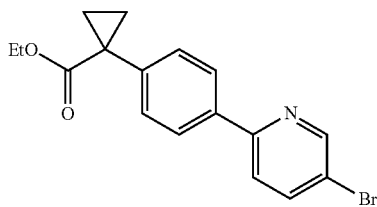

A solution of 2.17 g (20.5 mmol) of sodium carbonate in toluene (20 ml)-water (20 ml)-ethanol (5 ml) was degassed by bubbling with argon gas, and then 4.28 g (15.1 mmol) of 5-bromo-2-iodopyridine (Aldrich), 4.33 g (13.7 mmol) of 1-[4-(4,4,5,5-tetramethyl-1,3,2-dioxaborolane-2-yl)phenyl]cyclopropanecarboxylic acid ethyl ester (synthesized according to a process described in WO 12/078593) and 0.56 g (0.69 mmol) of [1,1'-bis(diphenylphosphino)ferrocene]palladium(II) dichloride methylene chloride adduct were added. The pressure was reduced once, the atmosphere was replaced with argon, and the mixture was heated and stirred at 100° C. for 11.5 hours. After completion of the reaction, the reaction mixture was cooled, and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=99:1 to 90:10 (V/V)), and the fractions containing the desired compound were concentrated under reduced pressure to obtain 2.58 g (7.45 mmol, yield 54%) of the title compound as a white solid.

Mass spectrum (EI, m/z): 345 [M]$^+$.

$^1$H-NMR spectrum (400 MHz, DMSO-d$_6$) δ: 8.78 (1H, dd, J=2.4, 0.5 Hz), 8.12 (1H, dd, J=8.5, 2.4 Hz), 8.04-7.98 (2H, m), 7.95 (1H, dd, J=8.6, 0.6 Hz), 7.47-7.42 (2H, m), 4.04 (2H, q, J=7.1 Hz), 1.52 (2H, dd, J=6.9, 4.0 Hz), 1.24 (2H, dd, J=7.1, 4.1 Hz), 1.10 (3H, t, J=7.1 Hz).

Reference Example 8

1-(4'-Bromo-2'-methoxy-[1,1'-biphenyl]-4-yl)cyclopropanecarboxylic acid ethyl ester

[Chemical Formula 271]

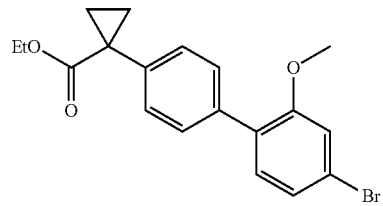

A solution of 1.2 g (3.8 mmol) of 4-bromo-1-iodo-2-methoxybenzene synthesized in analogy to Reference Example 5, 1.1 g (3.5 mmol) of 1-[4-(4,4,5,5-tetramethyl-1,3,2-dioxaborolane-2-yl)phenyl]cyclopropanecarboxylic acid ethyl ester (synthesized according to a process described in WO 12/078593) and 1.1 g (10 mmol) of sodium carbonate in 1,4-dioxane (15 ml)-water (10 ml) was degassed and subject to nitrogen. Then, 0.10 g (0.12 mmol) of [1,1'-bis(diphenylphosphino)ferrocene]palladium(II) dichloride methylene chloride adduct was added, and the mixture was heated and stirred under a nitrogen atmosphere at 80° C. for 1.5 hours. After completion of the reaction, to the reaction mixture was added water, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=94:6 to 75:25 (V/V)), and the fractions containing the desired compound were concentrated under reduced pressure to obtain 0.72 g (1.9 mmol, yield 55%) of the title compound as a white solid.

Mass spectrum (EI, m/z): 374 [M]$^+$.

$^1$H-NMR spectrum (400 MHz, CDCl$_3$) δ: 7.45-7.41 (2H, m), 7.39-7.35 (2H, m), 7.19 (1H, d, J=8.0 Hz), 7.15 (1H, dd, J=8.0, 1.8 Hz), 7.10 (1H, d, J=1.8 Hz), 4.12 (2H, q, J=7.1 Hz), 3.81 (3H, s), 1.61 (2H, dd, J=7.0, 4.0 Hz), 1.22 (2H, dd, J=7.0, 4.0 Hz), 1.19 (3H, t, J=7.1 Hz).

Reference Example 9

1-(4'-Chloro-2'-methoxy-[1,1'-biphenyl]-4-yl)cyclopropanecarboxylic acid ethyl ester

[Chemical Formula 272]

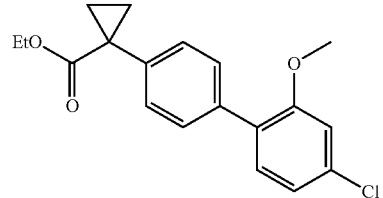

A solution of 2.0 g (9.0 mmol) of 1-bromo-4-chloro-2-methoxybenzene (Tokyo Chemical Industry Co., Ltd.), 2.6 g (8.2 mmol) of 1-[4-(4,4,5,5-tetramethyl-1,3,2-dioxaborolane-2-yl)phenyl]cyclopropanecarboxylic acid ethyl ester (synthesized according to a process described in WO 12/078593) and 2.7 g (25 mmol) of sodium carbonate in 1,4-dioxane (20 ml)-water (20 ml) was degassed and subjected to nitrogen replacement. Then, 0.21 g (0.25 mmol) of [1,1'-bis(diphenylphosphino)ferrocene]palladium(II) dichloride methylene chloride adduct was added, and the mixture was heated and stirred under a nitrogen atmosphere at 80° C. for 2 hours. After completion of the reaction, to the reaction mixture was added water, and the mixture was extracted with ethyl acetate. The organic layer was washed with saturated brine, subsequently dried over anhydrous magnesium sulfate, and concentrated under reduced pressure. The resulting residue was subjected to silica gel column chromatography, and the fraction having Rf=0.5 (developing solvent; hexane:ethyl acetate=90:10 (V/V)) was concentrated under reduced pressure to obtain 2.46 g (7.4 mmol, yield 90%) of the title compound as a white solid.

Mass spectrum (EI, m/z): 330 [M]$^+$.

$^1$H-NMR spectrum (400 MHz, CDCl$_3$) δ: 7.45-7.41 (2H, m), 7.39-7.35 (2H, m), 7.25 (1H, d, J=8.2 Hz), 7.00 (1H, dd, J=8.2, 2.0 Hz), 6.96 (1H, d, J=2.0 Hz), 4.12 (2H, q, J=7.1 Hz), 3.81 (3H, s), 1.61 (2H, dd, J=6.9, 3.9 Hz), 1.22 (2H, dd, J=7.0, 4.0 Hz), 1.19 (3H, t, J=7.1 Hz).

Reference Example 10

4-Bromo-4'-[1-(ethoxycarbonyl)cyclopropyl]-[1,1'-biphenyl]-2-carboxylic acid tert-butyl ester

[Chemical Formula 273]

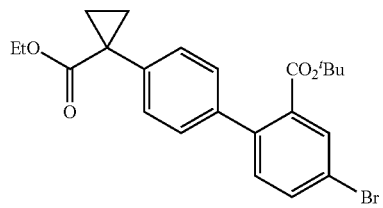

A solution of 1.5 g (2.9 mmol (purity 74% by weight)) of 5-bromo-2-iodobenzoic acid tert-butyl ester synthesized in Reference Example 6, 0.85 g (2.7 mmol) of 1-[4-(4,4,5,5-tetramethyl-1,3,2-dioxaborolane-2-yl)phenyl]cyclopropanecarboxylic acid ethyl ester (synthesized according to a process described in WO 12/078593) and sodium carbonate (0.85 g, 8.0 mmol) in 1,4-dioxane (10 ml)-water (5 ml) was degassed and subjected to nitrogen replacement. Then, 0.050 g (0.061 mmol) of [1,1'-bis(diphenylphosphino)ferrocene]palladium(II) dichloride methylene chloride adduct was added, and the mixture was heated and stirred under a nitrogen atmosphere at 80° C. for 2 hours. After completion of the reaction, to the reaction mixture was added water, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=94:6 to 75:25 (V/V)), and the fractions containing the desired compound were concentrated under reduced pressure to obtain 0.89 g (2.0 mmol, yield 69%) of the title compound as a white solid.

Mass spectrum (EI, m/z): 444 [M]$^+$.

$^1$H-NMR spectrum (400 MHz, CDCl$_3$) δ: 7.89 (1H, d, J=2.1 Hz), 7.59 (1H, dd, J=8.3, 2.1 Hz), 7.38-7.34 (2H, m), 7.24-7.18 (3H, m), 4.11 (2H, q, J=7.1 Hz), 1.63 (2H, dd, J=7.0, 4.0 Hz), 1.24 (9H, s), 1.19 (2H, dd, J=7.0, 4.0 Hz), 1.18 (3H, t, J=7.2 Hz).

Reference Example 11

1-{4-[5-(4,4,5,5-Tetramethyl-1,3,2-dioxaborolane-2-yl)pyridine-2-yl]phenyl}cyclopropanecarboxylic acid ethyl ester

[Chemical Formula 274]

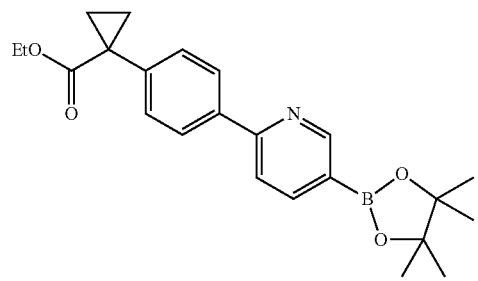

To 2.50 g (7.22 mmol) of 1-[4-(5-bromopyridine-2-yl)phenyl]cyclopropanecarboxylic acid ethyl ester synthesized in analogy to Reference Example 7, 2.2 g (8.7 mmol) of 4,4,4',4',5,5,5',5'-octamethyl-2,2'-bi(1,3,2-dioxaborolane) and 1.5 g (15 mmol) of potassium acetate was added 20 ml of 1,4-dioxane. The mixture was frozen and degassed by a dry ice-acetone bath, and subsequently the atmosphere was replaced with argon. Then, 466 mg (0.571 mmol) of [1,1'-bis(diphenylphosphino)ferrocene]palladium(II) dichloride methylene chloride adduct was added, and the mixture was degassed under reduced pressure. After the atmosphere was replaced with argon, the mixture was heated and stirred at 90° C. for 7 hours. After completion of the reaction, the reaction mixture was cooled, ethyl acetate and water were added, and insoluble matter was filtered with Celite 545 (trade name) to separate the layers. The resulting organic layer was dried over anhydrous magnesium sulfate and concentrated under reduced pressure. To the resulting residue was added hexane, the precipitated solid was collected by filtration to obtain 2.14 g (7.22 mmol, yield 75%) of the title compound as a brown solid.

Mass spectrum (EI, m/z): 393 [M]$^+$.

$^1$H-NMR spectrum (400 MHz, DMSO-d$_6$) δ: 8.85 (1H, dd, J=1.8, 0.9 Hz), 8.07-8.04 (2H, m), 8.07 (1H, dd, J=8.0, 1.8 Hz), 7.97 (1H, dd, J=8.0, 0.9 Hz), 7.48-7.43 (2H, m), 4.04 (2H, q, J=7.1 Hz), 1.52 (2H, dd, J=6.9, 3.9 Hz), 1.33 (12H, s), 1.24 (2H, dd, J=7.1, 4.1 Hz), 1.10 (3H, t, J=7.0 Hz).

Reference Example 12

1-[2'-Methoxy-4'-(4,4,5,5-tetramethyl-1,3,2-dioxaborolane-2-yl)-[1,1'-biphenyl]-4-yl]-cyclopropanecarboxylic acid ethyl ester

[Chemical Formula 275]

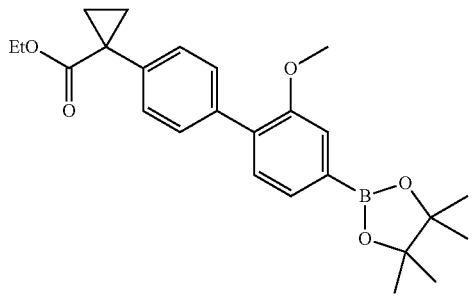

A solution of 0.72 g (1.9 mmol) of 1-(4'-bromo-2'-methoxy-[1,1'-biphenyl]-4-yl)cyclopropanecarboxylic acid ethyl ester synthesized in analogy to Reference Example 8, 0.60 g (2.4 mmol) of 4,4,4',4',5,5,5',5'-octamethyl-2,2'-bi(1,3,2-dioxaborolane) and 0.30 g (3.1 mmol) of potassium acetate in 1,4-dioxane (10 ml) was degassed and subjected to nitrogen replacement. Then, 0.10 g (0.12 mmol) of [1,1'-bis(diphenylphosphino)ferrocene]palladium(II) dichloride methylene chloride adduct was added, and the mixture was stirred under a nitrogen atmosphere under the heat-refluxing condition for 3 hours. After completion of the reaction, to the reaction mixture was added water, and the mixture was extracted with toluene. The organic layer was washed with saturated brine, subsequently dried over anhydrous magnesium sulfate, and concentrated under reduced pressure. The resulting residue was subjected to silica gel column chromatography (elution solvent; hexane:ethyl acetate=92:8 to 79:21 (V/V)), and the fractions containing the desired compound were concentrated under reduced pressure to obtain 0.81 g (1.9 mmol, yield: quantitative) of the title compound as a pale yellow solid.

Mass spectrum (EI, m/z): 422 [M]$^+$.

$^1$H-NMR spectrum (400 MHz, CDCl$_3$) δ: 7.52-7.46 (3H, m), 7.40-7.33 (4H, m), 4.12 (2H, q, J=7.1 Hz), 3.86 (3H, s), 1.60 (2H, dd, J=6.9, 3.9 Hz), 1.36 (12H, s), 1.22 (2H, dd, J=7.0, 4.0 Hz), 1.19 (3H, t, J=7.1 Hz).

The title compound was also synthesized as follows.

A solution of 2.46 g (7.43 mmol) of 1-(4'-chloro-2'-methoxy-[1,1'-biphenyl]-4-yl)cyclopropanecarboxylic acid ethyl ester synthesized in analogy to Reference Example 9, 2.43 g (9.57 mmol) of 4,4,4',4',5,5,5',5'-octamethyl-2,2'-bi(1,3,2-dioxaborolane) and 1.1 g (11 mmol) of potassium acetate in 1,4-dioxane (30 ml) was degassed and subjected to nitrogen replacement. Then, 0.30 g (0.37 mmol) of [1,1'-bis(diphenylphosphino)ferrocene]palladium(II) dichloride methylene chloride adduct and 0.30 g (1.1 mmol) of tricyclohexylphosphine were added, and the mixture was stirred under a nitrogen atmosphere under the heat-refluxing condition for 24 hours. Additionally, 0.15 g (0.18 mmol) of [1,1'-bis(diphenylphosphino)ferrocene]palladium(II) dichloride methylene chloride adduct and 0.15 g (0.54 mmol) of tricyclohexylphosphine were then added, and the mixture was stirred under a nitrogen atmosphere under the heat-refluxing condition for 5 hours. After completion of the reaction, the reaction mixture was cooled to room temperature, toluene was added, and insoluble matter was filtered. The filtrate was washed sequentially with a saturated aqueous sodium hydrogencarbonate solution and saturated brine, dried over anhydrous magnesium sulfate and then concentrated under reduced pressure. The resulting residue was subjected to silica gel column chromatography (elution solvent; hexane:ethyl acetate=92:8 to 79:21 (V/V)), the fractions containing the desired compound were concentrated under reduced pressure, and to the residue was added hexane. The solid was collected by filtration and washed with hexane to obtain 1.89 g (4.5 mmol, yield 60%) of the title compound as a white solid.

Reference Example 13

4'-[1-(Ethoxycarbonyl)cyclopropyl]-4-(4,4,5,5-tetramethyl-1,3,2-dioxaborolane-2-yl)-[1,1'-biphenyl]-2-carboxylic acid tert-butyl ester

[Chemical Formula 276]

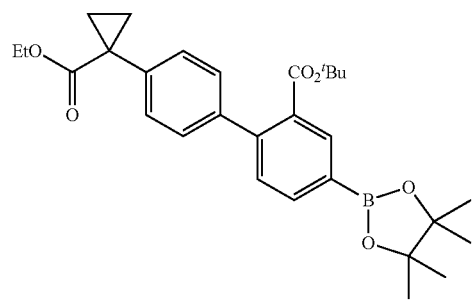

A solution of 0.88 g (2.0 mmol) of 4-bromo-4'-[1-(ethoxycarbonyl)cyclopropyl]-[1,1'-biphenyl]-2-carboxylic acid tert-butyl ester synthesized in analogy to Reference Example 10, 0.60 g (2.4 mmol) of 4,4,4',4',5,5,5',5'-octamethyl-2,2'-bi(1,3,2-dioxaborolane) and 0.30 g (3.1 mmol) of potassium acetate in 1,4-dioxane (10 ml) was degassed and subjected to nitrogen replacement. Then, 0.080 g (0.098 mmol) of [1,1'-bis(diphenylphosphino)ferrocene]palladium(II) dichloride methylene chloride adduct was added, and the mixture was stirred under a nitrogen atmosphere under the heat-refluxing condition for 3 hours. After completion of the reaction, to the reaction mixture was added water, and the mixture was extracted with toluene. The organic layer was washed with saturated brine, subsequently dried over anhydrous magnesium sulfate. The resulting residue was subjected to silica gel column chromatography (elution solvent; hexane:ethyl acetate=92:8 to 79:21 (V/V)), and the fractions containing the desired compound were concentrated under reduced pressure to obtain 0.94 g (1.9 mmol, yield 81%) of the title compound as a pale yellow solid.

Mass spectrum (EI, m/z): 492 [M]$^+$.

$^1$H-NMR spectrum (400 MHz, CDCl$_3$) δ: 8.19 (1H, d, J=0.9 Hz), 7.89 (1H, dd, J=7.6, 1.3 Hz), 7.39-7.32 (3H, m), 7.28-7.24 (2H, m), 4.11 (2H, q, J=7.1 Hz), 1.62 (2H, dd, J=6.9, 3.9 Hz), 1.36 (12H, s), 1.23 (9H, s), 1.21-1.15 (5H, m).

Reference Example 14

(RS)-1-{4'-[3-({[1-(2-Chlorophenyl)ethoxy]carbonyl}amino)thiophen-2-yl]-[1,1'-biphenyl]-4-yl}cyclopropanecarboxylic acid ethyl ester

[Chemical Formula 277]

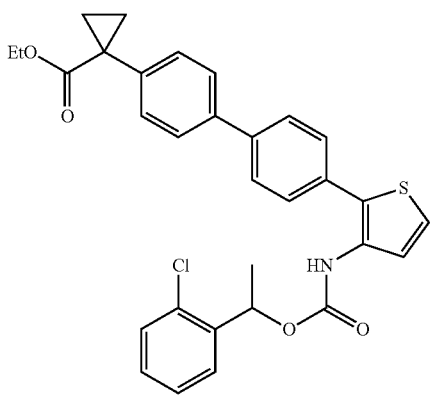

To a solution of 2.5 g (7.0 mmol) of (RS)-1-(2-chlorophenyl)ethyl (2-bromothiophen-3-yl)carbamate synthesized in analogy to Reference Example 1 and 3.1 g (8.4 mmol) of 1-[4'-(4,4,5,5-tetramethyl-1,3,2-dioxaborane-2-yl)-[1,1'-biphenyl]-4-yl]cyclopropanecarboxylic acid ethyl ester (synthesized according to a process described in WO 12/078593) in 1,2-dimethoxyethane (70 ml) were added 2.90 g (21.0 mmol) of potassium carbonate and 0.23 g (0.28 mmol) of [1,1'-bis(diphenylphosphino)ferrocene]palladium(II) dichloride methylene chloride adduct at room temperature while degassing by bubbling with nitrogen gas, and the mixture was stirred under an argon atmosphere under the heat-refluxing condition for one hour. After completion of the reaction, the reaction mixture was poured into water, and the mixture was extracted with ethyl acetate. The organic layer was dried over anhydrous magnesium sulfate and subsequently concentrated under reduced pressure, the resulting residue was subjected to silica gel column chromatography (elution solvent; hexane:ethyl acetate=96:4 to 71:29 (V/V)), and the fractions containing the desired compound were concentrated under reduced pressure to obtain 2.0 g (3.7 mmol, yield 52%) of the title compound.

Mass spectrum (EI, m/z): 545 [M]$^+$.

$^1$H-NMR spectrum (400 MHz, DMSO-d$_6$, 75° C.) δ: 8.94 (1H, brs), 7.70-7.65 (2H, m), 7.64-7.56 (4H, m), 7.50-7.39 (5H, m), 7.35 (1H, td, J=7.5, 1.4 Hz), 7.29 (1H, td, J=7.6, 1.8 Hz), 7.10 (1H, d, J=5.4 Hz), 6.00 (1H, q, J=6.5 Hz), 4.06 (2H, q, J=7.1 Hz), 1.52 (2H, dd, J=7.0, 4.1 Hz), 1.46 (3H, d, J=6.5 Hz), 1.22 (2H, dd, J=7.0, 4.0 Hz), 1.13 (3H, t, J=7.1 Hz).

Reference Example 15

2-{4'-[1-(Ethoxycarbonyl)cyclopropyl]-[1,1'-biphenyl]-4-yl}thiophene-3-carboxylic acid benzyl ester

[Chemical Formula 278]

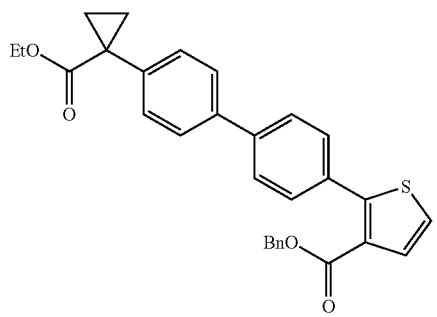

A solution of 5.01 g (12.8 mmol) of 1-[4'-(4,4,5,5-tetramethyl-1,3,2-dioxaborane-2-yl)-[1,1'-biphenyl]-4-yl]cyclopropanecarboxylic acid ethyl ester (synthesized according to a process described in WO 12/078593), 3.2 g (11 mmol) of 2-bromothiophene-3-carboxylic acid benzyl ester synthesized in analogy to Reference Example 2 and 3.7 g (27 mmol) of potassium carbonate in 1,4-dioxane (177 ml)-water (35 ml) was degassed by bubbling with argon, and then 1.8 g (1.6 mmol) of tetrakis(triphenylphosphine)palladium(0) was added, and the mixture was heated and stirred under an argon atmosphere at 80° C. for one hour and then at 100° C. for 20 minutes. After completion of the reaction, the reaction mixture was allowed to cool, and 150 ml of toluene and 50 ml of water were added to separate the layers. The organic layer was dried over anhydrous magnesium sulfate and concentrated under reduced pressure. The resulting residue was subjected to silica gel column chromatography (elution solvent; hexane:ethyl acetate=100:0 to 71:29 (V/V)), and the fractions containing the desired compound were concentrated under reduced pressure. The resulting solid was dissolved by adding methylene chloride, hexane was added, and the mixture was gradually concentrated under reduced pressure. The precipitated solid was collected by filtration to obtain 3.25 g (6.7 mmol, yield 63%) of the title compound as a white solid.

Mass spectrum (CI, m/z): 483 [M+1]$^+$.

$^1$H-NMR spectrum (400 MHz, DMSO-d$_6$) δ: 7.70-7.62 (5H, m), 7.57-7.53 (2H, m), 7.52 (1H, d, J=5.4 Hz), 7.47-7.43 (2H, m), 7.33-7.21 (5H, m), 5.20 (2H, s), 4.06 (2H, q, J=7.1 Hz), 1.52 (2H, dd, J=7.0, 4.1 Hz), 1.25 (2H, dd, J=7.0, 4.1 Hz), 1.12 (3H, t, J=7.1 Hz).

Reference Example 16

1-[4'-(3-Carbamoylthiophen-2-yl)-[1,1'-biphenyl]-4-yl]cyclopropanecarboxylic acid ethyl ester

[Chemical Formula 279]

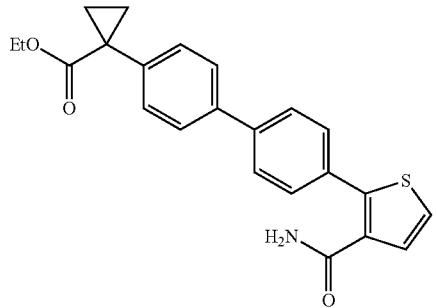

A solution of 8.0 g (20 mmol) of 1-[4'-(4,4,5,5-tetramethyl-1,3,2-dioxaborane-2-yl)-[1,1'-biphenyl]-4-yl]cyclopropanecarboxylic acid ethyl ester (synthesized according to a process described in WO 12/078593), 3.5 g (17 mmol) of 2-bromothiophene-3-carboxamide (synthesized according to WO 10/036497) and 5.4 g (51 mmol) of sodium carbonate in 1,4-dioxane (75 ml)-water (25 ml) was degassed, then 1.0 g (0.87 mmol) of tetrakis(triphenylphosphine)palladium(0) was added, and the mixture was heated and stirred under a nitrogen atmosphere at 90° C. for 14.5 hours. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=50:50 to 0:100 (V/V)), and the fractions containing the desired compound were concentrated under reduced pressure. To the resulting solid was added a small amount of ethyl acetate to form slurry which was filtered. The solid was washed with a small amount of ethyl acetate to obtain 4.8 g (12 mmol, yield 72%) of the title compound as a white solid.

Mass spectrum (EI, m/z): 391 [M]⁺.

(1H-NMR spectrum (400 MHz, CDCl₃) δ: 7.69-7.65 (2H, m), 7.62-7.54 (4H, m), 7.51 (1H, d, J=5.4 Hz), 7.46-7.42 (2H, m), 7.29 (1H, d, J=5.3 Hz), 5.51 (2H, brs), 4.12 (2H, q, J=7.1 Hz), 1.65 (2H, dd, J=6.9, 3.9 Hz), 1.23 (2H, dd, J=7.0, 4.0 Hz), 1.19 (3H, t, J=7.1 Hz).

Reference Example 17

2-{4'-[1-(Ethoxycarbonyl)cyclopropyl]-[1,1'-biphenyl]-4-yl}thiophene-3-carboxylic acid tert-butyl ester

[Chemical Formula 280]

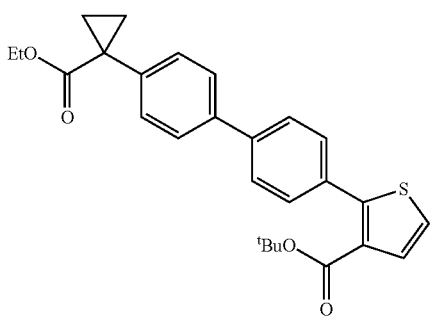

A solution of 0.80 g (2.0 mmol) of 1-[4'-(4,4,5,5-tetramethyl-1,3,2-dioxaboran-2-yl)-[1,1'-biphenyl]-4-yl]cyclopropanecarboxylic acid ethyl ester (synthesized according to a process described in WO 12/078593), 0.50 g (1.9 mmol) of 2-bromothiophene-3-carboxylic acid tert-butyl ester synthesized in analogy to Reference Example 3 and 0.61 g (5.8 mmol) of sodium carbonate in 1,4-dioxane (15 ml)-water (5 ml) was degassed, then 0.10 g (0.089 mmol) of tetrakis(triphenylphosphine)palladium(0) was added, and the mixture was heated and stirred under a nitrogen atmosphere at 90° C. for 14.5 hours. After completion of the reaction, the reaction mixture was allowed to cool, water was added, and the mixture was extracted with ethyl acetate. The organic layer was washed with saturated brine, dried over anhydrous magnesium sulfate, and concentrated under reduced pressure. The resulting residue was subjected to silica gel column chromatography, and the fraction having Rf=0.41 (developing solvent; hexane:ethyl acetate=90:10 (V/V)) was concentrated under reduced pressure to obtain 0.58 g (1.3 mmol, yield 68%) of the title compound as a white solid.

Mass spectrum (EI, m/z): 448 [M]⁺.

¹H-NMR spectrum (400 MHz, CDCl₃) δ: 7.64-7.60 (2H, m), 7.59-7.55 (2H, m), 7.55-7.51 (2H, m), 7.48 (1H, d, J=5.4 Hz), 7.45-7.41 (2H, m), 7.23 (1H, d, J=5.3 Hz), 4.13 (2H, q, J=7.1 Hz), 1.64 (2H, dd, J=6.9, 3.9 Hz), 1.38 (9H, s), 1.23 (2H, dd, J=7.2, 4.1 Hz), 1.20 (3H, t, J=7.2 Hz).

Reference Example 18

1-[4'-(3-Carbamoylthiophen-2-yl)-2'-nitro-[1,1'-biphenyl]-4-yl]cyclopropanecarboxylic acid ethyl ester

[Chemical Formula 281]

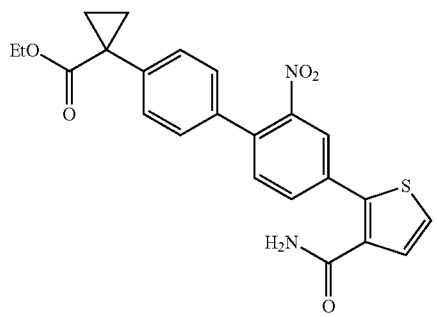

A solution of 376 mg (1.33 mmol) of 2-(4-chloro-3-nitrophenyl)thiophene-3-carboxamide synthesized in analogy to Reference Example 4 and 632 mg (2.00 mmol) of 1-[4-(4,4,5,5-tetramethyl-1,3,2-dioxaborolane-2-yl)phenyl]cyclopropanecarboxylic acid ethyl ester (synthesized according to a process described in WO 12/078593) in 1,4-dioxane (6 ml) was degassed, then 16.0 mg (0.150 mmol) of palladium acetate, 164 mg (0.585 mmol) of tricyclohexylphosphine, 705 mg (6.65 mmol) of sodium carbonate and 2 ml of water were added, and the mixture was heated and stirred under an argon atmosphere at 95° C. for 2 hours. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=63:37 to 42:58 (V/V)), and the fractions containing the desired compound were concentrated under reduced pressure to obtain 508 mg (1.16 mmol, yield 88%) of the title compound as a yellow foam.

Mass spectrum (CI, m/z): 437 [M+1]⁺.

1H-NMR spectrum (400 MHz, CD₂Cl₂) δ: 8.03 (1H, d, J=1.8 Hz), 7.82 (1H, dd, J=8.0, 1.9 Hz), 7.53 (1H, d, J=7.9 Hz), 7.45-7.41 (3H, m), 7.38 (1H, d, J=5.4 Hz), 7.33-7.29 (2H, m), 5.63 (2H, br s), 4.10 (2H, q, J=7.1 Hz), 1.62 (2H, dd, J=7.0, 4.0 Hz), 1.24 (2H, dd, J=7.0, 4.0 Hz), 1.19 (3H, t, J=7.2 Hz).

Reference Example 19

4-(3-Carbamoylthiophen-2-yl)-4'-[1-(ethoxycarbonyl)cyclopropyl]-[1,1'-biphenyl]-2-carboxylic acid tert-butyl ester

[Chemical Formula 282]

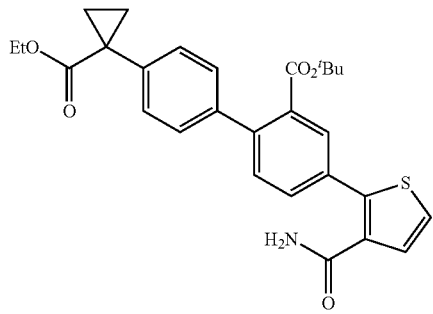

A solution of 0.94 g (1.9 mmol) of 4'-[1-(ethoxycarbonyl)cyclopropyl]-4-(4,4,5,5-tetramethyl-1,3,2-dioxaborolane-2-yl)-[1,1'-biphenyl]-2-carboxylic acid tert-butyl ester synthesized in analogy to Reference Example 13, 0.41 g (2.0 mmol) of 2-bromothiophene-3-carboxamide (synthesized according to WO 10/036497) and 0.63 g (5.9 mmol) of sodium carbonate in 1,4-dioxane (10 ml)-water (5 ml) was frozen and degassed, then 0.114 g (0.099 mmol) of tetrakis(triphenylphosphine)palladium(0) was added, and the mixture was heated and stirred under a nitrogen atmosphere at 90° C. for 16.5 hours. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=20:80 to 0:100 (V/V)), and the fractions containing the desired compound were concentrated under reduced pressure to obtain 0.90 g (1.8 mmol, yield 95%) of the title compound as a gray foam.

Mass spectrum (EI, m/z): 491 [M]$^+$.

$^1$H-NMR spectrum (400 MHz, CDCl$_3$) δ: 7.92 (1H, d, J=1.8 Hz), 7.66 (1H, dd, J=7.9, 2.0 Hz), 7.48 (1H, d, J=5.3 Hz), 7.43-7.37 (3H, m), 7.32 (1H, d, J=5.3 Hz), 7.30-7.26 (2H, m), 5.51 (2H, brs), 4.12 (2H, q, J=7.1 Hz), 1.64 (2H, dd, J=6.9, 3.9 Hz), 1.24 (9H, s), 1.23-1.16 (5H, m).

Reference Example 20

2-{4'-[1-(Ethoxycarbonyl)cyclopropyl]-2-methoxy-[1,1'-biphenyl]-4-yl}thiophene-3-carboxylic acid tert-butyl ester

[Chemical Formula 283]

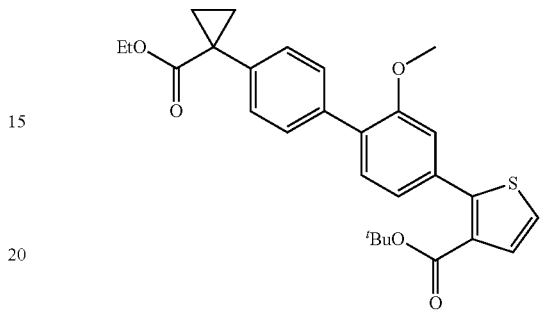

To 3.81 g (9.02 mmol) of ethyl 1-[2'-methoxy-4'-(4,4,5,5-tetramethyl-1,3,2-dioxaborolane-2-yl)-[1,1'-biphenyl]-4-yl]-cyclopropanecarboxylic acid ethyl ester synthesized in analogy to Reference Example 12 and 2.7 g (7.3 mmol (purity 71% by weight)) of 2-bromothiophene-3-carboxylic acid tert-butyl ester synthesized in Reference Example 3 in 1,4-dioxane (23 ml)-water (23 ml) was added 2.96 g (27.9 mmol) of sodium carbonate, and the mixture was degassed. Then, 540 mg (0.467 mmol) of tetrakis(triphenylphosphine)palladium(0) was added, and the mixture was heated and stirred at 90° C. for 7 hours. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. To the resulting residue was added ethyl acetate, the resulting insoluble matter was removed by filtration, and washed with a mixed solution of hexane-ethyl acetate (1:2 (V/V)). Subsequently, the mother liquid and the washings were combined, and concentrated under reduced pressure. Then, the mixture was dissolved in ethyl acetate, hexane was added until the solution became cloudy, and the precipitated solid was filtered and washed with hexane to obtain 3.09 g (5.55 mmol (purity 86% by weight), yield 61%) of the title compound as a white solid.

Mass spectrum (EI, m/z): 478 [M]$^+$.

$^1$H-NMR spectrum (400 MHz, CDCl$_3$) δ: 7.53-7.48 (2H, m), 7.47 (1H, d, J=5.4 Hz), 7.41-7.36 (2H, m), 7.34 (1H, d, J=7.8 Hz), 7.23 (1H, d, J=5.4 Hz), 7.12 (1H, dd, J=7.7, 1.6 Hz), 7.07 (1H, d, J=1.6 Hz), 4.13 (2H, q, J=7.1 Hz), 3.83 (3H, s), 1.62 (2H, dd, J=6.8, 4.0 Hz), 1.40 (9H, s), 1.23 (2H, dd, J=6.8, 3.8 Hz), 1.20 (3H, t, J=7.1 Hz).

Reference Example 21

2-Bromo-5-chlorothiophene-3-carboxamide

[Chemical Formula 284]

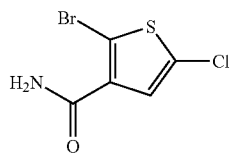

To a solution of 4.48 g (21.7 mmol) of 2-bromothiophene-3-carboxamide (synthesized according to WO 10/036497) in N,N-dimethylformamide (50 ml) was added 8.70 g (65.2 mmol) of N-chlorosuccinimide under an argon atmosphere while stirring, and the mixture was heated and stirred at 60° C. for 3 hours. After completion of the reaction, 50 ml of water and 100 ml of ethyl acetate were added under an ice bath, and subsequently 6.80 g (65.3 mmol) of sodium hydrogen sulfite was added while stirring. After the mixture was stirred at room temperature for 15 minutes, water was added to separate the layers. The organic layer was washed twice with 50 ml of a saturated aqueous sodium hydrogencarbonate solution and washed with saturated brine and subsequently dried over anhydrous magnesium sulfate, and the solvent was concentrated to about half of the volume under reduced pressure. To the resulting suspension was added hexane, the mixture was sonicated. Subsequently, the solid was collected by filtration, washed with hexane and dried to obtain 3.64 g (15.1 mmol, yield 70%) of the title compound as a white solid.

Mass spectrum (DUIS+, m/z): 240 [M+1]+.
$^1$H-NMR spectrum (400 MHz, DMSO-$d_6$) δ: 7.75 (1H, brs), 7.58 (1H, brs), 7.33 (1H, s).

The title compound was also synthesized as follows.

To a solution of 1.0 g (4.8 mmol) of 2-bromothiophene-3-carboxylic acid (Aldrich) in N,N-dimethylformamide (16 ml) was added 0.90 g (6.7 mmol) of N-chlorosuccinimide under a nitrogen atmosphere at room temperature while stirring, and the mixture was heated and stirred at 80° C. for one hour. After completion of the reaction, the reaction mixture was allowed to cool, water was added, acidified by adding 2N hydrochloric acid thereto, and the mixture was extracted with ethyl acetate. The organic layer was washed sequentially with an aqueous sodium hydrogen sulfite solution and saturated brine, dried over anhydrous magnesium sulfate, and concentrated under reduced pressure. To a solution of the resulting residue in methylene chloride (15 ml) was added dropwise 0.80 ml (9.1 mmol) of oxalyl chloride under a nitrogen atmosphere at 0° C. while stirring, the temperature was raised to room temperature, and the mixture was stirred for 30 minutes. Then, 3.7 mL (48 mmol) of 28% by weight aqueous ammonia was added dropwise at room temperature while stirring, and the mixture was stirred at room temperature for one hour. After completion of the reaction, to the reaction mixture was added water, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=69:31 to 48:52 (V/V)), and the fractions containing the desired compound were concentrated under reduced pressure to obtain 0.62 g (2.6 mmol, yield 53%) of the title compound as a white solid.

Reference Example 22

5-Bromo-2-{4'-[1-(ethoxycarbonyl)cyclopropyl]-[1,1'-biphenyl]-4-yl}thiophene-3-carboxylic acid benzyl ester

[Chemical Formula 285]

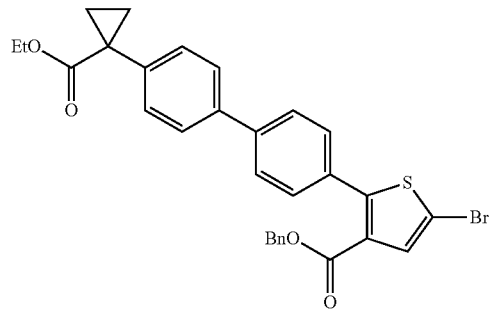

To a solution of 1.01 g (2.09 mmol) of 2-{4'-[1-(ethoxycarbonyl)cyclopropyl]-[1,1'-biphenyl]-4-yl}thiophene-3-carboxylic acid benzyl ester synthesized in analogy to Reference Example 15 in N,N-dimethylformamide (10 ml) was added 613 mg (3.44 mmol) of N-bromosuccinimide under an argon atmosphere at 80° C. while heating and stirring, and the mixture was heated and stirred at the same temperature for 2 hours. After completion of the reaction, the reaction mixture was allowed to cool, poured into water, and extracted with toluene twice. The organic layers were combined, washed sequentially with a saturated aqueous sodium hydrogencarbonate solution and a saturated aqueous ammonium chloride solution, dried over anhydrous magnesium sulfate, and concentrated under reduced pressure. To the resulting residue were added toluene and hexane sequentially, and the mixture was ultrasonically washed. The precipitate was collected by filtration and dried under reduced pressure to obtain 1.04 g (1.86 mmol, yield 89%) of the title compound as a white solid.

Mass spectrum (CI, m/z): 561 [M+1]+.
$^1$H-NMR spectrum (400 MHz, DMSO-$d_6$) δ: 7.70-7.62 (4H, m), 7.61 (1H, s), 7.57-7.53 (2H, m), 7.47-7.43 (2H, m), 7.33-7.22 (5H, m), 5.19 (2H, s), 4.05 (2H, q, J=7.1 Hz), 1.52 dd, J=7.0, 4.0 Hz), 1.25 (2H, dd, J=7.0, 4.0 Hz), 1.12 (3H, t, J=7.1 Hz).

Reference Example 23

5-Chloro-2-{4'-[1-(ethoxycarbonyl)cyclopropyl]-[1,1'-biphenyl]-4-yl}thiophene-3-carboxylic acid benzyl ester

[Chemical Formula 286]

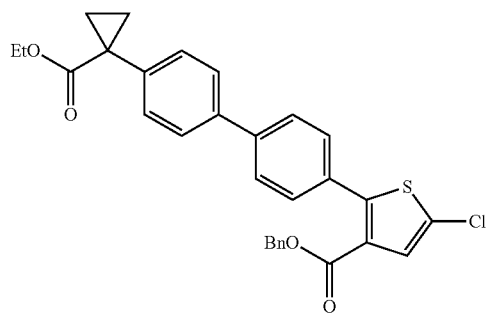

To a solution of 160 mg (0.33 mmol) of 2-{4'-[1-(ethoxycarbonyl)cyclopropyl]-[1,1'-biphenyl]-4-yl}thiophene-3-carboxylic acid benzyl ester synthesized in analogy to Reference Example 15 in N,N-dimethylformamide (2 ml) was added 100 mg (0.76 mmol) of N-chlorosuccinimide under an argon atmosphere at 80° C. while heating and stirring, and the mixture was heated and stirred at the same temperature for 2 hours. After completion of the reaction, the reaction mixture was allowed to cool, poured into water, and extracted with toluene twice. The organic layers were combined, washed sequentially with a saturated aqueous sodium hydrogencarbonate solution and a saturated aqueous ammonium chloride solution, dried over anhydrous magnesium sulfate, and subsequently concentrated under reduced pressure. The resulting residue was subjected to silica gel column chromatography (elution solvent; hexane:ethyl acetate=91:9 to 64:36 (V/V)), and the fractions containing the desired compound were concentrated under reduced pressure to obtain 150 mg (0.29 mmol, yield 87%) of the title compound as a white solid.

Mass spectrum (CI, m/z): 517 [M+1]$^+$.

$^1$H-NMR spectrum (400 MHz, DMSO-$d_6$) δ: 7.70-7.66 (2H, m), 7.66-7.61 (2H, m), 7.58-7.53 (2H, m), 7.52 (1H, s), 7.47-7.43 (2H, m), 7.33-7.22 (5H, m), 5.19 (2H, s), 4.05 (2H, q, J=7.1 Hz), 1.52 (2H, dd, J=7.0, 4.0 Hz), 1.25 (2H, dd, J=7.0, 4.0 Hz), 1.12 (3H, t, J=7.1 Hz).

Reference Example 24

1-[4'-(3-Carbamoyl-5-chlorothiophen-2-yl)-[1,1'-biphenyl]-4-yl]cyclopropanecarboxylic acid ethyl ester

[Chemical Formula 287]

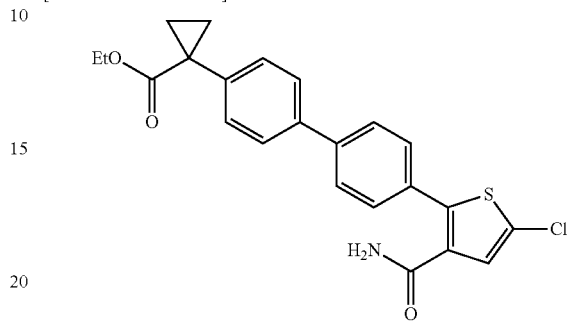

To a solution of 2.8 g (7.3 mmol) of 1-[4'-(3-carbamoyl-thiophen-2-yl)-[1,1'-biphenyl]-4-yl]cyclopropanecarboxylic acid ethyl ester synthesized in analogy to Reference Example 16 in 30 ml of N,N-dimethylformamide was added 1.2 g (9.0 mmol) of N-chlorosuccinimide under a nitrogen atmosphere at room temperature while stirring, and the mixture was stirred at room temperature for 14 hours and then heated and stirred at 80° C. for one hour. After completion of the reaction, to the reaction mixture was added water, and the mixture was extracted with toluene. The organic layer was washed sequentially with a 10% by weight aqueous sodium hydrogen sulfite solution and saturated brine, dried over anhydrous magnesium sulfate, and concentrated under reduced pressure. To the residue was added ethyl acetate, and the solid was collected by filtration to obtain 2.4 g (5.6 mmol, yield 77%) of the title compound as a white solid.

Mass spectrum (EI, m/z): 425 [M]$^+$.

$^1$H-NMR spectrum (400 MHz, CDCl$_3$) δ: 7.69-7.65 (2H, m), 7.58-7.53 (4H, m), 7.46-7.42 (2H, m), 7.33 (1H, s), 5.44 (2H, brs), 4.12 (2H, q, J=7.1 Hz), 1.65 (2H, dd, J=7.0, 4.0 Hz), 1.23 (2H, dd, J=7.0, 4.0 Hz), 1.19 (3H, t, J=7.1 Hz).

The title compound was also synthesized as follows.

A solution of 485.6 mg (2.02 mmol) of 2-bromo-5-chlorothiophene-3-carboxamide synthesized in analogy to Reference Example 21, 876.5 mg (2.234 mmol) of 1-[4-(4,4,5,5-tetramethyl-1,3,2-dioxaboran-2-yl)-[1,1'-biphenyl]-4-yl]cyclopropanecarboxylic acid ethyl ester (synthesized according to a process described in WO 12/078593) and 657.7 mg (6.21 mmol) of sodium carbonate in 1,4-dioxane (15 ml)-water (5 ml) was frozen and degassed in a dry ice-acetone bath to replace the atmosphere with argon. Further, 230 mg (0.199 mmol) of tetrakis(triphenylphosphine)palladium(0) was added, and the mixture was heated and stirred at 90° C. for 3 hours. After completion of the reaction, the reaction mixture was cooled, and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=64:36 to 43:57 (V/V)), and the fractions containing the desired compound were concentrated under reduced pressure. To the resulting residue was added a solution of hexane-ethyl acetate (2:1 (V/V)), and the precipitated solid was collected by filtration and dried under reduced pressure to obtain 705.0 mg (1.655 mmol, yield 82%) of the title compound as a white solid.

Reference Example 25

1-[4'-(3-Carbamoyl-5-chlorothiophen-2-yl)-2'-nitro-[1,1'-biphenyl]-4-yl]cyclopro-pylcarboxylic acid ethyl ester

[Chemical Formula 288]

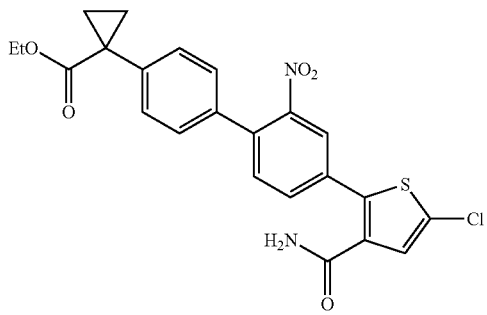

To a solution of 195 mg (0.447 mmol) of 1-[4'-(3-carbamoylthiophen-2-yl)-2'-nitro-[1,1'-biphenyl]-4-yl]cyclopropanecarboxylic acid ethyl ester synthesized in analogy to Reference Example 18 in N,N-dimethylformamide (2 ml) was added 56.0 mg (0.419 mmol) of N-chlorosuccinimide under an argon atmosphere at 80° C. while heating and stirring, and the mixture was heated and stirred at the same temperature for one hour. Additionally, 29.4 mg (0.220 mmol) of N-chlorosuccinimide was added, and the mixture was heated and stirred for one hour and 20 minutes. After completion of the reaction, the reaction mixture was allowed to cool, poured into water and extracted with tert-butyl methyl ether. The organic layer was washed sequentially with a saturated aqueous sodium carbonate solution, a saturated aqueous sodium hydrogen sulfite solution and saturated brine, dried over anhydrous magnesium sulfate, and concentrated under reduced pressure. The resulting residue was subjected to silica gel column chromatography (elution solvent; hexane:ethyl acetate=65:35 to 44:56 (V/V)), and the fractions containing the desired compound were concentrated under reduced pressure to obtain 166 mg (0.352 mmol, yield 79%) of the title compound as a yellow foam.

Mass spectrum (CI, m/z): 470 [M]$^+$.

$^1$H-NMR spectrum (400 MHz, CD$_2$Cl$_2$) δ: 7.98 (1H, d, J=1.8 Hz), 7.77 (1H, dd, J=8.0, 1.9 Hz), 7.54 (1H, d, J=8.0 Hz), 7.46-7.41 (2H, m), 7.32-7.28 (2H, m), 7.23 (1H, s), 5.58 (2H, brs), 4.09 (2H, q, J=7.1 Hz), 1.62 (2H, dd, J=7.0, 4.0 Hz), 1.23 (2H, dd, J=7.1, 4.1 Hz), 1.18 (3H, t, J=7.1 Hz).

Reference Example 26

4-(3-Carbamoyl-5-chlorothiophen-2-yl)-4'-[1-(ethoxycarbonyl)cyclopropyl]-[1,1'-biphenyl]-2-carboxylic acid tert-butyl ester

[Chemical Formula 289]

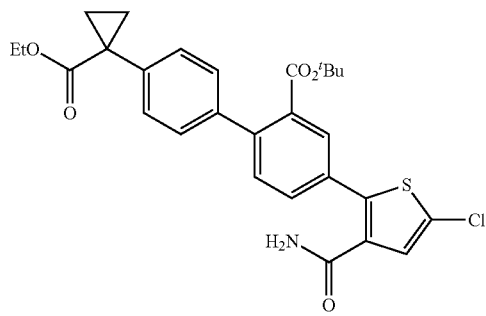

To a solution of 0.88 g (1.8 mmol) of 4-(3-carbamoylthiophen-2-yl)-4'-[1-(ethoxycarbonyl)cyclopropyl]-[1,1'-biphenyl]-2-carboxylic acid tert-butyl ester synthesized in analogy to Reference Example 19 in N,N-dimethylformamide (10 ml) was added 160 mg (1.20 mmol) of N-chlorosuccinimide under an argon atmosphere at 80° C. while heating and stirring, and the mixture was heated and stirred at the same temperature for 40 minutes. Additionally, 142 mg (1.06 mmol) of N-chlorosuccinimide was added, and the mixture was heated and stirred at the same temperature for 30 minutes. After completion of the reaction, the reaction mixture was allowed to cool, poured into water and extracted with tert-butyl methyl ether. The organic layer was washed sequentially with a saturated aqueous sodium carbonate solution and saturated brine, dried over anhydrous magnesium sulfate, and concentrated under reduced pressure. The resulting residue was subjected to silica gel column chromatography (elution solvent; hexane:ethyl acetate=75:25 to 37:63 (V/V)), and the fractions containing the desired compound were concentrated under reduced pressure to obtain 0.66 g (1.3 mmol, yield 70%) of the title compound as a yellow foam.

Mass spectrum (CI, m/z): 525 [M]$^+$.

$^1$H-NMR spectrum (400 MHz, DMSO-d$_6$, 75° C.) δ: 7.77 (1H, d, J=1.8 Hz), 7.65 (I H, dd, J=8.0, 2.0 Hz), 7.41-7.22 (8H, m), 4.06 (2H, q, J=7.1 Hz), 1.52 (2H, dd, J=7.0, 4.0 Hz), 1.22 (9H, s), 1.19 (2H, dd, J=7.0, 4.1 Hz), 1.12 (3H, t, J=7.1 Hz).

Reference Example 27

2-{4'-[1-(Ethoxycarbonyl)cyclopropyl]-[1,1'-biphenyl]-4-yl}-5-fluorothiophene-3-carboxylic acid tert-butyl ester

[Chemical Formula 290]

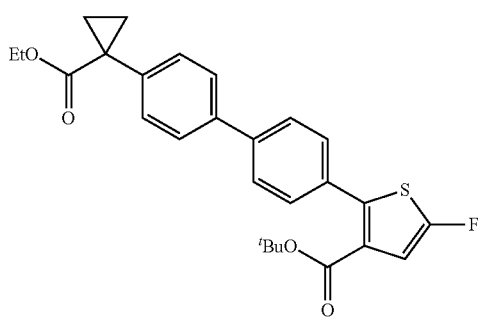

To a solution of 4.50 g (10.0 mmol) of 2-{4'-[1-(ethoxycarbonyl)cyclopropyl]-[1,1'-biphenyl]-4-yl}thiophene-3-carboxylic acid tert-butyl ester synthesized in analogy to Reference Example 17 in dehydration tetrahydrofuran (60 ml) was added dropwise 11 ml (12.0 mmol) of a 1.09M lithium diisopropylamide tetrahydrofuran-hexane solution (Kanto Chemical Co., Inc.) under an argon atmosphere over 5 minutes while cooling to −70° C. or lower in a dry ice-acetone bath, and the mixture was stirred at the same temperature for 30 minutes. Then, while cooling to −65° C. or lower, a solution of 4.75 g (15.1 mmol) of N-fluorodibenzenesulfonamide in tetrahydrofuran (15 ml) was added dropwise over 5 minutes, and the mixture was stirred at the same temperature for 30 minutes. Then, the temperature was gradually raised, 40 ml of a saturated aqueous ammonium chloride solution was added at −45° C. to stop the reaction, the temperature was raised to room temperature, and the mixture was extracted with ethyl acetate. The extracts were dried over anhydrous magnesium sulfate and concentrated under reduced pressure. To the resulting residue was added methylene chloride, and insoluble matter was filtered. Subsequently, the residue obtained by concentration under reduced pressure was subjected to silica gel column chromatography (elution solvent; hexane:ethyl acetate=100:0 to 79:21 (V/V)), and the fractions containing the desired compound were concentrated under reduced pressure to obtain 2.23 g (4.78 mmol, yield 48%) of the title compound as a white solid.

Mass spectrum (CI, m/z): 467 [M+1]$^+$.

$^1$H-NMR spectrum (400 MHz, DMSO-d$_6$) δ: 7.78-7.72 (2H, m), 7.68-7.63 (2H, m), 7.56-7.50 (2H, m), 7.46-7.41 (2H, m), 7.03 (1H, d, J=2.4 Hz), 4.05 (2H, q, J=7.1 Hz), 1.52 (2H, dd, J=6.9, 3.9 Hz), 1.31 (9H, s), 1.24 (2H, dd, J=7.1, 4.1 Hz), 1.12 (3H, t, J=7.1 Hz).

Reference Example 28

2-{4'-[1-(Ethoxycarbonyl)cyclopropyl]-2-methoxy-[1,1'-biphenyl]-4-yl}-5-fluorothiophene-3-carboxylic acid tert-butyl ester

[Chemical Formula 291]

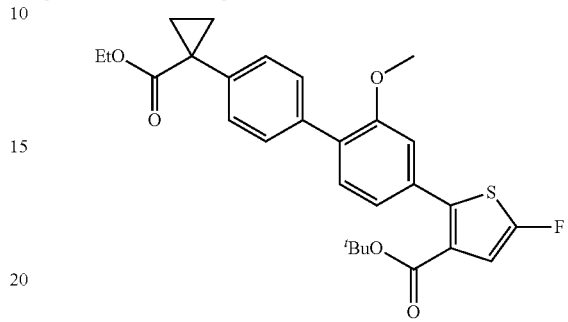

To a solution of 2.88 g (5.17 mmol (purity 86% by weight)) of 2-{4'-[1-(ethoxycarbonyl)cyclopropyl]-2-methoxy-[1,1'-biphenyl]-4-yl}thiophene-3-carboxylic acid tert-butyl ester synthesized in Reference Example 20 in tetrahydrofuran (37 ml) was added dropwise 6.56 ml (7.22 mmol) of a 1.1M lithium diisopropylamide/tetrahydrofuran solution under an argon atmosphere at −78° C. while stirring, and the mixture was stirred at the same temperature for 30 minutes. Then, a solution of 2.85 g (9.04 mmol) of N-fluorobenzenesulfonimide in tetrahydrofuran (9.5 ml) was added dropwise, and the mixture was stirred at the same temperature for 30 minutes. After completion of the reaction, to the reaction mixture were added a saturated aqueous ammonium chloride solution and ethyl acetate to separate the organic layer. The organic layer was washed with saturated brine, subsequently dried over anhydrous magnesium sulfate, and concentrated under reduced pressure. The resulting residue was subjected to silica gel column chromatography (elution solvent; hexane:dichloroethane=100:0 to 30:70 (V/V)), and the fractions containing the desired compound were concentrated under reduced pressure. The resulting residue was dissolved by adding hexane and warming, and then the mixture was sonicated. The precipitated solid was collected by filtration and washed with hexane to obtain 496 mg (1.00 mmol, yield 20%) of the title compound as a white solid.

Mass spectrum (DUIS$^+$, m/z): 497 [M+1]$^+$.

$^1$H-NMR spectrum (400 MHz, CDCl$_3$) δ: 7.52-7.46 (2H, m), 7.41-7.36 (2H, m), 7.33 (1H, d, J=7.8 Hz), 7.08 (1H, dd, J=7.8, 1.6 Hz), 7.03 (1H, d, J=1.5 Hz), 6.84 (1H, d, J=2.3 Hz), 4.13 (2H, q, J=7.1 Hz), 3.82 (3H, s), 1.62 (2H, dd, J=6.9, 3.9 Hz), 1.37 (9H, s), 1.23 (2H, dd, J=6.5, 3.5 Hz), 1.20 (3H, t, J=7.2 Hz).

Reference Example 29

1-{4-[5-(3-Carbamoyl-5-chlorothiophen-2-yl)pyridine-2-yl]phenyl}cyclopropanecarboxylic acid ethyl ester

[Chemical Formula 292]

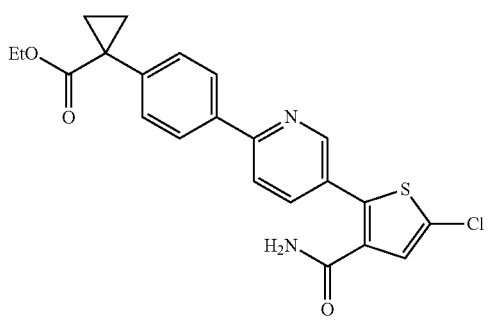

A solution of 481.9 mg (2.004 mmol) of 2-bromo-5-chlorothiophene-3-carboxamide synthesized in analogy to Reference Example 21, 866.6 mg (2.203 mmol) of 1-{4-[5-(4,4,5,5-tetramethyl-1,3,2-dioxaborolane-2-yl)pyridine-2-yl]phenyl}cyclopropanecarboxylic acid ethyl ester synthesized in analogy to Reference Example 11 and 656 mg (6.19 mmol) of sodium carbonate in 1,4-dioxane (15 ml)-water (5 ml) was frozen and degassed in a dry ice-acetone bath to replace the atmosphere with argon. Then, 230 mg (0.199 mmol) of tetrakis(triphenylphosphine)palladium(0) was added, and the mixture was heated and stirred at 90° C. for 6 hours. After completion of the reaction, the reaction mixture was cooled, and ethyl acetate and water were added to separate the layers. The organic layer was dried over anhydrous magnesium sulfate and concentrated under reduced pressure. The resulting residue was subjected to silica gel column chromatography (elution solvent; hexane:ethyl acetate=65:35 to 0:100 (V/V)), the fractions containing the desired compound were concentrated under reduced pressure, and the resulting solid was washed with a mixed solution of hexane-ethyl acetate (2:1 (V/V)) and dried under reduced pressure to obtain 633.8 mg (1.485 mmol, yield 74%) of the title compound as a pale yellow solid.

Mass spectrum (EI, m/z): 426 [M]$^+$.

$^1$H-NMR spectrum (400 MHz, DMSO-$d_6$) δ: 8.73 (1H, dd, J=2.3, 0.8 Hz), 8.09-8.04 (2H, m), 8.02 (1H, dd, J=8.4, 0.8 Hz), 7.95 (1H, dd, J=8.3, 2.3 Hz), 7.82 (1H, brs), 7.51 (1H, brs), 7.48-7.45 (2H, m), 7.44 (1H, s), 4.05 (2H, q, J=7.0 Hz), 1.52 (2H, dd, J=6.9, 4.0 Hz), 1.26 (2H, dd, J=7.1, 4.1 Hz), 1.11 (3H, t, J=7.1 Hz).

Reference Example 30

1-[4'-(3-Carbamoyl-5-chlorothiophen-2-yl)-2'-methoxy-[1,1'-biphenyl]-4-yl]cyclopropanecarboxylic acid ethyl ester

[Chemical Formula 293]

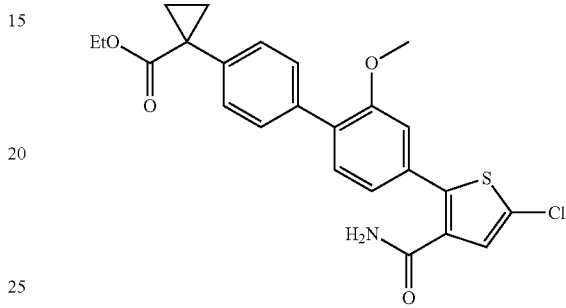

A solution of 2.0 g (4.7 mmol) of 1-[2'-methoxy-4'-(4,4,5,5-tetramethyl-1,3,2-dioxaborolane-2-yl)-[1,1'-biphenyl]-4-yl]-cyclopropanecarboxylic acid ethyl ester synthesized in analogy to Reference Example 12, 1.25 g (5.2 mmol) of 2-bromo-5-chlorothiophene-3-carboxamide synthesized in analogy to Reference Example 21 and 1.5 g (14 mmol) of sodium carbonate in 1,4-dioxane (30 ml)-water (10 ml) was degassed, then 0.30 g (0.26 mmol) of tetrakis(triphenylphosphine)palladium(0) was added, and the mixture was heated and stirred under a nitrogen atmosphere at 90° C. for 4.5 hours. After completion of the reaction, the reaction mixture was allowed to cool, water was added, and the mixture was extracted with ethyl acetate. The organic layer was washed with saturated brine, subsequently dried over anhydrous magnesium sulfate, and concentrated under reduced pressure. To the resulting residue was added ethyl acetate, and the solid was collected by filtration and washed with a small amount of ethyl acetate to obtain 1.53 g (3.4 mmol, yield 71%) of the title compound as a white solid.

Mass spectrum (EI, m/z): 455 [M]$^+$.

$^1$H-NMR spectrum (400 MHz, DMSO-$d_6$) δ: 7.73 (1H, brs), 7.50 (1H, brs), 7.48-7.43 (2H, m), 7.39-7.33 (31-1, m), 7.32 (1H, s), 7.25 (1H, d, J=1.6 Hz), 7.13 (1H, dd, J=7.8, 1.6 Hz), 4.05 (2H, q, J=7.1 Hz), 3.79 (3H, s), 1.51 (2H, dd, J=6.8, 4.0 Hz), 1.23 (2H, dd, J=7.0, 4.0 Hz), 1.12 (3H, t, J=7.1 Hz).

Reference Example 31

5-Bromo-2-{4'-[1-(ethoxycarbonyl)cyclopropyl]-[1,1'-biphenyl]-4-yl}thiophene-3-carboxylic acid

[Chemical Formula 294]

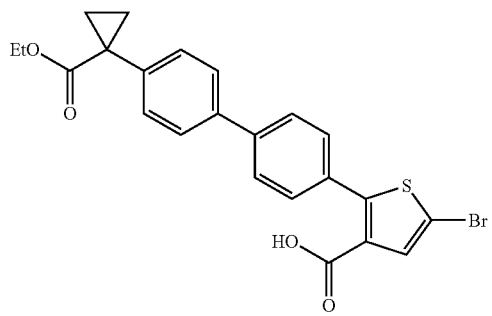

To a solution of 29.5 mg (0.053 mmol) of 5-bromo-2-{4'-[1-(ethoxycarbonyl)cyclopropyl]-[1,1'-biphenyl]-4-yl}thiophene-3-carboxylic acid benzyl ester synthesized in analogy to Reference Example 22 in 20 ml of methylene chloride was added dropwise 0.0060 ml (0.060 mmol) of a 1M boron tribromide/methylene chloride solution under an argon atmosphere with cooling by a dry ice-acetone bath. After dropwise addition, the acetone bath was removed. While the temperature was gradually raised to room temperature, the mixture was stirred for 2 hours. Then, cooling was carried out again by a dry ice-acetone bath, 0.025 ml (0.25 mmol) of a 1M boron tribromide/methylene chloride solution was added dropwise, and the reaction mixture was stored in the refrigerator (4° C.) for 2 days. Then, cooling was carried out under an argon atmosphere by an ice water bath, 0.025 ml (0.25 mmol) of a boron tribromide/methylene chloride solution was added dropwise, and the ice water bath was removed. While the temperature was gradually raised, the mixture was stirred for 15 minutes. The reaction mixture was poured into water and extracted with methylene chloride. The organic layer was dried over anhydrous magnesium sulfate and concentrated under reduced pressure. The resulting residue was subjected to silica gel column chromatography (developing solvent; hexane:ethyl acetate=67:33 to 0:100 (V/V)), and the fractions containing the desired compound were concentrated under reduced pressure. The resulting residue was subjected to silica gel column chromatography again (developing solvent; ethyl acetate:methanol=100:0 to 50:50 (V/V)), and the fractions containing the desired compound were concentrated under reduced pressure to obtain 0.018 g (0.038 mmol, yield 73%) of the title compound as a white solid.

Mass spectrum (ESI+, m/z): 471 [M+1]$^+$.

$^1$H-NMR spectrum (400 MHz, DMSO-d$_6$) δ: 12.29 (1H, brs), 7.75-7.69 (2H, m), 7.68-7.63 (2H, m), 7.61-7.55 (2H, m), 7.50 (1H, s), 7.46-7.41 (2H, m), 4.05 (2H, q, J=7.1 Hz), 1.51 (2H, dd, J=6.9, 4.0 Hz), 1.24 (2H, dd, J=7.0, 4.0 Hz), 1.11 (3H, t, J=7.1 Hz).

Reference Example 32

5-Chloro-2-{4'-[1-(ethoxycarbonyl)cyclopropyl]-[1,1'-biphenyl]-4-yl}thiophene-3-carboxylic acid

[Chemical Formula 295]

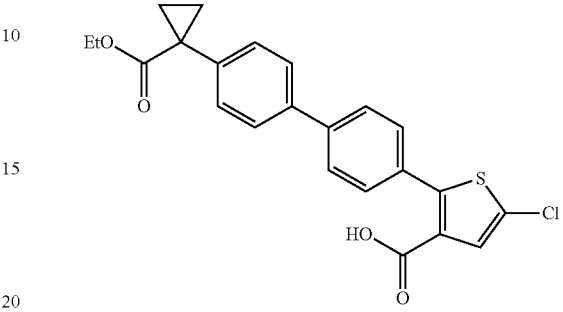

A solution of 145 mg (0.28 mmol) of 5-chloro-2-{4'-[1-(ethoxycarbonyl)cyclopropyl]-[1,1'-biphenyl]-4-yl}thiophene-3-carboxylic acid benzyl ester synthesized in analogy to Reference Example 23 in methylene chloride (1 ml) was cooled under an argon atmosphere by a dry ice-acetone bath, 0.38 ml (0.38 mmol) of a 1M boron tribromide/methylene chloride solution was added dropwise, and the mixture was stirred for one hour. Subsequently, the bath was changed to an ice water bath, and the mixture was stirred for 1.5 hours. After completion of the reaction, the reaction mixture was poured into ice water, and extracted with methylene chloride. The organic layer was dried over anhydrous magnesium sulfate and concentrated under reduced pressure. To the resulting residue was added hexane, and the solid was collected by filtration and dried under reduced pressure to obtain 0.072 g (0.28 mmol, yield 60%) of the title compound as a white solid.

Mass spectrum (CI, m/z): 427 [M+1]$^+$.

$^1$H-NMR spectrum (400 MHz, DMSO-d$_6$) δ: 12.97 (1H, brs), 7.75-7.70 (2H, m), 7.68-7.64 (2H, m), 7.60-7.56 (2H, m), 7.46-7.41 (3H, m), 4.05 (2H, q, J=7.1 Hz), 1.52 (2H, dd, J=6.9, 3.9 Hz), 1.24 (2H, dd, J=7.1, 4.1 Hz), 1.11 (3H-1, t, J=7.1 Hz).

Reference Example 33

2-{4'-[1-(Ethoxycarbonyl)cyclopropyl]-[1,1'-biphenyl]-4-yl}-5-fluorothiophene-3-carboxylic acid

[Chemical Formula 296]

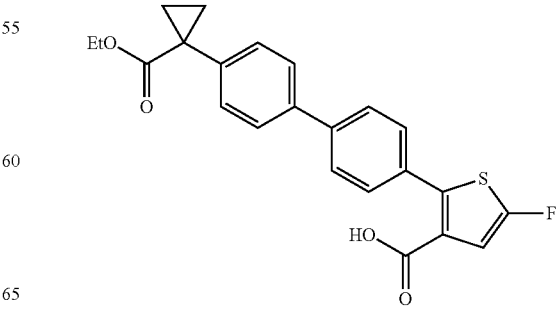

To a solution of 2.18 g (4.67 mmol) of 2-{4'-[1-(ethoxycarbonyl)cyclopropyl]-[1,1'-biphenyl]-4-yl}-5-fluorothiophene-3-carboxylic acid tert-butyl ester synthesized in analogy to Reference Example 27 in 20 ml of methylene chloride was added 5.0 ml (65 mmol) of trifluoroacetic acid while stirring under ice cooling under an argon atmosphere. After the mixture was stirred at the same temperature for one hour, it was further stirred at room temperature for 2 hours. After completion of the reaction, the mixture was concentrated under reduced pressure, and subsequently the residue was washed sequentially with diethyl ether and hexane to obtain 1.87 g (4.56 mmol, yield 98%) of the title compound as a white solid.

Mass spectrum (CI, m/z): 411 [M+1]$^+$.

$^1$H-NMR spectrum (400 MHz, DMSO-$d_6$) δ: 12.92 (1H, s), 7.74-7.70 (2H, m), 7.68-7.64 (2H, m), 7.60-7.55 (2H, m), 7.46-7.41 (2H, m), 7.05 (1H, d, J=2.4 Hz), 4.05 (2H, q, J=7.1 Hz), 1.52 (2H, dd, J=6.9, 3.9 Hz), 1.24 (2H, dd, J=7.0, 4.1 Hz), 1.11 (3H, t, J=7.1 Hz).

Reference Example 34

2-{4'-[1-(Ethoxycarbonyl)cyclopropyl]-2-methoxy-[1,1'-biphenyl]-4-yl}-5-fluorothiophene-3-carboxylic acid

[Chemical Formula 297]

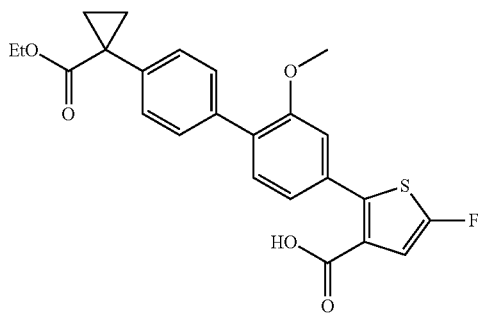

To a solution of 491 mg (0.989 mmol) of 2-{4'-[1-(ethoxycarbonyl)cyclopropyl]-2-methoxy-[1,1'-biphenyl]-4-yl}-5-fluorothiophene-3-carboxylic acid tert-butyl ester synthesized in analogy to Reference Example 28 in methylene chloride (4.4 ml) was added 1.1 ml (14 mmol) of trifluoroacetic acid under an argon atmosphere at room temperature, and the mixture was stirred at room temperature for 3 hours. After completion of the reaction, the reaction mixture was concentrated under reduced pressure, methylene chloride was added, and the mixture was concentrated under reduced pressure. Subsequently, hexane was added, and the mixture was concentrated under reduced pressure to obtain 436 mg (0.99 mmol, yield: quantitative) of the title compound as a white solid.

Mass spectrum (EI, m/z): 440 [M]$^+$.

$^1$H-NMR spectrum (400 MHz, CDCl$_3$) δ: 7.53-7.48 (2H, m), 7.40-7.37 (2H, m), 7.34 (1H, d, J=7.8 Hz), 7.14 (1H, d, =1.6 Hz), 7.13-7.10 (1H, m), 6.94 (1H, d, J=2.3 Hz), 4.12 (2H, q, J=7.1 Hz), 3.82 (3H, s), 1.62 (2H, dd, J=6.9, 3.9 Hz), 1.23 (2H, dd, J=7.0, 4.0 Hz), 1.20 (3H, t, J=7.1 Hz).

Reference Example 35

4-(3-Carbamoyl-5-chlorothiophen-2-yl)-4'-[1-(ethoxycarbonyl)cyclopropyl]-[1,1'-biphenyl]-2-carboxylic acid

[Chemical Formula 298]

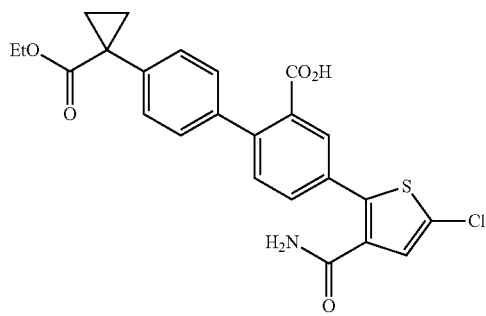

To a solution of 180 mg (0.342 mmol) of 4-(3-carbamoyl-5-chlorothiophen-2-yl)-4'-[1-(ethoxycarbonyl)cyclopropyl]-[1,1'-biphenyl]-2-carboxylic acid tert-butyl ester synthesized in analogy to Reference Example 26 in methylene chloride (4 ml) was added 0.5 ml (6.5 mmol) of trifluoroacetic acid, and the mixture was stirred at room temperature for 3.25 hours. Additionally, 0.5 ml (6.5 mmol) of trifluoroacetic acid was added, and the mixture was stirred at room temperature for 2.25 hours. After completion of the reaction, the reaction mixture was concentrated under reduced pressure, hexane was added, and the resulting solid was collected by filtration, washed with hexane and subsequently dried under reduced pressure to obtain 155 mg (0.330 mmol, yield 96%) of the title compound as a white solid.

Mass spectrum (CI, m/z): 469 [M]$^+$.

1H-NMR spectrum (400 MHz, DMSO-$d_6$, 75° C.) δ: 7.80 (1H, d, J=1.8 Hz), 7.65 (1H, dd, J=8.0, 2.1 Hz), 7.41 (1H, d, J=8.0 Hz), 7.38-7.28 (5H, m), 4.06 (2H, q, J=7.1 Hz), 1.52 (2H, dd, J=7.0, 4.0 Hz), 1.21 (2H, dd, J=7.0, 4.0 Hz), 1.13 (3H, t, J=7.0 Hz).

Reference Example 36

1-{2'-[(tert-Butoxycarbonyl)amino]-4'-(3-carbamoyl-5-chlorothiophen-2-yl)-[1,1'-biphenyl]-4-yl}cyclopropanecarboxylic acid ethyl ester

[Chemical Formula 299]

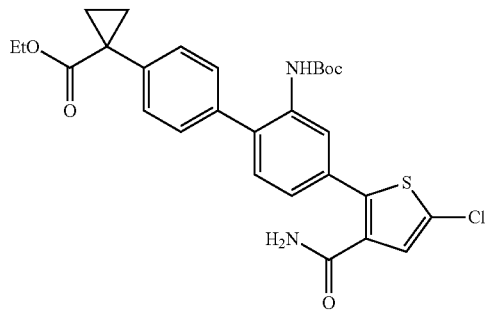

150 mg (0.319 mmol) of 4-(3-carbamoyl-5-chlorothiophen-2-yl)-4'-[1-(ethoxycarbonyl)cyclopropyl]-[1,1'-biphenyl]-2-carboxylic acid synthesized in analogy to Reference Example 35 was subjected to azeotropic dehydration treatment with toluene (2 ml), and the mixture was dried under reduced pressure. Subsequently, 2 ml of tert-butanol, 0.050 ml (0.36 mmol) of triethylamine and 0.090 ml (0.42 mmol) of diphenylphosphoryl azide were added under an argon atmosphere, and the mixture was heated and stirred at 80° C. for 3.5 hours. After completion of the reaction, the reaction mixture was allowed to cool and subjected to silica gel column chromatography (elution solvent; hexane:ethyl acetate=67:33 to 46:54 (V/V)), and the fractions containing the desired compound were concentrated under reduced pressure to obtain 113 mg (0.209 mmol, yield 65%) of the title compound as a white foam.

Mass spectrum (CI, m/z): 540 [M]$^+$.

1H-NMR spectrum (400 MHz, DMSO-d$_6$, 75° C.) δ: 7.99 (1H, brs), 7.58 (1H, d, J=1.9 Hz), 7.41-7.24 (9H, m), 4.06 (2H, q, J=7.1 Hz), 1.51 (2H, dd, J=6.9, 4.0 Hz), 1.29 (9H, s), 1.19 (2H, dd, J=7.1, 4.1 Hz), 1.13 (3H, t, J=7.1 Hz).

Reference Example 37

1-[4'-(3-Carbamoyl-5-chlorothiophen-2-yl)-[1,1'-biphenyl]-4-yl]cyclopropanecarboxylic acid

[Chemical Formula 300]

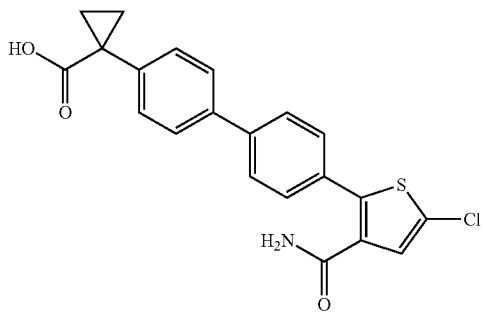

To a solution of 150 mg (0.35 mmol) of 1-(4'-(3-carbamoyl-5-chlorothiophen-2-yl)-[1,1'-biphenyl]-4-yl)cyclopropanecarboxylic acid ethyl ester synthesized in analogy to Reference Example 24 in ethanol (4 ml) was added 1.0 ml (4.0 mmol) of a 4N aqueous sodium hydroxide solution, and the mixture was heated and stirred at 50° C. for 2 hours. After completion of the reaction, the reaction mixture was allowed to cool and neutralized with 2N hydrochloric acid, and the solid was collected by filtration to obtain 140 mg (0.35 mmol, yield: quantitative) of the title compound as a white solid.

Mass spectrum (EI, m/z): 397 [M]$^+$.

$^1$H-NMR spectrum (400 MHz, DMSO-d$_6$) δ: 12.28 (1H, brs), 7.75 (1H, brs), 7.73-7.68 (2H, m), 7.65-7.60 (2H, m), 7.59-7.54 (2H, m), 7.47 (1H, brs), 7.45-7.40 (2H, m), 7.32 (1H, s), 1.48 (2H, dd, J=6.8, 3.9 Hz), 1.18 (2H, dd, J=6.8, 4.0 Hz).

Reference Example 38

4-Methylthiophene-3-carbaldehyde

[Chemical Formula 301]

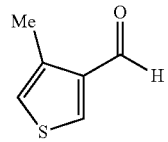

To a solution of 2.65 g (15.0 mmol) of 3-bromo-4-methylthiophene (Tokyo Chemical Industry Co., Ltd.) in diethyl ether (50 ml) was added dropwise 11 ml (18 mmol) of a 1.6M n-butyllithium/hexane solution under an argon atmosphere at −78° C., and the mixture was stirred at the same temperature for 30 minutes. Then, after the mixture was stirred at −30° C. to −20° C. for 30 minutes, 2.4 ml (31 mmol) of N,N-dimethylformamide was added dropwise at −30° C. to −20° C., and the mixture was stirred at room temperature for 16 hours. After completion of the reaction, to the reaction mixture was added a saturated aqueous ammonium chloride solution, and the mixture was extracted with diethyl ether. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=100:0 to 95:5 (V/V)), and the fractions containing the desired compound were concentrated under reduced pressure to obtain 270 mg (1.39 mmol (purity 65% by weight) of the title compound, yield 9%) as a pale yellow oil. Further, the unpurified fractions were concentrated under reduced pressure, the resulting residue was subjected to silica gel column chromatography (elution solvent; hexane:ethyl acetate=100:10 to 90:10 (V/V)), and the fractions containing the desired compound were concentrated under reduced pressure to obtain 675 mg (5.35 mmol, yield 36%) of the title compound as a pale yellow oil.

Mass spectrum (EI, m/z): 126 [M]$^+$.

$^1$H-NMR spectrum (400 MHz, CDCl$_3$) δ: 9.99 (1H, d, J=0.8 Hz), 8.06 (1H, d, J=3.3 Hz), 6.97-6.96 (1H, m), 2.49 (3H, d, J=1.0 Hz).

Reference Example 39

(RS)-1-(4-Methylthiophen-3-yl)ethanol

[Chemical Formula 302]

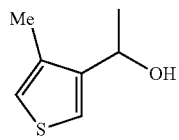

To a solution of 270 mg (1.39 mmol (purity 65% by weight)) of 4-methylthiophene-3-carbaldehyde synthesized in Reference Example 38 in tetrahydrofuran (5 ml) was added dropwise 2.4 ml (2.4 mmol) of a 0.99M methylmagnesium bromide/tetrahydrofuran solution under an argon atmosphere at 0° C., and the mixture was stirred at room temperature for 2 hours. After completion of the reaction, to the reaction mixture was added a saturated aqueous ammonium chloride solution, and the mixture was extracted with ethyl acetate. The similar reaction was carried out separately. To a solution of 672 mg (5.33 mmol) of 4-methylthiophene-3-carbaldehyde synthesized in Reference Example 38 in tetrahydrofuran (10 ml) was added dropwise 8.0 ml (7.9 mmol) of a 0.99M methylmagnesium bromide/tetrahydrofuran solution under an argon atmosphere at 0° C., and the mixture was stirred at room temperature for 2 hours. After completion of the reaction, to the reaction mixture was added a saturated aqueous ammonium chloride solution, and the mixture was extracted with ethyl acetate. The organic layers obatined from these two reactions were combined, washed sequentially with water and saturated brine, dried over anhydrous magnesium sulfate, and subsequently concentrated under reduced pressure. The resulting residue was subjected to silica gel column chromatography (elution solvent; hexane:ethyl acetate=90:10 to 70:30 (V/V)), and the fractions containing the desired compound were concentrated under reduced pressure to obtain 688 mg (4.84 mmol, yield 72%) of the title compound as a colorless oil.

Mass spectrum (EI, m/z): 142 [M]$^+$.

$^1$H-NMR spectrum (400 MHz, CDCl$_3$) δ: 7.22-7.20 (1H, m), 6.92 (1H, dq, J=3.3, 0.9 Hz), 4.92 (1H, qdd, J=6.4, 4.6, 0.9 Hz), 2.27 (3H, d, J=0.9 Hz), 1.67 (1H, d, J=4.6 Hz), 1.53 (3H, d, J=6.4 Hz).

Reference Example 40

(RS)-1-(4-Chlorothiophen-3-yl)ethanol

[Chemical Formula 303]

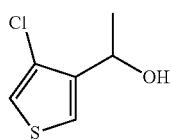

To a solution of 400 mg (2.73 mmol) of 4-chlorothiophene-3-carbaldehyde (Enamine Ltd) in tetrahydrofuran (5 ml) was added dropwise 3.0 ml (3.0 mmol) of a 0.99M methylmagnesium bromide/tetrahydrofuran solution under an argon atmosphere at 0° C., and the mixture was stirred at room temperature for 1.5 hours. After completion of the reaction, to the reaction mixture was added a saturated aqueous ammonium chloride solution, and the mixture was extracted with ethyl acetate. The organic layer was washed sequentially with water and saturated brine and dried over anhydrous magnesium sulfate. The organic layer was concentrated under reduced pressure, the resulting residue was subjected to silica gel column chromatography (elution solvent; hexane:ethyl acetate=90:10 to 70:30 (V/V)), and the fractions containing the desired compound were concentrated under reduced pressure to obtain 340 mg (2.09 mmol, yield 77%) of the title compound as a colorless oil.

Mass spectrum (EI, m/z): 162 [M]$^+$.

$^1$H-NMR spectrum (400 MHz, CDCl$_3$) δ: 7.30 (1H, dd, J=3.5, 0.8 Hz), 7.15 (1H, d, J=3.6 Hz), 5.00 (1H, qdd, J=6.5, 4.1, 0.8 Hz), 2.00 (1H, d, J=4.1 Hz), 1.54 (3H, d, J=6.5 Hz).

Reference Example 41

(RS)-1-(Isothiazol-4-yl)ethanol

[Chemical Formula 304]

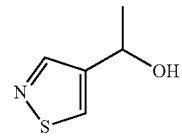

To a solution of 977 mg (8.64 mmol) of isothiazol-4-carbaldehyde in tetrahydrofuran (25 ml) was added dropwise 9.6 ml (9.5 mmol) of a 0.99M methylmagnesium bromide/tetrahydrofuran solution at −78° C. under an argon atmosphere while stirring. The temperature was raised to room temperature, and the mixture was stirred for 2.5 hours. After completion of the reaction, the reaction mixture was poured into a saturated aqueous ammonium chloride solution, to the mixed solution was added sodium chloride, and the mixture was extracted with ethyl acetate. The organic layer was dried over anhydrous magnesium sulfate and concentrated under reduced pressure. The resulting residue was subjected to silica gel column chromatography (elution solvent; hexane:ethyl acetate=63:37 to 37:63 (V/V)), and the fractions containing the desired compound were concentrated under reduced pressure to obtain 1.0 g (8.0 mmol, yield 93%) of the title compound as a pale yellow oil.

Mass spectrum (EI, m/z): 129 [M]$^+$.

$^1$H-NMR spectrum (400 MHz, DMSO-d$_6$) δ: 8.76 (1H, d, J=0.6 Hz), 8.53 (1H, s), 5.35 (1H, d, J=4.9 Hz), 4.94-4.86 (1H, m), 1.40 (3H, d, J=6.5 Hz).

Reference Example 42

1-(4-Methylthiophen-3-yl)ethanone

[Chemical Formula 305]

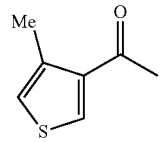

To a solution of 850 mg (5.98 mmol) of (RS)-1-(4-methylthiophen-3-yl)ethanol synthesized in analogy to Reference Example 39 in methylene chloride (30 ml) was added 2.53 g (11.7 mmol) of pyridinium chlorochromate under an argon atmosphere, and the mixture was stirred at room temperature for 2 hours. The reaction mixture was filtered using silica gel, and the filtrate was concentrated under reduced pressure. The resulting residue was subjected to silica gel column chromatography (elution solvent; hexane:ethyl acetate=100:0 to 80:20 (V/V)), and the fractions containing the desired compound were concentrated under reduced pressure to obtain 739 mg (5.27 mmol, yield 88%) of the title compound as a colorless oil.

Mass spectrum (CI, m/z): 141 [M+1]$^+$.

$^1$H-NMR spectrum (400 MHz, CDCl$_3$) δ: 7.99 (1H, d, J=3.1 Hz), 6.91 (1H, dq, J=3.1, 1.0 Hz), 2.53 (3H, s), 2.46 (3H, d, J=1.0 Hz).

The title compound was also synthesized as follows.

To a solution of 1.0 g (5.3 mmol) of 3-bromo-4-methylthiophen (Tokyo Chemical Industry Co., Ltd.) in diethyl ether (23 ml) was added dropwise 4.0 ml (6.4 mmol) of a 1.6M n-butyllithium hexane solution at −78° C. under an argon atmosphere, and the mixture was stirred at −78° C. for 15 minutes. Then, a solution of 0.70 ml (6.9 mmol) of N-methoxy-N-methyl acetamide in diethyl ether (1 ml) was added dropwise at −78° C., and the mixture was stirred at −78° C. for 15 minutes and then at room temperature for 23 hours. After completion of the reaction, to the reaction mixture was added a saturated aqueous ammonium chloride solution, and the mixture was extracted with ethyl acetate. The resulting organic layer was washed with water, subsequently dried over anhydrous magnesium sulfate, and concentrated under reduced pressure. The resulting residue was subjected to silica gel column chromatography (elution solvent; hexane:ethyl acetate=80:20 (V/V)), and the fractions containing the desired compound were concentrated under reduced pressure to obtain 552 mg (3.94 mmol, yield 75%) of the title compound as a pale yellow oil.

Reference Example 43

N-Methoxy-N-methylisothiazol-3-carboxamide

[Chemical Formula 306]

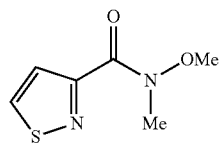

To a solution of 500 mg (3.87 mmol) of isothiazol-3-carboxylic acid (Apollo Scientific), 415 mg (4.25 mmol) of N,O-dimethylhydroxylamine hydrochloride and 30 mg (0.196 mmol) of 1-hydroxybenzotriazole monohydrate in methylene chloride (20 ml) were added 2.7 mL (15.46 mmol) of diisopropylamine and 1.49 g (7.77 mmol) of 1-(3-dimethylaminopropyl)-3-ethylcarbodiimide under an argon atmosphere, and the mixture was stirred at room temperature for 21 hours. After completion of the reaction, to the reaction mixture was added water, and the mixture was extracted with ethyl acetate. The resulting organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 60:40 (V/V)), and the fractions containing the desired compound were concentrated under reduced pressure to obtain 598 mg (3.47 mmol, yield 90%) of the title compound as a colorless oil Mass spectrum (EI, m/z): 172 [M]+.

$^1$H-NMR spectrum (400 MHz, CDCl$_3$) δ: 8.68 (1H, d, J=4.6 Hz), 7.69 (1H, d, J=4.0 Hz), 3.81 (3H, s), 3.47 (3H, brs).

Reference Example 44

N-Methoxy-N,2-dimethylthiophene-3-carboxamide

[Chemical Formula 307]

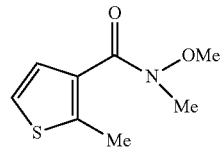

To a solution of 1.67 g (11.8 mmol) of 2-methylthiophene-3-carboxylic acid (synthesized according to a process described in Bioorganic and Medicinal Chemistry Letters, 21 (2011), pp. 5417-5422) in methylene chloride (20 ml) were added 1.26 g (12.9 mmol) of N,O-dimethylhydroxylamine hydrochloride, 90 mg (0.59 mmol) of 1-hydroxybenzotriazole monohydrate, 8.2 ml (47 mmol) of diisopropylamine and 4.50 g (23.5 mmol) of 1-(3-dimethylaminopropyl)-3-ethylcarbodiimide under an argon atmosphere, and the mixture was stirred at room temperature for 18 hours. After completion of the reaction, to the reaction mixture was added water, and the mixture was extracted with methylene chloride. The resulting organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 60:40 (V/V)), and the fractions containing the desired compound were concentrated under reduced pressure to obtain 1.85 g (9.99 mmol, yield 85%) of the title compound as a colorless oil.

Mass spectrum (EI, m/z): 185 [M]+.

$^1$H-NMR spectrum (400 MHz, CDCl$_3$) δ: 7.12 (1H, d, J=5.3 Hz), 7.02 (1H, d, J=5.4 Hz), 3.56 (3H, s), 3.32 (3H, s), 2.57 (3H, s).

Reference Example 45

1-(Isothiazol-3-yl)ethanone

[Chemical Formula 308]

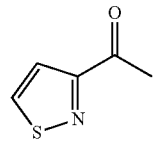

To a solution of 598 mg (3.47 mmol) of N-methoxy-N-methylisothiazol-3-carboxamide synthesized in analogy to Reference Example 43 in tetrahydrofuran (30 ml) was added dropwise 11.5 ml (34.5 mmol) of a 3.0M methylmagnesium chloride/tetrahydro solution at 0° C. under an argon atmosphere, and the mixture was stirred at room temperature for one hour. After completion of the reaction, to the reaction mixture was added a saturated aqueous ammonium chloride solution, and the mixture was extracted with ethyl acetate. The resulting organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=100:0 to 70:30 (V/V)), and the fractions containing the desired compound were concentrated under reduced pressure to obtain 86 mg (0.68 mmol, yield 19%) of the title compound as a yellow oil.

Mass spectrum (CI, m/z): 128 [M+1]$^+$.

$^1$H-NMR spectrum (400 MHz, CDCl$_3$) δ: 8.66 (1H, d, J=4.8 Hz), 7.82 (1H, d, J=4.6 Hz), 2.71 (3H, s).

Reference Example 46

1-(2-Methylthiophen-3-yl)ethanone

[Chemical Formula 309]

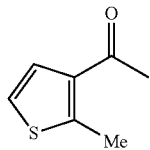

To a solution of 1.85 g (9.99 mmol) of N-methoxy-N,2-dimethylthiophene-3-carboxamide synthesized in analogy to Reference Example 44 in tetrahydrofuran (20 ml) was added dropwise 5.1 ml (15 mmol) of a 3.0M methylmagnesium chloride/tetrahydrofuran solution at 0° C. under an argon atmosphere, and the mixture was stirred at room temperature for 22.5 hours. After completion of the reaction, to the reaction mixture was added a saturated aqueous ammonium chloride solution, and the mixture was extracted with ethyl acetate. The resulting organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 60:40 (V/V)), and the fractions containing the desired compound were concentrated under reduced pressure to obtain 744 mg (5.31 mmol, yield 53%) of the title compound as a yellow oil.

Mass spectrum (EI, m/z): 140 [M]$^+$.

$^1$H-NMR spectrum (400 MHz, CDCl$_3$) δ: 7.35 (1H, d, J=5.4 Hz), 7.01 (1H, d, J=5.4 Hz), 2.74 (3H, s), 2.51 (3H, s).

Reference Example 47

(RS)-1-(2,4,5-Trifluorophenyl)ethanol

[Chemical Formula 310]

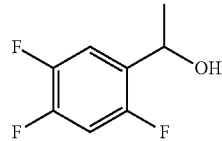

To a solution of 1.0 g (5.7 mmol) of 1-(2,4,5-trifluorophenyl)ethanone (Tokyo Chemical Industry Co., Ltd.) in ethanol (25 ml) was added 0.25 g (6.6 mmol) of sodium borohydride while stirring, and the mixture was stirred at room temperature for one hour. After completion of the reaction, the reaction mixture was concentrated under reduced pressure, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=97:3 to 76:24 (V/V)), and the fractions containing the desired compound were concentrated under reduced pressure to obtain 1.0 g (5.7 mmol, yield: quantitative) of the title compound as a colorless oil.

Mass spectrum (EI, m/z): 176 [M]$^+$.

$^1$H-NMR spectrum (400 MHz, CDCl$_3$) δ: 7.39-7.31 (1H, m), 6.89 (1H, td, J=9.8, 6.4 Hz), 5.19-5.12 (1H, m), 1.87 (1H, d, J=4.1 Hz), 1.48 (3H, d, J=6.4 Hz).

Reference Example 48

(RS)-1-(5-Fluoro-2-methylphenyl)ethanol

[Chemical Formula 311]

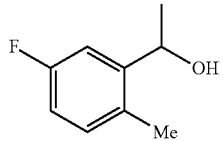

To a solution of 1.0 g (6.6 mmol) of 1-(5-fluoro-2-methylphenyl)ethanone (Alfa Aeser) in ethanol (25 ml) was added 0.30 g (7.9 mmol) of sodium borohydride while stirring, and the mixture was stirred at room temperature for one hour. After completion of the reaction, the reaction mixture was concentrated under reduced pressure, water was added, and the mixed solution was extracted with ethyl acetate. The organic layer was washed with saturated brine, subsequently dried over anhydrous magnesium sulfate, and concentrated under reduced pressure. The resulting residue was subjected to silica gel column chromatography, and the fraction having Rf=0.34 (developing solvent; hexane:ethyl acetate=80:20 (V/V)) was concentrated under reduced pressure to obtain 1.0 g (6.6 mmol, yield: quantitative) of the title compound as a colorless oil.

Mass spectrum (EI, m/z): 154 [M]$^+$.

$^1$H-NMR spectrum (400 MHz, CDCl$_3$) δ: 7.24 (1H, dd, J=10.2, 2.8 Hz), 7.07 (1H, dd, J=8.3, 5.8 Hz), 6.85 (1H, td, J=8.3, 2.8 Hz), 5.13-5.05 (1H, m), 2.28 (3H, s), 1.74 (1H, d, J=3.4 Hz), 1.44 (3H, d, J=6.4 Hz).

Reference Example 49

(RS)-1-(4-Fluoro-2-methylphenyl)ethanol

[Chemical Formula 312]

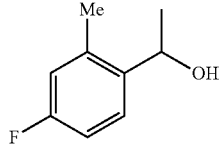

To a solution of 1.0 g (6.6 mmol) of 1-(4-fluoro-2-methylphenyl)ethanone (Matrix Scientific) in ethanol (25 ml) was added 0.30 g (7.9 mmol) of sodium borohydride while stirring, and the mixture was stirred at room temperature for one hour. After completion of the reaction, the reaction mixture was concentrated under reduced pressure, water was added, and the mixture was extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=90:10 to 69:31 (V/V)), and the fractions containing the desired compound were concentrated under reduced pressure to obtain 0.96 g (6.2 mmol, yield 95%) of the title compound as a colorless oil.

Mass spectrum (EI, m/z): 154 [M]$^+$.

$^1$H-NMR spectrum (400 MHz, CDCl$_3$) δ: 7.47 (1H, dd, J=8.5, 6.0 Hz), 6.91 (1H, td, =8.5, 2.7 Hz), 6.84 (1H, dd, J=9.7, 2.7 Hz), 5.10 (1H, qd, J=6.4, 3.5 Hz), 2.34 (3H, s), 1.68 (1H, d, J=3.5 Hz), 1.45 (3H, d, J=6.4 Hz).

Reference Example 50

(RS)-1-(Thiophen-3-yl)ethanol

[Chemical Formula 313]

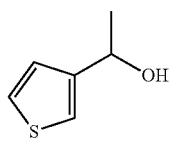

To a solution of 1.014 g (8.04 mmol) of 1-(thiophen-3-yl)ethanone (Tokyo Chemical Industry Co., Ltd.) in ethanol (80 ml) was added 353.0 mg (8.58 mmol) of sodium borohydride under an argon atmosphere while stirring, and the mixture was stirred at room temperature for 30 minutes. Additionally, 175.0 mg (4.63 mmol) of sodium borohydride was subsequently added, and the mixture was further stirred at room temperature for 3.5 hours. The reaction mixture was concentrated under reduced pressure, to the residue were added water and ethyl acetate, and the mixture was extracted with ethyl acetate twice. The organic layer was dried over anhydrous magnesium sulfate and concentrated under reduced pressure. The resulting residue was subjected to silica gel column chromatography (elution solvent; hexane:ethyl acetate=95:5 to 50:50 (V/V)), and the fractions containing the desired compound were concentrated under reduced pressure to obtain 1.025 g (8.00 mmol, yield 99.5%) of the title compound as a colorless oil.

Mass spectrum (EI, m/z): 128 [M]$^+$.

$^1$H-NMR spectrum (400 MHz, DMSO-d$_6$) δ: 7.43 (1H, dd, J=5.0, 2.9 Hz), 7.25 (1H, ddd, J=2.9, 1.2, 1.1 Hz), 7.08 (1H, dd, J=5.0, 1.2 Hz), 5.11 (1H, d, J=4.6 Hz), 4.79-4.72 (1H, m), 1.34 (3H, d, J=6.4 Hz).

Reference Example 51

(RS)-1-(Isothiazol-3-yl)ethanol

[Chemical Formula 314]

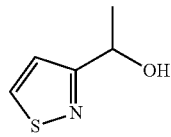

To a solution of 86 mg (0.68 mmol) of 1-(isothiazol-3-yl)ethanone synthesized in analogy to Reference Example 45 in ethanol (2 ml) was added 52 mg (1.4 mmol) of sodium borohydride under an argon atmosphere at 0° C., and the mixture was stirred at room temperature for 2 hours. After completion of the reaction, to the reaction mixture was added water, and the mixture was extracted with ethyl acetate. The resulting organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 60:40 (V/V)), and the fractions containing the desired compound were concentrated under reduced pressure to obtain 30 mg (0.23 mmol, yield 35%) of the title compound as a colorless oil.

Mass spectrum (CI, m/z): 130 [M+1]$^+$.

$^1$H-NMR spectrum (400 MHz, CDCl$_3$) δ: 8.65 (1H, d, J=4.6 Hz), 7.22 (1H, d, J=4.8 Hz), 5.06 (1H, q, J=6.2 Hz), 2.85 (1H, s), 1.58 (3H, d, J=6.7 Hz).

Reference Example 52

(RS)-1-(2-Methylthiophen-3-yl)ethanol

[Chemical Formula 315]

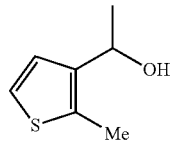

To a solution of 740 mg (5.28 mmol) of 1-(2-methylthiophen-3-yl)ethanone synthesized in analogy to Reference Example 46 in ethanol (10 ml) was added 200 mg (5.29 mmol) of sodium borohydride under an argon atmosphere at 0° C., and the mixture was stirred at room temperature for one hour. Additionally, 200 mg (5.29 mmol) of sodium borohydride was added at 0° C., and the mixture was stirred at room temperature for one hour. After completion of the reaction, to the reaction mixture was added water, and the mixture was extracted with ethyl acetate. The resulting organic layer was washed sequentially with water and saturated brine, subsequently dried over anhydrous magnesium sulfate, and concentrated under reduced pressure. The resulting residue was subjected to silica gel column chromatography (elution solvent; hexane:ethyl acetate=90:10 to 60:40 (V/V)), and the fractions containing the desired compound were concentrated under reduced pressure to obtain 613 mg (4.31 mmol, yield 82%) of the title compound as a colorless oil.

Mass spectrum (EI, m/z): 142 [M]+.

1H-NMR spectrum (400 MHz, CDCl3) δ: 7.05-7.04 (2H, m), 5.00 (1H, qd, J=6.4, 3.5 Hz), 2.44 (3H, s), 1.64 (1H, d, J=3.5 Hz), 1.48 (3H, d, J=6.4 Hz).

Reference Example 53

(R)-1-(Thiophen-3-yl)ethanol

[Chemical Formula 316]

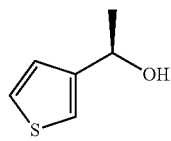

According to a process described in Journal of Organic Chemistry, 72 (2007) pp. 1639-1644, to a solution of 2.023 g (16.03 mmol) of 1-(thiophen-3-yl)ethanone (Aldrich) in tetrahydrofuran (100 ml), dried over Molecular Sieves 4A 1/16 (trade name, Wako Pure Chemical Industries, Ltd.) was added 0.446 g (1.61 mmol) of (S)-5,5-diphenyl-2-methyl-3,4-propano-1,3,2-oxazaborolidine (Aldrich) under an argon atmosphere at room temperature while stirring. Then, the temperature was adjusted to around −30° C. by a dry ice-ethanol bath, and 19.0 ml (17.1 mmol) of 0.9M borane-tetrahydrofuran complex (Tokyo Chemical Industry Co., Ltd.) was added dropwise over one hour while stirring, and the mixture was stirred at around −30° C. for one hour. After completion of the reaction, 50 ml of water was added, and then 100 ml of ethyl acetate and 5 ml of 1N hydrochloric acid were added to separate the layers. The resulting organic layer was washed with 50 ml of saturated brine, subsequently dried over anhydrous magnesium sulfate, and concentrated under reduced pressure. The resulting residue was subjected to silica gel column chromatography (elution solvent; hexane:ethyl acetate=95:5 to 74:26 (V/V)), and the fractions containing the desired compound were concentrated under reduced pressure to obtain 1.81 g (14.1 mmol, yield 88%, optical purity 82.9% ee) of the title compound as a colorless oil.

Optical Purity Analysis Conditions

Column: CHIRALCEL OJ-RH (trade name, Daicel Corporation)

Size: 0.46 cmI.D.×25 cmL.

Mobile phase: a 0.03% by volume aqueous trifluoroacetic acid solution/acetonitrile=75/25 (V/V)

Flow rate: 1.0 mL/min.

Temperature: 40° C.

Wavelength: 254 nm

1H-NMR spectrum (400 MHz, DMSO-d6) δ: 7.44 (1H, dd, J=5.0, 3.0 Hz), 7.25 (1H, ddd, J=3.0, 1.2, 0.9 Hz), 7.07 (1H, dd, J=5.0, 1.2 Hz), 5.11 (1H, d, J=4.8 Hz), 4.80-4.71 (1H, m), 1.34 (3H, d, J=6.4 Hz).

Reference Example 54

(R)-1-(4-Methylthiophen-3-yl)ethanol

[Chemical Formula 317]

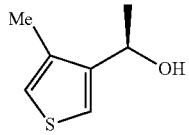

To a solution of 78 mg (0.28 mmol) of (S)-5,5-diphenyl-2-methyl-3,4-propano-1,3,2-oxazaborolidine (Aldrich) in tetrahydrofuran (1.0 ml) was added dropwise 3.4 ml (3.1 mmol) of 0.9M borane-tetrahydrofuran complex under an argon atmosphere at −30° C. to −27° C., and the mixture was stirred at −30° C. to −27° C. for 30 minutes. Then, a solution of 406 mg (2.90 mmol) of 1-(4-methylthiophen-3-yl)ethanone synthesized in analogy to Reference Example 42 in tetrahydrofuran (20 ml) was added dropwise at −30° C. to −27° C., and the mixture was stirred at −30° C. to −27° C. for one hour. After completion of the reaction, to the reaction mixture were added water and 1N hydrochloric acid, and the mixture was extracted with ethyl acetate. The resulting organic layer was washed with saturated brine, subsequently dried over anhydrous magnesium sulfate, and concentrated under reduced pressure. The resulting residue was subjected to silica gel column chromatography (elution solvent; hexane:ethyl acetate=95:5 to 70:30 (V/V)), and the fractions containing the desired compound were concentrated under reduced pressure to obtain 387 mg (2.72 mmol, yield 94%) of the title compound as a colorless oil.

Mass spectrum (EI, m/z): 142 [M]+.

1H-NMR spectrum (400 MHz, CDCl3) δ: 7.23-7.21 (1H, m), 6.92 (1H, dq, J=3.1, 0.9 Hz), 4.92 (1H, qdd, J=6.4, 4.8, 0.8 Hz), 2.27 (3H, d, J=0.9 Hz), 1.63 (1H, d, J=4.6 Hz), 1.53 (3H, d, J=6.4 Hz).

Reference Example 55

(R)-1-{2'-[(tert-Butoxycarbonyl)amino]-4'-(5-chloro-3-{[(1-phenylethoxy)carbonyl]-amino}thiophen-2-yl)-[1,1'-biphenyl]-4-yl}cyclopropanecarboxylic acid ethyl ester

[Chemical Formula 318]

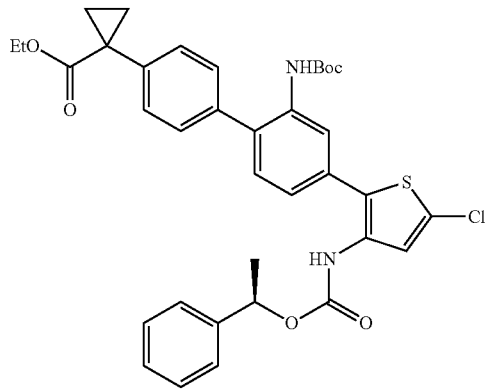

109 mg (0.201 mmol) of 1-{2'-[(tert-butoxycarbonyl)amino]-4'-(3-carbamoyl-5-chlorothiophen-2-yl)-[1,1'-biphenyl]-4-yl}cyclopropanecarboxylic acid ethyl ester synthesized in analogy to Reference Example 36 was subjected to azeotropic dehydration treatment with 2 ml of toluene, and the mixture was dried under reduced pressure. Under an argon atmosphere, 2 ml of toluene, 0.050 ml (0.62 mmol) of pyridine and 46 mg (0.38 mmol) of (R)-1-phenylethanol (Tokyo Chemical Industry Co., Ltd.) were added, then 110 mg (0.258 mmol) of [bis(trifluoroacetoxy)iodo]benzene was added, and the mixture was heated and stirred at 80° C. for 5 hours. After completion of the reaction, the reaction mixture was allowed to cool and subjected to silica gel column chromatography (elution solvent; hexane:ethyl acetate=67:33 to 55:45 (V/V)), and the fractions containing the desired compound were concentrated under reduced pressure to obtain 136 mg (0.173 mmol (purity 84% by weight), yield 86%) of the title compound as a yellow oil.

$^1$H-NMR spectrum (400 MHz, DMSO-$d_6$, 75° C.) δ: 8.95 (1H, brs), 7.94 (1H, brs), 7.60 (1H, d, J=1.8 Hz), 7.43-7.22 (11H, m), 7.12 (1H, s), 5.74 (1H, q, J=6.5 Hz), 4.06 (2H, q, J=7.1 Hz), 1.52 (2H, dd, J=6.9, 4.0 Hz), 1.48 (3H, d, J=6.5 Hz), 1.30 (9H, s), 1.19 (2H, dd, J=7.1, 4.1 Hz), 1.13 (3H, t, J=7.1 Hz).

Reference Example 56

(R)-1-{2'-[(tert-Butoxycarbonyl)amino]-4'-(5-chloro-3-{[(1-phenylethoxy)carbonyl]-amino}thiophen-2-yl)-[1,1'-biphenyl]-4-yl}cyclopropanecarboxylic acid

[Chemical Formula 319]

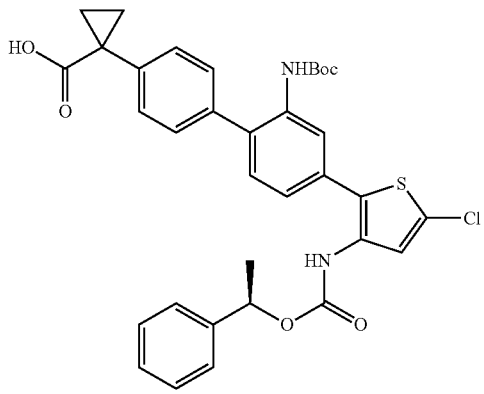

To a solution of 129 mg (0.164 mmol (purity 84% by weight)) of (R)-1-{2'-[(tert-butoxycarbonyl)amino]-4'-(5-chloro-3-{[(1-phenylethoxy)carbonyl]-amino}thiophen-2-yl)-[1,1'-biphenyl]-4-yl}cyclopropanecarboxylic acid ethyl ester synthesized in Reference Example 55 in isopropyl alcohol (2 ml) was added 1 ml (4 mmol) of a 4N aqueous sodium hydroxide solution, and the mixture was stirred at room temperature for 68 hours. After completion of the reaction, the reaction mixture was acidified by adding 1N hydrochloric acid thereto, and extracted with ethyl acetate. The organic layer was washed with saturated brine, subsequently dried over anhydrous magnesium sulfate, and concentrated under reduced pressure. The resulting residue was subjected to silica gel column chromatography (elution solvent; hexane:ethyl acetate=60:40 to 39:61 (V/V)), and the fractions containing the desired compound were concentrated under reduced pressure to obtain 70.2 mg (0.111 mmol, yield 68%) of the title compound as a white solid.

$^1$H-NMR spectrum (400 MHz, DMSO-$d_6$, 75° C.) δ: 11.99 (1H, brs), 8.96 (1H, brs), 7.93 (1H, brs), 7.61 (1H, d, J=1.8 Hz), 7.42-7.37 (2H, m), 7.36-7.23 (9H, m), 7.12 (1H, s), 5.74 (1H, q, J=6.6 Hz), 1.50-1.47 (2H, m), 1.48 (3H, d, J=6.5 Hz), 1.30 (9H, s), 1.13 (2H, dd, J=6.8, 4.0 Hz).

Test Example 1

Binding test of GTPγS to LPA1 receptor

5 μg of the membrane fraction of RH 7777 cells expressed with human LPA1 receptor (A324, ChanTest) was suspended in a reaction buffer (20 mM HEPES, 100 mM NaCl, 10 mM $MgCl_2$, 10 μM GDP, 5 μg saponin, 0.2% BSA, 0.1 nM [$^{35}$S]GTPγS (NEG030X, Perkin Elmer), pH 7.4), and the test compound dissolved in DMSO in various concentrations was added. After preincubation at 30° C. for 15 minutes, LPA (L7260, Sigma, the final concentration of 100 nM) was added, and the suspension was incubated at 30° C. for 30 minutes. The membrane fraction was collected onto a glass fiber filter (GF/B, Whatman) by using a cell harvester (M30, Brandel), and washed with a 10 mM phosphate buffer (pH 7.4). The radioactivity of the membrane fraction was measured using a liquid scintillation analyzer (2900TR, Packard) and the concentration of the test compound which inhibits the binding of LPA1 receptor and [$^{35}$S]GTPγS by 50%, ($IC_{50}$) was determined by non-linear regression analysis using EXSAS (version 7.6.0, Arm Systex).

The compound of the present invention showed the excellent activity in this test, and, for example, the $IC_{50}$ values of Compound Nos. I-11, I-24, I-28, I-38, I-42, I-51, I-52, I-56, I-60, I-76, I-100, I-104, I-112, I-122, I-126, I-140, and I-152 were 200 nM or less.

Test Example 2

Cell Migration Test

The cell migration test was carried out using Chemo-Tx (registered trademark) (116-8, Neuro Probe). A2058 human melanoma cells (obtained from European Collection of Cell Culture) were cultured in a serum-free EMEM medium for 24 hours, and then re-suspended in a 0.1% BSA-containing DMEM medium to obtain a cell suspension. The test compound dissolved in DMSO in various concentration was each added to the cell suspension, and the suspension was cultured at 37° C. for 15 minutes (the final DMSO concentration of 0.5%). LPA dissolved in a 0.1% BSA-containing DMEM medium (the final concentration of 100 nM) was added to Chemo-Tx 96 well plate, and a Chemo-Tx filter which had been coated with 0.001% Fibronectin on the both surfaces was put on the plate. The suspension of cultured cells (25,000 cells) was added onto the upper surface of the filter and further cultured at 37° C. for 3 hours, and the cells on the upper surface of the filter were removed. After the filter was removed and dried, the cells which had migrated to the lower surface of the filter were stained using Diff-Quik stain (16920, Sysmex). The absorbance of the filter (570 nm) was measured and the concentration of the test compound which inhibits the cell migration activity of LPA by 50%, ($IC_{50}$) was determined by non-linear regression analysis using EXSAS (version 7.6.0, Arm Systex).

The compound of the present invention showed the excellent activity in this test, and, for example, the $IC_{50}$ values of Compound Nos. I-24, I-28, I-38, I-42, I-51, I-52, I-56, I-60, I-64, I-68, I-72, I-76, I-100, I-104, I-112, I-122, I-126, I-136, I-140, I-148, I-152, I-171, I-196, I-350, I-354, I-358, I-362, I-366, I-370, I-374, I-378, I-388, I-396, I-420, I-424, I-428, I-432, I-442, I-446, I-450, I-454, I-458, I-466, I-469, I-477, I-481, I-490, I-498, I-502, I-534, I-595, I-596, I-605, I-606, I-621, I-625, I-630, I-639, I-640, I-649, I-650, I-657, I-674, I-779, I-780, I-783, I-791, I-808, I-811, I-815, I-823, and I-840 were 200 nM or less.

Test Example 3

LPA-induced histamine release test in mouse

LPA-induced histamine release test in mouse was carried out according to a method by Swaney et al. (The Journal of Pharmacology and Experimental Therapeutics, 336 (2011), pages 693-700). The test compound was suspended in 0.5% methylcellulose solution (133-14255, Wako), and orally administered to male CD1 mice (body weight: 30 to 40 g, supplied by Charles River Laboratories Japan) at a dose of 10 mL/kg. 4 hours after administration, LPA (857130P, Avanti) dissolved in a 0.1% BSA-containing PBS was administered via the tail vein (300 µg/mouse). Immediately, the mouse was anesthetized with isoflurane, and blood was collected via a vein 2 minutes after the administration of LPA. The blood was put into a test tube containing EDTA, and centrifuged at 4° C., 2,000×g, for 10 minutes to obtain the plasma.

The histamine concentration in the plasma was measured by EIA kit (62HTMPEB, Cisbio Bioassays).

The inhibition rate (%) in 0.5% methylcellulose solution administration group was calculated in each individual based on the plasma histamine concentration in the mouse to which the test compound had been administered, and the rate of individuals which showed the inhibition rate of 80% or more was expressed as the efficacy rate (%).

The compound of the present invention showed the excellent activity in this test, and the efficacy rate at the dose of 10 mg/kg was 50% or more, for example, in Examples I-24, I-28, I-38, I-42, I-52, I-56, I-60, I-64, I-68, I-100, I-104, I-112, I-122, I-126, I-136, I-152, I-196, I-350, I-354, I-358, I-362, I-366, I-370, I-374, I-378, I-388, I-420, I-424, I-428, I-432, I-442, I-450, I-458, I-596, I-606, I-639, I-640, I-649, I-650, I-657, I-780, and I-811.

Test Example 4

Bleomycin-induced Pulmonary Fibrosis Model

Bleomycin hydrochloride (Nippon Kayaku) is administered to a mouse to prepare a pulmonary fibrosis model. The test compound is orally administered every day from the day when bleomycin administration is started. On the $3^{rd}$ day to the $42^{nd}$ day after the treatment with bleomycin, bronchoalveolar lavage fluid (BALF) or lung is collected under anesthesia with isoflurane. BALF is centrifuged at 800×g for 10 minutes to obtain a supernatant. The protein concentration of the supernatant is measured using DC protein assay kit (500-0114, Biorad), and the collagen concentration is measured using Sircol solble collagen assay kit (S111, Biocolor). Further, a biomarker relating to inflammation or fibrosis in the supernatant is measured using an ELISA method. After the wet weight of the lung is measured, the hydroxyproline amount in the tissue is measured by modifying Woessner method (Archives of Biochemistry and Biophysics, 93 (1961), pages 440-447). A part of the lung is fixed with 10% formalin neutral buffer solution, and the histopathological changes are observed. The results are statistically analyzed using EXSAS (version 7.6.0, Arm Systex).

Test Example 5

Unilateral Ureteral Ligation (UUO) Renal Fibrosis Model

After a mouse was anesthetized with isoflurane, the abdomen was incised. The left ureter was ligated with a silk thread to prepare a UUO model. The test compound was orally administered every day from the day when UUO was prepared. On the $8^{th}$, $14^{th}$, or $21^{st}$ day after the preparation of UUO, the kidney was harvested and the wet weight was measured. RNA was extracted from a part of the kidney and the expression level of the marker gene of fibrosis was measured by a quantitative PCR method. Further, the hydroxyproline amount or the collagen amount in the renal tissue was measured. The results were statistically analyzed using EXSAS.

Test Example 6

Carbon Tetrachloride ($CCl_4$)-induced Hepatic Fibrosis Model

Diluted $CCl_4$ (035-01273, Wako Pure Chemical) is administered to a mouse twice a week to prepare a hepatic fibrosis model. The test compound is orally administered every day from the day when the $CCl_4$ administration is started. On the $3^{rd}$ day to the $28^{th}$ day after the $CCl_4$ administration is started, the liver is collected under anesthesia with isoflurane, and the wet weight is measured. RNA is extracted from a part of the liver, and the expression level of the marker gene of fibrosis is measured by a quantitative PCR method. Further, the hydroxyproline amount or the collagen amount in the hepatic tissue is measured. A part of the liver is fixed with 10% formalin neutral buffer solution, and the histopathological changes are observed. The results are statistically analyzed using EXSAS.

Test Example 7

Non-alcoholic Steatohepatitis (NASH) Model

A rat is fed with a methionine/choline-deficient (MCD) diet to prepare a NASH model. The rat is allowed to freely take an ordinary diet or the MCD diet for 20 weeks. The test compound is orally administered every day from the day when the feed with the MCD diet is started. After the breeding for 20 weeks, the liver is collected under anesthesia with isoflurane, and the wet weight is measured. RNA is extracted from a part of liver, and the expression of the marker gene of fibrosis is measured by a quantitative PCR method. Further, the hydroxyproline amount or the collagen amount in the hepatic tissue is measured. A part of the liver is fixed with 10% formalin neutral buffer solution, and the histopathological changes are observed. The results are statistically analyzed using EXSAS.

Based on the results of the above Test Examples 1 to 3, the α-halogen-substituted thiophene compound of the present invention has a LPA receptor-antagonist activity and it is particularly useful as a medicament for the treatment and/or prevention (preferably, a medicament for the treatment) of a disease accompanying fibrosis, an immunological or inflammatory disease, a central or peripheral nervous system disease, an urologic disease or a cancer-related disease.

INDUSTRIAL APPLICABILITY

The α-halogen-substituted thiophene compound represented by the general formula (I) of the present invention and, a pharmacologically acceptable salt thereof has a potent LPA receptor-antagonist activity and it is useful as a medicament (a medicament for the treatment and/or prevention of a disease accompanying fibrosis, an immunological or inflammatory disease, a central or peripheral nervous system disease, an urologic disease or a cancer-related disease).

The invention claimed is:

1. A compound represented by the formula (I):

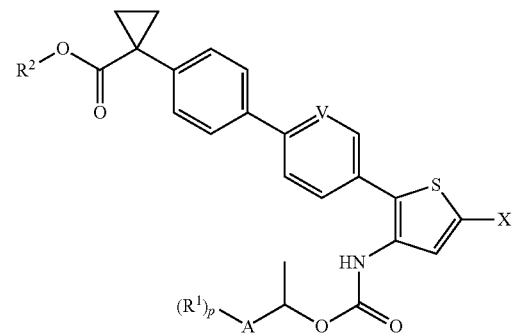

wherein
A represents, a phenyl ring;
$R^1$ is the same or different, and represents a halogen atom, or a $C_1$-$C_3$ alkyl group;
$R^2$ represents a hydrogen atom, or a $C_1$-$C_6$ alkyl group;
p represents an integer of 0 to 5;
V represents $CR^3$ wherein $R^3$ represents a hydrogen atom, an amino group, a nitro group, or a $C_1$-$C_3$ alkoxy group;
X represents a halogen atom,
or a pharmacologically acceptable salt thereof.

2. The compound according to claim 1 which is represented by the formula (Ia):

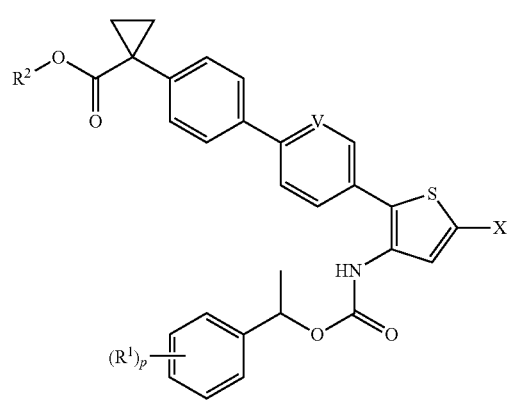

wherein
$R^1$ is the same or different, and represents a halogen atom, or a $C_1$-$C_3$ alkyl group,
$R^2$ represents a hydrogen atom, or a $C_1$-$C_6$ alkyl group;
p represents an integer of 0 to 5;
V represents CH;
X represents a halogen atom,
or a pharmacologically acceptable salt thereof.

3. The compound according to claim 2 wherein, in the formula (Ia), the group:

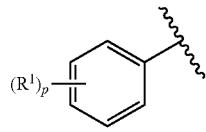

is selected from a group consisting of the groups:

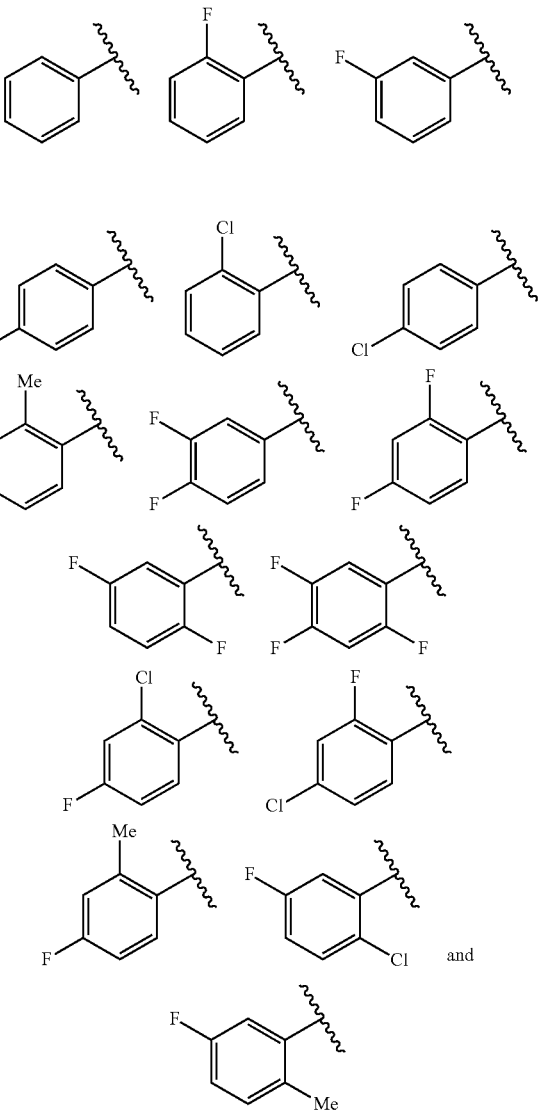

or a pharmacologically acceptable salt thereof.

4. The compound according to claim 2 wherein, in the formula (Ia), the group:

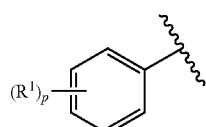

is selected from a group consisting of the groups:

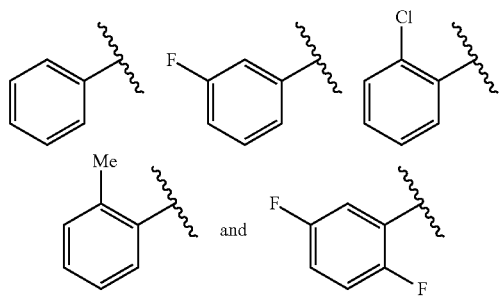

or a pharmacologically acceptable salt thereof.

5. (RS)-1-{4'-[5-bromo-3-({[1-(2-chlorophenyl)ethoxy]carbonyl}amino)thiophen-2-yl]-[1,1'-biphenyl]-4-yl}cyclopropanecarboxylic acid,
(RS)-1-{4'-[5-chloro-3-({[1-(2-chlorophenyl)ethoxy]carbonyl}amino)thiophen2-yl]-[1,1'-biphenyl]-4-yl}cyclopropanecarboxylic acid,
(R)-1-{4'-[5-chloro-3-({[1-(2-chlorophenyl)ethoxy]carbonyl}amino)thiophen2-yl]-[1,1'-biphenyl]-4-yl}cyclopropanecarboxylic acid,
(R)-1-[4'-(5-chloro-3-{[(1-phenylethoxy)carbonyl]amino}thiophen-2-yl)-[1,1'-biphenyl]-4-yl]cyclopropanecarboxylic acid,
(R)-1-{4'-[5-chloro-3-({[1-(2-fluorophenyl)ethoxy]carbonyl}amino)thiophen2-yl]-[1,1'-biphenyl]-4-yl}cyclopropanecarboxylic acid,
(R)-1-{4'-[5-chloro-3-({[1-(3-fluorophenyl)ethoxy]carbonyl}amino)thiophen-2-yl]-[1,1'-biphenyl]-4-yl}cyclopropanecarboxylic acid,
(R)-1-{4'-[5-chloro-3-({[1-(4-fluorophenyl)ethoxy]carbonyl}amino)thiophen2-yl]-[1,1'-biphenyl]-4-yl}cyclopropanecarboxylic acid,
(R)-1-{4'-[5-chloro-3-({[1-(4-chlorophenyl)ethoxy]carbonyl}amino)thiophen2-yl]-[1,1'-biphenyl]-4-yl}cyclopropanecarboxylic acid,
(R)-1-{4'-[5-chloro-3-({[1-(o-tolyl)ethoxy]carbonyl}amino)thiophen-2-yl][1,1'-biphenyl]-4-yl}cyclopropanecarboxylic acid,
(R)-1-{4'-[5-chloro-3-({[1-(2,4-difluorophenyl)ethoxy]carbonyl}amino)thiophen-2-yl]-[1,1'-biphenyl]-4-yl}cyclopropanecarboxylic acid,
(R)-1-{4'-[5-chloro-3-({[1-(2,5-difluorophenyl)ethoxy]carbonyl}amino)thiophen-2-yl]-[1,1'-biphenyl]-4-yl}cyclopropanecarboxylic acid,
(R)-1-{4'-[5-chloro-3-({[1-(3,4-difluorophenyl)ethoxy]carbonyl}amino)thiophen-2-yl]-[1,1'-biphenyl]-4-yl}cyclopropanecarboxylic acid,
(R)-1-{4'-[5-chloro-3-({[1-(2-chloro-4-fluorophenyl)ethoxy]carbonyl}amino)thiophen-2-yl]-[1,1'-biphenyl]-4-yl}cyclopropanecarboxylic acid,
(R)-1-[4'-(5-fluoro-3-{[(1-phenylethoxy)carbonyl]amino}thiophen-2-yl)-[1,1'-biphenyl]-4-yl]cyclopropanecarboxylic acid,
(R)-1-{4'-[5-fluoro-3-({[1-(2-fluorophenyl)ethoxy]carbonyl}amino)thiophen2-yl]-[1,1'-biphenyl]-4-yl}cyclopropanecarboxylic acid,
(R)-1-{4'-[5-fluoro-3-({[1-(4-fluorophenyl)ethoxy]carbonyl}amino)thiophen-2-yl]-[1,1'-biphenyl]-4-yl}cyclopropanecarboxylic acid,
(R)-1-{4'-[3-({[1-(2-chlorophenyl)ethoxy]carbonyl}amino)-5-fluorothiophen2-yl]-[1,1'-biphenyl]-4-yl}cyclopropanecarboxylic acid,
(R)-1-{4'-[3-({[1-(4-chlorophenyl)ethoxy]carbonyl}amino)-5-fluorothiophen2-yl]-[1,1'-biphenyl]-4-yl}cyclopropanecarboxylic acid,
(R)-1-{4'-[5-fluoro-3-({[1-(o-tolyl)ethoxy]carbonyl}amino)thiophen-2-yl][1,1'-biphenyl]-4-yl}cyclopropanecarboxylic acid,
(R)-1-{4'-[3-({[1-(3,4-difluorophenyl)ethoxy]carbonyl}amino)-5-fluorothiophen-2-yl]-[1,1'-biphenyl]-4-yl}cyclopropanecarboxylic acid,
(R)-1-{4'-[3-({[1-(2,4-difluorophenyl)ethoxy]carbonyl}amino)-5-fluorothiophen-2-yl]-[1,1'-biphenyl]-4-yl}cyclopropanecarboxylic acid,
(R)-1-{4'-[3-({[1-(2-chloro-4-fluorophenyl)ethoxy]carbonyl}amino)-5-fluorothiophen-2-yl]-[1,1'-biphenyl]-4-yl}cyclopropanecarboxylic acid,
(RS)-1-{4'-[3-({[1-(4-chloro-2-fluorophenyl)ethoxy]carbonyl}amino)-5 fluorothiophen-2-yl]-[1,1'-biphenyl]-4-yl}cyclopropanecarboxylic acid,
(RS)-1-{4'-[5-fluoro-3-({[1-(2,4,5-trifluorophenyl)ethoxy]carbonyl}amino)thiophen-2-yl]-[1,1'-biphenyl]-4-yl}cyclopropanecarboxylic acid
or a pharmacologically acceptable salt thereof.

6. The compound according to claim 1 wherein, in the general formula (I), V represents $CR^3$ in which $R^3$ represents an amino group, a nitro group, or a $C_1$-$C_3$ alkoxy group,
or a pharmacologically acceptable salt thereof.

7. The compound according to claim 6 which is represented by the formula (Ib):

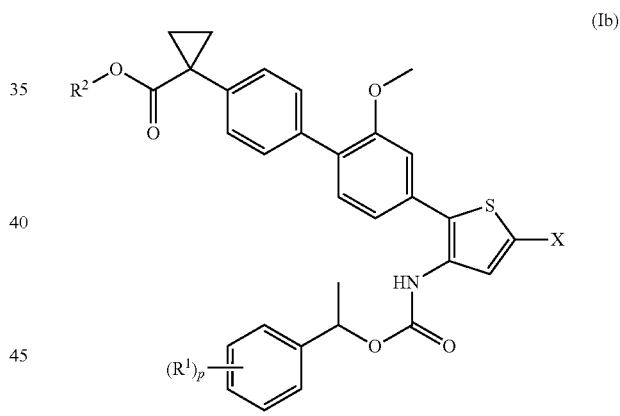

(Ib)

wherein
$R^1$ is the same or different, and represents a halogen atom, or a $C_1$-$C_3$ alkyl group;
$R^2$ represents a hydrogen atom or a $C_1$-$C_6$ alkyl group;
p represents an integer of 0 to 5;
X represents a halogen atom,
or a pharmacologically acceptable salt thereof.

8. The compound according to claim 7 wherein, in the formula (Ib), the group:

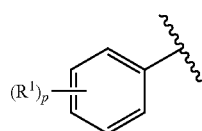

is selected from a group consisting of the groups:

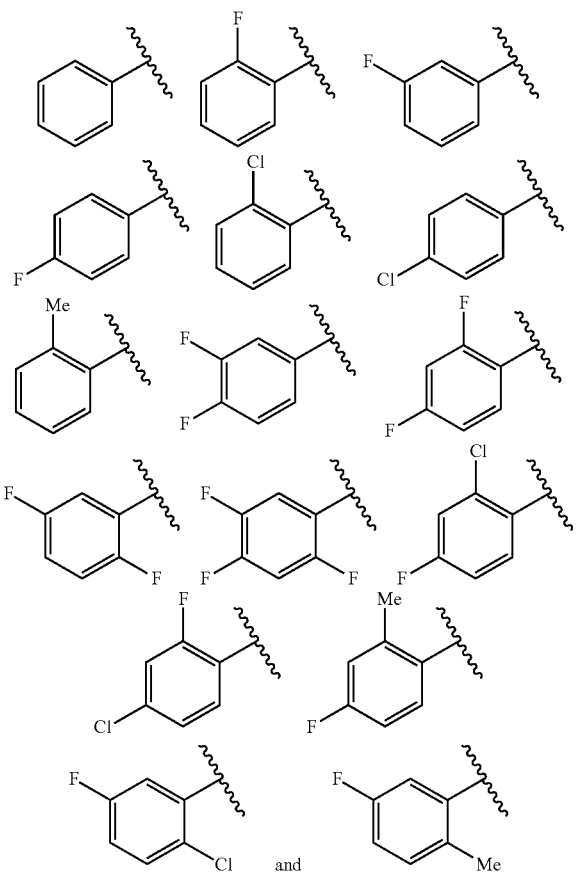

or a pharmacologically acceptable salt thereof.

9. The compound according to claim 7 wherein, in the formula (Ib), the group:

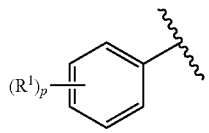

is selected from a group consisting of the groups:

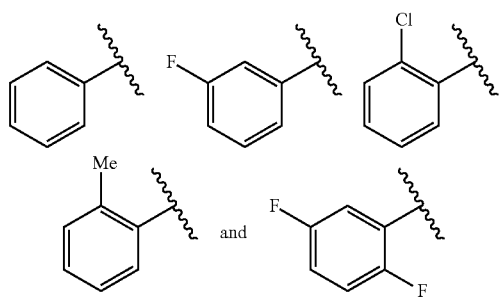

or a pharmacologically acceptable salt thereof.

10. The compound according to claim 7 which is selected from a group consisting of:

(R)-1-[4'-(5-chloro-3-{[(1-phenylethoxy)carbonyl]amino}thiophen-2-yl)-2'methoxy-[1,1'-biphenyl]-4-yl]cyclopropanecarboxylic acid,
(R)-1-{4'-[5-chloro-3-({[1-(2-fluorophenyl)ethoxy]carbonyl}amino)thiophen2-yl]-2'-methoxy-[1,1'-biphenyl]-4-yl}cyclopropanecarboxylic acid,
(R)-1-{4'-[5-chloro-3-({[1-(3-fluorophenyl)ethoxy]carbonyl}amino)thiophen2-yl]-2'-methoxy-[1,1'-biphenyl]-4-yl}cyclopropanecarboxylic acid,
(R)-1-{4'-[5-chloro-3-({[1-(4-fluorophenyl)ethoxy]carbonyl}amino)thiophen2-yl]-2'-methoxy-[1,1'-biphenyl]-4-yl}cyclopropanecarboxylic acid,
(R)-1-{4'-[5-chloro-3-({[1-(2-chlorophenyl)ethoxy]carbonyl}amino)thiophen2-yl]-2'-methoxy-[1,1'-biphenyl]-4-yl}cyclopropanecarboxylic acid,
(R)-1-{4'-[5-chloro-3-({[1-(4-chlorophenyl)ethoxy]carbonyl}amino)thiophen2-yl]-2'-methoxy-[1,1'-biphenyl]-4-yl}cyclopropanecarboxylic acid,
(R)-1-{4'-[5-chloro-3-({[1-(o-tolyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(3,4-difluorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(2,4-difluorophenyl)ethoxy]carbonyl}amino)thiophen-2-yl]-2'-methoxy-[1,1'-biphenyl]-4-yl}cyclopropanecarboxylic acid,
(RS)-1-{4'-[5-chloro-3-({[1-(2-chloro-5-fluorophenyl)ethoxy]carbonyl}amino)thiophen-2-yl]-2'-methoxy-[1,1'-biphenyl]-4-yl}cyclopropanecarboxylic acid,
(R)-1-{4'-[5-chloro-3-({[1-(2-chloro-4-fluorophenyl)ethoxy]carbonyl}amino)thiophen-2-yl]-2'-methoxy-[1,1'-biphenyl]-4-yl}cyclopropanecarboxylic acid,
(RS)-1-{4'-[5-chloro-3-({[1-(5-fluoro-2-methylphenyl)ethoxy]carbonyl}amino)thiophen-2-yl]-2'-methoxy-[1,1'-biphenyl]-4-yl}cyclopropanecarboxylic acid,
(RS)-1-{4'-[5-chloro-3-({[1-(4-fluoro-2-methylphenyl)ethoxy]carbonyl}amino)thiophen-2-yl]-2'-methoxy-[1,1'-biphenyl]-4-yl}cyclopropanecarboxylic acid,
(R)-1-[4'-(5-fluoro-3-{[(1-phenylethoxy)carbonyl]amino}thiophen-2-yl)-2'-methoxy-[1,1'-biphenyl]-4-yl]cyclopropanecarboxylic acid,
(R)-1-{4'-[5-fluoro-3-({[1-(2-fluorophenyl)ethoxy]carbonyl}amino)thiophen2-yl]-2'-methoxy-[1,1'-biphenyl]-4-yl}cyclopropanecarboxylic acid,
(R)-1-{4'-[5-fluoro-3-({[1-(3-fluorophenyl)ethoxy]carbonyl}amino)thiophen2-yl]-2'-methoxy-[1,1'-biphenyl]-4-yl}cyclopropanecarboxylic acid,
(R)-1-{4'-[5-fluoro-3-({[1-(4-fluorophenyl)ethoxy]carbonyl}amino)thiophen2-yl]-2'-methoxy-[1,1'-biphenyl]-4-yl}cyclopropanecarboxylic acid,
(R)-1-{4'-[3-({[1-(2-chlorophenyl)ethoxy]carbonyl}amino)-5-fluorothiophen2-yl]-2'-methoxy-[1,1'-biphenyl]-4-yl}cyclopropanecarboxylic acid,
(R)-1-{4'-[3-({[1-(4-chlorophenyl)ethoxy]carbonyl}amino)-5-fluorothiophen2-yl]-2'-methoxy-[1,1'-biphenyl]-4-yl}cyclopropanecarboxylic acid,
(R)-1-{4'-[5-fluoro-3-({[1-(o-tolyl)ethoxy]carbonyl}amino)thiophen-2-yl]-2'-methoxy-[1,1'-biphenyl]-4-yl}cyclopropanecarboxylic acid,
(R)-1-{4'-[3-({[1-(3,4-difluorophenyl)ethoxy]carbonyl}amino)-5-fluorothiophen-2-yl]-2'-methoxy-[1,1'-biphenyl]-4-yl}cyclopropanecarboxylic acid, (R)-1-{4'-[3-({[1-(2,5-difluorophenyl)ethoxy]
carbonyl}amino)-5-fluorothiophen-2-yl]-2'-methoxy-
[1,1'-biphenyl]-4-yl}cyclopropanecarboxylic acid, (R)-1-{4'-[3-({[1-(2,4-difluorophenyl)ethoxy]
carbonyl}amino)-5-fluorothiophen-2-yl]-2'-methoxy-
[1,1'-biphenyl]-4-yl}cyclopropanecarboxylic acid, (RS)-1-{4'-[3-({[1-(2-chloro-5-fluorophenyl)ethoxy]
carbonyl}amino)-5fluorothiophen-2-yl]-2'-methoxy-
[1,1'-biphenyl]-4-yl}cyclopropanecarboxylic acid, (R)-1-{4'-[3-({[1-(2-chloro-4-fluorophenyl)ethoxy]
carbonyl}amino)-5-fluorothiophen-2-yl]-2'-methoxy-
[1,1'-biphenyl]-4-yl}cyclopropanecarboxylic acid, (RS)-1-{4'-[5-fluoro-3-({[1-(5-fluoro-2-methylphenyl)
ethoxy]carbonyl}amino)thiophen-2-yl]-2'-methoxy-[1,
1'-biphenyl]-4-yl}cyclopropanecarboxylic acid, and (RS)-1-{4'-[5-fluoro-3-({[1-(4-fluoro-2-methylphenyl)
ethoxy]carbonyl}amino)thiophen-2-yl]-2'-methoxy-[1,
1'-biphenyl]-4-yl}cyclopropanecarboxylic acid, or a pharmacologically acceptable salt thereof.

11. (R)-1-{4'-[5-chloro-3-({[1-(2-chlorophenyl)ethoxy]carbonyl}amino)thiophen2-yl]-[1,1'-biphenyl]-4-yl}cyclopropanecarboxylic acid, or a pharmacologically acceptable salt thereof.

12. (R)-1-{4'-[5-chloro-3-({[1-(3-fluorophenyl)ethoxy]carbonyl}amino)thiophen2-yl]-[1,1'-biphenyl]-4-yl}cyclopropanecarboxylic acid, or a pharmacologically acceptable salt thereof.

13. (R)-1-{4'-[3-({[1-(2-chlorophenyl)ethoxy]carbonyl}amino)-5-fluorothiophen2-yl]-[1,1'-biphenyl]-4-yl}cyclopropanecarboxylic acid, or a pharmacologically acceptable salt thereof.

14. (R)-1-{4'-[5-fluoro-3-({[1-(o-tolyl)ethoxy]carbonyl}amino)thiophen-2-yl][1,1'-biphenyl]-4-yl}cyclopropanecarboxylic acid, or a pharmacologically acceptable salt thereof.

15. (R)-1-[4'-(5-chloro-3-{[(1-phenylethoxy)carbonyl]amino}thiophen-2-yl)2'-methoxy-[1,1'-biphenyl]-4-yl]cyclopropanecarboxylic acid, or a pharmacologically acceptable salt thereof.

16. (R)-1-{4'-[5-chloro-3-({[1-(2,5-difluorophenyl)ethoxy]carbonyl}-amino)thiophen-2-yl]-2'-methoxy-[1,1'-biphenyl]-4-yl}cyclopropanecarboxylic acid, or a pharmacologically acceptable salt thereof.

17. (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid, or a pharmacologically acceptable salt thereof.

18. A pharmaceutical composition comprising:
the compound or a pharmacologically acceptable salt thereof according to claim 1 as an active ingredient; and
an additive.

* * * * *